(12) United States Patent
Weir et al.

(10) Patent No.: US 8,790,933 B2
(45) Date of Patent: Jul. 29, 2014

(54) SCREENING

(75) Inventors: Malcolm Peter Weir, Welwyn Garden (GB); Fiona Hamilton Marshall, Welwyn Garden (GB)

(73) Assignee: Heptares Therapeutics Limited, Hertfordshire (GB)

( * ) Notice: Subject to any disclaimer, the term of this patent is extended or adjusted under 35 U.S.C. 154(b) by 539 days.

(21) Appl. No.: 12/809,181

(22) PCT Filed: Dec. 19, 2008

(86) PCT No.: PCT/GB2008/004223
§ 371 (c)(1),
(2), (4) Date: Oct. 20, 2010

(87) PCT Pub. No.: WO2009/081136
PCT Pub. Date: Jul. 2, 2009

(65) Prior Publication Data
US 2011/0027910 A1 Feb. 3, 2011

(30) Foreign Application Priority Data
Dec. 20, 2007 (GB) ................................. 0724860.2

(51) Int. Cl.
*G01N 33/567* (2006.01)
*C07K 14/705* (2006.01)

(52) U.S. Cl.
USPC ........................................ 436/501; 435/7.21

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner et al. | |
| 5,223,409 A | 6/1993 | Ladner et al. | |
| 5,290,681 A | 3/1994 | Kuroda et al. | |
| 5,585,277 A | 12/1996 | Bowie et al. | |
| 5,834,250 A | 11/1998 | Wells et al. | |
| 5,925,549 A | 7/1999 | Hsueh et al. | |
| 6,153,410 A | 11/2000 | Arnold et al. | |
| 6,448,377 B1 | 9/2002 | Kobilka et al. | |
| 6,537,749 B2 | 3/2003 | Kuimelis et al. | |
| 7,094,593 B1 | 8/2006 | Pausch et al. | |
| 7,115,377 B2 | 10/2006 | Yao et al. | |
| 7,462,457 B2 | 12/2008 | Beachy et al. | |
| 2002/0028443 A1 | 3/2002 | Short | |
| 2002/0147170 A1* | 10/2002 | Kopin et al. | 514/44 |
| 2003/0036092 A1 | 2/2003 | Iverson et al. | |
| 2003/0096297 A1* | 5/2003 | Gilchrist et al. | 435/7.1 |
| 2003/0129649 A1 | 7/2003 | Kobilka et al. | |
| 2004/0157268 A1 | 8/2004 | Kobilka et al. | |
| 2005/0136392 A1 | 6/2005 | Torres et al. | |
| 2005/0143402 A1 | 6/2005 | Cheetham et al. | |
| 2005/0287565 A1* | 12/2005 | Merchiers et al. | 435/6 |
| 2007/0154947 A1 | 7/2007 | Broach et al. | |
| 2007/0196389 A1 | 8/2007 | Caligiuri et al. | |
| 2010/0190188 A1 | 7/2010 | Henderson et al. | |
| 2011/0028700 A1 | 2/2011 | Heal | |
| 2011/0046351 A1 | 2/2011 | Weir et al. | |
| 2011/0112037 A1 | 5/2011 | Warne et al. | |
| 2012/0165507 A1 | 6/2012 | Jazayeri-Dezfuly et al. | |
| 2012/0270230 A1 | 10/2012 | Henderson et al. | |
| 2013/0224238 A1 | 8/2013 | Hutchings et al. | |

FOREIGN PATENT DOCUMENTS

| | | |
|---|---|---|
| EP | 0 184 187 A2 | 6/1986 |
| EP | 0 239 400 A2 | 9/1987 |
| EP | 0 397 834 B1 | 2/2000 |
| EP | 1 376 132 A1 | 1/2004 |
| EP | 1 505 074 A1 | 2/2005 |
| GB | 2 188 638 A | 10/1987 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 95/32425 A1 | 11/1995 |
| WO | WO 97/35881 A2 | 10/1997 |
| WO | WO 00/22129 A1 | 4/2000 |
| WO | WO 01/36471 A2 | 5/2001 |
| WO | WO 02/059346 | 8/2002 |
| WO | WO 02/068600 A2 | 9/2002 |
| WO | WO 03/035693 A2 | 5/2003 |
| WO | WO 2005/121755 A1 | 12/2005 |

(Continued)

OTHER PUBLICATIONS

Lu et al., Transmembrane Domains 4 and 7 of the M1 Muscarinic Acetylcholine Receptor are Critical for Ligand Binding and the Receptor Activation Switch, Sep. 7, 2001, The Journal of Biological Chemistry 276(36):34098-34104.*
Pogozheva et al., Interactions of Human Melanocortin 4 Receptor with Nonpeptide and Peptide Agonists, Aug. 30, 2005, Biochemistry 44(34):11329-11341.*
U.S. Appl. No. 60/080,686, filed Apr. 3, 1998, Kuimelis et al.
International Search Report and Written Opinion for PCT/GB2008/000986 mailed Jan. 19, 2009.
International Preliminary Report on Patentability for PCT/GB2008/000986 mailed Jul. 6, 2009.
International Search Report and Written Opinion for PCT/GB2008/004032 mailed Aug. 19, 2009.

(Continued)

*Primary Examiner* — John Ulm
(74) *Attorney, Agent, or Firm* — Wolf, Greenfield & Sacks, P.C.

(57) ABSTRACT

A method of producing a conformational specific binding partner of a GPCR, the method comprising: a) providing a mutant GPCR of a parent GPCR, wherein the mutant GPCR has increased stability in a particular conformation relative to the parent GPCR; b) providing a test compound; c) determining whether the test compound binds to the mutant GPCR when residing in a particular conformation; and d) isolating a test compound that binds to the mutant GPCR when residing in the particular conformation. Methods of producing GPCRs with increased stability relative to a parent GPCR are also disclosed.

17 Claims, 54 Drawing Sheets

(56) References Cited

FOREIGN PATENT DOCUMENTS

| WO | WO 2006/023248 A2 | 3/2006 |
|---|---|---|
| WO | WO 2008/068534 A2 | 6/2008 |
| WO | WO 2008/114020 A2 | 9/2008 |
| WO | WO 2009/071914 A2 | 6/2009 |
| WO | WO 2009/081136 A2 | 7/2009 |

OTHER PUBLICATIONS

International Preliminary Report on Patentability for PCT/GB2008/004032 issued Jun. 8, 2010.
International Search Report and Written Opinion for PCT/GB2008/004223 mailed Aug. 19, 2009.
International Preliminary Report on Patentability for PCT/GB2008/004223 issued Jun. 22, 2010.
International Search Report and Written Opinion for PCT/GB2009/000310 mailed Jun. 23, 2009.
International Preliminary Report on Patentability for PCT/GB2009/000310 mailed Aug. 26, 2010.
International Search Report and Written Opinion for PCT/GB2008/000740 mailed Jul. 28, 2008.
International Preliminary Report on Patentability for PCT/GB2008/000740 issued Sep. 7, 2010.
International Search Report and Written Opinion for PCT/GB2010/001227 mailed Jun. 20, 2011.
International Preliminary Report on Patentability for PCT/GB2010/001227 mailed Jan. 12, 2012.
Office Action mailed Feb. 14, 2012 for U.S. Appl. No. 12/450,358.
[No author listed] Uniprot Database Accession No. P08482. 1988. Muscarinic acetylcholine receptor M1.
[No author listed] Stephen White Laboratory at UC Irvine. Available at http://blanco.biomol.uci.edu. Downloaded May 29, 2012.
[No author listed] IUPHAR database. G protein-coupled receptors. Available at http://www.iuphar-db.org/GPCR/ReceptorFamiliesForward. Downloaded Apr. 28, 2010.
[No author listed] The CCP4 suite: programs for protein crystallography. Collaborative Computational Project, No. 4. Acta Crystallogr. 1994. D50:760-763.
Abagyan & Totrov. High-throughput docking for lead generation. Curr. Opin. Chem. Biol. 2001. 5:375-382.
Abagyan et al., ICM—a new method for protein modelling and design. Applications to docking and structure prediction from the distorted native conformation. J. Comput. Chem. 1994. 15:488-506.
Adams et al., PHENIX: building new software for automated crystallographic structure determination. Acta Crystallogr. 2002. D58:1948-1954.
Afonine et al., The Phenix refinement framework. CCP Newsletter. 2005. Contribution 8.
Alexandrov et al., Microscale Fluorescent Thermal Stability Assay for Membrane Proteins; Structure; 2008;16:351-359.
Ali & Caffrey. Membrane Protein Crystallization in Lipidic Mesophases: Detergent Effects. Biophys. J. 2000.79:394-405.
Alkhatib et al., HIV coreceptors: from discovery and designation to new paradigms and promise. Eur. J. Med. Res. 2007 12(9):375-384.
Altschul & Gish. Local alignment statistics. Methods in Enzymology. 1996. 266:460-480.
Altschul et al., Basic local alignment search tool. J. Mol. Biol. 1990. 215:403-410.
Altschul et al., Gapped BLAST and PSI-BLAST: a new generation of protein database search programs. Nucl Acids Res. 1997 25:3389-3402.
Alves et al., Plasmon Resonance Methods in GPCR Signaling and Other Membrane Events. Curr. Prot. & Peptide Sci. 2005 6:293-312.
Artymiuk et al., Graph theoretic methods for the analysis of structural relationships in biological macromolecules. J Amer. Soc. Info. Sci Tech. 2005 56(5):518-528.
Avlani et al., Critical role for the second extracellular loop in the binding of both orthosteric and allosteric G protein-coupled receptor ligands. J Biol Chem. 2007. 282:25677-25686.

Babcook et al., A novel strategy for generating monoclonal antibodies from single, isolated lymphocytes producing antibodies of defined specificities. PNAS. 1996 93:7843-7848.
Baker. The selectivity of β-adrenoceptor antagonists at the human β1, β2 and β3 adrenoceptors. British J. Pharmacol. 2005. 144:317-322.
Bakker et al., Constitutively Active Mutants of the Histamine H1 Receptor Suggest a Conserved Hydrophobic Asparagine-Cage That Constrains the Activation of Class A G Protein-Coupled Receptors. Mol. Pharmacol. 2008. 73:94-103.
Balbes et al., A Perspective of Modern Methods in Computer-Aided Drug Design. Reviews in Computational Chemistry. 1994. 5:337-380.
Baldwin et al., An alpha-carbon template for the transmembrane helices in the rhodopsin family of G-proteincoupled receptors. J. Mol. Biol. 1997. 272: 144-164.
Ballesteros & Weinstein. Integrated methods for the construction of three-dimensional models and computational probing of structure-function relations in G-proteincoupled receptors. Methods in Neurosciences. 1995 Sealfon, S.C.and Conn, P.M. (eds.). Academic Press San Diego, CA 366-428.
Ballesteros et al., Activation of the beta 2-adrenergic receptor involves disruption of an ionic lock between the cytoplasmic ends of transmembrane segments 3 and 6. J. Biol. Chem. 2001. 276:29171-29177.
Ballesteros et al., Structural mimicry in GPCR: Implications of the high-resolution structure of rhodopsin for structure-function analysis of rhodopsin-like receptors. Mol. Pharmacology 60, 1-19, 2001.
Bamber et al., Yeast mitochondrial ADP ATP carriers are monomeric in detergents. PNAS. 2006 103:16224-16229.
Baneres et al., Molecular Characterization of a Purified 5-HT4 Receptor. J. Biol. Chem. 2005. 208:20253-20260.
Baranski et al., C5a Receptor Activation. J. Biol. Chem. 1999. 274(22):15757-15765.
Barbas et al., Assembly of combinatorial antibody libraries on phage surfaces: The gene III site. PNAS. 1991 88:7978-7982.
Baroni et al., A Common Reference Framework for Analyzing/Comparing Proteins and Ligands. Fingerprints for Ligands and Proteins (FLAP): Theory and Application. J. Chem Inf. Mod. 2007. 47:279-294.
Barroso S. et al., 2000, Identification of Residues Involved in Neurotensin Binding and Modeling of the Agonist Binding Site in Neurotensin Receptor 1, Journal of Biological Chemistry, 275(1):328-336.
Barroso S. et al., 2002, Constitutive activation of the neurotensin receptor 1 by mutation of Phe358 in Helix seven, British Journal of Pharmacology, 135:997-1002.
Barry et al., Quantitative protein profiling using antibody arrays. Proteomics. 2004 4:3717-3726.
Bartlett et al., CAVEAT: A Program to Facilitate the Structure-Derived Design of Biologically Active Molecules. Molecular Recognition: Chemical and Biological Problems, 1989. S. M. Roberts, Editor, Royal Society of Chemistry. 78:182-196.
Bee et al., 2007, Functional analysis of transmembrane domain 2 of the M1 muscarinic acetylocholine receptor, J. Biol. Chem. 282(44):32471-32479.
Behr et al., Novel mutants of the human β1-adrenergic receptor reveal amino acids relevant for receptor activation. J. Biol. Chem. 2006. 281(26):18120-18125.
Berchiche et al., Direct Assessment of CXCR4 Mutant Conformations Reveals Complex Link between Receptor Structure and G(alpha)(i) Activation. J. Biol. Chem. 2007. 282(8):5111-5115.
Besenicar et al., Surface plasmon resonance in protein-membrane interactions. Chem. Phys. Lipids. 2006 141:169-178.
Black. Drugs from Emasculated Hormones: The Principle of Syntopic Antagonism (Nobel Lecture). Angew Chem. Int. Edit. 1989. 28:886-894.
Blundell et al., Knowledge-based prediction of protein structures and the design of novel molecules. Nature. 1987. 326:347-352.
Blundell et al., Knowledge-based protein modelling and design; 18th Sir Hans Krebs Lecture Eur. J. Biochem. 1988. 173:513-520.
Bockaert and Pin. Molecular tinkering of G protein-coupled receptors: an evolutionary success. EMBO J. 1999. 18:1723-1729.

(56) References Cited

OTHER PUBLICATIONS

Bockaert et al., GPCR-GIP networks: a first step in the discovery of new therapeutic drugs? Curr Opin Drug Discov and Dev. 2004. 7:649-657.
Bohm. The computer program LUDI: a new method for the de novo design of enzyme inhibitors. J. Comput. Aided Mol. Des. 1992. 6:61-78.
Bommarius et al., High-throughput screening for enhanced protein stability. Curr Opin Biotechnol. 2006. 17(6):606-610. Epub Oct. 17, 2006.
Bonner et al., Identification of a family of muscarinic acetylcholine receptor genes. Science. 1987. 237:527-532.
Boucard et al., Constitutive Activation of the Angiotensin II Type 1 Receptor Alters the Spatial Proximity of Transmembrane 7 to the Ligand-binding Pocket. J. Biol. Chem. 2003. 278(38):36628-36636. Epub Jul. 3, 2003.
Bowie. Stabilizing membrane proteins. Curr. Opin. Struct. Biol. 2001. 1 1(4):397-402.
Brenner & Lerner. Encoded combinatorial chemistry. PNAS. 1992. 89:5381-5383.
Brodeur et al., Mouse-Human Myeloma Partners for the Production of Heterohybridomas. Mono. Antib. Prod. Tech. Apps. 1987. 51-63.
Brunger et al., Recent developments for the efficient crystallographic refinement of macromolecular structures. Curr. Opin. Struct. Biol. 1998. 8(5):606-611.
Bruns et al., Human glutathione transferase A4-4 crystal structures and mutagenesis reveal the basis of high catalytic efficiency with toxic lipid peroxidation products. J Mol Biol. 1999. 288:427-439.
Burstein et al., The second intracellular loop of the m5 muscarinic receptor is the switch which enables G-protein coupling. J Biol Chem. 1998. 273:24322-24327.
Caron et al., Affinity chromatography of the beta-adrenergic receptor. J. Biol. Chem. 1979. 254:2923-2927.
Carrillo H. & Lipman D.J. The multiple sequence alignment problem in biology. SIAM J. Appl. Math. 1988; 48:1073-1082.
Carson. Ribbons 2.0. Appl. Crystallogr. 1991. 24:958-961.
Chan et al., Allosteric modulation of the muscarinic M4 receptor as an approach to treating schizophrenia. PNAS. 2008. 105:10978-10983.
Chapple et al., Multiplexed expression and screening for recombinant protein production in mammalian cells. BMC Biotechnol. 2006. 22:6-49.
Cherezov et al., A robotic system for crystallizing membrane and soluble proteins in lipidic mesophases. Acta. Crystallogr. D. Biol. Crystallogr. 2004. 60(Pt 10):1795-1807. Epub Sep. 23, 2004.
Cherezov et al., Crystallization Screens: Compatibility with the Lipidic Cubic Phase for in Meso Crystallization of Membrane Proteins. Biophys. J. 2001. 81:225-242.
Cherezov et al., High Resolution Crystal Structure of an Engineered Human β2-Adrenergic G protein-Coupled Receptor. Science. 2007. 318(5854):1258-1265. Epub Oct. 25, 2007.
Cherezov et al., Room to Move: Crystallizing Membrane Proteins in Swollen Lipidic Mesophases. J. Mol. Biol. 2006. 357:1605-1618.
Christopoulos. Allosteric binding sites on cell-surface receptors: Novel targets for drug discovery. Nat. Rev. Drug Discov. 2002. 1:198-210.
Clackson et al., Making antibody fragments using phage display libraries. Nature. 1991. 352:624-628.
Claeysen et al., A single mutation in the 5-HT4 receptor (5-HT4-R D100(3.32)A) generates a Gs-coupled receptor activated exclusively by synthetic ligands (RASSL).J Biol Chem. Jan. 10, 2003;278(2):699-702. Epub Nov. 18, 2002.
Cohen et al., Molecular modeling software and methods for medicinal chemistry. J. Med. Chem. 1990. 33:883-894.
Conklin et al., Engineering GPCR signaling pathways with RASSLs. Nat Methods. Aug. 2008;5(8):673-8.
Cooper. Advances in membrane receptor screening and analysis. J. Mol. Recognit. 2004. 17(4):286-315.
Cooper. Non-optical screening platforms: the next wave in label-free screening? Drug Discov. Today. 2006. 11(23-24):1068-1074. Epub Oct. 20, 2006.
Cornell et al., A Second Generation Force Field for the Simulation of Proteins, Nucleic Acids, and Organic Molecules. JACS. 1995. 117(19):5179-5197.
D'Antona et al., A cannabinoid receptor I mutation proximal to the DRY motif results in constitutive activty and reveals intramolecular interactions involved in receptor activation. Brain Research. 2006 1108(1):1-11.
D'Antona et al., Mutations of CB1 T210 Produce Active and Inactive Receptor Forms: Correlations with Ligand Affinity, Receptor Stability, and Cellular Localization. Biochemistry. 2006. 45:5606-5617.
Day et al., A monoclonal antibody for G protein-coupled receptor crystallography. Nat Methods. 2007. 4(11):927-929.
Degrip. Thermal Stability of Rhodopsin and Opsin in Some Novel Detergents. Methods in Enzymology. 1982. 81:256-265.
Devereux et al., A comprehensive set of sequence analysis programs for the VAX; Nucl. Acids Rec. 12:387-395, 1984.
Dignam. Preparation of extracts from higher eukaryotes. Methods in Enzymology. 1990. 182:194-203.
Domazet et al., The second transmembrane domain of the human type 1 angiotensin II receptor participates in the formation of the ligand binding pocket and undergoes integral pivoting movement during the process of receptor activation. J Biol Chem. May 1, 2009;284(18):11922-9. Epub Mar. 9, 2009.
Dupriez et al. Aequorin-based functional assays for G-protein-coupled receptors, ion channels and tyrosine kinase receptors. Receptors Channels. 2002. 8(5-6):319-330.
Dyson et al., Identification of soluble protein fragments by gene fragmentation and genetic selection. Nucl. Acid Research. 2008. 36:e51.
Dyson et al., Production of soluble mammalian proteins in *Escherichia coli*: identification of protein features that correlate with successful expression. BMC Biotechnology. 2004. 4:32.
Eddy et al., Maximum Discrimination Hidden Markov Models of Sequence Consensus. J. Comput Biol. 1995. 2(1):9-23.
Eglen. Functional G protein-coupled receptor assays for primary and secondary screening. Comb. Chem. High Throughput Screen. 2005. 8(4):311-318.
Eisen et al., HOOK: a program for finding novel molecular architectures that satisfy the chemical and steric requirements of a macromolecule binding site. Proteins:Structure, Function and Genetics. 1994.19(3):199-221.
Eldridge et al., Empirical scoring functions: I. the development of a fast empirical scoring function to estimate the binding affinity of ligands in receptor complexes. J. Comp. Aided Mol. Des. 1997. 11(5):425-445.
Ernst et al., Intrinsic biophysical monitors of transducin activation: fluorescence, UV-visible spectroscopy, light scattering, and evanescent field techniques. Meth. Enzymol. 2000. 315:471-489.
Evans & McCoy. An introduction to molecular replacement. Acta Crystallogr. 2008. D64:1-10.
Faham et al., Side-chain contributions to membrane protein structure and stability. J. Mol. Biol. 2004. 335:297-305.
Fanelli. Theoretical study on mutation-induced activation of the luteinizing hormone receptor. J. Mol. Biol. 2000. 296(5):1333-1351.
Fang et al., G protein-coupled receptor microarrays for drug discovery. Drug Discovery Today. 2003. 8:755-761.
Felix et al., Immunoadsorption as a new therapeutic principle for treatment of dilated cardiomyopathy. Eur. Heart J. Supplements. 2002. 4:163-168.
Ferracci et al., Real time analysis of intact organelles using surface plasmon resonance. Anal. Biochem. 2004. 334:367-375.
Ferro & Hermans. A different best rigid body molecular fit routine. Acta Cryst. 1977. A33:345-347.
Fetrow & Bryant. New programs for protein tertiary structure prediction. Biotechnology. 1993. 11(4):479-484.
Folkertsma et al., A family-based approach reveals the function of residues in the nuclear receptor ligand-binding domain. J. Mol. Biol. 2004. 341(2):321-335.
Foord et al., International Union of Pharmacology. XLVI. G Protein-Coupled Receptor List. Pharmacol. Rev. 2005. 57:279-288.

(56) References Cited

OTHER PUBLICATIONS

Foord S.M. & Marshall F.H. RAMPs: accessory proteins for seven transmembrane domain receptors, Trends Pharmacol Sci. 20(5):184-187 1999.
Frändberg et al., Cysteine Residues Are Involved in Structure and Function of Melanocortin 1 Receptor: Substitution of a Cysteine Residue in Transmembrane Segment Two Converts an Agonist to Antagonist. Biochem. Biophys. Res. Commun. 2001. 281(4):851-857.
Frielle et al., Cloning of the cDNA for the human-β-adrenergic receptor. PNAS. 1987. 84:7920-7924.
Fuchs et al., Targeting recombinant antibodies to the surface of *Escherichia coli*: fusion to a peptidglycan associated lipoprotein. Biotechnology. 1991. 9:1369-1372.
Gales et al., Real-time monitoring of receptor and G-protein interactions in living cells, Nat. Methods. 2(3):177-184 (2005).
Garcia-Lopez et al., Strategies for design of non peptide CCK1R agonist/antagonist ligands. Curr. Top. Med. Chem. 2007. 7(12):1180-1194.
Gardella et al., Transmembrane residues of the parathyroid hormone (PTH)/PTH-related peptide receptor that specifically affect binding and signaling by agonist ligands. J Biol Chem. May 31, 1996;271(22):12820-5.
Garrard et al., $F_{ab}$ assembly and enrichment in a monovalent phage display system. Biotechnology. 1991. 9:1373-1377.
Gerber et al., An Activation Switch in the Ligand Binding Pocket of the C5a Receptor. J. Biol. Chem. 2001. 276(5):3394-3400.
Gether et al., Structural Instability of a Constitutively Active G Protein-coupled Receptor Agonist-Independent Activation Due to Conformational Flexibility. J. Biol. Chem. 1997. 272:2587-2590.
Gether. Uncovering Molecular Mechanisms Involved in Activation of G Protein-Coupled Receptors. Endocr. Rev. 2000. 21:90-113.
Gillet et al., SPROUT—a program for structure generation. J. Comput. Aided Mol. Des.1993. 7:127-153.
Ginalski, Comparative modeling for protein structure prediction. Curr. Op. Struct. Biol. 2006. 16(2):172-177.
Gish & States. Identification of protein coding regions by database similarity search. Nature Genetics. 1993. 3:266-272.
Goding. Production of Monoclonal Antibodies: Principles and Practice. Academic Press. 1986. 59-103.
Goodford. A Computational Procedure for Determining Energetically Favorable Binding Sites on Biologically Important Macromolecules. J. Med. Chem. 1985. 28:849-857.
Goodsell et al., Automated docking of substrates to proteins by simulated annealing. Proteins: Structure, Function and Genetics. 1990. 8:195-202.
Gram et al., In vitro selection and affinity maturation of antibodies from a naïve combinatorial immunoglobulin library. PNAS. 1992. 89:3576-3580.
Graneli et al., Characterization of a proton pumping transmembrane protein incorporated into a supported three-dimensional matrix of proteoliposomes. Anal. Biochem. 2007. 367:87-94.
Graneli et al., Utilizing adsorbed proteoliposomes trapped in a non-ruptured state on SiO2 for amplified detection of membrane proteins. Biosens. Bioelectron. 2004. 20:498-504.
Gray et al., Identification of Two Serine Residues Essential for Agonist-Induced 5-HT2a Receptor Desensitization. Biochemistry. 2003. 42(36):10853-10862.
Gray. High-resolution protein-protein docking. Curr. Opin. Struct. Biol. 2006. 16:183-193.
Greer et al., Application of the Three-Dimensional Structures of Protein Target Molecules in Structure-Based Drug Design. J. Med. Chem. 1994. 37:1035-1054.
Greer. Comparative modeling of homologous proteins. Methods in Enzymology. 1991. 202:239-252.
Greer. Model structure for the inflammatory protein C5a. Science. 1985. 228:1055-1060.
Griffiths et al. Human anti-self antibodies with high specificity from phage display libraries. EMBO J. 1993. 12:725-734.
Grindley et al., Identification of Tertiary Structure Resemblance in Proteins Using a Maximal Common Subgraph Isomorphism Algorithm. J. Mol. Biol. 1993. 229:707-721.
Grisshamer et al. Expression of a rat neurotensin receptor in *Escherichia coli*. Biochem J. 1993. 295(2):571-576.
Grisshammer & Tate. Overexpression of integral membrane proteins for structural studies. Q. Rev. Biophys. 1995. 28:315-422.
Groves & Dustin. Supported planar bilayers in studies on immune cell adhesion and communication. Immunol. Meth. 2003. 278:19-32.
Groves. Membrane array technology for drug discovery. Curr. Op. Drug Discov. Develop. 2002. 5:606-612.
Gschwend & Kuntz. Orientational sampling and rigid-body minimization in molecular docking revisited: on-the-fly optimization and degeneracy removal. J. Comput. Aided Mol. Des. 1996. 10:123-132.
Guida. Software for structure-based drug design. Curr. Opin. Struct. Biol. 1994. 4:777-781.
Gupta & Devi. The use of receptor-specific antibodies to study G-protein-coupled receptors. Mt. Sinai J. Med. 2006. 73(4):673-681.
Gupta et al., Conformation State-sensitive Antibodies to G-protein-coupled Receptors. J. Biol. Chem. 2007. 282(8): 5116-5124.
Halperin et al., Principles of docking: An overview of search algorithms and a guide to scoring functions. Proteins. 2002. 47:409-443.
Hamuro et al., Hydrogen/deuterium-exchange (H/D-Ex) of PPARγLBD in the presence of various modulators. Protein Science. 2006. 15(8):1883-1892.
Han et al., Constitutive activation of opsin by mutation of methionine 257 on transmembrane helix 6. Biochemistry. Jun. 2, 1998;37(22):8253-61.
Harding et al., Direct analysis of a GPCR-agonist interaction by surface plasmon resonance. Eur. Biophys. J. Biophys. Let. 2006. 35:709-712.
Harding. Metal-ligand geometry relevant to proteins and in proteins: sodium and potassium. Acta Crystallogr. 2002. D58:872-874.
Hawkins et al., Selection of phage antibodies by binding affinity: mimicking affinity maturation. J. Mol. Biol. 1992. 226:889-896.
Hay et al., Bacteriophage Cloning and *Escherichia coli* Expression of a Human IgM Fab. Hum. Antibod. Hybridomas. 1992. 3:81-85.
Hendrickson. Transformations to optimize the superposition of similar structures. Acta Crystallogr. 1979. A35:158-163.
Henikoff & Henikoff. Amino acid substitution matrices from protein blocks. Proc Natl Acad Sci U.S.A. Nov. 15, 1992; 89(22):10915-10919.
Hoffmann et al., A FlAsH-based FRET approach to determine G protein-coupled receptor activation in living cells. Nat Methods. Mar. 2005;2(3):171-6. Epub Feb. 17, 2005.
Holm & Sander. Dali/FSSP classification of three-dimensional protein folds. Nucl. Acids Res. 1997. 25:231-234.
Holm & Sander. Mapping the Protein Universe. Science. 1996. 273:595-602.
Hoogenboom et al., Multi-subunit proteins on the surface of filamentous phage: methodologies for displaying antibody (Fab) heavy and light chains. Nuc. Acid Res. 1991. 19:4133-4137.
Hopkins & Groom. The druggable genome. Nature Rev. Drug Discovery. 2002. 1:727-730.
Hoppe & Schomburg. Prediction of protein thermostability with a direction- and distance-dependent knowledge-based potential. Protein Science. 2005. 14:2682-2692.
Huang et al., A probabilistic method to correlate ion pairs with protein thermostability. Applied Bioinformics. 2004. 3(1):21-29.
Hubbell et al., Rhodopsin structure, dynamics, and activation: a perspective from crystallography, site-directed spin labeling, sulfhydryl reactivity, and disulfide cross-linking. Adv. Protein Chem. 2003. 63:243-290.
Hulme & Curtis. Purification of recombinant M1 muscarinic acetylcholine receptor. Biochemical Society Transactions. 1998. 26:S361.
Hunte et al., Structure at 2.3 Å resolution of the cytochrome bc1 complex from the yeast *Saccharomyces cerevisiae* co-crystallized with an antibody Fv fragment. Structure. 2000. 8:669-684.
Hus et al. Assignment strategy of proteins with known structure. J. Magn. Reson. 2002. 157(1):119-123.
Huse et al., Generation of a large combinatorial library of the immunoglobulin repertoire in phage lambda. Science. 1989. 246:1275-1281.

(56) References Cited

OTHER PUBLICATIONS

Ikuta et al., Crystallographic Approach to Identification of Cyclin-dependent Kinase 4 (CDK4)-specific Inhibitors by Using CDK4 Mimic CDK2 Protein. J. Biol. Chem. 2001. 276:27548-27554.
Isogaya et al., Binding pockets of the β1 and β2 adrenergic receptors for subtype-selective agonists. Mol. Pharmacol. 1999. 56(5):875-885.
Isogaya et al., Identification of a Key Amino Acid of the β2-Adrenergic Receptor for High Affinity Binding of Salmeterol. Mol. Pharmacol. 1998. 54:616-622.
Jaakola et al., The 2.6 Å Crystal Structure of a Human A2A Adenosine Receptor Bound to an Antagonist. Science. 2008. 322:1211-1217.
Jaenicke & Bohm. The stability of proteins in extreme environments. Current Opinion in Structural Biology. 1998. 8:738-748.
Jahns et al., Direct evidence for a β1-adrenergic receptor-directed autoimmune attack as a cause of idiopathic dilated cardiomyopathy. J. Clinical Investigation. 2004. 113(10):1419-1429.
Jahns et al., Modulation of Beta1-Adrenoceptor Activity by Domain-Specific Antibodies and Heart Failure-Associated Autoantibodies. J. Am. Coll. Cardiol. 2000. 36(4):1280-1287.
Jameson et al., Real-time Detection of Basal and Stimulated G Protein GTPase Activity Using Fluorescent GTP Analogues. J. Biol. Chem. 2005. 280(9):7712-7719.
Jane-wit D. et al., β1-Adrenergic Receptor Autoantibodies Mediate Dilated Cardiomyopathy by Agonistically Inducing Cardiomyocyte Apoptosis. Circulation. 2007. 116(4):399-410. Epub Jul. 9, 2007.
Jap et al., 2D crystallization: from art to science; Ultramicroscopy. 1992. 46(1-4):45-84.
Jerne & Nordin. Plaque formation in agar in single antibody-producing cells. Science. 1963. 140:405.
Johnson & Chriswell. Human antibody engineering. Curr. Op. Structural Biol. 1993. 3:564-571.
Johnson et al., A 1,536-well 35S GTPgammaS scintillation proximity binging assay for ultra-high-throughput screening of an orphan galphai-coupled GPCR. Assay Drug Dev Technol 6, 327-337 (2008).
Johnson et al., Knowledge-based protein modeling. Crit Rev Biochem Mol Biol. 1994. 29:1-68.
Jones et al., Development and validation of a genetic algorithm for flexible docking. J Mol. Biol. 1997. 267:727-748.
Jones et al., Docking small-molecule ligands into active sites. Curr. Opin. Biotech. 1995. 6:652-656.
Jones et al., Improved methods for building protein models in electron density maps and the location of errors in these models. Acta Crystallogr. 1991. A47:110-119.
Jones et al., Molecular Recognition of Receptor Sites Using a Genetic Algorithm with a Description of Desolvation. J Mol Biol. 1995. 245:43-53.
Kabsch, A discussion of the solution for the best rotation to relate two sets of vectors. Acta Crystallogr. 1978. A34:827-828.
Kabsch., A solution of the best rotation to relate two sets of vectors. Acta Crystallogr. 1976. A32:922-23.
Karlin & Altschul. Applications and statistics for multiple high-scoring segments in molecular sequences. PNAS. 1993. 90:5873-5877.
Karlsson & Lofas. Flow-Mediated On-Surface Reconstitution of G-Protein Coupled Receptors for Applications in Surface Plasmon Resonance Biosensors. Anal. Biochem. 2002. 300(2):132-138.
Kearsley. On the orthogonal transformation used for structural comparisons. Acta Crystallogr. 1989. A45:208-210.
Kenakin et al., Protean agonists. Keys to active receptor states? Ann. N.Y. Acad. Sci. 1997. 812:116-125.
Kenakin. Inverse, protean, and ligand-selective agonism: matters of receptor conformation. FASEB J. 2001. 15(3):598-611.
Kent et al., Development of a Generic Dual-Reporter Gene Assay for Screening G-Protein-Coupled Receptors. J. Biomol. Screen. 2005. 10(5):437-446.
Kent et al., G-protein-coupled receptor heterodimerization: assay technologies to clinical significance. Curr. Opin. Drug Discov. Devel. 2007. 10(5):580-589.

Kerr et al., Encoded combinational peptide libraries containing non-natural amino acids. JACS. 1993. 115:2529-2531.
Kikkawa et al., The Role of the Seventh Transmembrane Region in High Affinity Binding of a b2-Selective Agonist TA-2005. Mol. Pharmacol. 1998. 53:128-134.
Klco et al., Essential role for the second extracellular loop in C5a receptor activation. Nat Struct Mol Biol. 2005. 12:320-326.
Kleywegt & Jones. A super position. CCP4/ESF-EACBM Newsletter on Protein Crystallography. 1994. 31:9-14.
Kobilka & Deupi. Conformation complexity of G-protein coupled receptors. Trends in Pharmacological Sciences. 2007. 28(8):397-406.
Kobilka & Schertler. New G-protein-coupled receptor crystal structures: insights and limitations. Trends Pharm. Sci. 2008. 29(2):79-83.
Köhler & Milstein. Continuous cultures of fused cells secreting antibody of predefined specificity. Nature. 1975. 256:495-497.
Komolov et al., Surface Plasmon Resonance Study of G Protein/Receptor Coupling in a Lipid Bilayer-Free System. Anal. Chem. 2006. 78:1228-1234.
Kozbor et al., A human hybrid myeloma for production of human monoclonal antibodies. J. Immunol. 1984. 133:3001-3005.
Kristiansen. Molecular mechanisms of ligand binding, signalling, and regulation within the superfamily of G-protein-coupled receptors: molecular modelling and mutagenesis approaches to receptor structure and function. Pharmacology and therapeutics. 2004. 103:21-80.
Kuhlbrandt. Three-dimensional crystallization of membrane proteins. Q. Rev. Biophys. 1988. 21:429-477.
Kuhlbrandt. Two-dimensional crystallization of membrane proteins. Q. Rev. Biophys. 1992. 25(1):1-49.
Kukkonen et al., Muscarinic Toxin 7 Selectivity is Dictated by Extracellular Receptor Loops. J. Biol. Chem. 2004. 279:50923-50929.
Kuntz et al., A Geometric Approach to Macromolecule-Ligand Interactions. J. Mol. Biol. 1982. 161:269-288.
Kuroda et al., Systems for the detection and analysis of protein-protein interactions. Appl. Microbiol. Biotechnol. 2006. 71(2):127-136.
Kyte & Doolittle. A Simple Method for Displaying the Hydropathic Character of a Protein. J. Mol. Biol. 1982. 157:105-132.
Labbé-Jullié C. et al., 1998, Mutagenesis and Modeling of the Neurotensin Receptor NTR1, Journal of Biological Chemistry, 273(26):16351-16357.
Lamb et al., Modulation of the ligand binding properties of the transcription repressor NmrA by GATA-containing DNA and site-directed mutagenesis. Prot. Sci. 2004. 13(12):3127-3138.
Landau & Rosenbusch. Lipidic cubic phases: A novel concept for the crystallization of membrane proteins. PNAS USA. 1996. 93:14532-14535.
Lane et al., Protean agonism at the dopamine D2 receptor: (S)-3-(3-hydroxyphenyl)-N-propylpiperidine is an agonist for activation of Goα1 but an antigonist/inverse agonist for Giα1, Giα2, and Giα3. Mil Pharmacol. 2007 71(5):1349-1359. Epub Feb. 7, 2007.
Lang et al., Structure-activity relationship studies: Methods and ligand design for g-protein coupled peptide receptors. Curr. Prot. Peptide Sci. 2006. 7:335-353.
Latronico et al., Gonadotropin-Independent Precocious Puberty Due to Luteinizing Hormone Receptor Mutations in Brazilian Boys: A Novel Constitutively Activating Mutation in the First Transmembrane Helix. J. Clin. Endocrinol. Metabl. 2000. 85(12):4799-4805.
Lattion et al., Constitutively active mutants of the β1-adrenergic receptor. FEBS Letters 1999 457(3):302-306.
Lattman. Use of Rotation and Translation Functions. Meth. Enzymol. 1985. 115:55-77.
Lau et al., Changing single side chains can greatly enhance the resistance of a membrane protein to irreversible inactivation. J. Mol. Biol. 1999. 290:559-564.
Lauri & Bartlett. CAVEAT: A Program to Facilitate the Design of Organic Molecules. J. Comp. Aided Mol. Design. 1994. 8:51-66.

(56) References Cited

OTHER PUBLICATIONS

Lee et al., Alanine scanning mutagenesis of conserved arginine/lysine-arginine/lysine-x-x-arginie/lysine G protein/activating motifs on M1 muscarinic acetylcholine receptors. Molecular Pharmacology. 1996 50(1):140-148.

Lee et al., D2 Dopamine receptor homodimerization is mediated by multiple sites of interaction, including an intermolecular interaction involving transmembrane domain 4. Biochemistry. 2003. 42(37):11023-31.

Lee et al., State of the art in studying protein folding and protein structure predictio using molecular dynamics methods. J. Mol. Graph & Modelling. 2001. 19(1):146-149.

Lefèvre et al., Alanine-stretch scanning mutagenesis: a simple and efficient method to probe protein structure and function. Nucl. Acids Res. 1997. 25(2):447-448.

Lehmann et al., The consensus concept for thermostability engineering of proteins: further proof of concept. Protein Engineering. 2002. 15(5):403-411.

Leifert et al., G-Protein-Coupled Receptors in Drug Discovery: Nanosizing Using Cell-Free Technologies and Molecular Biology Approaches. J. Biomol. Screening. 2005. 10:765-779.

Leroy et al., G Protein-coupled receptor-mediated ERK1/2 phosphorylation: towards a generic sensor of GPCR activation. J. Recept. Signal. Transduct. Res. 2007. 27(1):83-97.

Lewis & Lofthouse. Adverse reactions with beta-adrenoceptor blocking drugs: an update. Drug Safety. 1993. 9:272-279.

Li et al., Distinct Structural Changes in a G Protein-coupled Receptor Caused by Different Classes of Agonist Ligands. J. Biol. Chem. 2007. 282(36):26284-26293.

Li et al., Random Mutagenesis of the M3 Muscarinic Acetylcholine Receptor Expressed in Yeast. J. Biol. Chem. 2005. 280:5664-5675.

Li et al., Structure of Bovine Rhodopsin in a Trigonal Crystal Form. J. Mol. Biol. 2004. 343:1409-1438.

Liu & Wu. Analysis of the coupling of G12/13 to G protein-coupled receptors using a luciferase reporter assay. Methods Mol. Biol. 2004. 237:145-149.

Lohse et al. Kinetic analysis of G protein-coupled receptor signaling using fluorescence resonance energy transfer in living cells. Adv Protein Chem 2007 74:167-188.

Luecke et al., Structure of bacteriorhodopsin at 1.55 A resolution. J. Mol. Biol. 1999. 291(4):899-911.

Maclean et al., Encoded combinatorial chemistry: Synthesis and screening of a library of highly functionalized pyrrolidines. PNAS. 1997. 94:2805-2810.

Madabushi et al., Evolutionary Trace of G Protein-coupled Receptors Reveals Clusters of Residues That Determine Global and Class-specific Functions; J Biol Chem 2004 279(9):8126-8132.

Magnani et al., Co-evolving stability and conformational homogeneity of the human adenosine A2a receptor. PNAS. 2008. 105(31):10744-10749.

Makino et al., Automated flexible ligand docking method and its application for database search. J Comput. Chem. 1997. 18:1812-1825.

Marshall. Heterodimerization of G-protein-coupled receptors in the CNS. Curr. Opin. Pharmacol. 2001. 1(1):40-44.

Martin et al., A simple vector system to improve performance and utilisation of recombinant antibodies. BMC Biotechnology. 2006. 6:46.

Martin et al., Apolipoprotein A-I Assumes a "Looped Belt" Conformation on Reconstituted High Density Lipoprotein. J. Biol. Chem. 2006. 281(29):20418-20426.

Martin. 3D Database searching in drug design. J. Med. Chem. 1992. 35:2145-2154.

Martin-Garcia et al., Interaction with CD4 and Antibodies to CD4-Induced Epitopes of the Envelope gp120 from a Microglial Cell-Adapted Human Immunodeficiency Virus Type 1 Isolate. J. Virology. 2005. 79:6703-6713.

Mathews & Rossmann. Comparison of Protein Structures. Methods of Enzymology. 1985. 115:397-420.

Matsui et al., Specific removal of β1-adrenoceptor autoantibodies by immunoabsorption in rabbits with autoimmune cardiomyopathy improved cardiac structure and function. J. Mol. Cell Cardiol. 2006. 41(1):78-85. epub Jun. 14, 2006.

McCafferty et al., Phage antibodies: filamentous phage displaying antibody variable domains. Nature. 1990. 348:552-554.

McCoy. Phaser crystallographic software. Acta Crystallogr. 2007. 40:658-674.

McCoy. Solving Structures of protein complexes by molecular replacement with Phaser. Acta Crystallogr. 2007. D63:32-41.

McLachlan. Gene duplications in the structural evolution of chymotrypsin. J. Mol. Biol. 1979. 128, 49-79.

Mehler et al., Ab initio computational modelling of loops in G-protein-coupled receptors: Lessons from the crystal structure of rhodopsin. Proteins Structures Function and Bioinformatics. 2006. 64(3):673-690.

Meng et al., Automated docking with grid-based energy evaluation. J. Comp. Chem. 1992. 13:505-524.

Mezzasalma et al., Enhancing recombinant protein quality and yield by protein stability profiling. J. Biolmol. Screening. 2007. 12(3):418-428.

Michaelson et al., Antibodies to muscarinic acetylcholine receptors in myasthenia gravis. Biochem. Biophys. Res. Commun. 1982. 104(1):52-57.

Milligan & White. Protein—protein interactions at G-protein-coupled receptors. Trends Pharmacol. Sci. 2001. 22:513-518.

Milligan. G protein-coupled receptor dimerisation: Molecular basis and relevance to function. Biochim. Biophys Acta. 2007. 1768(4):825-835.

Milstein & Cuello. Hybrid hybridomas and their use in immunohistochemistry. Nature. 1983. 305:537-540.

Minic et al., Immobilization of native membrane-bound rhodopsin on biosensor surfaces. Biochim. Biophys. Acta—General Subjects. 2005. 1924:324-332.

Minneman et al., A Comparison of the Beta-Adrenergic Receptor of the Turkey Erythrocyte with Mammalian Beta1 and Beta2 Receptors. Mol. Pharmacol. 1980. 17:1-7.

Miranker et al., Functionality Maps of Binding Sites: A Multiple Copy Simultaneous Search Method Proteins: Structure, Function and Genetics. 1991. 11:29-34.

Misquitta et al. Membrane Protein Crystallization in Lipidic Mesophases with Tailored Bilayers. Structure. 2004. 12:2113-2124.

Moran et al., Radio frequency tag encoded combinatorial library method for the discovery of tripeptide-substituted cinnamic acid inhibitors of the protein tyrosine phosphatase PTB1B. JACS. 1995. 117:10787-10788.

Morris et al., Automated docking using a Lamarckian genetic algorithm and an empirical binding free energy function. J. Comput. Chem. 1998. 19:1639-1662.

Morrison. Success in specification. Nature. 1994. 368:812-813.

Mozsolits et al., Surface plasmon resonance spectroscopy in the study of membrane-mediated cell signalling. J. Peptide Sci. 2003. 9:77-89.

Munson & Rodbard. Ligand: a versatile computerized approach for characterization of ligand-binding systems. Anal. Biochem. 1980. 107:220-239.

Murakami et al., Crystal structure of squid rhodopsin. Nature. May 15, 2008;453(7193):363-7.

Myburgh et al., A single amino acid substitution in transmembrane helix VI results in overexpression of the human GnRH receptor. Eur. J. Endocrinol. 1998. 139(4):438-447.

Navarro et al., Receptor-Dependent G-Protein activation in Lipidic Cubic phase. Biopolymers. 2002. 67:167-177.

Navaza. AMoRe: an Automated Package for Molecular Replacement. Acta Cryst. 1994. D50:157-163.

Navia & Murko. Use of structural information in drug design. Curr Opin Struc Biol. 1992. 2:202-210.

Navratilova et al., Analyzing ligand and small molecule binding activity of solubilized GPCRs using biosensor technology. Anal. Biochem. 2006. 355:132-139.

Nawaratne et al., New insights into the function of M4 muscarinic acetylcholine receptors gained using a novel allosteric modulator and

(56) References Cited

OTHER PUBLICATIONS a DREADD (designer receptor exclusively activated by a designer drug). Mol Pharmacol. Oct. 2008;74(4):1119-31. Epub Jul. 15, 2008.
Needleman SB & Wunsch C.D. A general method applicable to the search for similarities in the amino acid sequence of two proteins. J Mol Biol Mar. 1970; 48(3):443-453.
Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Newman-Tancredi et al., Agonist and inverse agonist efficacy at human recombinant serotonin 5-HT1A receptors as a function of receptor:G-protein stoichiometry. Neurophamacology. 1997. 36:451-459.
Nicolaou et al., Radiofrequency encoded combinatorial chemistry. Angew. Chem. Int. Ed. Engl. 1995. 34:2289-2291.
Nishibata et al., Automatic creation of drug candidate structures based on receptor structure. Starting point for artificial lead generation. Tetrahedron. 1991. 47:8985-8990.
Nunomura et al., Regulation of Protein 4.1R, p55, and Glycophorin C Ternary Complex in Human Erythrocyte Membrane. J. Biol. Chem. 2000. 275:24540-24546.
Ohlmeyer et al., Complex synthetic chemical libraries indexed with molecular tags. PNAS. 1993. 90:10922-10926.
Oldham et al., Mapping allosteric connections from the receptor to the nucleotide-binding pocket of heterotrimeric G proteins. PNAS. 2007. 104(19):7927-7932.
Omerovic et al., Induction of Cardiomyopathy in Immunodeficiency Mice by Transfer Patients with Idiopathic Dilated Cardiomyopathy. Autoimmunity. 2000. 32(4):271-280.
Osbourn et al., Directed selection of MIP-1 alpha neutralizing CCR5 antibodies from a phage display human antibody library. Nature Biotechnology. 1998. 16:778-781.
Ostermeier & Michel. Crystalization of Membrane Proteins. Curr. Opin. Struct. Biol. 1997. 7:697-701.
Ott et al., Engineering and functional immobilization of opioid receptors. Prot. Eng. Design & Selection. 2005. 18:153-160.
Overington et al., How many drug targets are there? Natur Rev. Drug Discovery. 2006. 5:993-996.
Palczewski et al., Crystal Structure of Rhodopsin: A G Protein-Coupled Receptor. Science. 2000. 289:739-745.
Palmer et al., Treatment of systemic lupus erythematosus by extracorporeal immunoadsorption. Lancet. 1988. 2(8605):272.
Pardo et al., The role of internal water molecules in the structure and function of the rhodopsin family of G protein-coupled receptors. Chembiochem. Jan. 2, 2007;8(1):19-24.
Park et al., Characterization of radioligand binding to a transmembrane receptor reconstituted into Lipobeads. FEBS Lett. 2004. 567:344-348.
Parker & Ross. Truncation of the Extended Carboxyl-terminal Domain Increases the Expression and Regulatory Activity of the Avian,& Adrenergic Receptor. J. Biol. Chem. 1991. 266:9987-9996.
Parker et al., Carboxyl terminal domains in the avian β1-adrenergic receptor that regulate agonist-promoted endocytosis. J. Biol. Chem. 1995. 270:6482-6487. Erratum in: J Biol Chem 1995. 270(17):10358.
Parker et al., Reconstitutively Active G Protein-coupled Receptors Purified from Baculovirus-infected Insect Cells. J. Biol. Chem. 1991. 266:519-527.
Parsons et al., Directing phage selections towards specific epitopes. Protein Engineering. 1996. 9:1043-1049.
Perez. From Plants to Man: The GPCR "Tree of Life". Mol. Pharmacol. 2005. 67:1383-1384.
Pin et al., Evolution, structure, and activation mechanism of family 3/C G-protein-coupled receptor, Pharm. & Ther. 2003 98 325-354.
Plant et al., Phospholipid/alkanethiol bilayers for cell-surface receptor studies by surface plasmon resonance. Analyt. Biochem. 1995. 226(2):342-348.

Ponsioen et al. Detecting cAMP-induced Epac activation by fluorescence resonance energy transfer: epac as a novel cAMP indicator, 2004 EMBO Rep.;5(12):1176-1180.
Qian et al., High-resolution structure prediction and the crystallographic phase problem. Nature. 2007. 450:259-264.
Quick & Javitch. Monitoring the function of membrane transport proteins in detergent-solubilized form. PNAS. 2007. 104(9):3603-3608.
Rarey et al., A fast flexible docking method using an incremental construction algorithm. J. Mol. Biol. 1996. 261:470-489.
Rasmussen et al., Crystal structure of the human β2 adrenergic g-protein-coupled receptor. Nature. 2007. 450:383-387.
Rasmussen et al., Mutation of a Highly Conserved Aspartic Acid in the β2 Adrenergic Receptor: Constitutive Activation, Structural Instability, and Conformational Rearrangement of Transmembrane Segment 6. Molecular Pharmacol. 1999. 56:175-84.
Riekel et al., Protein crystallography microdiffraction. Curr. Opin. Struct. Biol. 2005. 15(5):556-562.
Rigaut et al., A generic protein purification method for protein complex characterization and proteome exploration. Nature Biotechnol. 1999. 17(10):1030-1032.
Roberts & Strange. Mechanisms of inverse agonist action at D2 dopamine receptors. Br. J. Pharmacol. 2005. 145:34-42.
Robinson-Rechavi et al., Contribution of Electrostatic Interactions, Compactness and Quaternary Structure to Protein Thermostability: Lessons from Structural Genomics of *Thermotoga maritima*. J. Mol. Biol. 2006. 356:547-557.
Rodgers et al., Development of displacement binding and GTPγS scintillation proximity assays for the identification of antagonists of the μ-opiod receptor. Assay Drug Dev. Technol. 2003. 1(5):627-636.
Rosenbaum et al., GPCR Engineering Yields High-Resolution Structural Insights into b2-Adrenergic Receptor Function. Science. 2007. 318:1266-1273.
Rossmann & Argos. A Comparison of the Heme Binding Pocket in Globins and Cytochrome b. J. Biol. Chem. 1975. 250:7525-7532.
Roth et al., Stabilization of the β2-adrenergic Receptor 4-3-5 Helix Interface by Mutagenesis of Glu-122 3.41, A Critical Residue in GPCR Structure. J. Mol. Biol. 2008. 376:1305-1319.
Rovati et al., The Highly Conserved DRY Motif of Class A G Protein-Coupled Receptors: Beyond the Ground State. Mol. Pharmacol. 2007. 71(4):959-964.
Rummel et al., Lipidic Cubic Phases: New Matrices for the Three-Dimensional Crystallization of Membrane Proteins. J. Struct. Biol. 1998. 121:82-91.
Sali & Blundell. Comparative protein modelling of satisfaction by spatial restraints. J. Mol. Biol. 1993. 234(3):779-815.
Samama et al., A mutation-induced activated state of the β2-adrenergic receptor. J Biol Chem. 1993 268(7):4625-4636.
Sarkar et al., Directed evolution of a G protein-coupled receptor for expression, stability, and binding selectivity. PNAS. 2008. 105(39):14808-14813.
Savinainen et al., Identification of WIN55212-3 as a competitive neutral antagonist of the human cannabinoid CB2 receptor. Br. J. Pharmacol. 2005. 145:636-645.
Sayle et al., RASMOL: biomolecular graphics for all. Trends in Biochemical Sciences. 1995. 20:374-376.
Scarselli et al., Multiple Residues in the Second Extracellular Loop Are Critical for M3 Muscarinic Acetylcholine Receptor Activation. J. Biol. Chem. 2007. 282:7385-7396.
Schaffner & Weissmann. A Rapid, Sensitive, and Specific Method for the Determination of Protein in Dilute Solution. Anal. Biochem. 1973. 56:502-514.
Schena et al., Quantitative monitoring of gene expression patterns with a complementary DNA microarray. Science. 1995. 270:467-470.
Schnare et al. Comprehensive comparison of structural characteristics in eukaryotic cytoplasmic large subunit (23S-like) ribosomal RNA. J. Mol. Biol. 1996. 256:701-719.
Schofield et al., Application of phage display to high throughput antibody generation and characterization. Genome Biology. 2007. 8(11):R254.

(56) References Cited

OTHER PUBLICATIONS

Schultz et al., Requirement of Specific Intrahelical Interactions for Stabilizing the Inactive Conformation of Glycoprotein Hormone Receptors. J. Biol. Chem. 2000. 275(48):37860-37869.

Screpanti et al., Crucial Steps in the Structure Determination of the Na+/H+ Antiporter NhaA in its Native Conformation. J. Mol. Biol. 2006. 362:192-202.

Sebestyen et al., Efficiency and limitations of the 'portioning-mixing' peptide synthesis. Pept. Proc. Eur. Pept. Symp. 22nd 1992. 1993. 63-64.

Sen et al., Functional studies with membrane-bound and detergent-solubilized alpha2-adrenergic receptors expressed in Sf9 cells. Biochim Biophys Acta. 2005 1712(1):62-70. Epub Apr. 26, 2005.

Serrano-Vega et al., Conformational thermostabilisation of the β1-adrenergic receptor in a detergent-resistant form. PNAS. 2008 105(3):877-882.

Shi & Javitch. The second extracellular loop of the dopamine D2 receptor lines the binding-site crevice. PNAS 2004. 101:440-445.

Shi et al., Beta2 adrenergic receptor activation. Modulation of the proline kink in transmembrane 6 by a rotamer toggle switch. J Biol Chem. Oct. 25, 2002;277(43):40989-96. Epub Aug. 6, 2002.

Shibata et al. Thermostabilization of the Neurotensin Receptor NTS1, J. Mol. Biol. 2009 390(2):262-277.

Skerra. 'Anticalins': a new class of engineered ligand-binding proteins with antibody-like properties. J. Biotechnol. 2001. 74(4):257-275.

Sobek et al., Microarray technology as a universal tool for high-throughput analysis of biological systems. Combinat. Chem. & High Throughput Screening. 2006. 9:365-380.

Spalding et al., Structural Requirements of Transmembrane Domain 3 for Activation by the M1 Muscarinic Receptor Agonists AC-42, AC-260584, Clozapine, and N-Desmethylclozapine: Evidence for Three Distinct Modes of Receptor Activation. Mol. Pharmacol. 2006. 70:1974-1983.

Standfuss et al., Crystal Structure of a thermally stable rhodopsin mutant. J Mol Biol. 2007 372(5):1179-1188.

Steipe et al., Sequence statistics reliably predict stabilizing mutations in a protein domain. J. Mol. Biol. 1994. 240:188-192.

Stenlund et al., Capture and reconstitution of G protein-coupled receptors on a biosensor surface. Analytical Biochemistry. 2003. 316:243-250.

Stock et al., Robotic nanolitre protein crystallisation at the MRC Laboratory of Molecular Biology. Prog. Biophys. Mil. Biol. 2005. 88:311-327.

Sugimoto et al., Beta(1)-selective agonist (−)-1-(3,4-dimethoxyphenetylamino)-3-(3,4-dihydroxy)-2-propanol [(−)-RO363] differentially interacts with key amino acids responsible for beta(1)-selective binding in resting and active states. J Pharmacol Exp Ther. Apr. 2002;301(1):51-8.

Sung et al., Rhodopsin Mutations Responsible for Autosomal Dominant Retinitis Pigmentosa. J. Biol. Chem. 1993. 268(35):26645-26649.

Sutcliffe et al., Knowledge based modelling of homologous proteins, part I: three-dimensional frameworks derived from the simultaneous superposition of multiple structures. Protein Eng. 1987. 1:377-384.

Swaminath et al., Sequential Binding of Agonists to the 2 Adrenoceptor. J. Biol. Chem. 2004. 279(1):686-691.

Szklarz & Halpert. Use of homology modeling in conjunction with site-directed mutagenesis for analysis of structure-function relationships of mammalian cytochromes P450. Life Sci. 1997. 61:2507-2520.

Tan et al., FGF and stress regulate CREB and ATF-1 via a pathway involving p38 MAP kinase and MAPKAP kinase-2. EMBO J. 1996. 15(17):4629-4642.

Tao et al., Chimeras of the Rat and Human FSH Receptors (FSHRs) Identify Residues that Permit or Suppress Transmembrane 6 Mutation-Induced Constitutive Activation of the FSHR via Rearrangements of Hydrophobic Interactions Between Helices 6 and 7. Mol. Endocrinol. 2002. 16(8):1881-1892.

Tate. Overexpression of mammalian integral membrane proteins for structural studies. FEBS Lett. 2001. 504:94-98.

Tate. Baculovirus-Mediated Expression of Neurotransmitter Transporters. Methods Enzymol. 1998. 296:443-455.

Teng et al., Control of feeding behavior in C. elegans by human G protein-coupled receptors permits screening for agonist-expressing bacteria. PNAS. 2008. 105(39):14826-14831.

Teng et al., Expression of mammalian GPCRs in C. elegans generates novel behavioural responses to human ligands. BMC Biology. 2006. 4:22.

Themmen & Huhtaniemi. Mutations of Gonadotropins and Gonadotropin Receptors: Elucidating the Physiology and Pathophysiology of Pituitary-Gonadal Function. Endocr. Rev. 2000. 21(5):551-583.

Thompson et al., CLUSTAL W: improving the sensitivity of progressive multiple sequence alignment through sequence weighting, position-specific gap penalties and weight matrix choice Nucl. Acids Res. 1994. 22:4673-4680.

Topiol & Sabio. Use of the X-ray structure of the β2-adrenergic receptor for drug discovery Bioorganic & Medicinal Chemistry. 2008. 18(5):1598-1602.

Traunecker et al., Bispecific single chain molecules (Janusins) target cytotoxic lymphocytes on HIV infected cells. EMBO J. 1991. 10:3655-3659.

Tucker & Grisshammer. Purification of a rat neurotensin receptor expressed in Escherichia coli. Biochem. J. 1996. 317(Pt. 3):891-899.

Urizar et al. An activation switch in the rhodopsin family of G protein-coupled receptors: The Thyrotropin receptor J. Biol Chem 2005 280(17):17135-17141.

Vagin & Teplyakov. MOLREP: an automated program for molecular replacement. J. Appl. Cryst. 1997. 30:1022-1025.

Vakser. Evaluation of GRAMM low-resolution docking methodology on hemagglutinin-antibody complex. Proteins, Suppl. 1997. 1:226-230.

Venturi & Hunte. Monoclonal antibodies for the structural analysis of the Na+/H+ antiporter NhaA from Escherichia coli. Biochimica et aBiophysica Acta. 2003. 1610:46-50.

Walters et al., Virtual screening—an overview. Drug Discovery Today. 1998. 3(4):160-178.

Wang. Basic Amino Acids at the C-Terminus of the Third Intracellular Loop Are Required for the Activation of Phospholipase C by Cholecystokinin-B Receptors. J. Neurochem. 1997. 68(4):1728-1735.

Warne et al., Structure of a β1-adrenergic G protein-coupled receptor. Nature. 2008. 454:486-491.

Warne et al., Expression and purification of truncated, non-glycosylated turkey beta-adrenergic receptors for crystallization. Biochim. Biophys. Acta. 2003. 1610:133-140.

Warne et al., The purification of G-protein coupled receptors for crystallization, Structural Biology of Membrane Proteins, Royal Society of Chemistry. 2006. 51-71.

Weber et al., A 1,536-Well cAMP Assay for Gs- and Gi-Coupled Receptors Using Enzyme Fragmentation Complementation. Assay Drug Dev. Technol. 2004. 2(1):39-49.

Weiβ & Grisshammer. Purification and characterization of the human adenosine A2a receptor functionally expressed in Escherichia coli. Eur. J. Biochem. 2002. 269:82-92.

Wess. Molecular Basis of Receptor/G-Protein-Coupling Selectivity. Pharmacol. Ther. 1998. 80:231-264.

White. The progress of membrane protein structure determination. Protein Science. 2004. 13:1948-1949.

Williams & Addona. The integration of SPR biosensors with mass spectrometry: possible applications for proteome analysis. Trends Biotechnol. 2000. 18(2):45-48.

Williams. Biotechnology match making: screening orphan ligands and receptors. Curr. Opin. Biotechnol. 2000. 11(1):42-46.

Winter & Milstein. Man-made antibodies. Nature. 1991. 349:293-299.

Winter et al., Surface binding affinity measurements from order transitions of lipid-membrane-coated colloidal particles. Anal. Chem. 2006. 78:174-180.

Wurch et al., Chimeric Receptor Analysis of the Ketanserin Binding Site in the Human 5-Hydroxytryptamine 1D Receptor: Importance of

(56) References Cited

OTHER PUBLICATIONS the Second Extracellular Loop and Fifth Transmembrane Domain in Antagonist Binding. Mol. Pharmacol. 1998. 54(6):1088-1096.
Wyckoff. Diffractometry. Methods in Enzymology. 1985. 114:330-386.
Yano et al., Phe576 Plays an Important Role in the Secondary Structure and Intracellular Signaling of the Human Luteinizing Hormone/Chorionic Gonadotropin Receptor. J. Clin. Endocrinol. Metabl. 1997. 82(8):2586-2591.
Yao et al., Coupling ligand structure to specific conformational switches in the β2-adrenoceptor: Nat. Chem. Biol. 2006. 2(8):417-422.
Yarden et al., The avian beta-adrenergic receptor: Primary structure and membrane topology. Proc. Natl. Acad. Sci. USA. 1986. 83:6795-6799.
Yohannan et al., The evolution of transmembrane helix kinks and the structural diversity of G protein-coupled receptors. PNAS. 2004. 101(4):959-963.
Yokogawa et al., Bead-linked Proteoliposomes: A Reconstitution Method for NMR Analyses of Membrane Protein-Ligand Interactions. J. Am. Chem. So. 2005. 127:12021-12027.
Zeitoun, O. et al., 2006, Mutagenesis within Helix 6 of the Human β1-Adrenergic Receptor Identifies Lysine324 as a Residue Involved in Imparting the High-Affinity Binding State of Agonists, Molecular Pharmacology, 70(3):838-850.
Zhang et al., Structure modelling of all identified G-protein coupled receptors in the human genome. PloS Computational Biology. 2006. 2(2):88-99.
Zhao et al. A homogeneous enzyme fragement complementation-based {beta}-Arrestin translocation assay for high-throughput screening of G-Protein-Coupled receptors: J. Biomol Screen 2008;13(8):737-747; Epub 2008.
Zheng et al., An efficient one-step site-directed and site-saturation mutagenesis protocol. Nucl. Acids Res. 2004. 32:e115.
Zhou & Bowie. Building a Thermostable Membrane Protein. J. Biol. Chem. 2000. 275:6975-6979.

Zurawski et al., A novel biosensor assay for screening peptide antagonism of the interaction between HIV-1 envelope, CD4 and membrane-embedded CCR5. Biopolymers. 2003. 71:388-389. Abstract P395.
Duthey et al., A single subunit (GB2) is required for G-protein activation by the heterodimeric $GABA_b$ receptor. J Biol Chem. Feb. 1, 2002;277(5):3236-41. Epub Nov. 15, 2001.
González et al., Cellular fluorescent indicators and voltage/ion probe reader (VIPR™) tools for ion channel and receptor drug discovery. Receptors Channels. 2002;8(5-6):283-95.
Hudson et al., High-content screening of known G protein-coupled receptors by arrestin translocation. Methods Enzymol. 2006;414:63-78.
Lehmann et al., The consensus concept for thermostability engineering of proteins. Biochim Biophys Acta. Dec. 29, 2000;1543(2):408-415.
Robertson et al., The properties of thermostabilised G protein-coupled receptors (StaRs) and their use in drug discovery. Neuropharmacology 60: 36-44, 2011.
Scopes, 4.7 Precipitation by Selective Denaturation. General Principles. Purification: Principles and Practice. $3^{rd}$ Edition. 1994:95.
Shoichet et al., Structure-based drug screening for G-protein-coupled receptors. Trends in Pharma Science 33(5): 268-272, 2012.
Voet et al., Protein Stability. Chapter 7: Three-Dimensional Structures of Proteins; Section 7-4. Protein Stability. Biochemistry $2^{nd}$ Edition. 1995. 179-180.
Zhang et al., Adopting selected hydrogen bonding and ionic interactions from *Aspergillus fumigatus* phytase structure improves the thermostability of *Aspergillus niger* PhyA phytase. Appl Environ Microbiol. May 2007;73(9):3069-76. Epub Mar. 9, 2007.
Alberts et al., Solubilizing membrane proteins with a mild detergent. Molecular Biology of the Cell 2002;4th Edition. New York: Garland Science. Figure 10-24.
Hulme et al.,Phenotypic classification of mutants: a tool for understanding ligand binding and activation of muscarinic acetylcholine receptors. Biochem Soc Trans. Aug. 2007;35(Pt 4):742-5.
Schimerlik, Overview of membrane protein solubilization. Current Protocols in Neuroscience. 2001;5.9.1-5.9.5. Abstract.

\* cited by examiner

|         | Turkey β1 | Human β1 | Human β2 | Human β3 |
|---------|-----------|----------|----------|----------|
| Turkey β1 | 100% | 76% | 55% | 54% |
| Human β1 |  | 100% | 60% | 59% |
| Human β2 |  |  | 100% | 50% |
| Human β3 |  |  |  | 100% |

|         | Human AA2a | Human AA2b | Human AA1 | Human AA3 |
|---------|------------|------------|-----------|-----------|
| Human AA2a | 100% | 59% | 46% | 38% |
| Human AA2b |  | 100% | 43% | 35% |
| Human AA1 |  |  | 100% | 47% |
| Human AA3 |  |  |  | 100% |

|         | Rat NTR1 | Human NTR1 | Human NTR2 |
|---------|----------|------------|------------|
| Rat NTR1 | 100% | 91% | 44% |
| Human NTR1 |  | 100% | 42% |
| Human NTR2 |  |  | 100% |

Figure 27

SCREENING

RELATED APPLICATIONS

This application is a national stage filing under 35 U.S.C. §371 of international application PCT/GB2008/004223, filed Dec. 19, 2008, which was published under PCT Article 21(2) in English, the disclosure of which is incorporated in its entirety herein by reference. This application claims the benefit under §119(a)-(d) of United Kingdom Application No. 0724860.2, filed Dec. 20, 2007, the entire disclosure of which is incorporated herein by reference.

BACKGROUND OF THE INVENTION

The present invention relates to the screening of binding partners of G-protein coupled receptors (GPCRs) and particularly to conformation specific binding partners of GPCRs.

The listing or discussion of an apparently prior-published document in this specification should not necessarily be taken as an acknowledgement that the document is part of the state of the art or is common general knowledge.

SUMMARY OF THE INVENTION

Many GPCRs represent important therapeutic targets which could be exploited by biotherapeutics such as antibodies. The generation of therapeutic antibodies for GPCRs has been extremely difficult due in part to the lack of a suitable immunogen. The usual route is to take small peptide fragments of the receptor for immunization however these do not retain their native conformation and often result in binding partners that can bind to and label the receptor but have no functional agonist or antagonist activity. Due to the unique physical conformation of GPCRs it is also known that biotherapeutics such as antibodies recognise combinations of polypeptide 'loops', features that are lost when peptide fragments are used in isolation. It is well known that the local membrane environment of GPCRs maintains the tertiary conformation of the protein, and governs which epitopes are present on the extracellular surface. These epitopes can in theory be recognised by biotherapeutics, however it is non-trivial to raise biotherapeutics, such as antibodies, to membranes or membrane fragments containing a target GPCR as these preparations inevitably contain other non-target GPCRs and membrane-associated proteins, and other membrane components such as lipoproteins, apolipoproteins, lipids, phosophoinsositol lipids and liposacharides which can act as non-desired antigens in the biotherapeutic selection and production process.

Aspects of the invention relate to methods of producing a binding partner of a GPCR, the method comprising: (a) providing a mutant GPCR of a parent GPCR, wherein the mutant GPCR has increased stability in a particular conformation relative to the parent GPCR; (b) providing one or more test compounds; (c) determining whether the or each test compound binds to the mutant GPCR when residing in a particular conformation; and (d) isolating one or more test compounds that bind to the mutant GPCR when residing in the particular conformation.

In some embodiments, methods further comprise determining whether the or each test compound binds to the parent GPCR when residing in the particular conformation and isolating the or each test compound that also binds the parent GPCR when residing in the particular conformation.

In some embodiments, the mutant GPCR is immobilised onto a solid support. In some embodiments, the support is any of a bead, a column, a slide, a chip or a plate. In some embodiments, the mutant GPCR is immobilised onto the support via a covalent interaction. In some embodiments, the support is coated with a polymeric support, such as carboxylated dextran. In some embodiments, the mutant GPCR is immobilised on the support via a non-covalent interaction.

In some embodiments, the support is coated with any of avidin, streptavidin, a metal ion, an antibody to the parent GPCR or an antibody to a molecular tag attached to the mutant GPCR. In some embodiments, the mutant GPCR is immobilised via the C-terminus or an intracellular domain such that the extracellular domains are outward facing. In some embodiments, the mutant GPCR is immobilised via the N-terminus or an extracellular domain such that the intracellular domains are outward facing.

In some embodiments, the mutant GPCR comprises a molecular tag at the C-terminus or N-terminus. In some embodiments, the tag is any of a FLAG tag, a His tag, a c-Myc tag, a DDDDK tag, an HSV tag, a Halo tag or a biotin tag. In some embodiments, the mutant GPCR is in a whole cell preparation, in a cell membrane fragment, solubilised in detergent, in a lipid monolayer, in a lipid bilayer, in a bead-linked lipid particle, in a solid-supported lipid layer or in a proteoliposome.

In some embodiments, the test compound is immobilised on a solid support. In some embodiments, the solid support is any of a bead, a column, a slide, a chip or a plate. In some embodiments, the mutant GPCR and the test compound are not immobilised on a solid support.

In some embodiments, the test compound is any of a polypeptide; an anticalin; a peptide; an antibody; a chimeric antibody; a single chain antibody; an aptamer; a darpin; a Fab, $F(ab')_2$, Fv, ScFv or dAb antibody fragment; a small molecule; a natural product; an affibody; a peptidomimetic; a nucleic acid; a peptide nucleic acid molecule; a lipid; a carbohydrate; a protein based on a modular framework including ankyrin repeat proteins, armadillo repeat proteins, leucine rich proteins, tetrariopeptide repeat proteins or Designed Ankyrin Repeat Proteins (DARPins); or proteins based on lipocalin or fibronectin domains or Affilin scaffolds based on either human gamma crystalline or human ubiquitin.

In some embodiments, the test compound is provided as a biological sample. In some embodiments, the sample is any of blood, serum, plasma, spinal fluid, a tissue extract or a cell extract.

In some embodiments, the test compound is a library of test compounds. In some embodiments, the library is any of a peptide library, a protein library, an antibody library, a recombinant combinatorial antibody library or a scFV or Fab phage display library. In some embodiments, the test compound is labelled with any of a peptide tag, a nucleic acid tag, a chemical tag, a fluorescent tag or a radio frequency tag.

In some embodiments, the antibody is an antibody to a mutant GPCR of a parent GPCR, wherein the mutant GPCR has increased stability in a particular conformation relative to the parent GPCR. In some embodiments, the antibody is produced by immunising a lymphocyte with an immunogen of the mutant GPCR. In some embodiments, the lymphocyte is immunised in vivo. In some embodiments, the lymphocyte is immunised in vitro. In some embodiments, the immunogen of the mutant GPCR is all of the mutant GPCR, a fragment thereof or a fusion protein thereof.

In some embodiments, the immunogen of a mutant GPCR is provided in a whole cell preparation, in a cell membrane fragment, solubilised in detergent, in a lipid monolayer, in a lipid bilayer, in a bead-linked lipid particle, in a solid-supported lipid layer or in a proteoliposome. In some embodiments, the immunogen is provided with an adjuvant. In some embodiments, the adjuvant is Titremax or Ribi's adjuvant emulsion.

In some embodiments, methods further comprise modifying the isolated test compound that binds to a mutant GPCR when residing in a particular conformation and determining whether the modified test compound binds to the mutant GPCR when residing in a particular conformation. In some embodiments, methods further comprise determining whether the modified test compound binds to the parent GPCR when residing in the particular conformation.

In some embodiments, more than one mutant GPCR is provided and it is determined whether the test compound binds to each mutant GPCR when residing in a particular conformation; and the test compound which binds to each mutant GPCR when residing in the particular conformation is isolated.

In some embodiments, a mutant GPCR of a first parent GPCR and a mutant GPCR of a second parent GPCR are provided and it is determined whether the test compound binds to each mutant GPCR when residing in a particular conformation; and the test compound which binds to each mutant GPCR when residing in the particular conformation is isolated.

In some embodiments, more than one mutant GPCR is provided and a test compound is selected that binds to a first mutant GPCR but which does not bind, or binds less strongly than to the first mutant GPCR, to at least one other mutant GPCR.

In some embodiments, methods further comprise (i) determining if the isolated test compound affects the function of the GPCR to which it binds and (ii) isolating a test compound that affects the function of the GPCR to which it binds.

In some embodiments, in step (i) it is determined if the isolated test compound affects the binding of the GPCR to its natural ligand or analog thereof. In some embodiments, in step (ii) a test compound that decreases binding between the GPCR and its natural ligand or analog thereof is isolated. In some embodiments, in step (ii) a test compound that increases binding between the GPCR and its natural ligand or analog thereof is isolated. In some embodiments, in step (i) it is determined if the isolated test compound modulates activation of the GPCR to which it binds.

In some embodiments, in step (ii) a test compound which modulates any of calcium mobilisation, cAMP levels, kinase pathway activity, gene transcription from a reporter gene under control of the GPCR to which the test compound binds, β-arrestin recruitment, activation of G proteins, GTPase activity or [35S]GTPγS binding is selected.

In some embodiments, in step (ii) an agonist test compound that increases activation of the GPCR to which it binds, is isolated. In some embodiments, in step (ii) an antagonist test compound that decreases activation of the GPCR to which it binds, is isolated.

In some embodiments, the mutant GPCR is provided by: (a) providing one or more mutants of a parent GPCR; (b) selecting a ligand, the ligand being one which binds to the parent GPCR when the GPCR is residing in a particular conformation; (c) determining whether the or each mutant GPCR has increased stability with respect to binding the selected ligand compared to the stability of the parent GPCR with respect to binding that ligand; and (d) selecting those mutants that have an increased stability compared to the parent GPCR with respect to binding the selected ligand. In some embodiments, the one or more mutants are brought into contact with the selected ligand prior to step (c). In some embodiments, the one or more mutants are provided in a solubilised form. In some embodiments, the particular conformation in which the GPCR resides in step (c) corresponds to the class of ligand selected in step (b).

In some embodiments, the selected ligand is from the agonist class of ligands and the particular conformation is an agonist conformation, or the selected ligand is from the antagonist class of ligands and the particular conformation is an antagonist conformation. In some embodiments, the selected ligand is from the agonist class of ligands and the particular conformation in which the GPCR resides in step (c) is the agonist conformation.

In some embodiments, the binding affinity of the mutant for the selected ligand is substantially the same or greater than the binding affinity of the parent for the selected ligand. In some embodiments, the method is repeated for one or more rounds, with the selected mutants having increased stability in step (a) representing the parent GPCR in a subsequent round of the method.

In some embodiments, a mutant GPCR is selected which has increased stability to any one or more of heat, a detergent, a chaotropic agent and an extreme of pH. In some embodiments, a mutant GPCR with increased thermostability is selected. In some embodiments, the ligand is any one of a full agonist, a partial agonist, an inverse agonist, an antagonist. In some embodiments, the ligand is a polypeptide which binds to the GPCR. In certain embodiments, the polypeptide is any of an antibody, an ankyrin, a G protein, an RGS protein, an arrestin, a GPCR kinase, a receptor tyrosine kinase, a RAMP, a NSF, a GPCR, an NMDA receptor subunit NR1 or NR2a, or calcyon, a fibronectin domain framework, or a fragment or derivative thereof that binds to the GPCR.

In some embodiments, in step (b) two or more ligands are selected, the presence of each causes the GPCR to reside in the same particular conformation. In some embodiments, a mutant GPCR is selected which has reduced ability to bind a ligand of a different class to the ligand selected in step (b) compared to its parent. In some embodiments, the GPCR is any one of a β-adrenergic receptor, an adenosine receptor and a neurotensin receptor.

In some embodiments, the mutant GPCR is provided by: (a) carrying out the method of any one of the preceeding embodiments; (b) identifying the position or positions of the mutated amino acid residue or residues in the mutant GPCR or GPCRs which has been selected for increased stability, and (c) synthesising a mutant GPCR which contains a replacement amino acid at one or more of the positions identified. In some embodiments, the mutant GPCR contains a plurality of mutations compared to the parent GPCR.

In some embodiments, the mutant GPCR is provided by: (i) identifying in the amino acid sequence of one or more mutants of a first parent GPCR with increased stability relative to the first parent GPCR, the position or positions at which the one or more mutants have at least one different amino acid residue compared to the first parent GPCR, and (ii) making one or more mutations in the amino acid sequence that defines a second GPCR at the corresponding position or positions, to provide one or more mutants of a second parent GPCR with increased stability relative to the second parent GPCR.

In some embodiments, the one or more mutants of a first parent GPCR are provided according to methods described herein. In some embodiments, the second GPCR is of the same GPCR class or family as the first parent GPCR. In some embodiments, the second GPCR is a GPCR which has at least 20% sequence identity with the first parent GPCR.

In some embodiments, producing a mutant GPCR with increased stability relative to its parent GPCR, the method comprising: (i) providing one or more mutants of a first parent GPCR with increased stability relative to the first parent GPCR; (ii) identifying in a structural membrane protein model the structural motif or motifs in which the one or more mutants have at least one different amino acid residue compared to the first parent GPCR, and (iii) making one or more mutations in the amino acid sequence that defines a corresponding structural motif or motifs in a second parent GPCR, to provide one or more mutants of a second parent GPCR with increased stability relative to the second parent GPCR.

In some embodiments, the structural membrane protein model is a model of an integral membrane protein. In some embodiments, the integral membrane protein has at least 20% sequence identity with the mutant of the first parent GPCR in step (i) across the protein domain in which the mutant has at least one different amino acid relative to the first parent GPCR. In some embodiments, the integral membrane protein is a GPCR. In some embodiments, the GPCR is of the same GPCR class or family as the first parent GPCR.

In some embodiments, the structural membrane protein model is a model of human $\beta_2$ adrenergic receptor or bovine rhodopsin. In some embodiments, the structural motif is any of a helical interface, a helix kink, a helix opposite a helix kink, a helix surface pointing into the lipid bilayer, a helix surface pointing into the lipid bilayer at the hydrophobic-hydrophilic boundary layer, a loop region or a protein binding pocket.

In some embodiments, the second parent GPCR is the first parent GPCR. In some embodiments, the second parent GPCR is not the first parent GPCR. In some embodiments, the second parent GPCR is a GPCR which has at least 20% sequence identity with the first parent GPCR. In some embodiments, the second GPCR is of the same GPCR class or family as the first parent GPCR.

In some embodiments, methods further comprise: (I) selecting a ligand, the ligand being one which binds to the second parent GPCR when the GPCR is residing in a particular conformation; (II) determining whether the or each mutant of the second parent GPCR when residing in a particular conformation has increased stability with respect to binding the selected ligand compared to the stability of the second parent GPCR when residing in the same particular conformation with respect to binding that ligand, and (III) selecting those mutants that have an increased stability compared to the second parent GPCR with respect to binding the selected ligand. In some embodiments, the particular conformation in which the GPCR resides in step (II) corresponds to the class of ligand selected in step (I).

In some embodiments, the selected ligand is from the agonist class of ligands and the particular conformation is an agonist conformation, or the selected ligand is from the antagonist class of ligands and the particular conformation is an antagonist conformation. In some embodiments, the ligand is any one of a full agonist, a partial agonist, an inverse agonist, an antagonist. In some embodiments, the ligand is a polypeptide which binds to the GPCR. In certain embodiments, the polypeptide is any of an antibody, an ankyrin, a G protein, an RGS protein, an arrestin, a GPCR kinase, a receptor tyrosine kinase, a RAMP, a NSF, a GPCR, an NMDA receptor subunit NR1 or NR2a, or calcyon, a fibronectin domain framework, or a fragment or derivative thereof that binds to the GPCR.

In some embodiments, the binding affinity of the one or more mutants of the second GPCR is substantially the same or greater than the binding affinity of the second parent GPCR for the selected ligand. In some embodiments, the mutant GPCR provided in step (a) is any one of a β-adrenergic receptor, an adenosine receptor, a neurotensin receptor or a muscarinic receptor.

In some embodiments, the mutant GPCR provided in step (a) has, compared to its parent receptor, at least one different amino acid at a position which corresponds to any one or more of the following positions: (i) according to the numbering of the turkey β-adrenergic receptor as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338, (ii) according to the numbering of the human adenosine $A_{2a}$ receptor as set out in FIGS. 10A and 10B: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, (iii) according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399, and (iv) according to the numbering of the muscarinic receptor as set out in FIGS. 17A, 17B and 17C: Leu 65, Met 145, Leu 399, Ile 383 and Met 384.

In some embodiments, the mutant GPCR provided in step (a) is a mutant β-adrenergic receptor which, when compared to its corresponding parent receptor, has a different amino acid at a position which corresponds to any one or more of the following positions according to the numbering of the turkey β-adrenergic receptor as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

In some embodiments, the mutant β-adrenergic receptor has an amino acid sequence which is at least 20% identical to that of the turkey β-adrenergic receptor whose sequence is set out in FIGS. 9A and 9B.

In some embodiments, the mutant GPCR provided in step (a) is a mutant β-adrenergic receptor which has at least one different amino acid residue in a structural motif in which the mutant receptor compared to its parent receptor has a different amino acid at a position which corresponds to any of the following positions according to the numbering of the turkey β-adrenergic receptor as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

In some embodiments, the mutant GPCR provided in step (a) is a mutant adenosine receptor which, when compared to its corresponding parent receptor, has a different amino acid at a position which corresponds to any one or more of the following positions according to the numbering of the human adenosine $A_{2a}$ receptor as set out in FIGS. 10A and 10B: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315. In some embodiments, the mutant adenosine receptor has an amino acid sequence which is at least 20% identical to that of the human adenosine $A_{2a}$ receptor whose sequence is set out in FIGS. 10A and 10B.

In some embodiments, the mutant GPCR provided in step (a) is a mutant adenosine receptor which has at least one different amino acid residue in a structural motif in which the mutant receptor compared to its parent receptor has a different amino acid at a position which corresponds to any of the following positions according to the numbering of the human adenosine $A_{2a}$ receptor as set out in FIGS. 10A and 10B: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

In some embodiments, the mutant GPCR provided in step (a), is a mutant neurotensin receptor which, when compared to its corresponding parent receptor, has a different amino acid at a position which corresponds to any one or more of the following positions according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399. In some embodiments, the mutant neurotensin receptor has an amino acid sequence which is at least 20% identical to that of the rat neurotensin receptor whose sequence is set out in FIGS. 11A and 11B.

In some embodiments, the mutant GPCR provided in step (a) is a mutant neurotensin receptor which has at least one different amino acid residue in a structural motif in which the mutant receptor compared to its parent receptor has a different amino acid at a position which corresponds to any of the following positions according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

In some embodiments, the mutant GPCR provided in step (a) is a mutant muscarinic receptor which, when compared to the corresponding wild-type muscarinic receptor, has a different amino acid at a position which corresponds to any one or more of the following positions according to the numbering of the human muscarinic receptor as set out in FIGS. 17A, 17B and 17C: Leu 65, Met 145, Leu 399, Ile 383 and Met 384. In some embodiments, the mutant muscarinic receptor has an amino acid sequence which is at least 20% identical to that of the rat neurotensin receptor whose sequence is set out in FIGS. 17A, 17B and 17C.

In some embodiments, the mutant GPCR provided in step (a) is a mutant muscarinic receptor which has at least one different amino acid residue in a structural motif in which the mutant receptor compared to its parent receptor has a different amino acid at a position which corresponds to any of the following positions according to the numbering of the human muscarinic receptor as set out in FIGS. 17A, 17B and 17C: Leu 65, Met 145, Leu 399, Ile 383 and Met 384.

Further aspects of the invention involve methods of producing a binding partner of a GPCR, the method comprising synthesising a binding partner identifiable by carrying out the methods described herein. In some embodiments, a binding partner is obtained by any of the methods described herein. In some embodiments, the binding partner is conformation-specific. In some embodiments, the binding partner is any of a polypeptide; an anticalin; a peptide; an antibody; a chimeric antibody; a single chain antibody; an aptamer; a darpin; a Fab, $F(ab')_2$, Fv, ScFv or dAb antibody fragment; a small molecule; a natural product; an affibody; a peptidomimetic; a nucleic acid; a peptide nucleic acid molecule; a lipid; a carbohydrate; a protein based on a modular framework including ankyrin repeat proteins, armadillo repeat proteins, leucine rich proteins, tetrariopeptide repeat proteins or Designed Ankyrin Repeat Proteins (DARPins); or proteins based on lipocalin or fibronectin domains or Affilin scaffolds based on either human gamma crystalline or human ubiquitin.

In some embodiments, the binding partner is an antibody. In some embodiments, the binding affinity of the mutant GPCR for the binding partner is substantially the same or greater than the binding affinity of the parent GPCR for the binding partner. In some embodiments, the mutant GPCR has increased stability in a particular conformation relative to the parent GPCR and wherein when a target substance binds to said mutant GPCR, a detectable signal is produced.

Further aspects of the invention relate to biosensors, wherein the mutant GPCR is provided as defined in any of the methods described herein. In some embodiments, the detectable signal is any of a change in colour; fluorescence; evanescence; surface plasmon resonance; electrical conductance or charge separation; ultraviolet, visible or infrared absorption; luminescence; chemiluminescence; electrochemiluminescence; fluorescence anisotropy; fluorescence intensity; fluorescence lifetime; fluorescence polarisation; fluorescence energy transfer; molecular mass; electron spin resonance; nuclear magnetic resonance; hydrodynamic volume or radius; specific gravity; scintillation; field effect resistance; electrical impedance; acoustic impedance; quantum evanescence; resonant scattering; fluorescent quenching; fluorescence correlation spectroscopy; acoustic load; acoustic shear wave velocity; binding force; or interfacial stress.

In some embodiments, the biosensor is a flow-based biosensor, such as a quartz crystal microbalance biosensor, an evanescent wave biosensor, a planar wave guide biosensor, a surface Raman sensor, or a surface plasmon resonance biosensor. In some embodiments, the target substance is any of a molecule, a biomolecule, a peptide, a protein, a carbohydrate, a lipid, a GPCR ligand, a synthetic molecule, a drug, a drug metabolite or a disease biomarker.

BRIEF DESCRIPTION OF THE DRAWINGS

The invention will now be described in more detail with respect to the following Figures and Examples wherein:

FIGS. 9A and 9B Alignment of the turkey β-adrenergic receptor with human β1, ⊕2 and β3 receptors. The sequences depicted in FIGS. 9A and 9B correspond to SEQ ID NOs.: 1-4, respectively.

FIGS. 10A and 10B Alignment of human adenosine receptors. The sequences depicted in FIGS. 10A and 10B correspond to SEQ ID NOs.: 5-9, respectively.

FIGS. 11A and 11B Alignment of neurotensin receptors. The sequences depicted in FIGS. 11A and 11B correspond to SEQ ID NOs.: 9-11, respectively.

FIG. 27 Percentage identity of the turkey β1 adrenergic receptor, human adenosine receptor and rat neurotensin receptor to human β adrenergic receptors, human adenosine receptors and human neurotensin receptors, respectively.

DETAILED DESCRIPTION OF THE INVENTION

Figure 1:
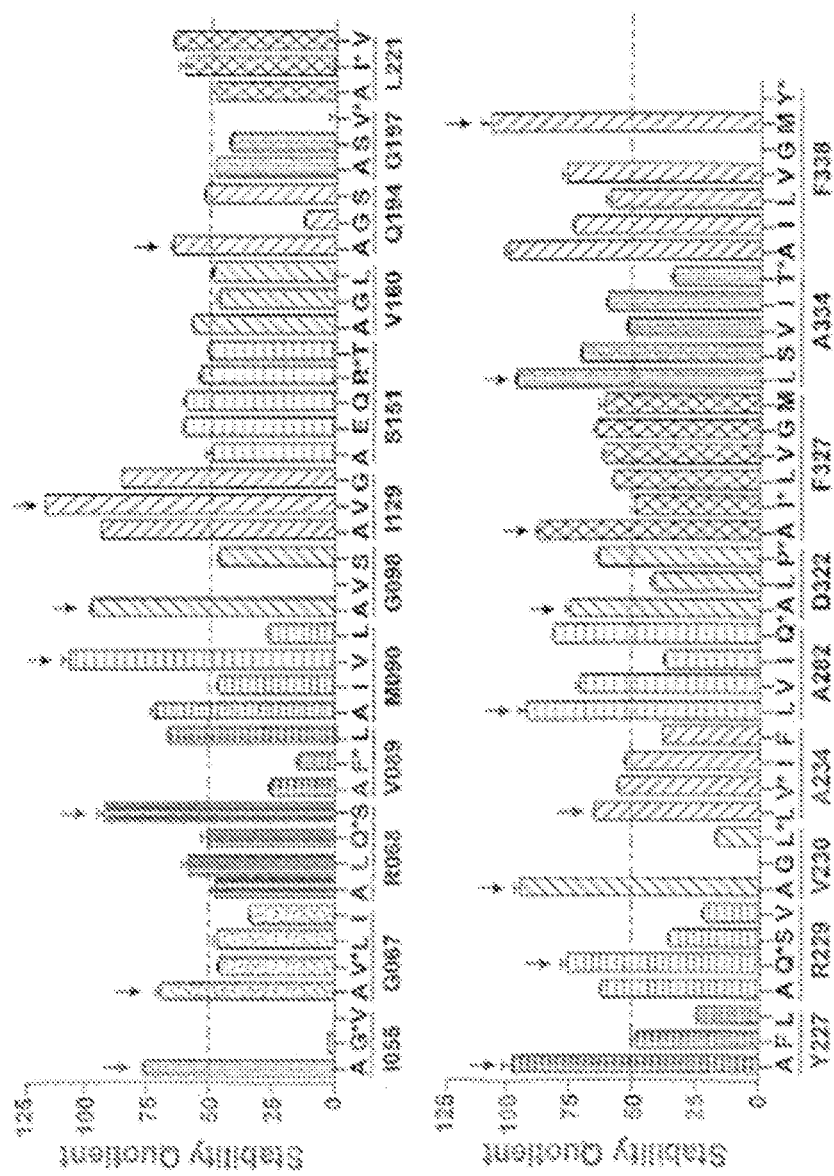
FIG. 1 Amino acid changes in βAR that lead to thermostability. Stability quotient indicates the % remaining binding activity of the mutants after heating the sample for 30 min at 32° C. All values are normalized to $\beta AR_{34-424}$ (50%, showed as a discontinuous line) to remove any experimental variability between assays. Bars show the stability for each mutant. The letters on the x-axis indicate the amino acid present in the mutant. The original amino acid and its position in $\beta AR_{34-424}$ is indicated below. Bars corresponding to the same amino acid in βAR$_{34-424}$ are in the same colour with arrows indicating the best mutations. Errors were calculated from duplicate measurements; the best mutants were subsequently re-assayed to determine the Tm for each individual mutation and to give an accurate rank order of stability for each mutant (see Example 1).

GPCRs constitute a very large family of proteins that control many physiological processes and are the targets of many effective drugs. Thus, they are of considerable pharmacological importance. A list of GPCRs is given in Foord et al (2005) *Pharmacol Rev.* 57, 279-288, which is incorporated herein by reference. GPCRs are generally unstable when isolated, and despite considerable efforts, it has only been possible to crystallise bovine rhodopsin, which naturally is exceptionally stable and the beta 2 adrenergic receptor which was crystallised as a fusion protein or in complex with an antibody fragment.

GPCRs are druggable targets, and reference is made particularly to Overington et al (2006) *Nature Rev. Drug Discovery* 5, 993-996 which indicates that over a quarter of present drugs have a GPCR as a target.

GPCRs are thought to exist in multiple distinct conformations which are associated with different pharmacological classes of ligand such as agonists and antagonists, and to cycle between these conformations in order to function (Kenakin T. (1997) *Ann N Y Acad Sci* 812, 116-125). Switching between conformations contributes to the difficulty in obtaining crystal structures of receptors.

The generation of conformation specific binding partners to GPCRs is hindered by several factors. For example, GPCRs generally have poor stability when removed from their native membrane environment that severely restricts the range of conditions that can be explored without their immediate denaturation or precipitation. The inability to produce purified GPCRs in their native conformation prevents their use in a wide range of screening paradigms which depend on the use of purified receptors. Thus, GPCR screening has traditionally depended on assays in which the receptor is present in cell membranes or whole cells.

We have developed a methodology for the stabilisation of a GPCR in a particular biologically relevant conformation. Such receptors have a number of advantages as immunogens and/or selection and screening reagents for the generation of binding partners. In particular, they are useful for the generation of conformation-specific binding partners, which will frequently have functional properties, and have previously proven very difficult to generate.

For example, the stability of native, correctly folded receptor throughout the expression, solubilisation and purification steps facilitates a high yield of purified GPCR (milligram quantities from lab-scale cell culture). Furthermore, the stability of folded protein in a range of detergents and solubilisation buffers and additives, without distortion of function, enables optimisation of conditions for immunization, for immobilization on solid surfaces without denaturation (e.g. plastic plates, resins, beads or slides, directly or via affinity tags such as poly-Histidine tags), for the purpose of antibody production and screening or for library screening (such as affibody, antibody, phage or small molecule libraries). For library screening, reduction in non-specific binding by removal of membranous matter and cell-surface "sticky antigens" will give a major improvement in signal/noise. Use of short-chain detergents with highly polar or charged head groups (such as lauryldimethylamine-oxide, octyl D-glucoside or octyl D-maltoside) is also made possible, which will reveal a greater proportion of the antigenic surfaces of the GPCR which are masked by longer-chain detergents such as n-dodecyl beta-D-maltoside (Bamber et al PNAS103 (2006) 16224-16229). The trapping of particular functional conformations of the receptor will also increase the likelihood of generating conformation-specific, functional binding partners.

Accordingly, a first aspect of the invention provides a method of producing a binding partner of a GPCR, the method comprising:

a) providing a mutant GPCR of a parent GPCR, wherein the mutant GPCR has increased stability in a particular conformation relative to the parent GPCR;

b) providing one or more test compounds;

c) determining whether the or each test compound binds to the mutant GPCR when residing in the particular conformation; and d) isolating those test compounds that bind to the mutant GPCR when residing in the particular conformation.

By "binding partner" we mean a molecule that binds to a particular GPCR. Preferably, the molecule binds selectively to the GPCR. For example, it is preferred if the binding partner has a $K_d$ value (dissociation constant) which is at least five or ten times lower (i.e. higher affinity) than for at least one other GPCR, and preferably more than 100 or 500 times lower. More preferably, the binding partner of a GPCR has a $K_d$ value more than 1000 or 5000 times lower than for at least one other GPCR. However, it will be appreciated that the limits will vary dependent upon the nature of the binding partner. Thus, typically, for small molecule binding partners, the binding partner typically has a $K_d$ value which is at least 50 times or 100 times lower than for at least one other GPCR. Typically, for antibody binding partners, the binding partner typically has a $K_d$ value which is at least 500 or 1000 times lower than for at least one other GPCR.

The use of stabilised GPCRs trapped in particular conformations will increase the likelihood of producing conformation-specific binding partners. Accordingly, it is appreciated that the method may be used to produce a conformation-specific binding partner of a GPCR. Thus, the method may also be used to identify binding partners that have functional activity such as agonists or antagonists (or other pharmacological categories) which will be determined by the conformation in which the GPCR was stabilised.

By "conformation specific", we mean that the binding partner of the GPCR binds selectively to a particular conformation of the GPCR and thus has a $K_d$ value for that conformation which is lower than for other conformations of the same GPCR. Thus, a conformation specific binding partner will bind to one conformation of a GPCR (and may cause the GPCR to adopt this conformation), but does not bind as strongly to another conformation that the GPCR may be able to adopt. It will be appreciated therefore that, while the difference in affinity between two conformations and the conformation specific binding partner may be small, typically it will be sufficient to alter the equilibrium between conformational states and encourage the GPCR to adopt a particular conformation. Thus, a conformational specific binding partner may be considered to be one which traps a GPCR in a conformation of biological relevance (e.g. ligand bound state). Typically, a conformation specific binding partner has a $K_d$ value (dissociation constant) which is at least five or ten times lower (i.e. higher affinity) than for at least one other conformation of the GPCR conformation, and preferably between 100-10000 times lower.

Typically, the conformational specific binding partner binds to the GPCR with a $K_d$ of from mM to pM or from mM to fM, such as in the range from μM to nM or in the range from nM to pM.

Kd values can be determined readily using methods well known in the art and as described, for example, below.

At equilibrium $Kd=[R][L]/[RL]$ where the terms in brackets represent the concentration of
Receptor-ligand complexes [RL],
unbound receptor [R], and
unbound ("free") ligand [L].

In order to determine the Kd the value of these terms must be known. Since the concentration of receptor is not usually known then the Hill-Langmuir equation is used where Fractional occupancy=$[L]/[L]+Kd$.

In order to experimentally determine a Kd then, the concentration of free ligand and bound ligand at equilibrium must be known. Typically, this can be done by using a radiolabelled or fluorescently labelled ligand which is incubated with the receptor (present in whole cells or homogenised membranes) until equilibrium is reached. The amount of free ligand vs bound ligand must then be determined by separating the signal from bound vs free ligand. In the case of a radioligand this can be done by centrifugation or filtration to separate bound ligand present on whole cells or membranes from free ligand in solution. Alternatively a scintillation proximity assay is used. In this assay the receptor (in membranes) is bound to a bead containing scintillant and a signal is only detected by the proximity of the radioligand bound to the receptor immobilised on the bead.

The affinity constant may also be determined in a functional assay ($K_B$). Here the receptor in a whole cell or membrane is activated by an agonist ligand and a response measured (e.g. mobilisation of intracellular calcium, G protein activation, increase or decrease in adenylate cyclise or cAMP, activation of a signal transduction pathway such as a MAP-kinase pathway or activation of gene transcription). The ability of an antagonist to inhibit agonist activity can be measured and for a competitive antagonist is equal to the affinity constant.

The stability of the mutant GPCRs in a range of detergents, surfactants and solubilisation buffers enables their purification outside of their normal membrane environment. Therefore, the GPCR can be provided in an isolated form removed from non-desired antigens such as non-target GPCRs, membrane associated proteins and other membrane components such as lipoproteins, apolipoproteins, lipis, phosphoinositol lipids and liposaccharides. Thus the method of the invention allows for the selection of a binding partner of a GPCR in the absence of such non-desired antigens. Thus the invention produces binding partners that have enhanced selectivity for a GPCR over other membrane components.

Mutations of the parent GPCR that confer stability in a particular conformation are not expected to affect the binding of the parent GPCR residing in a particular conformation to a particular binding partner. However, it is appreciated that once a binding partner has been isolated by assessing binding to a mutant GPCR residing in a particular conformation, binding of that binding partner to the parent GPCR residing in the same particular conformation may also be assessed.

Thus, in one embodiment the method further comprises:
(e) determining whether the or each test compound binds to the parent GPCR when residing in the particular conformation; and
(f) isolating those test compounds that also bind the parent GPCR when residing in the particular conformation.

Typically, the selected binding partner binds to the mutant GPCR when residing in a particular conformation with a similar potency to its binding to the parent GPCR when residing in the same particular conformation. Typically, the $K_d$ values for the particular binding partner binding the mutant GPCR and the parent GPCR are within 5-10 fold of each other, such as within 2-3 fold. Typically, the binding of the binding partner to the mutant GPCR compared to the parent GPCR would not be more than 5 times weaker and not more than 10 times stronger.

Typically, the selected binding partner binds to the mutant GPCR with approximately equal affinity (that is to say typically within 2-3 fold) or greater affinity than does the parent receptor, when residing in the same conformation. For agonist-conformation mutants, the mutants typically bind the agonist-conformation specific binding partners with the same or higher affinity than the parent GPCR and typically bind antagonist-conformation specific binding partners with the same or lower affinity than the parent GPCR. Similarly for antagonist-conformation mutants, the mutants typically bind the antagonist-conformation specific binding partners with the same or higher affinity than the parent GPCR and typically bind agonist-conformation specific binding partners with the same or lower affinity than the parent GPCR.

Selectivity of binding partners for particular conformations of GPCR or for particular GPCRs and calculation of $K_d$s can be determined using binding assays well known in the art and as described, for example, below. Typically, $K_d$ values are calculated using conventional GPCR assays in membranes wherein the binding affinity at different compound concentrations is measured. Examples of suitable assays include surface plasmon resonance assays and competition assays which are well known in the art and are described below.

Typically, the mutant GPCR used in the present aspect is selected and prepared using any of the methods as described below.

Providing a Mutant GPCR of a Parent GPCR

A mutant GPCR with increased stability relative to its parent GPCR can be provided by the methods described below, and by any of the methods disclosed in PCT applications WO 2008/114020 and PCT/GB2008/004032.

Method 1

A method for selecting a mutant G-protein coupled receptor (GPCR) with increased stability, comprises
(a) providing one or more mutants of a parent GPCR,
(b) selecting a ligand, the ligand being one which binds to the parent GPCR when the GPCR is residing in a particular conformation,
(c) determining whether the or each mutant GPCR has increased stability with respect to binding the selected ligand compared to the stability of the parent GPCR with respect to binding that ligand, and
(d) selecting those mutants that have an increased stability compared to the parent GPCR with respect to binding of the selected ligand.

The inventors have appreciated that, in order to improve the likelihood of crystallisation of a GPCR in a biologically relevant form (which is therefore pharmacologically useful), it is desirable not only to increase the stability of the protein, but also for the protein to have this increased stability when in a particular conformation. The conformation is determined by a selected ligand, and is a biologically relevant conformation in particular a pharmacologically relevant conformation. Thus, the method of selection may be considered to be a method for selecting mutants of a GPCR which have increased stability of a particular conformation, for example they may have increased conformational thermostability. The method may be used to create stable, conformationally locked GPCRs by mutagenesis. The selected mutant GPCRs are effectively purer forms of the parent molecules in that a much higher proportion of them occupies a particular conformational state. The deliberate selection of a chosen receptor conformation resolved from other conformations by use of a ligand (or ligands) that bind preferentially to this conformation is therefore an important feature of the selection method. The method may also be considered to be a method for selecting mutant GPCRs which are more tractable to crystallisation. This is because it is well known that decreased homogeneity or increased pleiotropy within a population of molecules does not favour crystallisation, and further, that an increased number of conformations of a particular molecule does not favour crystallisation.

Thus a further method for selecting a mutant G-protein coupled receptor (GPCR) with increased stability, comprises
(a) providing one or more mutants of a parent GPCR,
(b) selecting a ligand, the ligand being one which binds to the parent GPCR when the GPCR is residing in a particular conformation,
(c) determining whether the or each mutant GPCR when residing in the particular conformation has increased stability with respect to binding the selected ligand compared to the stability of the parent GPCR when residing in the same particular conformation with respect to binding that ligand, and
(d) selecting those mutants that have an increased stability compared to the parent GPCR with respect to binding of the selected ligand.

In a review of the druggable genome by Hopkins & Groom (2002) *Nature Rev. Drug Discovery* 1, 727-730, Table 1 contains a list of protein families many of which are GPCRs. Overington et al (2006) *Nature Rev. Drug Discovery* 5, 993-996 provides more details of drug targets, and FIG. 1 indicates that more than a quarter of current drugs target GPCRs. There are 52 GPCR targets for orally available drugs out of a total of 186 total targets in this category.

Suitable GPCRs for use in the practice of the invention include, but are not limited to β-adrenergic receptor, adenosine receptor, in particular adenosine $A_{2a}$ receptor, and neurotensin receptor (NTR). Other suitable GPCRs are well known in the art and include those listed in Hopkins & Groom supra. In addition, the International Union of Pharmacology produce a list of GPCRs (Foord et al (2005) *Pharmacol. Rev.* 57, 279-288, incorporated herein by reference and this list is periodically updated at iuphar-db.org/GPCR/ReceptorFamiliesForward). It will be noted that GPCRs are divided into different classes, principally based on their amino acid sequence similarities. They are also divided into families by reference to the natural ligands to which they bind. All GPCRs are included in the scope of the invention.

The amino acid sequences (and the nucleotide sequences of the cDNAs which encode them) of many GPCRs are readily available, for example by reference to GenBank. In particular, Foord et al supra gives the human gene symbols and human, mouse and rat gene IDs from Entrez Gene (ncbi.nlm.nih.gov/entrez). It should be noted, also, that because the sequence of the human genome is substantially complete, the amino acid sequences of human GPCRs can be deduced therefrom.

Although the GPCR may be derived from any source, it is particularly preferred if it is from a eukaryotic source. It is particularly preferred if it is derived from a vertebrate source such as a mammal or a bird. It is particularly preferred if the GPCR is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic GPCR (such as an avian or mammalian GPCR) may be expressed in a prokaryotic host cell, such as *E. coli*, but be considered to be avian- or mammalian-derived, as the case may be.

In some instances, the GPCR may be composed of more than one different subunit. For example, the calcitonin gene-related peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657).

The mutants of the parent GPCR may be produced in any suitable way and provided in any suitable form. Thus, for example, a series of specific mutants of the parent protein may be made in which each amino acid residue in all or a part of the parent protein is independently changed to another amino acid residue. For example, it may be convenient to make mutations in those parts of the protein which are predicted to be membrane spanning. The three-dimensional structure of rhodopsin is known (Li et al (2004) *J Mol Biol* 343, 1409-1438; Palczewski et al (2000) Science 289, 739-745), and it is possible to model certain GPCRs using this structure. Thus, conveniently, parts of the GPCR to mutate may be based on modelling. Similarly, computer programs are available which model transmembrane regions of GPCRs based on hydrophobicity (Kyle & Dolittle (1982) *J. Mol. Biol.* 157, 105-132), and use can be made of such models when selecting parts of the protein to mutate. Conventional site-directed mutagenesis may be employed, or polymerase chain reaction-based procedures well known in the art may be used. It is possible, but less desirable, to use ribosome display methods in the selection of the mutant protein.

Typically, each selected amino acid is replaced by Ala (ie Ala-scanning mutagenesis), although it may be replaced by any other amino acid. If the selected amino acid is Ala, it may conveniently be replaced by Leu. Alternatively, the amino acid may be replaced by Gly (ie Gly-scanning mutagenesis), which may allow a closer packing of neighbouring helices that may lock the protein in a particular conformation. If the selected amino acid is Gly, it may conveniently be replaced by Ala.

Although the amino acid used to replace the given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic.

Alternatively, the mutants may be produced by a random mutagenesis procedure, which may be of the whole protein or of a selected portion thereof. Random mutagenesis procedures are well known in the art.

Conveniently, the mutant GPCR has one replaced amino acid compared to the parent protein (ie it is mutated at one amino acid position). In this way, the contribution to stability of a single amino acid replacement may be assessed. However, the mutant GPCR assayed for stability may have more than one replaced amino acid compared to the parent protein, such as 2 or 3 or 4 or 5 or 6 replacements.

As is discussed in more detail below, combinations of mutations may be made based on the results of the selection method. It has been found that in some specific cases combining mutations in a single mutant protein leads to a further increase in stability. Thus, it will be appreciated that the method of selection can be used in an iterative way by, for example, carrying it out to identify single mutations which increase stability, combining those mutations in a single mutant GPCRs which is the GPCR then provided in part (a) of the method. Thus, multiply-mutated mutant proteins can be selected using the method.

The parent GPCR need not be the naturally occurring protein. Conveniently, it may be an engineered version which is capable of expression in a suitable host organism, such as *Escherichia coli*. For example, as described in Example 1, a convenient engineered version of the turkey β-adrenergic receptor is one which is truncated and lacks residues 1-33 of the amino acid sequence (ie $\beta AR_{34-424}$). The parent GPCR may be a truncated form of the naturally occurring protein (truncated at either or both ends), or it may be a fusion, either to the naturally occurring protein or to a fragment thereof. Alternatively or additionally, the parent GPCR, compared to a naturally-occurring GPCR, may be modified in order to improve, for example, solubility, proteolytic stability (eg by truncation, deletion of loops, mutation of glycosylation sites or mutation of reactive amino acid side chains such as cysteine). In any event, the parent GPCR is a protein that is able to bind to the selected ligand which ligand is one which is known to bind the naturally occurring GPCR. Conveniently, the parent GPCR is one which, on addition of an appropriate ligand, can affect any one or more of the downstream activities which are commonly known to be affected by G-protein activation.

However, it will be appreciated that the stability of the mutant is to be compared to a parent in order to be able to assess an increase in stability.

A ligand is selected, the ligand being one which binds to the parent GPCR when residing in a particular conformation. Typically, the ligand will bind to one conformation of the parent GPCR (and may cause the GPCR to adopt this conformation), but does not bind as strongly to another conformation that the GPCR may be able to adopt. Thus, the presence of the ligand may be considered to encourage the GPCR to adopt the particular conformation. Thus, the method may be considered to be a way of selecting mutant GPCRs which are trapped in a conformation of biological relevance (eg ligand bound state), and which are more stable with respect to that conformation.

Preferably the particular conformation in which the GPCR resides in step (c) corresponds to the class of ligand selected in step (b).

Preferably the selected ligand is from the agonist class of ligands and the particular conformation is an agonist conformation, or the selected ligand is from the antagonist class of ligands and the particular conformation is an antagonist conformation.

Preferably the selected ligand is from the agonist class of ligands and the particular conformation in which the GPCR resides in step (c) is the agonist conformation.

Preferably, the selected ligand binding affinity for the mutant receptor should be equal to or greater than that for the wild type receptor; mutants that exhibit significantly reduced binding to the selected ligand are typically rejected.

By "ligand" we include any molecule which binds to the GPCR and which causes the GPCR to reside in a particular conformation. The ligand preferably is one which causes more than half of the GPCR molecules overall to be in a particular conformation.

Many suitable ligands are known.

Typically, the ligand is a full agonist and is able to bind to the GPCR and is capable of eliciting a full (100%) biological response, measured for example by G-protein coupling, downstream signalling events or a physiological output such as vasodilation. Thus, typically, the biological response is GDP/GTP exchange in a G-protein, followed by stimulation of the linked effector pathway. The measurement, typically, is GDP/GTP exchange or a change in the level of the end product of the pathway (eg cAMP, cGMP or inositol phosphates). The ligand may also be a partial agonist and is able to bind to the GPCR and is capable of eliciting a partial (<100%) biological response.

The ligand may also be an inverse agonist, which is a molecule which binds to a receptor and reduces its basal (ie unstimulated by agonist) activity sometimes even to zero.

The ligand may also be an antagonist, which is a molecule which binds to a receptor and blocks binding of an agonist, so preventing a biological response. Inverse agonists and partial agonists may under certain assay conditions be antagonists.

The above ligands may be orthosteric, by which we include the meaning that they combine with the same site as the endogenous agonist; or they may be allosteric or allotopic, by which we include the meaning that they combine with a site distinct from the orthosteric site. The above ligands may be syntopic, by which we include the meaning that they interact with other ligand(s) at the same or an overlapping site. They may be reversible or irreversible.

In relation to antagonists, they may be surmountable, by which we include the meaning that the maximum effect of agonist is not reduced by either pre-treatment or simultaneous treatment with antagonist; or they may be insurmountable, by which we include the meaning that the maximum effect of agonist is reduced by either pre-treatment or simultaneous treatment with antagonist; or they may be neutral, by which we include the meaning the antagonist is one without inverse agonist or partial agonist activity. Antagonists typically are also inverse agonists.

Ligands for use in the selection method may also be allosteric modulators such as positive allosteric modulators, potentiators, negative allosteric modulators and inhibitors. They may have activity as agonists or inverse agonists in their own right or they may only have activity in the presence of an agonist or inverse agonist in which case they are used in combination with such molecules in order to bind to the GPCR.

Neubig et al (2003) *Pharmacol. Rev.* 55, 597-606, incorporated herein by reference, describes various classes of ligands.

Preferably, the above-mentioned ligands are small organic or inorganic moieties, but they may be peptides or polypeptides. Typically, when the ligand is a small organic or organic moiety, it has a $M_r$ of from 50 to 2000, such as from 100 to 1000, for example from 100 to 500.

Typically, the ligand binds to the GPCR with a $K_d$ of from mM to pM, such as in the range of from µM (micromolar) to nM. Generally, the ligands with the lowest Kd are preferred.

Small organic molecule ligands are well known in the art, for example see the Examples below. Other small molecule ligands include 5HT which is a full agonist at the 5HT1A receptor; eltoprazine which is a partial agonist at the 5HT1A receptor (see Newman-Tancredi et al (1997) *Neuropharmacology* 36, 451-459); (+)-butaclamol and spiperone are dopamine D2 receptor inverse agonists (see Roberts & Strange (2005) *Br. J. Pharmacol.* 145, 34-42); and WIN55212-3 is a neutral antagonist of CB2 (Savinainen et al (2005) *Br. J. Pharmacol.* 145, 636-645).

The ligand may be a peptidomimetic, a nucleic acid, a peptide nucleic acid (PNA) or an aptamer. It may be an ion such as $Na^+$ or $Zn^{2+}$, a lipid such as oleamide, or a carbohydrate such as heparin.

The ligand may be a polypeptide which binds to the GPCR. Such polypeptides (by which we include oligopeptides) are typically from $M_r$ 500 to $M_r$ 50,000, but may be larger. The polypeptide may be a naturally occurring GPCR-interacting protein or other protein which interacts with the GPCR, or a derivative or fragment thereof, provided that it binds selectively to the GPCR in a particular conformation. GPCR-interacting proteins include those associated with signalling and those associated with trafficking, which often act via PDZ domains in the C terminal portion of the GPCR.

Polypeptides which are known to bind certain GPCRs include any of a G protein, an arrestin, a RGS protein, G protein receptor kinase, a RAMP, a 14-3-3 protein, a NSF, a periplakin, a spinophilin, a GPCR kinase, a receptor tyrosine kinase, an ion channel or subunit thereof, an ankyrin and a Shanks or Horner protein. Other polypeptides include NMDA receptor subunits NR1 or NR2a, calcyon, or a fibronectin domain framework. The polypeptide may be one which binds to an extracellular domain of a GPCR, such as fibulin-1. The polypeptide may be another GPCR, which binds to the selected GPCR in a hetero-oligomer. A review of protein-protein interactions at GPCRs is found in Milligan & White (2001) *Trends Pharmacol. Sci.* 22, 513-518, or in Bockaert et al (2004) *Curr. Opinion Drug Discov. Dev.* 7, 649-657 incorporated herein by reference.

The polypeptide ligand may conveniently be an antibody which binds to the GPCR. By the term "antibody" we include an immunoglobulin whether natural or partly or wholley synthetically produced. Examples include immunoglobulin isotypes and their isotypic subclasses, and monoclonal antibodies and fragments thereof comprising an antigen binding domains such as Fab, F(ab')2, single chain Fv (scFv), Fv, domain antibodies (dAbs) and diabodies. Mention is also made of camelid antibodies and engineered camelid antibodies. Such molecules which bind GPCRs are known in the art and in any event can be made using well known technology. Suitable antibodies include ones presently used in radioimmunoassay (RIAs) for GPCRs since they tend to recognise conformational epitopes.

The polypeptide may also be a binding protein based on a modular framework, such as ankyrin repeat proteins, armadillo repeat proteins, leucine rich proteins, tetratriopeptide repeat proteins or Designed Ankyrin Repeat Proteins (DARPins) or proteins based on lipocalin or fibronectin domains or Affilin scaffolds based on either human gamma crystalline or human ubiquitin.

In one embodiment of the selection method, the ligand is covalently joined to the GPCR, such as a G-protein or arrestin fusion protein. Some GPCRs (for example thrombin receptor) are cleaved N-terminally by a protease and the new N-terminus binds to the agonist site. Thus, such GPCRs are natural GPCR-ligand fusions.

It will be appreciated that the use of antibodies, or other "universal" binding polypeptides (such as G-proteins which are known to couple with many different GPCRs) may be particularly advantageous in the use of the method on "orphan" GPCRs for which the natural ligand, and small molecule ligands, are not known.

Once the ligand has been selected, it is then determined whether the or each mutant GPCR has increased stability with respect to binding the selected ligand compared to the parent GPCR with respect to binding that ligand. It will be appreciated that this step (c) is one in which it is determined whether the or each mutant GPCR has an increased stability (compared to its parent) for the particular conformation which is determined by the selected ligand. Thus, the mutant GPCR has increased stability with respect to binding the selected ligand as measured by ligand binding or whilst binding the selected ligand. As is discussed below, it is particularly preferred if the increased stability is assessed whilst binding the selected ligand.

The increased stability is conveniently measured by an extended lifetime of the mutant under the imposed conditions which may lead to instability (such as heat, harsh detergent conditions, chaotropic agents and so on). Destabilisation under the imposed condition is typically determined by measuring denaturation or loss of structure. As is discussed below, this may manifest itself by loss of ligand binding ability or loss of secondary or tertiary structure indicators.

Figure 12:
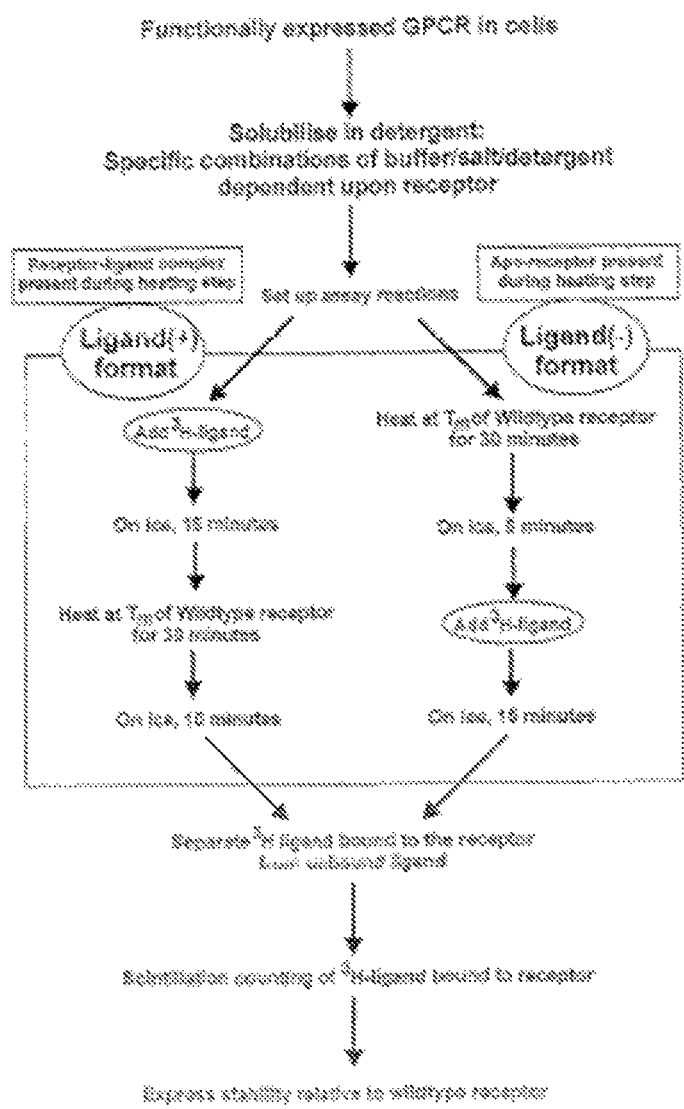
FIG. 12 Flow chart showing the two different assay formats of ligand (+) and ligand (−) used to determine receptor thermostablity.
Figure 13A:
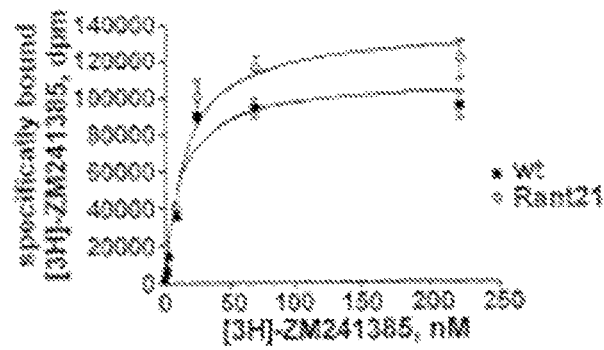
FIGS. 13A-F Pharmacological profile of thermostable mutant adenosine A2a receptor, Rant21. Saturation binding of (A) antagonist and (B) agonist to solubilised receptors. (C-F) Inhibition of [$^3$H]ZM241385 binding by increasing concentrations of antagonists (C) XAC and (D) Theophylline, and agonists (E) NECA and (F) R-PIA; binding of [$^3$H] ZM241385 (10 nM) in the absence of unlabelled ligand was set to 100%. Each solubilised receptor was incubated with ligands for one hour on ice in binding buffer (50 mM Tris pH7.5 and 0.025% DDM) containing 400 mM NaCl (A, C-F). Data shown are from two independent experiments with each data point measured in triplicate. K$_D$ and K$_i$ values are given in Table (iii).
Figure 13B:
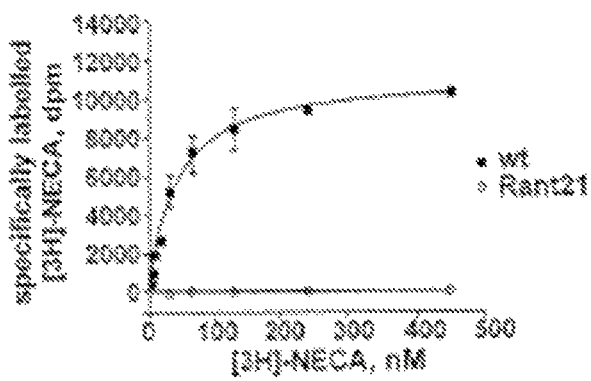
Figure 13C:
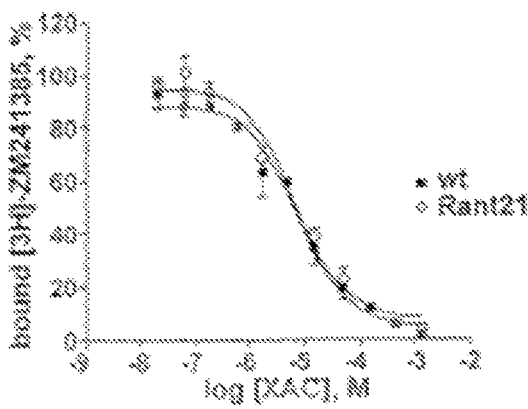
Figure 13D:
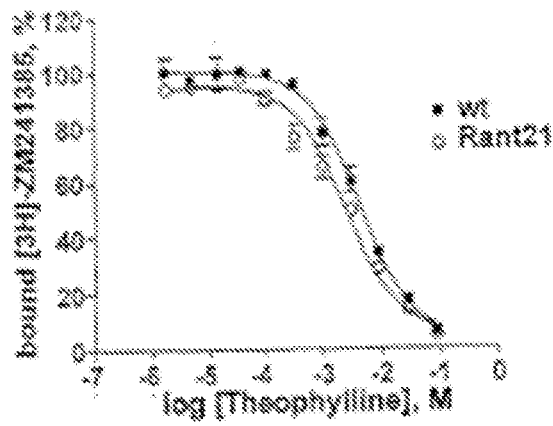
Figure 13E:
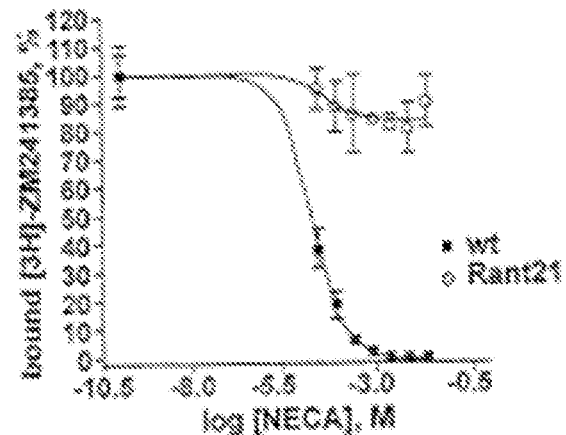
Figure 13F:
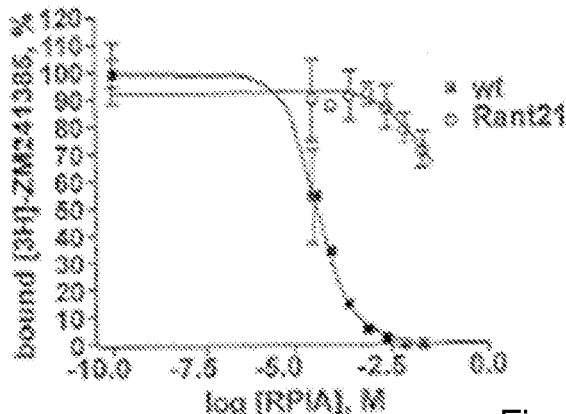
Figure 14A:
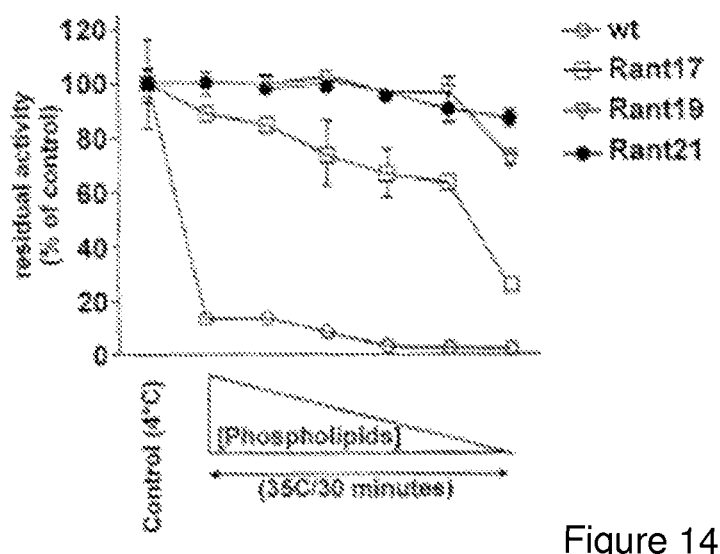
FIGS. 14A and 14B Thermostable mutants show a decreased dependence on lipids (A) and an increased survival at higher concentration of DDM (B) upon heating compared to the wild-type receptor. Receptors were solubilised in 1% DDM (diluted in 50 mM Tris pH7.5 and 400 mM NaCl) and immobilised on Ni-NTA agarose for the IMAC step. Exchange of buffer containing the appropriate concentration of DDM and/or lipids was performed during washes and elution from the Ni-NTA beads.
Figure 14B:
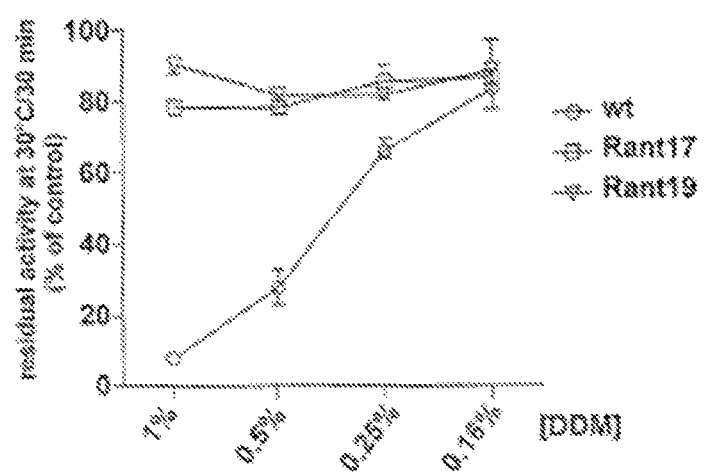

As is described with respect to FIG. 12 below (which depicts a particular, preferred embodiment), there are different assay formats which may be used to determine stability of the mutant GPCR.

In one embodiment the mutant GPCR may be brought into contact with a ligand before being subjected to a procedure in which the stability of the mutant is determined (the mutant GPCR and ligand remaining in contact during the test period). Thus, for example, when the method is being used to select for mutant GPCRs which in one conformation bind to a ligand and which have improved thermostablity, the receptor is contacted with the ligand before being heated, and then the amount of ligand bound to the receptor following heating may be used to express thermostability compared to the parent receptor. This provides a measure of the amount of the GPCR which retains ligand binding capacity following exposure to the denaturing conditions (eg heat), which in turn is an indicator of stability.

In an alternative (but less preferred) embodiment, the mutant GPCR is subjected to a procedure in which the stability of the mutant is determined before being contacted with the ligand. Thus, for example, when the method is being used to select for mutant membrane receptors which in one conformation bind to a ligand and which have improved thermostability, the receptor is heated first, before being contacted with the ligand, and then the amount of ligand bound to the receptor may be used to express thermostability. Again, this provides a measure of the amount of the GPCR which retains ligand binding capacity following exposure to the denaturing conditions.

In both embodiments, it will be appreciated that the comparison of stability of the mutant is made by reference to the parent molecule under the same conditions.

It will be appreciated that in both of these embodiments, the mutants that are selected are ones which have increased stability when residing in the particular conformation compared to the parent protein.

The preferred route may be dependent upon the specific GPCR, and will be dependent upon the number of conformations accessible to the protein in the absence of ligand. In the embodiment described in FIG. 12, it is preferred if the ligand is present during the heating step because this increases the probability that the desired conformation is selected.

From the above, it will be appreciated that the selection method includes a method for selecting a mutant GPCR with increased thermostability, the method comprising (a) providing one or more mutants of a parent GPCR, (b) selecting an antagonist or an agonist which binds the parent GPCR, (c) determining whether the or each mutant has increased thermostability when in the presence of the said antagonist or agonist by measuring the ability of the mutant GPCR to bind the selected said antagonist or agonist at a particular temperature and after a particular time compared to the parent GPCR and (d) selecting those mutant GPCRs that bind more of the selected said antagonist or agonist at the particular temperature and after the particular time than the parent GPCR under the same conditions. In step (c), a fixed period of time at the particular temperature is typically used in measuring the ability of the mutant GPCR to bind the selected said antagonist or agonist. In step (c), typically a temperature and a time is chosen at which binding of the selected said antagonist or agonist by the parent GPCR is reduced by 50% during the fixed period of time at that temperature (which is indicative that 50% of the receptor is inactivated; "quasi" Tm).

Conveniently, when the ligand is used to assay the GPCR (ie used to determine if it is in a non-denatured state), the ligand is detectably labelled, eg radiolabelled or fluorescently labelled. In another embodiment, ligand binding can be assessed by measuring the amount of unbound ligand using a secondary detection system, for example an antibody or other high affinity binding partner covalently linked to a detectable moiety, for example an enzyme which may be used in a colorimetric assay (such as alkaline phosphatase or horseradish peroxidase). FRET methodology may also be used. It will be appreciated that the ligand used to assay the mutant GPCR in determining its stability need not be the same ligand as selected in step (b) of the method.

Although it is convenient to measure the stability of the parent and mutant GPCR by using the ability to bind a ligand as an indicator of the presence of a non-denatured protein, other methods are known in the art. For example, changes in fluorescence spectra can be a sensitive indicator of unfolding, either by use of intrinsic tryptophan fluorescence or the use of extrinsic fluorescent probes such as 1-anilino-8-napthaleneulfonate (ANS), for example as implemented in the Thermofluor™ method (Mezzasalma et al, J Biomol Screening, 2007, April; 12(3):418-428). Proteolytic stability, deuterium/hydrogen exchange measured by mass spectrometry, blue native gels, capillary zone electrophoresis, circular dichroism (CD) spectra and light scattering may also be used to measure unfolding by loss of signals associated with secondary or tertiary structure. However, all these methods require the protein to be purified in reasonable quantities before they can be used (eg high pmol/nmol quantities), whereas the method described in the Examples makes use of pmol amounts of essentially unpurified GPCR.

In a preferred embodiment, in step (b) two or more ligands of the same class are selected, the presence of each causing the GPCR to reside in the same particular conformation. Thus, in this embodiment, one or more ligands (whether natural or non-natural) of the same class (eg full agonist or partial agonist or antagonist or inverse agonist) may be used. Including multiple ligands of the same class in this process, whether in series or in parallel, minimises the theoretical risk of inadvertently engineering and selecting multiply mutated receptor conformations substantially different to the parent, for example in their binding site, but still able, due to compensatory changes, to bind ligand. The following steps may be used to mitigate this risk:

1. Select a chemically distinct set (eg n=2-5) of ligands, in a common pharmacological class as evidenced by for example a binding or functional or spectroscopic assay. These ligands should be thought to bind to a common spatial region of the receptor, as evidenced for example by competitive binding studies using wild type and/or mutated receptors, and/or by molecular modelling, although they will not necessarily express a common pharmacophore.

2. Make single or multiple receptor mutants intended to increase stability, and assay for tight binding using the full set of ligands. The assays can be parallelised, multiplexed or run in series.

3. Confirm authenticity of stabilised receptor mutant by measurement for example of the binding isotherm for each ligand, and by measurement of the stability shift with ligand (the window should typically be narrowed compared to wild type).

In order to guard against changes in apparent affinity caused by perturbations to the binding site upon mutation, preferably ligands of the same pharmacological class, but different chemical class, should be used to profile the receptor. These should typically show similar shifts in affinity (mutant versus parent, e.g. wild type) in spite of having different molecular recognition properties. Binding experiments should preferably be done using labelled ligand within the same pharmacological class.

Nonetheless it should be recognised that conformational substrates may exist that are specific to chemical classes of ligand within the same pharmacological class, and these may be specifically stabilised in the procedure depending on the chemical class of the selected ligand.

Typically the selected ligand binds to the mutant GPCR with a similar potency to its binding to the parent GPCR. Typically, the $K_d$ values for the particular ligand binding the mutant GPCR and the parent GPCR are within 5-10 fold of each other, such as within 2-3 fold. Typically, the binding of the ligand to the mutant GPCR compared to the parent GPCR would be not more than 5 times weaker and not more than 10 times stronger.

Typically, mutant receptors which have been stabilised in the selected conformation should bind the selected ligand with approximately equal affinity (that is to say typically within 2-3 fold) or greater affinity than does the parent receptor. For agonist-conformation mutants, the mutants typically bind the agonists with the same or higher affinity than the parent GPCR and typically bind antagonists with the same or lower affinity than the parent GPCR. Similarly for antagonist-conformation mutants, the mutants typically bind the antagonists with the same or higher affinity than the parent GPCR and typically bind agonists with the same or lower affinity than the parent GPCR.

Mutants that exhibit a significant reduction (typically greater than 2-3 fold) in affinity for the selecting ligand are typically rejected.

Typically, the rank order of binding of a set of ligands of the same class are comparable, although there may be one or two reversals in the order, or there may be an out-tier from the set.

In a further embodiment, two or more ligands that bind simultaneously to the receptor in the same conformation may be used, for example an allosteric modulator and orthosteric agonist.

For the avoidance of doubt, and as is evident from the Examples, it is not necessary to use multiple ligands for the method to be effective.

In a further embodiment, it may be advantageous to select those mutant GPCRs which, while still being able to bind the selected ligand, are not able to bind, or bind less strongly than the parent GPCR, a second selected ligand which is in a different class to the first ligand. Thus, for example, the mutant GPCR may be one that is selected on the basis that it has increased stability with respect to binding a selected antagonist, but the mutant GPCR so selected is further tested to determine whether it binds to a full agonist (or binds less strongly to a full agonist than its parent GPCR). Mutants are selected which do not bind (or have reduced binding of) the full agonist. In this way, further selection is made of a GPCR which is locked into one particular conformation.

It will be appreciated that the selected ligand (with respect to part (b) of the method) and the further (second) ligand as discussed above, may be any pair of ligand classes, for example: antagonist and full agonist; full agonist and antagonist; antagonist and inverse agonist; inverse agonist and antagonist; inverse agonist and full agonist; full agonist and inverse agonist; and so on.

It is preferred that the mutant receptor binds the further (second) ligand with an affinity which is less than 50% of the affinity the parent receptor has for the same further (second) ligand, more preferably less than 10% and still more preferably less than 1% or 0.1% or 0.01% of affinity for the parent receptor. Thus, the $K_d$ for the interaction of the second ligand with mutant receptor is higher than for the parent receptor. As is shown in Example 1, the mutant β-adrenergic receptor βAR-m23 (which was selected by the selection method using an antagonist) binds an agonist 3 orders of magnitude more weakly than its parent (ie $K_d$ is 1000× higher). Similarly, in Example 2, the mutant adenosine A2a receptor Rant21 binds agonist 2-4 orders of magnitude more weakly than its parent.

This type of counter selection is useful because it can be used to direct the mutagenesis procedure more specifically (and therefore more rapidly and more efficiently) along a pathway towards a pure conformation as defined by the ligand.

Preferably, the mutant GPCR is provided in a suitable solubilised form in which it maintains structural integrity and is in a functional form (eg is able to bind ligand). An appropriate solubilising system, such as a suitable detergent (or other amphipathic agent) and buffer system is used, which may be chosen by the person skilled in the art to be effective for the particular protein. Typical detergents which may be used include, for example, dodecylmaltoside (DDM) or CHAPS or octylglucoside (OG) or many others. It may be convenient to include other compounds such as cholesterol hemisuccinate or cholesterol itself or heptane-1,2,3-triol. The presence of glycerol or proline or betaine may be useful. It is important that the GPCR, once solubilised from the membrane in which it resides, must be sufficiently stable to be assayed. For some GPCRs, DDM will be sufficient, but glycerol or other polyols may be added to increase stability for assay purposes, if desired. Further stability for assay purposes may be achieved, for example, by solubilising in a mixture of DDM, CHAPS and cholesterol hemisuccinate, optionally in the presence of glycerol. For particularly unstable GPCRs, it may be desirable to solubilise them using digitonin or amphipols or other polymers which can solubilise GPCRs directly from the membrane, in the absence of traditional detergents and maintain stability typically by allowing a significant number of lipids to remain associated with the GPCR. Nanodiscs may also be used for solubilising extremely unstable membrane proteins in a functional form.

Typically, the mutant GPCR is provided in a crude extract (eg of the membrane fraction from the host cell in which it has been expressed, such as *E. coli*). It may be provided in a form in which the mutant protein typically comprises at least 75%, more typically at least 80% or 85% or 90% or 95% or 98% or 99% of the protein present in the sample. Of course, it is typically solubilised as discussed above, and so the mutant GPCR is usually associated with detergent molecules and/or lipid molecules.

A mutant GPCR may be selected which has increased stability to any denaturant or denaturing condition such as to any one or more of heat, a detergent, a chaotropic agent or an extreme of pH.

In relation to an increased stability to heat (ie thermostability), this can readily be determined by measuring ligand binding or by using spectroscopic methods such as fluorescence, CD or light scattering at a particular temperature. Typically, when the GPCR binds to a ligand, the ability of the GPCR to bind that ligand at a particular temperature may be used to determine thermostability of the mutant. It may be convenient to determine a "quasi $T_m$" ie the temperature at which 50% of the receptor is inactivated under stated conditions after incubation for a given period of time (eg 30 minutes). Mutant GPCRs of higher thermostability have an increased quasi Tm compared to their parents.

In relation to an increased stability to a detergent or to a chaotrope, typically the GPCR is incubated for a defined time in the presence of a test detergent or a test chaotropic agent and the stability is determined using, for example, ligand binding or a spectroscopic method as discussed above.

In relation to an extreme of pH, a typical test pH would be chosen (eg in the range 4.5 to 5.5 (low pH) or in the range 8.5 to 9.5 (high pH)).

Because relatively harsh detergents are used during crystallisation procedures, it is preferred that the mutant GPCR is stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant GPCR is more stable to any of $C_9$ maltoside or glucoside, $C_8$ maltoside or glucoside, LDAO and SDS, and so it is preferred that these detergents are used for stability testing.

Because of its ease of determination, it is preferred that thermostability is determined, and those mutants which have an increased thermostability compared to the parent protein with respect to the selected condition are chosen. It will be appreciated that heat is acting as the denaturant, and this can readily be removed by cooling the sample, for example by placing on ice. It is believed that thermostability may also be a guide to the stability to other denaturants or denaturing conditions. Thus, increased thermostability is likely to translate into stability in denaturing detergents, especially those that are more denaturing than DDM, eg those detergents with a smaller head group and a shorter alkyl chain and/or with a charged head group. We have found that a thermostable GPCR is also more stable towards harsh detergents.

When an extreme of pH is used as the denaturing condition, it will be appreciated that this can be removed quickly by adding a neutralising agent. Similarly, when a chaotrope is used as a denaturant, the denaturing effect can be removed by diluting the sample below the concentration in which the chaotrope exerts its chaotropic effect.

In a particular embodiment of the selection method, the GPCR is β-adrenergic receptor (for example from turkey) and the ligand is dihydroalprenolol (DHA), an antagonist.

In a further preferred embodiment of the selection method, the GPCR is the adenosine $A_{2a}$ receptor ($A_{2a}R$) (for example, from man) and the ligand is ZM 241385 (4-[2-[[7-amino-2-(2-furyl) [1,2,4]-triazolo[2,3-α][1,3,5]triazin-5-yl]amino] ethyl]phenol), an antagonist or NECA (5'-N-ethylcarboxamido adenosine), an agonist.

In a still further preferred embodiment of the selection method, the GPCR is the neurotensin receptor (NTR) (for example, from rat) and the ligand is neurotensin, an agonist.

Method 2

A method for preparing a mutant GPCR selected as above comprises:
  (a) carrying out a method to select a mutant GPCR as described above,
  (b) identifying the position or positions of the mutated amino acid residue or residues in the mutant GPCR or GPCRs which has been selected for increased stability, and
  (c) synthesising a mutant GPCR which contains a mutation at one or more of the positions identified.

As can be seen in the Examples, surprisingly, changes to a single amino acid within the GPCR may increase the stability of the protein compared to the parent protein with respect to a particular condition in which the protein resides in a particular conformation. Thus, in one embodiment of the method of the second aspect of the invention, a single amino acid residue of the parent protein is changed in the mutant protein. Typically, the amino acid residue is changed to the amino acid residue found in the mutant tested in the method of the first aspect of the invention. However, it may be replaced by any other amino acid residue, such as any naturally-occurring amino acid residue (in particular, a "codeable" amino acid residue) or a non-natural amino acid. Generally, for convenience, the amino acid residue is replaced with one of the 19 other codeable amino acids. Preferably, it is the replaced amino acid residue which is present in the mutant selected in the selection method described above.

Also as can be seen in the Examples, a further increase in stability may be obtained by replacing more than one of the amino acids of the parent protein. Typically, each of the amino acids replaced is one which has been identified using the selection method described above. Typically, each amino acid identified is replaced by the amino acid present in the mutant protein although, as noted above, it may be replaced with any other amino acid.

Typically, the mutant GPCR contains, compared to the parent protein, from 1 to 10 replaced amino acids, preferably from 1 to 8, typically from 2 to 6 such as 2, 3, 4, 5 or 6 replaced amino acids.

It will be appreciated that the multiple mutants may be subject to the selection method. In other words, multiple mutants may be provided in step (a) of the selection. It will be appreciated that multiply mutagenised GPCRs may be made, whose conformation has been selected to create a very stable multiple point mutant protein.

The mutant GPCRs may be prepared by any suitable method. Conveniently, the mutant protein is encoded by a suitable nucleic acid molecule and expressed in a suitable host cell. Suitable nucleic acid molecules encoding the mutant GPCR may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and *Trichoplusiani* cells. Suitable animal host cells include HEK 293, COS, S2, CHO, NSO, DT40 and so on. It is known that some GPCRs require specific lipids (eg cholesterol) to function. In that case, it is desirable to select a host cell which contains the lipid. Additionally or alternatively the lipid may be added during isolation and purification of the mutant protein. It will be appreciated that these expression systems and host cells may also be used in the provision of the mutant GPCR in part (a) of the selection method.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

It is appreciated that it may be determined whether the selected or prepared mutant GPCR is able to couple to a G protein. It is also preferred if it is determined whether the selected or prepared mutant GPCR is able to bind a plurality of ligands of the same class as the selecting ligand with a comparable spread and/or rank order of affinity as the parent GPCR.

Method 3

Figure 17A:
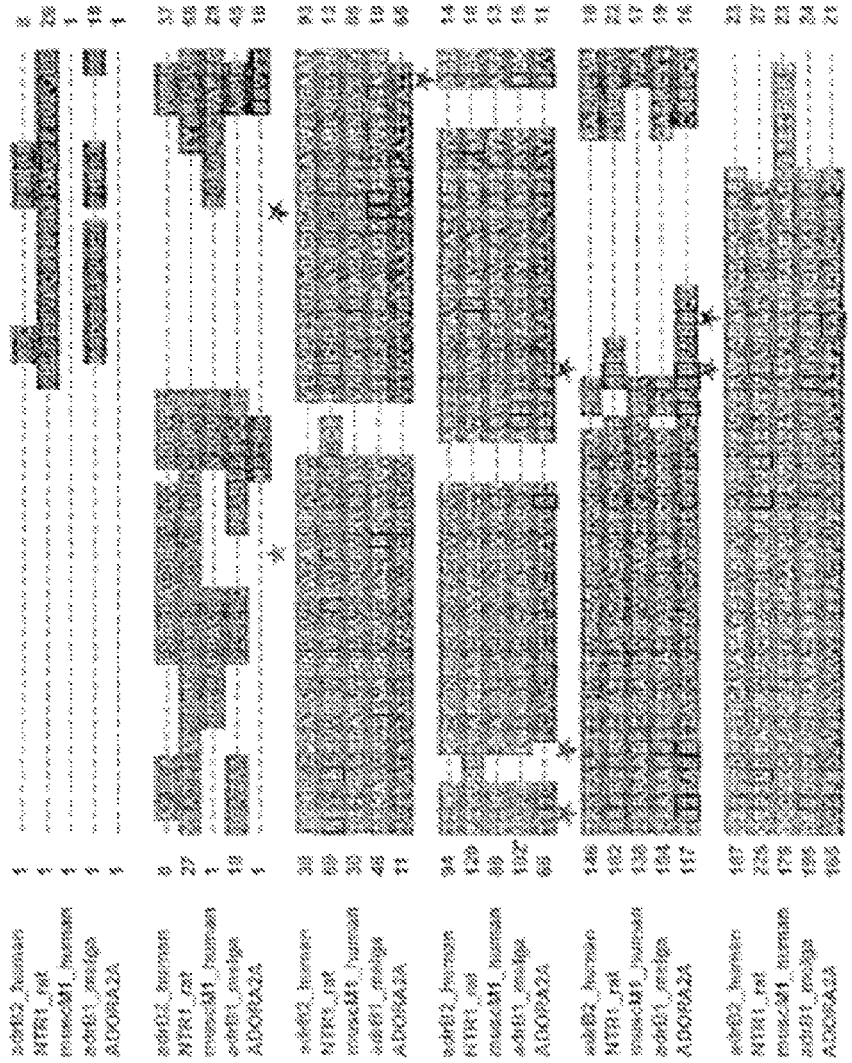
FIGS. 17A-C Multiple sequence alignment of human beta-2AR, rat NTR1, turkey beta-1 AR, human Adenosine A2aR and human muscarinic M1 receptors. In each sequence, thermostabilising mutations are marked with a box. Mutations occurring in two or more sequences are denoted with a star. The sequences depicted in FIGS. 17A, 17B, and 17C correspond to SEQ ID NOs.: 3, 9, 12, 1, and 5, respectively.
Figure 17B:
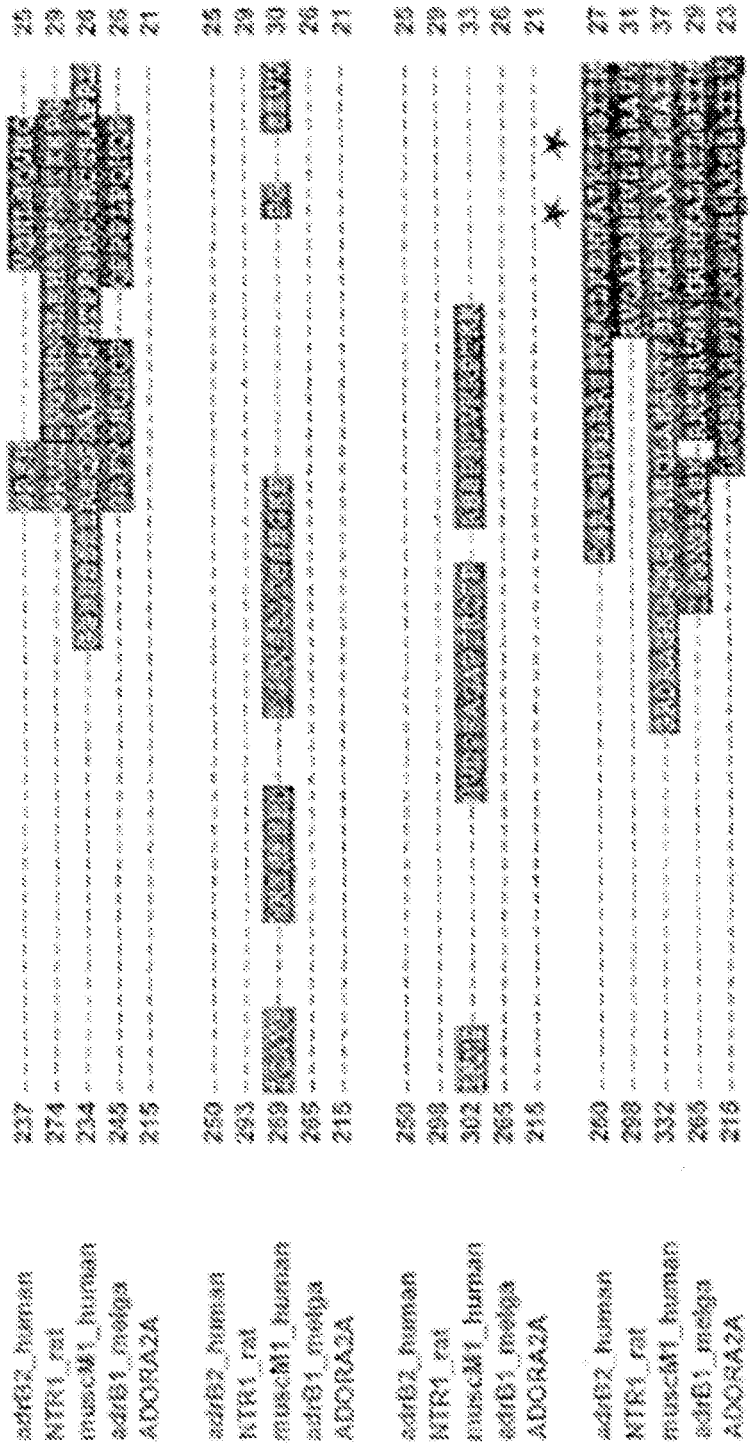
Figure 17C:
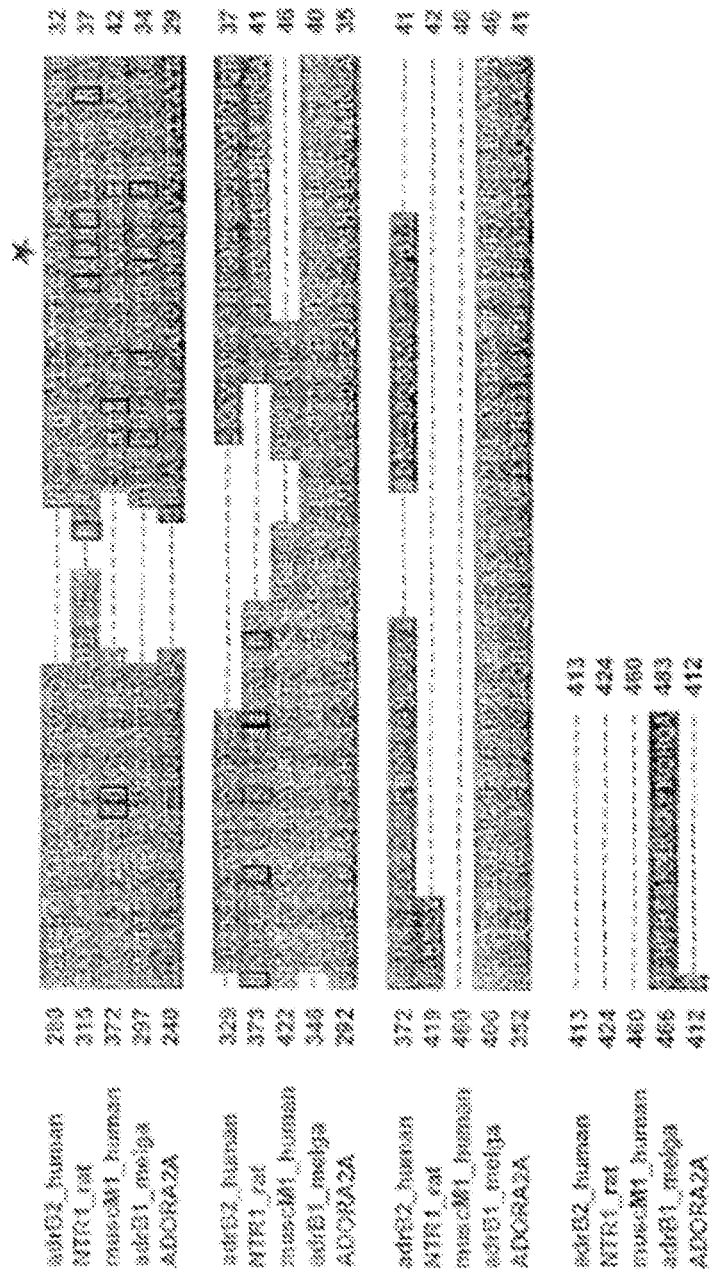

As shown in Examples 1-3 and described above, thermostabilising mutations are scattered widely throughout the sequences of the turkey beta1 adrenergic receptor, human adenosine receptor, rat neurotensin receptor and human muscarinic receptor. FIGS. 17A, 17B and 17C provide an alignment of these sequences with the sequence of the human beta-2AR such that when the thermostabilising mutations are positioned onto the sequences then, in 11 instances out of a total of 70, two sequences contain mutations at the same position (denoted in FIGS. 17A, 17B and 17C with a star). Thus it will be appreciated that once one or more stabilising mutations have been identified in one GPCR, a further GPCR with increased stability can be generated by aligning the amino acid sequences of the GPCRs and making the same one or more mutations at the corresponding position or positions. This concept is clearly exemplified in FIG. 26 wherein the six thermostabilising mutations in turkey β1-m23 were transferred directly to the human β2 receptor. The resultant mutant, β2-m23, had a Tm 12° C. higher than that of the human β2 receptor.

Accordingly, a further method for producing a mutant GPCR with increased stability relative to its parent GPCR comprises (i) identifying in the amino acid sequence of one or more mutants of a first parent GPCR with increased stability relative to the first parent GPCR, the position or positions at which the one or more mutants have at least one different amino acid residue compared to the first parent GPCR, and (ii) making one or more mutations in the amino acid sequence that defines a second GPCR at the corresponding position or positions, to provide one or more mutants of a second parent GPCR with increased stability relative to the second parent GPCR.

The one or more mutants of a first parent GPCR may be selected or prepared according to the selection or preparation methods described above. Hence, this method may also be used to create stable, conformationally locked GPCRs by mutagenesis. For example, following the selection of mutant GPCRs which have increased stability in a particular conformation, the stabilising mutation can be identified and the amino acid at a corresponding position in a second GPCR replaced to produce a mutant GPCR with increased stability in a particular conformation relative to a second parent GPCR.

For the avoidance of doubt the first parent GPCR may be a GPCR which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

Typically, identifying the position or positions at which the one or more mutants have at least one different amino acid residue compared to the first parent GPCR involves aligning their amino acid sequences with that of the parent GPCR, for example using the Clustal W program (Thompson et al., 1994).

By "corresponding position or positions", we include the meaning of the position in the amino acid sequence of a second GPCR which aligns to the position in the amino acid sequence of the first GPCR, when the first and second GPCRs are compared by alignment, for example by using MacVector and Clustal W. For example, as shown in the alignment in FIGS. 17A, 17B and 17C, the six stabilising mutations in turkey β1-m23, R68S, M90V, Y227A, A282L, F327A and F338M, are at positions which correspond to residues K60, M82, Y219, C265, L310 and F321 respectively in the human β2 receptor.

Having identified the corresponding position or positions in the amino acid sequence of a second GPCR, the amino acids at those positions are replaced with another amino acid. Typically, the amino acids are replaced with the same amino acids which replaced the amino acids at the corresponding positions in the mutant of the first parent GPCR (unless they are already that residue). For example, at position 68 in turkey β1-m23 (R68S), an arginine residue was replaced with a serine residue. Therefore, at the corresponding position in the human β2 receptor, position 60 (K60), the lysine residue is preferably replaced with a serine residue.

Mutations can be made in an amino acid sequence, for example, as described above and using techniques well-established in the art.

It will be appreciated that the second GPCR may be any other GPCR. For example, stabilising mutations in a GPCR from one species may be transferred to a second GPCR from another species. Similarly, stabilising mutations in one particular GPCR isoform may be transferred to a second GPCR which is a different isoform. Preferably, the second parent GPCR is of the same GPCR class or family as the first parent GPCR. Phylogenetic analyses have divided GPCRs into three main classes based on protein sequence similarity, i.e., classes 1, 2, and 3 whose prototypes are rhodopsin, the secretin receptor, and the metabotropic glutamate receptors, respectively (Foord et al (2005) *Pharmacol. Rev.* 57, 279-288). Thus, the second GPCR may be a GPCR which is of the same GPCR class as the first parent GPCR. Similarly, GPCRs have been divided into families by reference to natural ligands such as glutamate and GABA. Thus, the second GPCR may be of the same GPCR family as the first parent GPCR. A list of GPCR classes and families has been produced by the International Union of Pharmacology (Foord et al (2005) *Pharmacol. Rev.* 57, 279-288) and this list is periodically updated at iuphar-db.org/GPCR/ReceptorFamiliesForward.

It will be appreciated that the second parent GPCR must be able to be aligned with the first parent GPCR such that the corresponding positions of the mutations in the first GPCR can be determined in the second GPCR. Thus typically, the second parent GPCR has at least 20% sequence identity to the first parent GPCR and more preferably at least 30%, 40%, 50%, 60%, 70%, 80% or 90% sequence identity to the first parent GPCR. However, some GPCRs have low sequence identity (e.g. family B and C GPCRs) and at the same time are very similar in structure. Thus the 20% sequence identity threshold is not absolute.

Method 4

The inventors have reasoned that the identification of structural motifs in which the one or more mutations in a mutant GPCR with increased stability reside, will be useful in producing further mutant GPCRs with increased stability.

Accordingly, a further method for producing a mutant G-protein coupled receptor (GPCR) with increased stability relative to its parent GPCR comprises:

a. providing one or more mutants of a first parent GPCR with increased stability relative to the first parent GPCR b. identifying in a structural membrane protein model the structural motif or motifs in which the one or more mutants have at least one different amino acid residue compared to the first parent GPCR, and c. making one or more mutations in the amino acid sequence that defines a corresponding structural motif or motifs in a second parent GPCR, to provide one or more mutants of a second parent GPCR with increased stability relative to the second parent GPCR.

Figure 15:
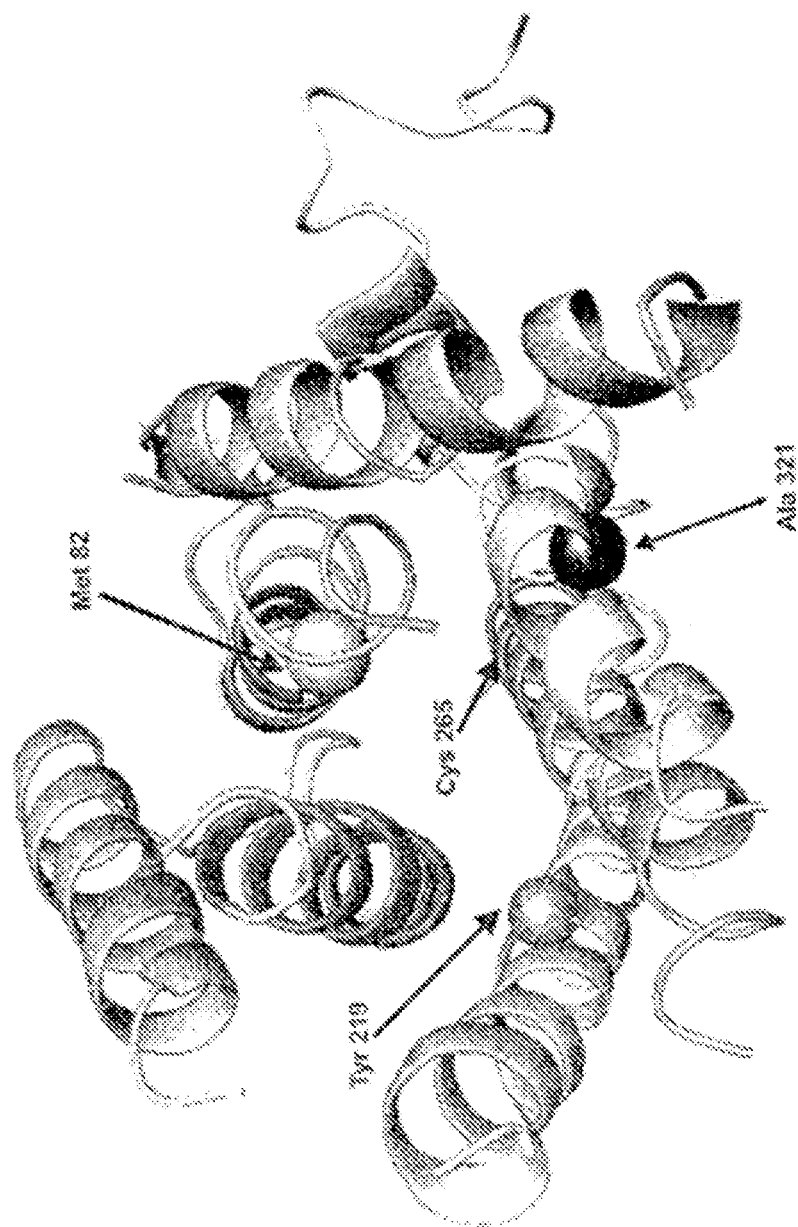
FIG. 15 Mapping of the M90V, Y227A, A282L and F338M m23 mutations in turkey beta1 adrenergic receptor onto homologous residues (M82, Y219, C265 and A321 respectively) in the human beta2 adrenergic receptor structure (Rasmussen et al (2007) Nature 15; 383-387; pdb accession codes 2R4R and 2R4S) reveals their position at a helical interface and helical kink respectively. Amino acid residues in equivalent positions to the thermostabilising mutations in the turkey β1 adrenergic receptor are shown as labelled space filling models.
Figure 16:
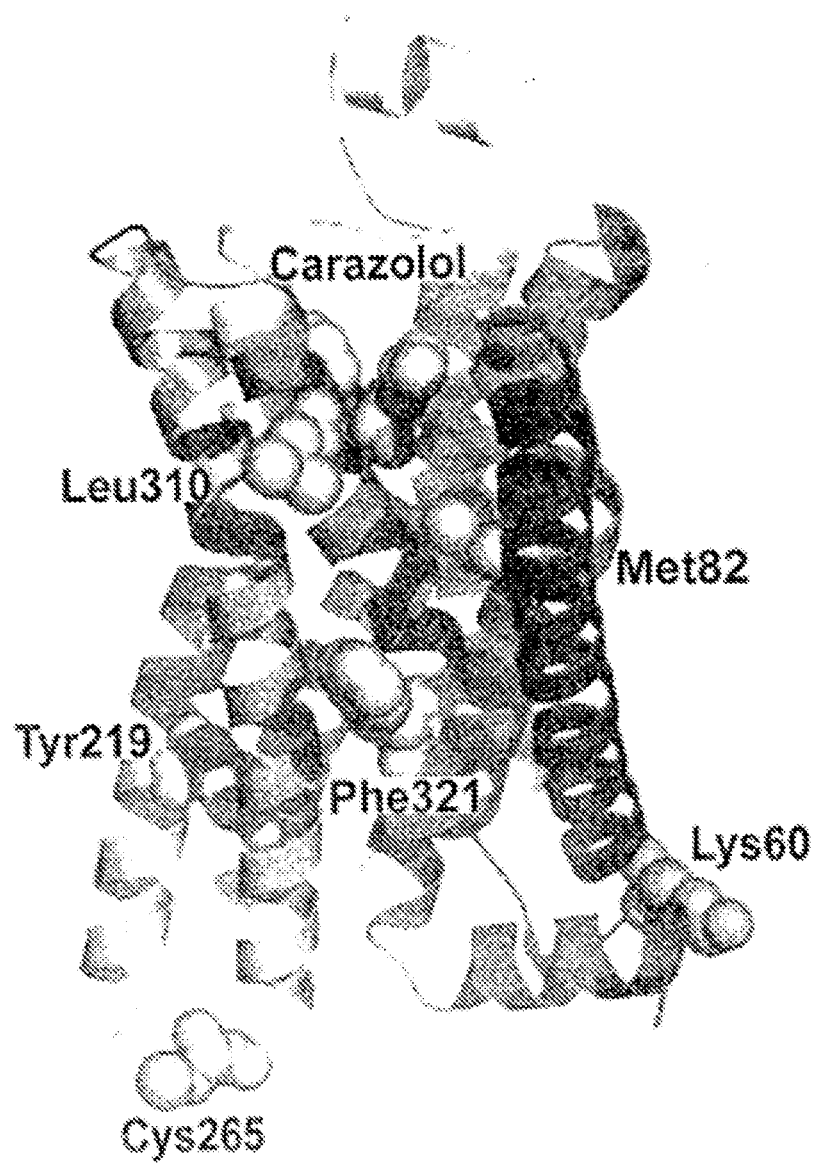
FIG. 16 Mapping of m23 mutations in turkey beta1 adrenergic receptor onto homologous residues in the human beta2 adrenergic receptor structure (Cherezov et al (2007) Science, 318:1258-65; pdb accession code 2RH1). The Cα trace of the β2AR is shown with the fusion moiety (T4 lysozyme) removed. The six mutations in βAR-m23 (R68S, M90V, Y227A, A282L, F327A, F338M) are equivalent to amino acid residues K60, M82, Y219, C265, L310, F321 in the human β2AR. Lys60 is on the intracellular end of Helix 1 and points into the lipid-water interface. Met82 is near the middle of Helix 2 and points into the ligand binding pocket; the nearest distance between the substrate carazolol and the Met side chain is 5.7 Å. Tyr219 is towards the intracellular end of helix 5 and is at the helix5-helix 6 interface. Cys265 is at the end of the loop region between helices 5 and 6 and points away from the transmembrane regions. Leu310 and Phe321 are both in helix 7 and both point out into the lipid bilayer.

Mapping stabilising mutations onto one or more known structural models can be used to identify particular structural motifs in which such stabilising mutations reside. We have mapped stabilising mutations of the β1-adrenergic receptor onto structural models of the β2-adrenergic receptor (Rasmussen et al (2007) *Nature* 450, 383-387; Cherezov et al (2007) *Science* 318:1258-65; Rosenbaum et al (2007) *Science* 318:1266-1273) in order to identify such motifs. For example, Table (vi) lists the turkey β1-adrenergic receptor mutations which we have mapped onto the human β2-adrenergic receptor and describes the corresponding structural motifs in which they reside. As discussed in Example 4, mapping of the Y227A mutation (equivalent to Y219 in the human $\beta_2$ receptor) onto the human $\beta_2$-adrenergic receptor reveals its position at the interface between helices such that the mutation may improve packing at the helical interface (see FIGS. 15, 16 and 23). Similarly, mapping of the M90V mutation (equivalent to M82 in the human $\beta_2$ receptor) onto the human β₂-adrenergic receptor reveals it to be in helix 2 at a point where the helix is kinked (see FIGS. 15, 16 and 20). Other mutations were found to reside in further structural motifs including transmembrane helix surfaces pointing into the lipid bilayer, hydrophobic-hydrophilic boundary regions, protein binding pockets and loop regions (see Table (vi) and FIGS. 18-19, 21-22 and 24-25).

Such structural motifs, by virtue of them containing stabilising mutations, are important in determining protein stability. Therefore, targeting mutations to these motifs will facilitate the generation of stabilised mutant GPCRs. Indeed, there were several instances where more than one mutation mapped to the same structural motif. For example, the Y227A, V230A and A234L mutations in the turkey β1 adrenergic receptor mapped to the same helical interface, the V89L and M90V mutations mapped to the same helical kink and the F327A and A334L mutations mapped to the same helical surface pointing towards the lipid bilayer (Table (vi)). Thus, when one stabilising mutation has been identified, the determination of the structural motif in which that mutation is located will enable the identification of further stabilising mutations.

The one or more mutants of a first parent GPCR may be selected or prepared according to any of the methods described above. Hence, this method may also be used to create stable, conformationally locked GPCRs by mutagenesis. For example, following the selection of mutant GPCRs which have increased stability in a particular conformation, the structural motifs in which such stabilising mutations reside can be identified. Making one or more mutations in the amino acid sequence that defines the corresponding structural motif in another GPCR can then be used to produce a mutant GPCR with increased stability in a particular conformation relative to its parent GPCR.

We have performed a multiple sequence alignment of the human beta-2AR, rat NTR1, turkey beta-1 AR, human Adenosine A2aR and human muscarinic M1 receptor amino acid sequences (FIGS. 17A, 17B and 17C) which shows that, when the thermostabilising mutations identified (see Examples 1-3) are positioned on the sequences then, in 11 instances out of a total of 70, two sequences contain mutations at the same position (denoted in FIGS. 17A, 17B and 17C with a star). Without wishing to be bound by any theory, the inventors believe that thermostabilising mutations at these positions should be of enhanced transferability for mapping onto a structural membrane protein model. Thus in one embodiment, the mutant of the first parent GPCR is a mutant human beta-2AR, rat NTR1, turkey beta-1 AR, human Adenosine A2aR or human muscarinic M1 receptor which, when compared to its corresponding parent receptor, has a different amino acid at a position which corresponds to any one or more of the following positions according to the numbering of the human beta2 AR as set out in FIGS. 17A, 17B and 17C: Ala 59, Val 81, Ser 143, Lys 147, Val 152, Glu 180, Val 222, Ala 226, Ala 271, Leu 275 and Val 317.

In order to identify the structural motif or motifs, the stabilising mutations are mapped onto a known structure of a membrane protein.

By "membrane protein" we mean a protein that is attached to or associated with a membrane of a cell or organelle. Preferably, the membrane protein is an integral membrane protein that is permanently integrated into the membrane and can only be removed using detergents, non-polar solvents or denaturing agents that physically disrupt the lipid bilayer.

The structural model of a membrane protein may be any suitable structural model. For example, the model may be a known crystal structure. Examples of GPCR crystal structures include bovine rhodopsin (Palczewski, K. et al., Science 289, 739-745. (2000)) and human β₂ adrenergic receptor (Rasmussen et al, Nature 450, 383-7 (2007); Cherezov et al (2007) *Science* 318:1258-65; Rosenbaum et al (2007) *Science* 318:1266-1273). The coordinates for the human β₂ adrenergic receptor structure can be found in the RCSB Protein Data Bank under accession codes: 2rh1, 2r4r and 2r4s. Alternatively, the structural model may be a computer generated model based upon homology or using de novo structure prediction methods (Qian et al *Nature* (2007) 450: 259-64).

It will be appreciated that stabilising mutations of a given mutant GPCR can be mapped onto a structural model of any membrane protein which has sufficient structural similarity to the GPCR. In particular, the domain of the membrane protein must have sufficient structural similarity to the GPCR domain in which the stabilising mutation resides, for a given mutation to be transferable.

A protein domain is typically defined as a discretely folded assembly of secondary structure elements which may stand alone as a single protein or be part of a larger protein in combination with other domains. It is commonly a functional evolutionary unit.

GPCRs are essentially single domain proteins excluding those with large N-terminal domains. Therefore, typically, the structural model is of a membrane protein which comprises at least one domain that has sufficient structural similarity to the GPCR.

Structural similarity can be determined indirectly by the analysis of sequence identity, or directly by comparison of structures.

With regard to sequence identity, the amino acid sequence encoding the GPCR domain in which the mutant has at least one different amino acid residue compared to the first parent GPCR, is aligned with an amino acid sequence encoding a domain of a membrane protein for which a structural model is available. It will be appreciated that one or more of these sequences may contain an inserted sequence or N-terminal or C-terminal extensions which are additional to the core conserved domain. For optimal alignment, such sequences are removed so as not to skew the analysis. Membrane proteins with sufficient sequence identity across the domain in question may then be used as the structural model for mapping mutations. It has been shown for soluble protein domains that their 3D structure is broadly conserved above 20% sequence identity and well conserved above 30% identity, with the level of structural conservation increasing as sequence identity increases up to 100% (Ginalski, K. Curr Op Struc Biol (2006) 16, 172-177). Thus, it is preferred if the structural membrane protein model is a model of a membrane protein which contains a domain that shares at least 20% sequence identity with the mutant GPCR domain containing the at least one different amino acid residue compared to the first parent GPCR, and more preferably at least 30%, 40%, 50%, 60%, 70%, 80% or 90% sequence identity, and yet more preferably at least 95% or 99% sequence identity.

Sequence identity may be measured by the use of algorithms such as BLAST or PSI-BLAST (Altschul et al, NAR (1997), 25, 3389-3402) or methods based on Hidden Markov Models (Eddy S et al, J Comput Biol (1995) Spring 2 (1) 9-23). Typically, the percent sequence identity between two polypeptides may be determined using any suitable computer program, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994). The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

In addition to sequence identity, structural similarity can be determined directly by comparison of structural models. Structural models may be used to detect regions of structural similarity not evident from sequence analysis alone, and which may or may not be contiguous in the sequence. For example, family B and C GPCRs are thought to share similar structures; however, their sequence identity is very low. Similarly, the water transporting aquaporins spinach SoPip2, E. coli AqpZ, Methanococcus AqpM, rat Aqp4, human Aqp1 and sheep Aqp0 share low sequence identity but all have similar structures.

Structural models of high fidelity may be constructed for proteins of unknown structure using standard software packages such as MODELLER (Sali A and Blundell T, J Mol Biol (1993) 234(3) 779-815), wherein the structure is modelled on a known structure of a homologous protein. Such modelling improves with increasing sequence identity. Typically, the sequence identity between the sequence of unknown structure and a sequence of known 3D structure is more than 30% (Ginalski, K. Curr Op Struc Biol (2006) 16, 172-177). In addition, de novo structure prediction methods based on sequence alone may be used to model proteins of unknown structure (Qian et al, (2007) Nature 450:259-64).

Once structures have been experimentally determined or derived by modelling, regions of structural similarity may be detected by direct comparison of two or more 3D structures. They may, for example, comprise secondary structure elements of a particular architecture and topology which can be detected by the use of software such as DALI (Holm, L and Sander, C (1996) Science 273, 595-603). They may comprise local arrangements of amino acid side chains and the polypeptide backbone, or specific sets of atoms or groups of atoms in a particular spatial arrangement, which may for example also be detected by the use of graph theoretical representations (Artymiuk, P et al, (2005) J Amer Soc Info Sci Tech 56 (5) 518-528). In this approach, the atoms or groups of atoms within the proteins or regions of proteins to be compared are typically represented as the nodes of a graph, with the edges of the graph describing the angles and distances between the nodes. Common patterns in these graphs indicate common structural motifs. This approach may be extended to include any descriptor of atoms or groups of atoms, such as hydrogen bond donor or acceptor, hydrophobicity, shape, charge or aromaticity; for example proteins may be spatially mapped according to such descriptors using GRID and this representation used as a basis for similarity searching (Baroni et al (2007) J Chem Inf Mod 47, 279-294). Descriptions of the methods, availability of software, and guidelines for user-defined selection of parameters, thresholds and tolerances are described in the references given above.

In a preferred embodiment, the structural membrane protein model is a structural GPCR model. It will be appreciated that the structural model of a GPCR may be a model of the first parent GPCR. For example, stabilising mutations within a mutant GPCR having increased stability can be directly mapped onto the first parent GPCR structure and the structural motifs in which such mutations are located, identified. Where the structure of the first parent GPCR is unknown, structural models of other GPCRs may be used. For example, stabilising mutations in a GPCR from one species may be mapped onto a known structural model of the same GPCR from another species. Similarly, stabilising mutations in one particular GPCR isoform may be mapped onto a known structural model of another GPCR isoform. Moreover, stabilising mutations from one GPCR may be mapped onto a GPCR of the same class or family. A list of GPCR classes and families has been produced by the International Union of Pharmacology (Foord et al (2005) Pharmacol. Rev. 57, 279-288) and this list is periodically updated at iuphar-db.org/GPCR/ReceptorFamiliesForward.

As described above, it will be appreciated that the structural model may be of any GPCR provided it has sufficient structural similarity across the domain in which the mutant GPCR has at least one different amino acid compared to the first parent GPCR. Thus, it is preferred if the GPCR shares at least 20% sequence identity with the mutant of the first parent GPCR across the protein domain containing the at least one different amino acid residue compared to the first parent GPCR, and more preferably at least 30%, 40%, 50%, 60%, 70%, 80% or 90% sequence identity, and yet more preferably at least 95% or 99% sequence identity. However, the inventors recognise that the 20% sequence identity threshold is not absolute. GPCRs with less than 20% sequence identity to the first parent GPCR may also serve as a structural model to which stabilising mutations are transferred, wherein the low sequence identity is counterbalanced by other similarities, including, for example, the presence of the same sequence motifs, binding to the same G-protein or having the same function, or having substantially the same hydropathy plots compared to the first parent GPCR.

Mapping of stabilising mutations onto the structural model can be done using any suitable method known in the art. For example, typically, the amino acid sequence of the GPCR for which the structural model is available is aligned with the amino acid sequence of the mutant of the first parent GPCR. The position or positions of the at least one different amino acid residue in the mutant GPCR relative to the first parent GPCR can then be located in the amino acid sequence of the GPCR for which a structural model is available.

By 'structural motif' we include the meaning of a three dimensional description of the location in a GPCR structural model of a thermostabilising mutation. For example, the structural motif may be any secondary or tertiary structural motif within the GPCR. By 'tertiary structural motif' we include any descriptor of atoms or groups of atoms, such as hydrogen bond donor or acceptor, hydrophobicity, shape, charge or aromaticity. For example, proteins may be spatially mapped according to such descriptors using GRID and this representation used as a basis for defining a structural motif (Baroni et al (2007) J Chem Inf Mod 47, 279-294).

Table (vi) lists the structural motifs in which the turkey β1 adrenergic receptor stabilising mutations were found to reside. As seen from the table, the mutations are positioned in a number of distinct localities. Three mutations are in loop regions that are predicted to be accessible to aqueous solvent. Eight mutations are in the transmembrane α-helices and point into the lipid bilayer; three of these mutations are near the end of the helices and may be considered to be at the hydrophobic-hydrophilic boundary layer. Eight mutations are found at the interfaces between transmembrane α-helices, three of which are either within a kinked or distorted region of the helix and another two mutations occur in one helix but are adjacent to one or more other helices which contain a kink adjacent in space to the mutated residue. These latter mutations could affect the packing of the amino acids within the kinked region, which could result in thermostabilisation. Another mutation is in a substrate binding pocket.

Accordingly, in one embodiment, the structural motif is any of a helical interface, a helix kink, a helix opposite a helix kink, a helix surface pointing into the lipid bilayer, a helix surface pointing into the lipid bilayer at the hydrophobic-hydrophilic boundary layer, a loop region or a protein binding pocket.

Identifying a structural motif in which a stabilising mutation resides suggests the importance of that motif in protein stability. Therefore, making one or more mutations in the amino acid sequence that defines a corresponding structural motif or motifs in a second parent GPCR, should provide one or more mutants of a second parent GPCR with increased stability relative to the second parent GPCR.

The amino acid sequence which defines a structural motif is the primary amino acid sequence of the amino acid residues which combine in the secondary or tertiary structure of the protein to form the structural motif. It will be appreciated that such a primary amino acid sequence may comprise contiguous or non-contiguous amino acid residues. Thus, identifying the amino acid sequence which defines the structural motif will involve determining the residues involved and subsequently defining the sequence. Mutations can be made in an amino acid sequence, for example as described above and using techniques well-established in the art.

By "corresponding structural motif or motifs", we mean the analogous structural motif or motifs identified in the structural model which are present in the second parent GPCR. For example, if a helical interface was identified, the corresponding helical interface in the second parent GPCR would be the interface between the helices which are analogous to the helices present in the structural model. If a helical kink was identified, the corresponding helical kink would be the kink in the helix which is analogous to the kinked helix present in the structural model. An analogous structural motif or motifs in the second parent GPCR can be identified by searching for similar amino acid sequences in the sequence of the second parent GPCR which define the motif or motifs in the structural model, for example, by sequence alignment. Moreover, computer based algorithms are widely available in the art that can be used to predict the presence of protein motifs based on an amino acid sequence. Thus, based upon the relative position of a particular motif within the amino acid sequence and its position relative to other motifs, an analogous structural motif can readily be identified. It will be appreciated that if a structural model of the second parent GPCR is available, the analogous structural motif or motifs can be directly mapped onto the structure of the protein. Typically, the amino acid sequence defining the analogous structural motif has at least 20% sequence identity with the sequence defining the motif in the structural model, more preferably at least 30%, 40%, 50%, 60%, 70%, 80% and 90% sequence identity and yet more preferably 95% and 99% sequence identity.

In one embodiment, the second parent GPCR is the first parent GPCR. For the avoidance of doubt, the second parent GPCR may have the naturally-occurring sequence of the first parent GPCR, or it may be a truncated form or it may be a fusion, either to the naturally occurring protein or to a fragment thereof, or it may contain mutations compared to the naturally-occurring sequence, providing that it retains ligand-binding.

In an alternative embodiment, the second parent GPCR is not the first parent GPCR. For example, a mutant of a first parent GPCR may have been identified that has increased stability but it is desired to generate a mutant of a different GPCR with increased stability. Preferably, the second parent GPCR is of the same GPCR class or family as the first parent GPCR as described above. However, it will be appreciated that the second parent GPCR may be any known GPCR provided that it shares sufficient structural similarity with the first parent GPCR, such that it contains a corresponding structural motif in which the stabilising mutation of the mutant of the first parent GPCR resides. Thus typically, the second parent GPCR has at least 20% sequence identity to the first parent GPCR and more preferably at least 30%, 40%, 50%, 60%, 70%, 80% or 90% sequence identity. However, as mentioned above, some GPCRs have low sequence identity (e.g. family B and C GPCRs) but are similar in structure. Thus the 20% sequence identity threshold is not absolute.

Since there are potentially thousands of mutations that can be screened in a GPCR for increased stability, it is advantageous to target particular mutations which are known to be important in conferring stability. Therefore, it will be appreciated that the methods 3 and 4 may be used in a method of selecting mutant GPCRs with increased stability. In particular, carrying out methods 3 and 4 can be used to target mutations to particular amino acid residues or to amino acid sequences which define structural motifs important in determining stability.

Accordingly, in one embodiment, methods 3 and 4 further comprise:
(I) selecting a ligand, the ligand being one which binds to the second parent GPCR when the GPCR is residing in a particular conformation
(II) determining whether the or each mutant of the second parent GPCR when residing in a particular conformation has increased stability with respect to binding the selected ligand compared to the stability of the second parent GPCR when residing in the same particular conformation with respect to binding that ligand, and
(III) selecting those mutants that have an increased stability compared to the second parent GPCR with respect to binding the selected ligand.

It will be noted that steps (I), (II) and (III) correspond to steps (b), (c) and (d) of method 1 described above. Accordingly, preferences for the ligand and methods of assessing stability are as defined above with respect to method 1.

Any mutant GPCR with increased stability relative to its parent GPCR, for example those provided by any of methods 1-4 described above, may be used in the present invention. For example, mutant GPCRs with increased stability compared to their parent GPCRs, particularly those with increased thermostability may be used. Particular examples of mutant GPCRs suitable for use in the present invention are provided below.

In one embodiment, the mutant GPCR is a mutant GPCR which has, compared to its parent receptor, at least one different amino acid at a position which corresponds to any one or more of the following positions: (i) according to the numbering of the turkey β-adrenergic receptor as set out in FIGS. 9A and 9B: Ile 55, Gly 67, Arg 68, Val 89, Met 90, Gly 67, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, (iii) according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399, and (iv)

according to the numbering of the muscarinic receptor as set out in FIGS. 17A, 17B and 17C: Leu 65, Met 145, Leu 399, Ile 383 and Met 384.

Alignment of the turkey β1 AR, human adenosine receptor, rat neurotensin receptor and human muscarinic receptor amino acid sequences in FIGS. 17A, 17B and 17C, show that in 11 instances out of 70, two sequences contain mutations art the same position, namely at the following positions according to the numbering of the human beta2 AR as set out in FIGS. 17A, 17B and 17C: Ala 59, Val 81, Ser 143, Lys 147, Val 152, Glu 180, Val 222, Ala 226, Ala 271, Leu 275 and Val 317. Therefore, in a further embodiment, the mutant GPCR is one which has, compared to its parent receptor, a different amino acid at any one of these positions.

Mutant β-Adrenergic Receptor

β-adrenergic receptors are well known in the art. They share sequence homology to each other and bind to adrenalin.

Figure 9A:
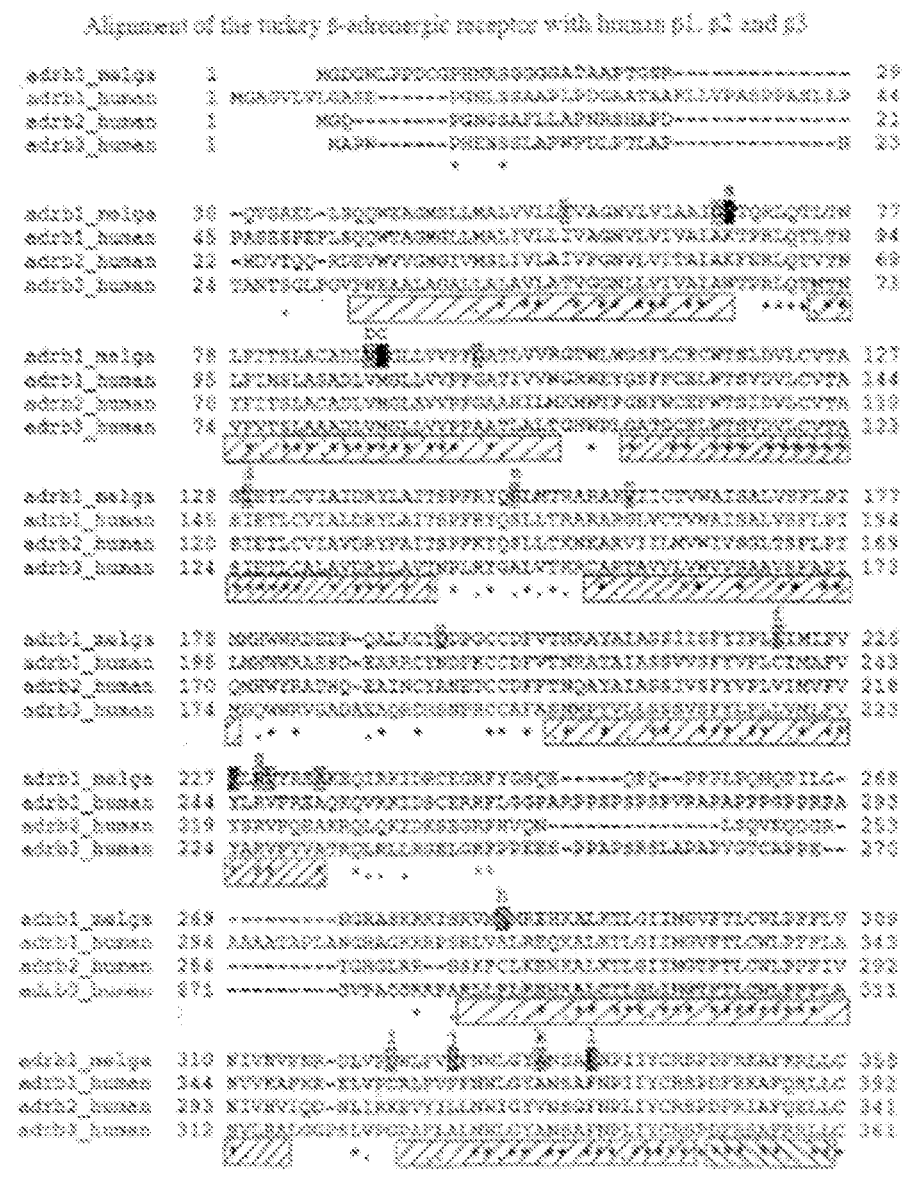
Figure 9B:
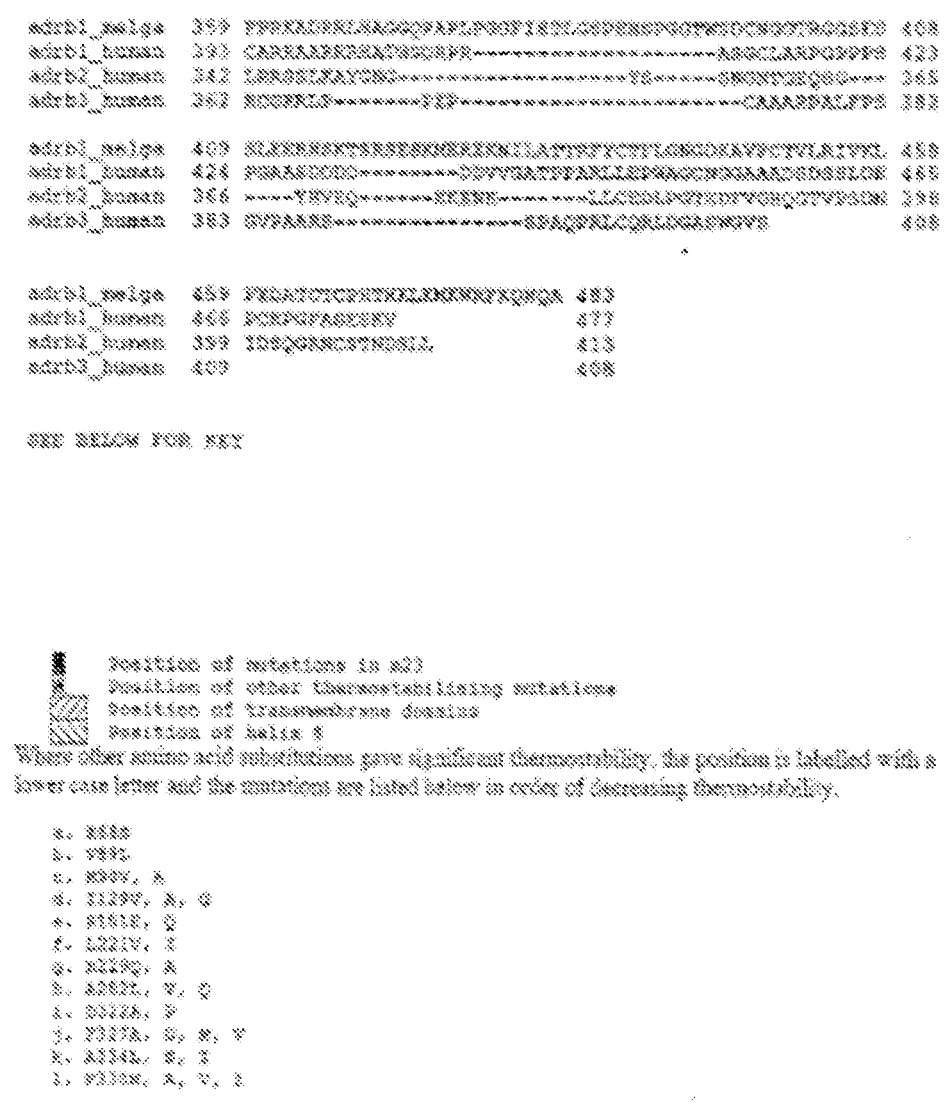

In one embodiment, the mutant GPCR is a mutant β-adrenergic receptor which, when compared to the corresponding wild-type β-adrenergic receptor, has a different amino acid at a position which corresponds to any one or more of the following positions according to the numbering of the turkey β-adrenergic receptor as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

The mutant β-adrenergic receptor may be a mutant of any β-adrenergic receptor provided that it is mutated at one or more of the amino acid positions as stated by reference to the given turkey β-adrenergic receptor amino acid sequence.

It is particularly preferred if the mutant GPCR is one which has at least 20% amino acid sequence identity when compared to the given turkey β-adrenergic receptor sequence, as determined using MacVector and CLUSTALW (Thompson et al (1994) *Nucl. Acids Res.* 22, 4673-4680). More preferably, the mutant receptor has at least 30% or at least 40% or at least 50% amino acid sequence identity. There is generally a higher degree of amino acid sequence identity which is conserved around the orthosteric ("active") site to which the natural ligand binds.

As is described in Example 1 and FIG. 1 below, individual replacement of the following amino acid residues in the parent turkey β-adrenergic sequence (as shown in FIGS. 9A and 9B) lead to an increase in thermostability: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

Thus, a mutant turkey β-adrenergic receptor in which, compared to its parent, one or more of these amino acid residues have been replaced by another amino acid residue may be used. Mutant β-adrenergic receptors from other sources in which one or more corresponding amino acids in the parent receptor are replaced by another amino acid residue may also be used.

In one embodiment the mutant GPCR is a mutant β-adrenergic receptor which has at least one different amino acid residue in a structural motif in which the mutant receptor compared to its parent receptor has a different amino acid at a position which corresponds to any of the following positions according to the numbering of the turkey β-adrenergic receptor as set out in FIGS. 9A and 9B: Ile 55, Gly 67, Arg 68, Val 89, Met 90, Gly 98, Ile 129, Ser 151, Val 160, Gln 194, Gly 197, Leu 221, Tyr 227, Arg 229, Val 230, Ala 234, Ala 282, Asp 322, Phe 327, Ala 334, Phe 338.

For the avoidance of doubt, the parent may be a β-adrenergic receptor which has a naturally-occurring sequence, or it may be a truncated form or it may be a fusion, either to the naturally occurring protein or to a fragment thereof, or it may contain mutations compared to the naturally-occurring sequenced provided that it retains ligand-binding ability.

By "corresponding amino acid residue" we include the meaning of the amino acid residue in another β-adrenergic receptor which aligns to the given amino acid residue in turkey β-adrenergic receptor when the turkey β-adrenergic receptor and the other β-adrenergic receptor are compared using MacVector and CLUSTALW.

FIGS. 9A and 9B show an alignment between turkey β-adrenergic receptor and human β1, β2 and β3 β-adrenergic receptors.

It can be seen that Ile 72 of human β1 corresponds to Ile 55 of turkey β-adrenergic receptor; Ile 47 of human β2 corresponds to Ile 55 of turkey β-adrenergic receptor; and Thr51 of human β3 corresponds to Ile 55 of turkey β-adrenergic receptor. Other corresponding amino acid residues in human β1, β2 and β3 can readily be identified by reference to FIGS. 9A and 9B.

It is preferred that the particular amino acid is replaced with an Ala. However, when the particular amino acid residue is an Ala, it is preferred that it is replaced with a Leu (for example, see turkey β-adrenergic Ala 234, Ala 282 and Ala 334 in FIG. 1).

It is preferred if the mutant β-adrenergic receptor has a different amino acid compared to its parent at more than one amino acid position since this is likely to give greater stability. Particularly preferred human β1 receptor mutants are those in which one or more of the following amino acid residues are replaced with another amino acid residue: K85, M107, Y244, A316, F361 and F372. Typically, the given amino acid residue is replaced with Ala or Val or Met or Leu or Ile (unless they are already that residue).

Mutant human β1 receptors which have combinations of 3 or 4 or 5 or 6 mutations as described above are preferred.

Particularly preferred human β2 receptor mutants are those in which one or more of the following amino acids are replaced with another amino acid residue: K60, M82, Y219, C265, L310 and F321. Typically, the given amino acid residue is replaced with Ala or Val or Met or Leu or Ile (unless they are already that residue).

Mutant human β2 receptors which have combinations of 3 or 4 or 5 or 6 mutations as described above are preferred.

Figure 26:
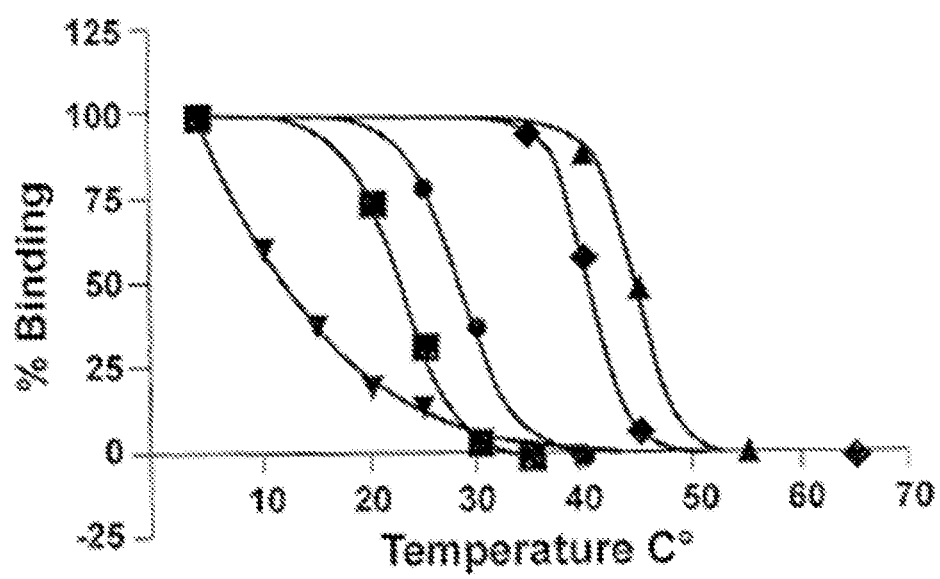
FIG. 26 Comparison of the thermostabilities of three β adrenergic receptors (turkey β1 (■), human β1 (▼) and human β2 (●)) and two thermostabilised receptors (turkey β1-m23 (▲) and human β2-m23 (♦)). The six thermostabilising mutations in β1-m23 (R68S, M90V, Y227A, A282L, F327A, F338M) were all transferred directly to the human β2 receptor (K60S, M82V, Y219A, C265L, L310A, F321M) making β2-m23, based upon the alignment in FIGS. 9A and 9B. The resulting mutants were transiently expressed in mammalian cells, solubilised in 0.1% dodecylmaltoside and assayed for thermostability in the minus-ligand format (heating the apo-state, quenching on ice, adding 3H-DHA). The apparent Tms for turkey β1 and β2-m23 were 23° C. and 45° C. respectively, giving a ΔTm of 22° C. as seen previously in E. coli expressed receptor. The Tms for human β2 and β2-m23 were 29° C. and 41° C. respectively, showing that the apo receptor was stabilised by 12° C. This exemplifies the principle of the transferability of thermostabilising mutations from one receptor to another receptor, which in this case are 59% identical. The human β1 receptor (Tm~12° C.) is much less stable than the turkey β1 receptor.
Figure 28A:
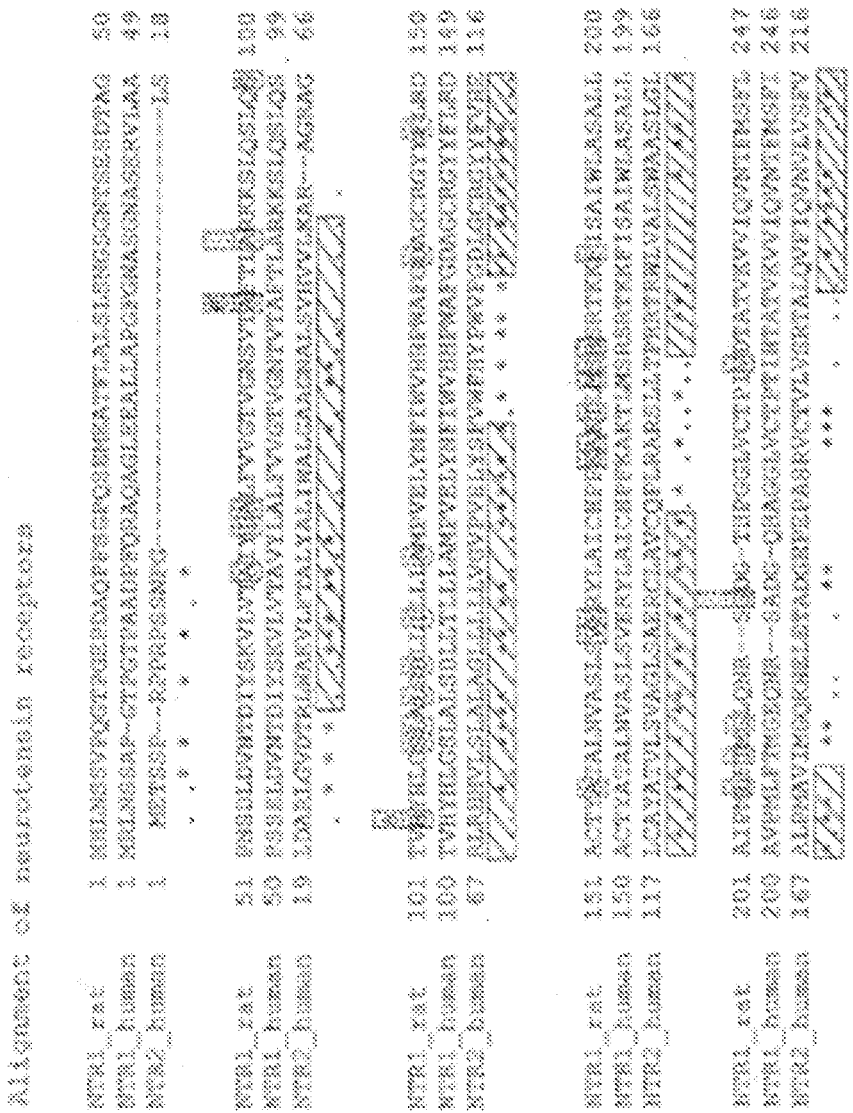
FIGS. 28A and 28B Alignment of neurotensin receptors. The sequences depicted in FIGS. 28A and 28B correspond to SEQ ID NOs.: 9-11, respectively.
Figure 28B:
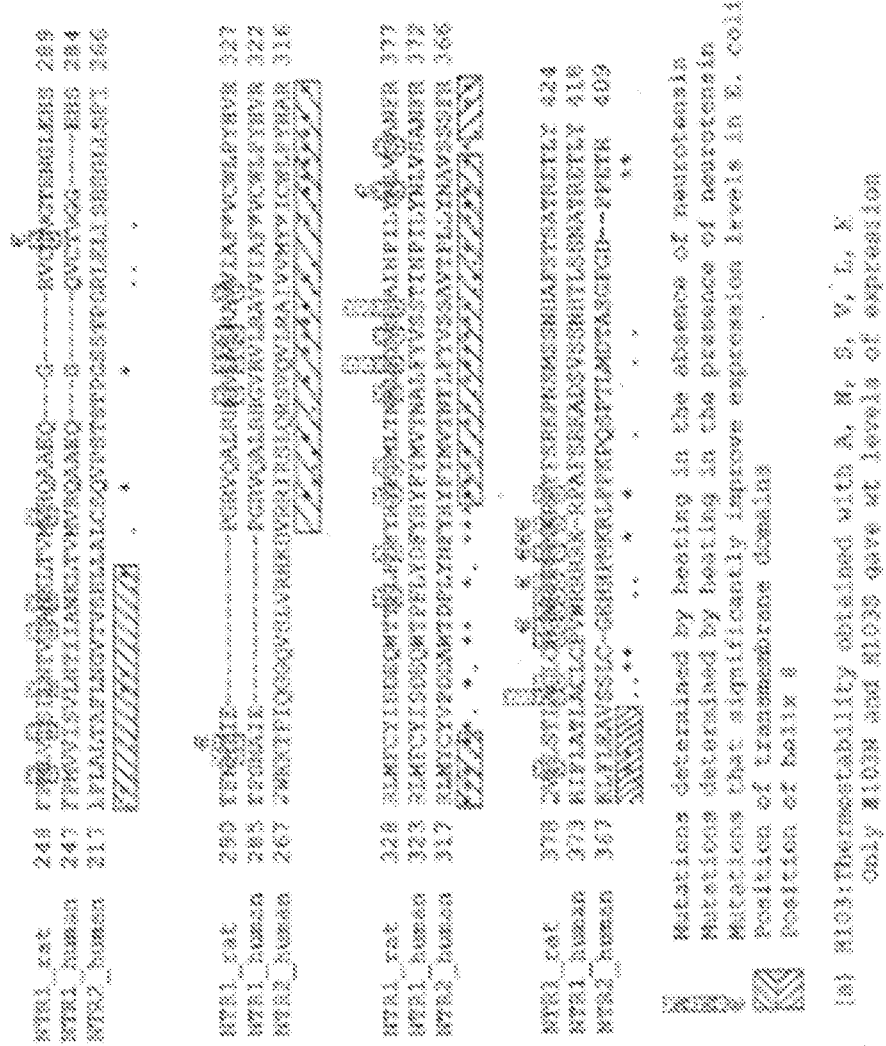

FIG. 26 shows the effect on thermostability when six thermostabilising mutations in β1-m23 (R68S, M90V, Y227A, A282L, F327A, F338M) were transferred directly to the human β2 receptor (equivalent mutations K60S, M82V, Y219A, C265L, L310A, F321M), making human β2-m23. The Tms for human β2 and β2-m23 were 29° C. and 41° C. respectively, thus exemplifying the transferability of thermostabilising mutations from one receptor to another receptor. Accordingly, a particularly preferred human β2 receptor mutant is one which comprises the mutations K60S, M82V, Y219A, C265L, L310A, F321M.

Particularly preferred human β3 receptor mutants are those in which one or more of the following amino acids are replaced with another amino acid residue: W64, M86, Y224, P284, A330 and F341. Typically, the given amino acid residue is replaced with Ala or Val or Met or Leu or Ile (unless they are already that residue).

Mutant human β3 receptors which have combinations of 3 or 4 or 5 or 6 mutations as described above are preferred.

Particularly preferred combinations of mutations are described in detail in Tables 1 and 2 in Example 1, and suitable mutants include the mutant turkey β-adrenergic receptors, and also include mutant β-adrenergic receptors where amino acids in corresponding position have been replaced by another amino acid, typically the same amino acid as indicated in Tables 1 and 2 in Example 1.

Particularly preferred mutants are those which contain mutations in the amino acids which correspond to the given amino acid residue by reference to turkey β-adrenergic receptor: (R68S, Y227A, A282L, A334L) (see m6-10 in Table 2 below); (M90V, Y227A, F338M) (see m7-7 in Table 2 below); (R68S, M90V, V230A, F327A, A334L) (see m10-8 in Table 2 below); and (R68S, M90V, Y227A, A282L, F327A, F338M) (see m23 in Table 2 below).

Mutant Adenosine Receptor

Adenosine receptors are well known in the art. They share sequence homology to each other and bind to adenosine.

Figure 10A:
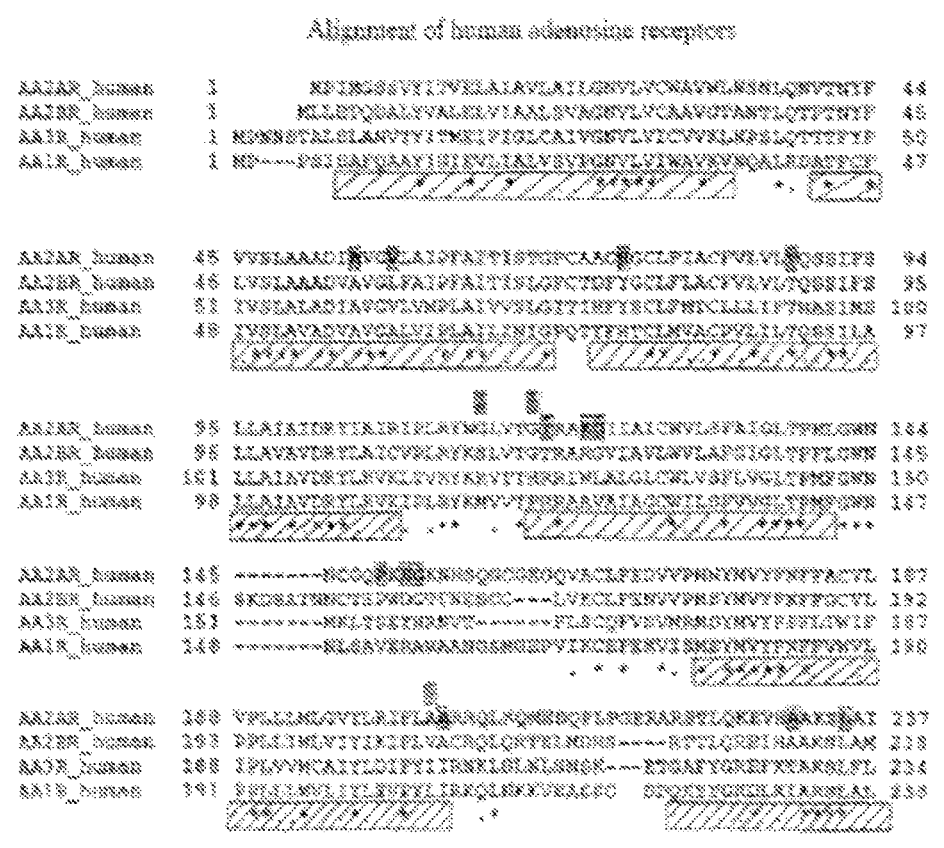
Figure 10B:
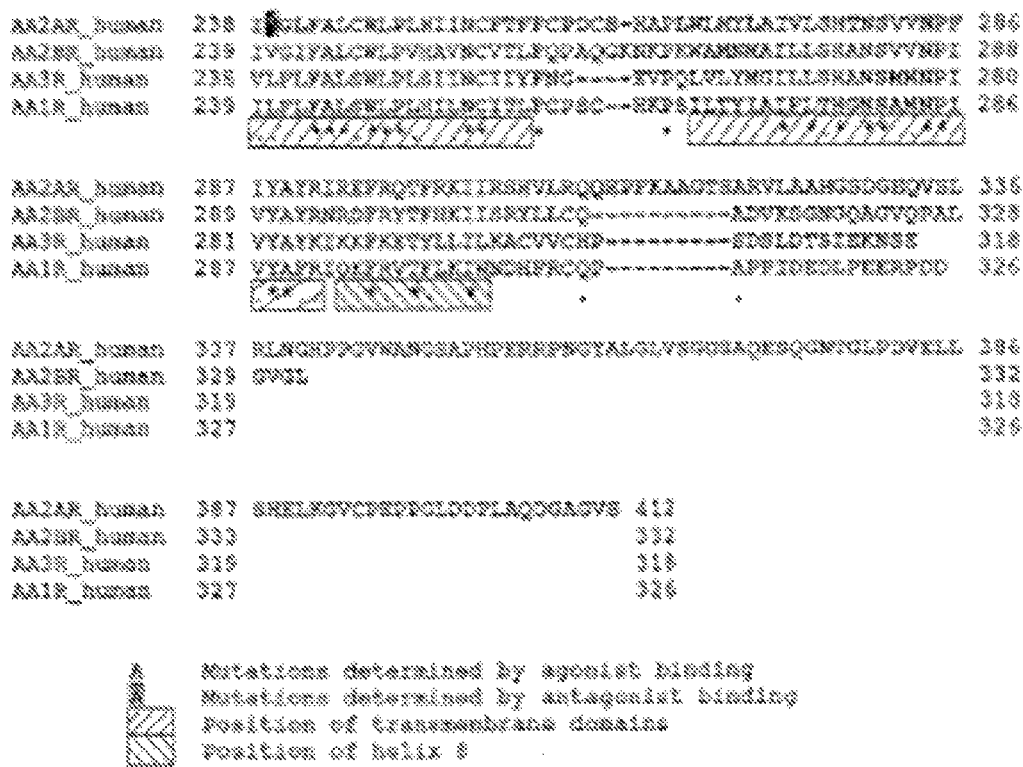

In one embodiment, the mutant GPCR is a mutant adenosine receptor which, when compared to the corresponding wild-type adenosine, has a different amino acid at a position which corresponds to any one or more of the following positions according to the numbering of the human adenosine $A_{2a}$ receptor as set out in FIGS. 10A and 10B: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315, Ala 54, Val 57, His 75, Thr 88, Gly 114, Gly 118, Thr 119, Lys 122, Gly 123, Pro 149, Glu 151, Gly 152, Ala 203, Ala 204, Ala 231, Leu 235, Val 239.

The mutant adenosine receptor may be a mutant of any adenosine receptor provided that it is mutated at one or more of the amino acid positions as stated by reference to the given human adenosine $A_{2a}$ receptor amino acid sequence.

It is particularly preferred if the mutant GPCR is one which has at least 20% amino acid sequence identity when compared to the given human adenosine $A_{2a}$ receptor sequence, as determined using MacVector and CLUSTALW. Preferably, the mutant GPCR has at least 30% or at least 40% or at least 50% or at least 60% sequence identity. Typically, there is a higher degree of sequence conservation at the adenosine binding site.

As is described in Example 2 below, individual replacement of the following amino acid residues in the human adenosine $A_{2a}$ receptor sequence (as shown in FIGS. 10A and 10B) lead to an increase in thermostability when measured with the agonist 5'-N-ethylcarboxamidoadenosine (NECA):

Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

Replacement of the following amino acid residues in the human $A_{2a}$ receptor sequence (as shown in FIGS. 10A and 10B) lead to an increase in thermostability when measured with the antagonist ZM 241385 (4-[2-[[7-amino-2-(2-furyl)[1,2,4]-triazolo[2,3-a][1,3,5]triazin-5-yl]amino]ethyl]phenol):

Ala 54, Val 57, His 75, Thr 88, Gly 114, Gly 118, Thr 119, Lys 122, Gly 123, Pro 149, Glu 151, Gly 152, Ala 203, Ala 204, Ala 231, Leu 235, Val 239.

Thus, a mutant human adenosine $A_{2a}$ receptor in which, compared to its parent, one or more of these amino acid residues have been replaced by another amino acid residue may be used. Mutant adenosine receptors from other sources in which one or more corresponding amino acids in the parent receptor are replaced by another amino acid residue may also be used.

In one embodiment, the mutant GPCR is a mutant adenosine receptor which has at least one different amino acid residue in a structural motif in which the mutant receptor compared to its parent receptor has a different amino acid at a position which corresponds to any of the following positions according to the numbering of the human adenosine $A_{2a}$ receptor as set out in FIGS. 10A and 10B: Gly 114, Gly 118, Leu 167, Ala 184, Arg 199, Ala 203, Leu 208, Gln 210, Ser 213, Glu 219, Arg 220, Ser 223, Thr 224, Gln 226, Lys 227, His 230, Leu 241, Pro 260, Ser 263, Leu 267, Leu 272, Thr 279, Asn 284, Gln 311, Pro 313, Lys 315.

For the avoidance of doubt, the parent may be an adenosine receptor which has a naturally-occurring sequence, or it may be a truncated form or it may be a fusion, either to the naturally-occurring protein or to a fragment thereof, or it may contain mutations compared to the naturally-occurring sequence, provided that it retains ligand-binding ability.

By "corresponding amino acid residue" we include the meaning of the amino acid residue in another adenosine receptor which aligns to the given amino acid residue in human adenosine $A_{2a}$ receptor when the human adenosine $A_{2a}$ receptor and the other adenosine receptor are compared using MacVector and CLUSTALW.

FIGS. 10A and 10B show an alignment between human adenosine $A_{2a}$ receptor and three other human adenosine receptors (A2b, A3 and A1).

It can be seen that, for example, Ser 115 in the $A_{2b}$ receptor (indicated as AA2BR) corresponds to Gly 114 in the $A_{2a}$ receptor. Similarly, it can be seen that Ala 60 in the $A_3$ receptor (indicated as AA3R) corresponds to Ala 54 in the $A_{2a}$ receptor, and so on. Other corresponding amino acid residues in human adenosine receptors $A_{2b}$, $A_3$ and $A_1$ can readily be identified by reference to FIGS. 10A and 10B.

It is preferred that the particular amino acid in the parent is replaced with an Ala. However, when the particular amino acid residue in the parent is an Ala, it is preferred that it is replaced with a Leu.

It is preferred that the mutant adenosine receptor has a different amino acid compared to its parent at more than one amino acid position. Particularly preferred human adenosine A2b receptors are those in which one or more of the following amino acid residues are replaced with another amino acid residue: A55, T89, R123, L236 and V240. Typically, the given amino acid residue is replaced with Ala or Val or Met or Leu or Ile (unless they are already that residue).

Mutant human adenosine A2b receptors which have combinations of 3 or 4 or 5 mutations as described above are preferred.

Particularly preferred human adenosine A3 receptors are those in which one or more of the following amino acid residues are replaced with another amino acid residue: A60, T94, W128, L232 and L236. Typically, the given amino acid residue is replaced with Ala or Val or Met or Leu or Ile (unless they are already that residue).

Mutant human adenosine A3 receptors which have combinations of 3 or 4 or 5 mutations as described above are preferred.

Particular preferred human adenosine A1 receptors are those in which one or more of the following residues are replaced: A57, T91, A125, L236, and L240. Typically, the given amino acid residue is replaced with Ala or Val or Met or Leu or Ile (unless they are already that residue).

Particularly preferred combinations of mutations are described in detail in Example 2. Suitable mutants include these mutant human adenosine $A_{2a}$ receptors, and also include other mutant adenosine receptors where amino acids in corresponding positions have been replaced by another amino acid, typically the same amino acid as indicated in Example 2.

Particularly preferred adenosine receptor mutants are those which contain mutations in the amino acids which correspond to the given amino residue by reference to human adenosine A2a receptor: (A54L, K122A, L235A) (Rant 17); (A54L, T88A, V239A, A204L) (Rant 19); and (A54L, T88A, V239A, K122A) (Rant 21).

Mutant Neurotensin Receptor

Neurotensin receptors are known in the art. They share sequence homology and bind neurotensin.

Figure 11A:
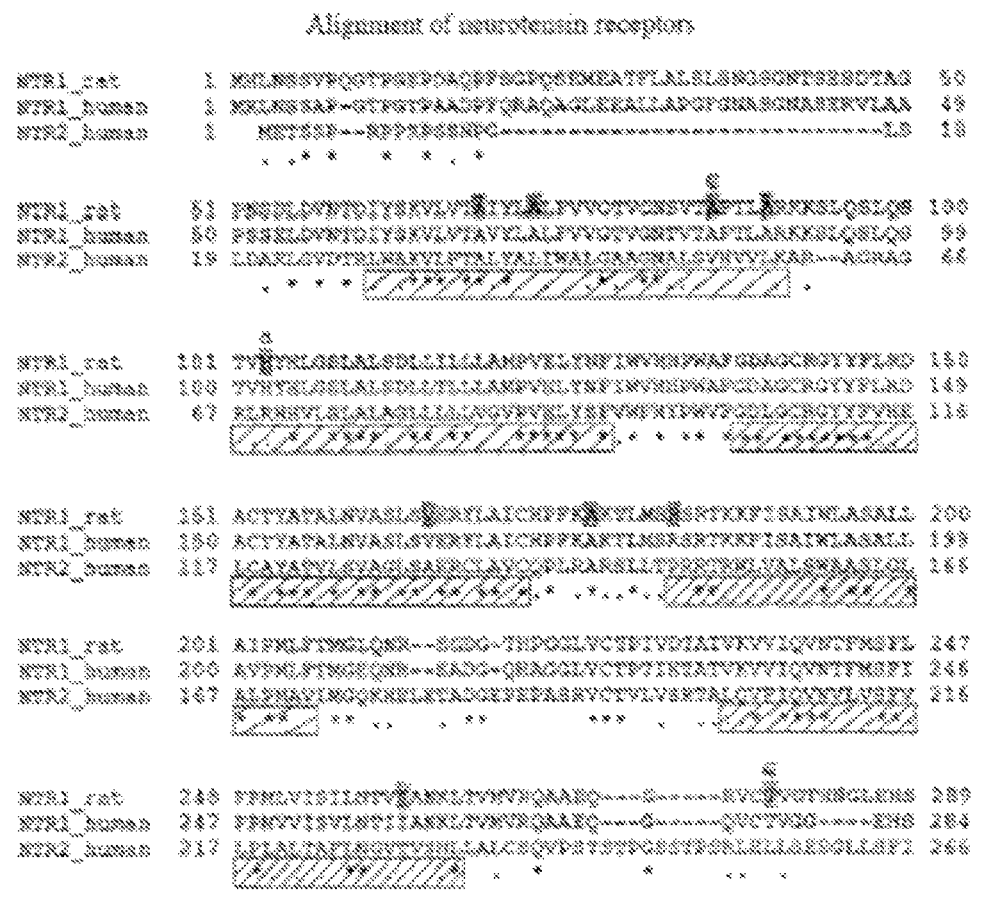
Figure 11B:
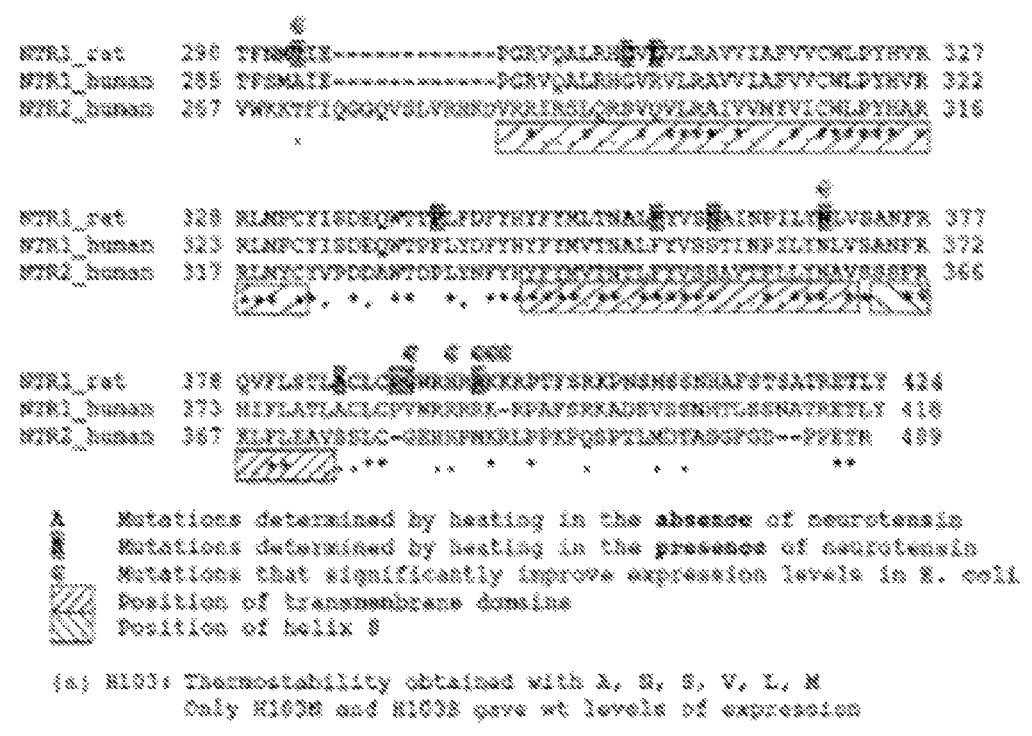

In one embodiment, the mutant GPCR is a mutant neurotensin receptor which, when compared to the corresponding wild-type neurotensin receptor, has a different amino acid at a position which corresponds to any one or more of the following positions according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

It is particularly preferred if the mutant GPCR is one which has at least 20% amino acid sequence identity when compared to the given rat neurotensin receptor sequence, as determined using MacVector and CLUSTALW. Preferably, the mutant GPCR has at least 30% or at least 40% or at least 50% amino acid sequence identity.

The mutant neurotensin receptor may be a mutant of any neurotensin receptor provided that it is mutated at one or more of the amino acid positions as stated by reference to the given rat neurotensin receptor amino acid sequence.

As is described in Example 3 below, individual replacement of the following amino acid residues in the rat neurotensin receptor sequence (as shown in FIGS. 11A and 11B and 28A and 28B) lead to an increase in thermostability when considered with respect to the absence of neurotensin. Leu 72, Ala 86, Ala 90, Ser 100, His 103, Ser 108, Leu 109, Leu 111, Asp 113, Ile 116, Ala 120, Asp 139, Phe 147, Ala 155, Lys 176, Thr 179, Met 181, Ser 182, Phe 189, Leu 205, Thr 207, Gly 209, Gly 215, Leu 256, Asn 262, Val 268, Met 293, Asp 345, Tyr 349, Tyr 351, Ala 356, Phe 358, Ser 362, Ala 385, Cys 386, Trp 391, Arg 392, His 393, Lys 397, Pro 399.

As is described in Example 3 below, individual replacement of the following amino acid residues in the rat neurotensin receptor sequence (as shown in FIGS. 11A and 11B and 28A and 28B) lead to an increase in thermostability when considered with respect to the presence of neurotensin. Ala 69, Ala 73, Ala 86, Ala 90, His 103, Val 165, Glu 166, Ala 177, Arg 183, Gly 215, Val 229, Met 250, Ile 253, Ile 260, Thr 279, Thr 294, Gly 306, Leu 308, Val 309, Leu 310, Val 313, Phe 342, Phe 358, Val 360, Ser 362, Asn 370, Ser 373, Phe 380, Ala 385, Pro 389, Gly 390, Arg 395.

Thus, a mutant rat neurotensin receptor in which, compared to its parent, one or more of these amino acid residues have been replaced by another amino acid residue may be used. Mutant neurotensin receptors from other sources in which one or more corresponding amino acids in the parent receptor are replaced by another amino acid residue may also be used.

In one embodiment the mutant GPCR is a mutant neurotensin receptor which has at least one different amino acid residue in a structural motif in which the mutant receptor compared to its parent receptor has a different amino acid at a position which corresponds to any of the following positions according to the numbering of the rat neurotensin receptor as set out in FIGS. 11A and 11B: Ala 69, Leu 72, Ala 73, Ala 86, Ala 90, Ser 100, His 103, Ser 108, Leu 109, Leu 111, Asp 113, Ile 116, Ala 120, Asp 139, Phe 147, Ala 155, Val 165, Glu 166, Lys 176, Ala 177, Thr 179, Met 181, Ser 182, Arg 183, Phe 189, Leu 205, Thr 207, Gly 209, Gly 215, Val 229, Met 250, Ile 253, Leu 256, Ile 260, Asn 262, Val 268, Asn 270, Thr 279, Met 293, Thr 294, Gly 306, Leu 308, Val 309, Leu 310, Val 313, Phe 342, Asp 345, Tyr 349, Tyr 351, Ala 356, Phe 358, Val 360, Ser 362, Asn 370, Ser 373, Phe 380, Ala 385, Cys 386, Pro 389, Gly 390, Trp 391, Arg 392, His 393, Arg 395, Lys 397, Pro 399.

For the avoidance of doubt the parent may be a neurotensin receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another neurotensin receptor which aligns to the given amino acid residue in rat neurotensin receptor when the rat neurotensin receptor and the other neurotensin receptor are compared using MacVector and CLUSTALW.

FIGS. 11A and 11B show an alignment between rat neurotensin receptor and two human neurotensin receptors 1 and 2. It can be seen, for example, that Ala 85 of the human neurotensin receptor 1 corresponds to Ala 86 of the rat neurotensin receptor, that Phe 353 of the human neurotensin receptor 1 corresponds to Phe 358 of the rat neurotensin receptor, and so on. Other corresponding amino acid residue in the human neurotensin receptors 1 and 2 can readily be identified by reference to FIGS. 11A and 11B.

It is preferred that the particular amino acid in the parent is replaced with an Ala. However, when the particular amino acid residue in the parent is an Ala, it is preferred that it is replaced with a Leu.

It is preferred that the mutant neurotensin receptor has a different amino acid compared to its parent at more than one amino acid position. Particularly preferred human neurotensin receptors (NTR1) are those in which one or more of the following amino acid residues are replaced with another amino acid residue: Ala 85, His 102, Ile 259, Phe 337 and Phe 353. Typically, the given amino acid residues is replaced with Ala or Val or Met or Leu or Ile (unless they are already that residue).

Mutant human neurotensin receptors (NTR1) which have combinations of 3 or 4 or 5 mutations as described above are preferred.

Particularly preferred human neurotensin receptors (NTR2) are those in which one or more of the following amino acid residues are replaced with another amino acid residue: V54, R69, T229, P331 and F347. Typically, the given amino acid residue is replaced with Ala or Val or Met or Leu or Ile (unless they are already that residue). Mutant human neurotensin receptors (NTR2) which have combinations of 3 or 4 or 5 mutations as described above are preferred.

Particularly preferred combinations of mutations are described in detail in Example 3. Suitable mutants include these mutant rat neurotensin receptors, and also include other mutant neurotensin receptors where amino acids in corresponding positions have been replaced by another amino acid, typically the same amino acid as indicated in Example 3.

Particularly preferred neurotensin receptor mutants are those which contain mutations in the amino acid residues which correspond to the given amino acid residue by reference to the rat neurotensin receptor: (F358A, A86L, I260A, F342A) (Nag7m); (F358A, H103A, I260A, F342A) (Nag7n).

Mutant Muscarinic Receptor

Muscarinic receptors are known in the art. They share sequence homology and bind muscarine.

In one embodiment, the mutant GPCR is a mutant muscarinic receptor which, when compared to the corresponding wild-type muscarinic receptor, has a different amino acid at a position which corresponds to any one or more of the following positions according to the numbering of the human muscarinic receptor M1 as set out in FIGS. 17A, 17B and 17C: Leu 65, Met 145, Leu 399, Ile 383 and Met 384.

It is particularly preferred if the mutant GPCR is one which has at least 20% amino acid sequence identity when compared to the given human muscarinic receptor sequence, as determined using MacVector and CLUSTALW. Preferably, the mutant GPCR has at least 30% or at least 40% or at least 50% amino acid sequence identity.

The mutant muscarinic receptor may be a mutant of any muscarinic receptor provided that it is mutated at one or more of the amino acid positions as stated by reference to the given muscarinic receptor amino acid sequence.

Thus, a mutant human muscarinic receptor in which, compared to its parent, one or more of these amino acid residues have been replaced by another amino acid residue may be used. Mutant muscarinic receptors from other sources in which one or more corresponding amino acids in the parent receptor are replaced by another amino acid residue may also be used.

For the avoidance of doubt the parent may be a muscarinic receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

In one embodiment, the mutant GPCR is a mutant muscarinic receptor. For example, the mutant muscarinic receptor may have at least one different amino acid residue in a structural motif in which the mutant receptor compared to its parent receptor has a different amino acid at a position which corresponds to any of the following positions according to the numbering of the human muscarinic receptor as set out in FIGS. 17A, 17B and 17C: Leu 65, Met 145, Leu 399, Ile 383 and Met 384.

By "corresponding amino acid residue" we include the meaning of the amino acid residue in another muscarinic receptor which aligns to the given amino acid residue in human muscarinic receptor when the human muscarinic receptor and the other muscarinic receptor are compared using MacVector and CLUSTALW.

It is preferred that the particular amino acid is replaced with an Ala. However, when the particular amino acid residue is an Ala, it is preferred that it is replaced with a Leu.

It is preferred that the mutant GPCRs used in the invention have increased stability to any one of heat, a detergent, a chaotropic agent and an extreme of pH.

It is preferred if the mutant GPCRs used in the invention have increased thermostability.

It is preferred that the mutant GPCRs used in the invention, including the mutant β-adrenergic, adenosine and neurotensin receptors, have an increased thermostability compared to its parent when in the presence or absence of a ligand thereto. Typically, the ligand is an antagonist, a full agonist, a partial agonist or an inverse agonist, whether orthosteric or allosteric. As discussed above, the ligand may be a polypeptide, such as an antibody.

It is preferred that the mutant GPCRs used in the invention, for example a mutant β-adrenergic receptor or a mutant adenosine receptor or a mutant neurotensin receptor or a mutant muscarinic receptor is at least 2° C. more stable than its parent preferably at least 5° C. more stable, more preferably at least 8° C. more stable and even more preferably at least 10° C. or 15° C. or 20° C. more stable than its parent. Typically, thermostability of the parent and mutant receptors are measured under the same conditions. Typically, thermostability is assayed under a condition in which the GPCR resides in a particular conformation. Typically, this selected condition is the presence of a ligand which binds the GPCR.

It is preferred that the mutant GPCRs used in the invention, when solubilised and purified in a suitable detergent has a similar thermostability to bovine rhodopsin purified in dodecyl maltoside. It is particularly preferred that the mutant GPCR retains at least 50% of its ligand binding activity after heating at 40° C. for 30 minutes. It is further preferred that the mutant GPCR retains at least 50% of its ligand binding activity after heating at 55° C. for 30 minutes.

For the avoidance of doubt, the mutant GPCR provided in step (a) of the method of the first aspect of the invention may be extended or truncated, contain internal deletions or insertions or otherwise altered beyond introduction of stabilising mutations; for example by introduction or deletion of sites for posttranslational modification e.g. glycosylation or phosphorylation or fatty acylation. It may also be chemically modified synthetically, for example by peptide semisynthesis or crosslinking or alkylation. In any event, the mutant GPCR provided has increased stability in a particular conformation relative to its parent GPCR.

Selection of Binding Partners

Selection for binding partners against membrane proteins has previously proven to be a difficult task. The preparation of the required pure antigen is problematic. Membrane proteins are often detergent-solubilised and they are purified as protein-detergent complexes. The type and concentration of detergent is crucial to keep the protein in its native conformation. Some detergents may prevent proteins from binding to plastic and polystyrene surfaces used as common ELISA supports. In addition, adsorption to the solid phase can cause partial denaturation of the protein.

In contrast, the increased stability of mutant GPCRs confers several advantages when the GPCRs are used as immunogens or selection reagents for screening, enabling them to be used as such in a variety of contexts.

Accordingly, in one embodiment, the mutant GPCR may be in a whole cell preparation, a cell membrane fragment, solubilised in detergent or it may be incorporated into a lipid monolayer, a lipid bilayer, a bead-linked lipid particle, another solid-supported lipid layer or a proteoliposome. It is appreciated that when the GPCR is immobilised, the lipid layers may be supported directly as a layer on the surface of the solid support or may be tethered as a layer or vesicle as described in Cooper M. A. J Mol Recognit. 2004 July-August; 17(4):286-315.

The inventors recognise that high throughput membrane-receptor screening is facilitated by immobilising membranes on beads or on surfaces that can be arrayed or otherwise multiplexed. Typically, membrane proteins are deposited on a surface together with lipid in the form of proteoliposomes. The most commonly employed methods for the formation of proteoliposomes start with either prokaryote or eukaryote cells. Membrane proteins can be isolated either in a mixed micelle with detergent, dissolved in an organic solvent or aggregated as membrane fragments by sonication in buffer. Once isolated and purified, the membrane proteins can be reconstituted into vesicles by: a) organic solvent-mediated reconstitutions (for example reverse-phase evaporation, rehydration of lipid-protein films), b) mechanical means (for example sonication, French press, freeze-thaw), or c) detergent-mediated means (for example dialysis, dilution, or direct incorporation into pre-formed vesicles or into bicelles)

The detergent solubilised form of the mutant GPCR may be a partly pure or highly pure preparation. Purification, enabled by the improved stability and optimisation of solubilisation conditions, confers the advantage of removal of extraneous "sticky" antigens and lipids and other cell surface material such as carbohydrate to which, for example, phage may stick to. This is particularly beneficial when the 'extraneous' material is charged or hydrophobic since phage particles, for example, are known to stick to hydrophobic or charged surfaces non-specifically. Moreover, certain phage antibodies may themselves bind promiscuously to antigens. A normal level of purity, as assessed by SDS-PAGE, is 80-95%. Therefore, preferably the detergent solubilised form of the mutant GPCR is at least 80% pure, or at least 85% pure, and still more preferably at least 90%, or at least 93%, or at least 95%, pure of other proteins. As is known in the art, higher levels of purity, e.g. at least 99%, can be achieved using additional purification techniques.

Solubilised receptor preparations are typically made in a buffer of 20 mM Tris (pH 7.0), 0.1M $(NH_4)_2SO_4$, 10% glycerol, 0.07% CHS, 0.33% DOM, 0.33% Chaps, 0.33 mM DOPC/DOPS (7:3), and 1 protease inhibitor tablet per 50 ml buffer. For solubilization trials, 0.5 ml of this solubilization buffer is added to approximately $2\times10^6$ cells, and these cell suspensions are sonicated using a probe sonicator (6×1-s pulses) and placed on a rocker at 4° C. After 2 h, the solutions are centrifuged at 4° C. for 20 min at 14,000 rpm using a tabletop centrifuge. The supernatants containing solubilised receptor are then transferred to new tubes and kept frozen at −80° C. until analysis.

Preparations of mutant GPCRs formed from membrane fragments or membrane-detergent extracts are reviewed in detail in Cooper M. A. J Mol Recognit. 2004 July-August; 17(4):286-315, incorporated herein by reference. Of particular interest are methods adapted from Graham, J. M.; Higgins, J. A. *Membrane Analysis*; Springer-Verlag: New York, 1997 and Dignam, J. D. *Methods in Enzymology* 1990, 182, 194-203. For example, one method is as follows; i) Spin 500 ml of a suitable cell culture (e.g. CHO, Sf9) at 1000 g for 10 min, re-suspend pellet in ca. twice the pellet volume of a suitable ice-cold 20 mM tris-HCl pH 8, 1 mM EDTA, 1 mM EGTA, 0.1 mM PMSF, 2 µg/ml aprotinin, and 10 µg/ml leupeptin, ii) Homogenize with a Dounce homogenizer (type A) for 10 strokes, then centrifuge at 30,000 g for 20 min, iii) Re-suspend pellet with 50 ml of 20 mM tris HCl pH 8, 3 mM MgCl, 10 ug/ml DNAase I plus PMSF, 2 µg/ml aprotinin and 10 µg/ml leupeptin (solution B) and re-homogenize, iv) Centrifuge at 30,000 g for 20 min. and resuspend pellet in 20 ml of solution B and homogenize again, v) Store at 4° C. for immediate use after snap freezing.

The mutant GPCR may be engineered to include a molecular tag at the C terminus or N-terminus as is well known in the art. The tag may be any of a FLAG tag, a His tag, a c-Myc tag, a DDDDK tag, an HSV tag, a Halo tag or a biotin tag. Such tags can be used to facilitate phage-based selection protocols in solution and may also be used to confer binding to a solid support. Moreover, such tags will facilitate selection and enrichment of mutant GPCRs from impure preparations using affinity columns, affinity filters, magnetic beads and other examples of selective solid supported reagents, filtration, centrifugation, size-exclusion chromatography and dialysis amongst other methods The increased stability of mutant GPCRs in a range of detergents and solubilisation buffers and additives lends them particularly well to being immobilised onto solid surfaces. Thus, in one embodiment the mutant GPCR is immobilised onto a solid support. Various supports are known in the art and include, for example, beads, columns, slides, chips or plates. Immobilisation may be via covalent or non-covalent interaction.

Where immobilisation is via a non-covalent interaction, the support may be coated with any of avidin, streptavidin, a metal ion, an antibody to the parent GPCR or an antibody to a molecular tag attached to the mutant GPCR. For example, the tag may be one recognised by an antibody such as a FLAG tag, or may be a poly-histidine tag enabling binding to a metal ion such as nickel or cobalt, as described for example in Venturi et al, Biochemica et Biophysica Acta 1610 (2003) 46-50. Alternatively, the mutant GPCR may be chemically modified for example with a biotin tag which can be bound to a surface coated with avidin or streptavidin. Moreover, a mutant GPCR may be immobilised via an antibody raised to the native receptor sequence.

Where immobilisation is via a covalent interaction, the support may be coated with a polymeric support such as carboxylated dextran. For example, the mutant GPCR may be covalently immobilised onto a surface coated with a carboxylated polymer via amine coupling. For example, water-soluble carbodiimide mediated activation of a carboxymethylated support such as dextran or hyaluronic acid allows for direct covalent capture of a mutant GPCR via available amino moieties of the protein to form a stable amide linkage. Alternatively, GPCRs can be engineered or further derivatised with sulfydryl-reactive reagents (e.g. pyridinyldithioethanamine (PDEA) or 3-(2-pyridinyldithio)propioic acid N-hydroxysuccinimide ester) (SPDP)) which allows reaction with free surface thiols (e.g. native free Cys, Met residues or with an engineered C-terminal Cys residue) to form a reversible disulfide linkage. In a similar manner, stable thioether bonds may be formed using maleimide coupling reagents such as sulfosuccinimidyl-4-(N-maleimidomethyl)cyclohexanecarboxylate (Sulfo-SMCC) and N-(γ-maleimidobutyrloxy)sulfosuccinimide ester (GMBS). A solid support may also be derivatised with cystamine to effect coupling with disulfide-activated GPCRs. Furthermore, treatment with hydrazine followed by a reductive amination enables coupling with aldheydes. The aldehyde groups may be native to the receptor or formed by mild oxidation of any cis-diols present in the solid support (present in sugar residues of carbohydrates such as dextran, agarose, sepharose, hyaluronic acid and polyaginate). In addition to the above, amino-presenting surfaces can be treated with commercially available bifunctional linking reagents to effect coupling with free amino or sulfhydryl groups on the receptor as described by (Ernst, O. P. et al. *Meth. Enzymol.* 2000, 315, 471-489 and Nunomura, W. e et al. *J. Biol. Chem.* 2000, 275, 24540-24546).

The orientation of the mutant GPCR will depend on the desired outcome of the binding partner identification. For example, for the identification of therapeutic small molecules or antibodies, the mutant GPCR will typically be immobilised via the C-terminus or other intracellular domain to enable the extracellular domains to be outward facing in the assay. To identify native intracellular GPCR binding partners or agents which interfere with GPCR binding, the mutant GPCR is typically immobilised by the N-terminus or extracellular domain. Immobilisation by the N-terminus or extracellular domain may also identify therapeutic molecules that bind to the intracellular domain. However, it will be appreciated that for such molecules to be active in vivo, they must be able to pass through the cell membrane.

In an alternative embodiment, the mutant GPCR is not immobilised and is, for example, solubilised in detergent or present in a whole cell preparation. In this case, the test compound (for example, a library of test compounds) may be immobilised on a solid support, such as a chip surface. A variety of techniques are known in the art for immobilising compounds onto a chip surface, and any may be utilised. For example, suitable techniques include photolithography (Affymetrix, Santa Clara, Calif.), mechanical microspotting (Schena et al., Science (1995) vol. 270, p. 467-470; Synteni, Fremont, Calif.) and ink jetting (Incyte Pharmaceuticals, Palo Alto, Calif.; and Protogene, Palo Alto, Calif.). The address of the test compound/GPCR mutant pair on the chip is used to reveal the identity of the test compound. Other suitable methods are described, for example, in Fang, Y. et al. *Drug Discovery Today* 2003, 8, 755-761, and references Alves, I. D. et al. Curr. Prot. & Peptide Sci. 2005, 6, 293-312; Barry, R. et al. Proteomics 2004, 4, 3717-3726; Besenicar, M. et al. Chem. Phys. Lipids 2006, 141, 169-178; Cocklin, S. et al. Prot. Sci. 2004, 13, 194-194; Cooper, M. A. J. of Mol. Recognit. 2004, 17, 286-315; Fang, Y. et al. Drug Discov. Today 2003, 8, 755-761; Ferracci, G. et al. Anal. Biochem. 2004, 334, 367-375; Graneli, A. et al. Anal. Biochem. 2007, 367, 87-94; Graneli, A. et al. Biosens. Bioelectron. 2004, 20, 498-504; Groves, J. T. Curr. Op. Drug Discov. Develop. 2002, 5, 606-612; Groves, J. T. et al. J. Immunol. Meth. 2003, 278, 19-32; Harding, P. J. et al. Eur. Biophys. J. Biophys. Let. 2006, 35, 709-712; Komolov, K. E. et al. Anal. Chem. 2006, 78, 1228-1234; Kuroda, K. et al. App. Psychophys. Biofeedback 2006, 31, 127-136; Lang, M. J. et al. Curr. Prot. Peptide Sci. 2006, 7, 335-353; Leifert, W. R. et al. J. Biomol. Screening 2005, 10, 765-779; Martin-Garcia, J. et al. J. Virology 2005, 79, 6703-6713; Minic, J. et al. Biochim. Biophys. Acta-General Subjects 2005, 1724, 324-332; Mozsolits, H. et al. J. Peptide Sci. 2003, 9, 77-89; Navratilova, I. et al. Anal. Biochem. 2006, 355, 132-139; Ott, D. et al. Prot. Eng. Design & Selection 2005, 18, 153-160; Park, P. S. H. et al. Febs Lett. 2004, 567, 344-348; Sobek, J. et al. Combinat. Chem. & High Throughput Screening 2006, 9, 365-380; Stenlund, P. et al. Analytical Biochemistry 2003, 316, 243-250; Winter, E. M. et al. Anal. Chem. 2006, 78, 174-180; Yokogawa, M. et al. J. Am. Chem. So. 2005, 127, 12021-12027; Zurawski, J. A. et al. Biopolymers 2003, 71, 388-389, all of which are incorporated herein by reference.

In one embodiment, neither the GPCR nor the test compound are immobilised, for example in phage-display selection protocols in solution.

The ability to produce milligram quantities of purified GPCRs, stabilised in a particular conformation, enables screening approaches which would not be available to native GPCRs present in biological membranes. Thus, the method of the invention may be used to identify ligands of 'orphan' GPCRs where the natural ligand is unknown. Ligands of orphan GPCRs may be identified from biological samples such as blood or tissue extracts or from libraries of ligands. Similarly, ligands of mutant GPCRs may be identified where the ligands were interacting proteins such as accessory proteins. It is also appreciated that peptide or protein therapeutics may be identified by the methods of the invention as could conformation-specific antibodies. For example, antibodies prepared as described below could be assessed for conformational-specific GPCR binding. In particular, antibodies may be identified from supernatants obtained from B-cells taken from immunised animals, from hybridomas obtained following immortalisation of B-cells from the immunised animal or from recombinant antibody libraries which may be expressed on phage particles or through an in vitro expression system such as ribosome display. The methods of the invention may also be used to determine the mechanism of action of compounds where the mechanism of action has not previously been known. For example, a mixture of GPCRs representing the 'GPCRome' or a subset thereof could be screened against compounds to identify if their mechanism of action was via binding to a GPCR. In addition, the invention may be used as a biochemical affinity purification system wherein particular compounds are purified from a mixture of compounds.

The test compound may be provided as a biological sample. In particular, the sample could be any suitable sample taken from an individual. For example, the sample may be a fluid sample such as blood, serum, plasma or spinal fluid. Alternatively, the sample could be a tissue or cell extract.

In one embodiment, the one or more test compounds is a polypeptide. For example, the test compound may be a particular type of polypeptide which is known to bind to certain GPCRs but where the identification of a conformation-specific polypeptide is desired. Alternatively, the polypeptide may be a candidate therapeutic molecule, for example an anticalin (Skerra *J Biotechnol* (2001) 74(4):257-75).

In one embodiment, the one or more test compounds is a peptide.

In one embodiment, the one or more test compounds is an affibody, a peptidomimetic, a nucleic acid, a peptide nucleic acid (PNA) or an aptamer, or a lipid or a carbohydrate.

In one embodiment, the one or more test compounds is a binding protein based on a modular framework, such as ankyrin repeat proteins, armadillo repeat proteins, leucine rich proteins, tetrariopeptide repeat proteins or Designed Ankyrin Repeat Proteins (DARPins) or proteins based on lipocalin or fibronectin domains or Affilin scaffolds based on either human gamma crystalline or human ubiquitin.

In one embodiment, the one or more test compounds is a small molecule, for example a molecule less than 5000 daltons, or the one or more test compounds is a natural product.

In one embodiment, the one or more test compounds is an antibody. For example, the test compound may be an antibody that has been raised against a mutant GPCR of a parent GPCR, wherein the mutant GPCR has increased stability in a particular conformation relative to the parent GPCR. Preferably, the mutant GPCR is the same mutant GPCR as was provided in step (a).

As used herein, the term "antibody" includes but is not limited to polyclonal, monoclonal, chimaeric, single chain, Fab fragments and fragments produced by a Fab expression library. Such fragments include fragments of whole antibodies which retain their binding activity for a target substance, Fv, F(ab') and F(ab')2 fragments, as well as genetically engineering derivatives of antibodies such as single chain antibodies (scFv), fusion proteins, domain antibodies (dAbs) and diabodies. For example, it will be appreciated that recombinant DNA technology may be used to produce further antibodies or chimeric molecules which retain the binding specificity of an original antibody. Such technology may involve fusing the DNA encoding the immunoglobulin variable region, or the complementarity determining regions (CDRs), of an antibody to the constant regions, or constant regions plus framework regions of a different immunoglobulin, as described, for example, in EP-A-184187, GB 2188638A or EP-A-239400. Moreover, a hybridoma or other cell producing an antibody may be subject to genetic mutation or other changes which may or may not alter the binding specificity of antibodies produced. Thus, since antibodies can be modified in a number of ways, the term "antibody" is to be construed as covering any specific binding member or substance having a binding domain with the required specificity. The term therefore includes antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent fused to another polypeptide are therefore included. Furthermore, antibodies and fragments thereof may be human or humanised antibodies, as is well known in the art.

Various procedures known within the art may be used to raise antibodies against a mutant GPCR, or against fragments or fusions thereof.

For example, an antibody to a mutant GPCR having increased stability relative to a parent GPCR may be produced by immunising a lymphocyte with an immunogen of the mutant GPCR, screening the antibodies so produced for an antibody which binds to the GPCR, and isolating the antibody. By 'immunising a lymphocyte' we include both in vivo immunisation, where a whole animal is immunised and in vitro immunisation, where lymphocytes are immunised in vitro, for example as described in U.S. Pat. No. 5,290,681.

Preferably, the immunogen of a mutant GPCR is generally all of the mutant GPCR but may also be a part of the mutant GPCR, for example a fragment of the mutant GPCR. For example, the production of a stabilised GPCR may facilitate identification of a part of the GPCR not previously obvious from the native conformation that would benefit from a targeted immunisation approach. The fragment of the mutant GPCR may be any part of the GPCR which is able to elicit an immune response such as an antibody response. It is known that peptides having as few as 5 amino acids may elicit an antibody response, although typically larger peptides are used. Thus, the fragment of the immunogen may have at least 5 amino acids, typically from 5 to 1000 amino acids, such as 5 to 500, 5 to 200, 5 to 100, 5 to 50, 5 to 40, 5 to 30, 5 to 20, for example 5, 6, 7, 8, 9, 10, 11, 12, 13, 14, 15, 16, 17, 18, 19 or 20 amino acids.

Furthermore, the immunogen may be a fusion of the mutant GPCR, wherein the GPCR is fused to a second protein known to be immunogenic to lymphocytes. Examples of such immunogenic proteins include but are not limited to keyhole limpet hemocyanin, serum albumin, bovine thyroglobulin, and soybean trypsin inhibitor. The immunogen may also further include an adjuvant to enhance the immunological response to a mutant GPCR in a mammal in vivo. Various adjuvants used to increase the immunological response include, but are not limited to, Freund's (complete and incomplete), mineral gels (e.g., aluminum hydroxide), surface-active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. An additional example of an adjuvant that can be employed includes MPL-TDM adjuvant (monophosphoryl Lipid A, synthetic trehalose dicorynomycolate). The choice of adjuvant can be important in maintaining the structure of the GPCR and, for this reason, Titremax and oil in water emulsions such as Ribi's adjuvant emulsion are particularly preferred. Stabilised mutant GPCRs may also be linked together on a backbone to produce polyvalent molecules to further increase antigenicity.

It is appreciated that the immunogen of the mutant GPCR may be a variant of the mutant GPCR, provided that it is able to elicit an immune response to the mutant GPCR and does not significantly reduce the stability of the mutant GPCR. Such variants include polypeptides which have one or more amino acid substitutions compared to the mutant GPCR, and as many as 5% substitutions. Typically, the substitutions are conservative substitutions where, for example, a "variant" refers to a protein wherein at one or more positions there have been amino acid insertions, deletions, or substitutions, either conservative or non-conservative, provided that such changes result in a protein that is still able to elicit an immune response against the mutant GPCR and does not significantly reduce the stability of the mutant GPCR. By "conservative substitutions" is intended combinations such as Gly, Ala; Val, Ile, Leu; Asp, Glu; Asn, Gln; Ser, Thr; Lys, Arg; and Phe, Tyr. Such variants of a mutant GPCR can be made using standard methods of protein engineering and site-directed mutagenesis.

It is appreciated that the immunogen may also be a polynucleotide encoding the stabilised GPCR or fragment thereof. For example, the polynucleotide may be taken up into cells in vivo and expressed on the cell surface where it will stimulate an immune response.

The immunogen of a mutant GPCR may be provided as a whole cell preparation, in a cell membrane fragment, solubilised in detergent, in a lipid monolayer, in a lipid bilayer, in a bead-linked lipid particle, in a solid-supported lipid layer or in a proteoliposome, as described above.

For the production of polyclonal antibodies, various suitable host animals (e.g., rabbit, goat, chicken, mouse or other mammal) may be immunized by one or more injections with the immunogen. The polyclonal antibody molecules directed against the immunogenic protein can be isolated from the mammal (e.g., from the serum or egg yolk) and further purified by well known techniques, such as affinity chromatography using protein A or protein G, which provide primarily the IgG fraction of immune serum Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent.

Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

Alternatively, monoclonal antibodies can be generated using the 'Selected Lymphocyte Antibody Method' (SLAM) as is well known in the art and described, for example, in Babcook et al. (1996) *Proc. Natl. Acad. Sci.* 93:7843-7848. Briefly, a single lymphocyte that is producing an antibody with a desired specificity or function within a large population of lymphoid cells is identified. Usually, lymphoid cells derived from an in vivo immunization are screened for those that produce antibodies which bind to selected antigens using an adapted haemolytic plaque assay (Jerne & Nordin, 1963, Science, 140:405) and the genetic information that encodes the specificity of the antibody subsequently retrieved from that lymphocyte.

Monoclonal antibodies can also be made by recombinant DNA methods, such as those described in U.S. Pat. No. 4,816, 567. DNA encoding monoclonal antibodies raised against mutant GPCRs with increased stability can be readily isolated and sequenced using conventional procedures (e.g., by using oligonucleotide probes that are capable of binding specifically to genes encoding the heavy and light chains of murine antibodies). The hybridoma cells described above serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

It will be appreciated that single-chain antibodies specific to GPCRs can also be produced (see e.g., U.S. Pat. No. 4,946,778). Antibody fragments that contain the idiotypes to the mutant GPCR may also be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments. A general review of the techniques involved in the synthesis of antibody fragments which retain their specific binding sites is found in Winter & Milstein (1991) *Nature* 349, 293-299.

Bispecific antibodies may also be produced. Bispecific antibodies are monoclonal, preferably human or humanized, antibodies that have binding specificities for at least two different antigens. In the present case, one of the binding specificities is for a mutant GPCR. The second binding target is any other antigen, and advantageously is a cell-surface protein or receptor, including another GPCR or receptor subunit. For example, bispecific antibodies would be useful for pairs of GPCRs which can form heterodimers (Milligan. Biochim Biophys Acta. 2007 April; 1768(4):825-35). In this case, the bispecific antibody may selectively target specific heterodimeric receptors. Bispecific antibodies may also be useful for viral entry co-receptors where one of the co-receptors is a GPCR, e.g. CD4 and the GPCRs CCR5 or CXCR4 (Alkhatib G, Berger E A. Eur J Med Res. 2007 Oct. 15; 12(9):375-84). Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., 1991 EMBO J., 10:3655-3659.

It is appreciated that in some instances high throughput screening of test compounds is preferred and that the method may be used as a "library screening" method, a term well known to those skilled in the art. Thus, the test compound may be a library of test compounds. For example, the library may be a peptide or protein library produced, for example, by ribosome display or an antibody library prepared either in vivo, ex vivo or in vitro. Methodologies for preparing and screening such libraries are known in the art.

Thus, rather than the test compound being an antibody raised against a mutant GPCR with increased stability in a particular conformation relative to its parent GPCR and then testing its binding to that GPCR, the test compound may be an antibody library. Thus another method for generating antibodies specific to a GPCR involves screening expression libraries encoding immunoglobulin genes, or portions thereof, expressed in bacteria, yeast, filamentous phages, ribosomes or ribosomal subunits or other display systems. In this method, large libraries of antibody sequences or antibody fragment sequences are obtained from diverse sources such healthy donors, patients or animals (healthy or not). These sequences are cloned and expressed in an appropriate system and antibodies typically selected by binding to a GPCR with increased stability immobilised on a solid surface.

A particular example of an antibody library is a recombinant combinatorial antibody library, for example a scFv or Fab phage display library, prepared using human VL and VH cDNAs prepared from mRNA derived from human lymphocytes (McCafferty et al., Nature 348:552-553 (1990)). According to this technique, antibody V domain genes are cloned in-frame into either a major or minor coat protein gene of a filamentous bacteriophage, such as M 13 or fd, and displayed as functional antibody fragments on the surface of the phage particle. Because the filamentous particle contains a single-stranded DNA copy of the phage genome, selections based on the ability of the antibody to bind to the GPCR with increased stability also result in selection of the gene encoding the antibody exhibiting those properties. Phage display can be performed in a variety of formats; for their review see, e.g., Johnson, Kevin S. and Chiswell, David J., Current Opinion in Structural Biology 3:564-57 1 (1993). Moreover, examples of methods and reagents particularly amenable for use in generating and screening antibody display libraries can be found in, for example, Ladner et al. U.S. Pat. No. 5,223, 409; Kang et al. PCT Publication No. WO 92/18619; Dower et al. PCT Publication No. WO 91/17271; Winter et al. PCT Publication No. WO 92/20791; Markland et al PCT Publication No. WO 92/15679; Breitling et al. PCT Publication No. WO 93/01288; McCafferty et al. PCT Publication No. WO 92/01047; Garrard et al. PCT Publication No. WO 92/09690;

Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J. Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982.

The methods may also be used to identify a polynucleotide capable of expressing a polypeptide binding partner of a GPCR, for example as described above in relation to phage display methods. Aliquots of an expression library in a suitable vector may be tested for the ability to give the required result. It will be appreciated that several cycles of identifying pools of polynucleotides comprising a polynucleotide having the required property and then rescreening those polynucleotides may be required in order to identify a single species of polynucleotide with the required property.

The invention includes screening methods to identify drugs or lead compounds of use in treating a disease or condition. It is appreciated that screening assays which are capable of high throughput operation are particularly preferred.

It is appreciated that in the methods described herein, which may be drug screening methods, a term well known to those skilled in the art, the test compound may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes or the blood:brain barrier, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

Thus in one embodiment, the method further comprises modifying a test compound which has been shown to bind to the mutant GPCR when residing in a particular conformation, and determining whether the modified test compound binds to the mutant GPCR when residing in the particular conformation. It will be appreciated that it may be further determined whether the modified test compound also binds to the parent GPCR when residing in the particular conformation.

Various methods may be used to determine binding between a GPCR and a test compound including, for example, enzyme linked immunosorbent assays (ELISA), surface plasmon resonance assays, chip-based assays, immunocytofluorescence, yeast two-hybrid technology and phage display which are common practice in the art and are described, for example, in Plant et al (1995) *Analyt Biochem,* 226(2), 342-348. and Sambrook et al (2001) Molecular Cloning A Laboratory Manual. Third Edition. Cold Spring Harbor Laboratory Press, Cold Spring Harbor, N.Y. Other methods of detecting binding between a test compound and the GPCR include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

Where the mutant GPCR is provided as a whole cell preparation, a membrane protoplast or a proteoliposome, it will be appreciated that biophysical techniques such as patch clamping, magic angle spinning NMR, fluorescence correlation spectroscopy, fluorescence resonance energy transfer and analytical ultracentrifugation may be used to analyse binding of the mutant GPCR to the test compound (as described in New, R. C., *Liposomes: a practical approach.* 1st ed.; Oxford University Press: Oxford, 1990, and Graham, J. M.; Higgins, J. A., *Membrane Analysis*. Springer-Verlag: New York, 1997.) Methods which allow quantitative, non-invasive determination of both the affinity and kinetics of such interactions include direct assays that allow continuous monitoring of membrane-protein binding, or in some cases by ultra-rapid separation of bound and free interactants followed by quantification of the membrane-bound and membrane-free analyte.

It will be appreciated that a bound test compound can be detected using a unique label or tag associated with the compound such as a peptide label, a nucleic acid label (Kerr et al., JACS (1993) vol. 115, p. 2529-2531; and Brenner & Lerner, Proc. Natl. Acad. Sci. USA (1992) vol. 89, p. 5381-5383), a chemical label (Ohlmeyer et al., Proc. Natl. Acad. Sci. USA (1993) vol. 90, p. 109222-10926; and Maclean et al., Proc. Natl. Acad. Sci. USA (1997) vol. 94, p. 2805-2810); a fluorescent label (Yamashita & Weinstock (SmithKline Beecham Corporation), WO95/32425 (1995); and Sebestyen et al., Pept. Proc. Eur. Pept. Symp. 22nd 1992 (1993), p. 63-64), or a radio frequency tag (Nicolaou et al., Angew. Chem. Int. Ed. Engl. (1995) vol. 34, p. 2289-2291; and Moran et al., JACS (1995) vol. 117, p. 10787-10788).

Where the test compound is an antibody against a mutant GPCR with increased stability, produced using any of the methods described above, binding is preferably assayed using immunoprecipitation or by an in vitro binding assay, such as radioimmunoassay (RIA) or enzyme-linked immunoabsorbent assay (ELISA). Such techniques and assays are known in the art. For example, in an ELISA, typically, the stabilised GPCR is immobilised on a microtitre plate or other solid surface. The plates are first incubated with BSA or other similar protein to block non-specific binding sites. Samples containing the antibody (such as serum or egg yolk or hybridoma cell culture supernatant) are then added to the plate and the antibodies allowed to bind to the immobilised GPCR. Bound antibodies are detected by the addition of a second detection antibody which binds to the first antibody and allows detection via its conjugation to an enzyme which catalyzes a reaction which can be subsequently detected. In addition, the binding affinity of antibodies can also be determined by the Scatchard analysis of Munson and Pollard, Anal. Biochem, 107:220 (1980). Preferably, antibodies having a high degree of specificity and a high binding affinity for the target GPCR are isolated.

It will be appreciated that where the antibody is a monoclonal antibody derived from a hybridoma, the hybridoma clones identified as expressing specific antibody can subsequently be subcloned by limiting dilution procedures and grown using standard methods. Suitable culture media for this purpose include, for example, Dulbecco's Modified Eagle's Medium and RPMI-1640 medium. Alternatively, the hybridoma cells can be grown in vivo as ascites in a mammal. The monoclonal antibodies secreted by the subclones can then be isolated or further purified from the culture medium or ascites fluid by conventional immunoglobulin purification procedures such as, for example, protein A-Sepharose, hydroxylapatite chromatography, gel electrophoresis, dialysis, or affinity chromatography.

Where the test compound is a phage display antibody library, binding to a stabilised GPCR may be assessed as follows. Typically, the mutant GPCR with increased stability is coated onto wells of a microtiter plate overnight at 4° C. The wells are washed in PBS and blocked for 1 hour at 37° C. in MPBS (3% milk powder in PBS). Purified phage from a phagemid library e.g. expressing a repertoire of human scFv (10 transducing units (tu)) are then blocked for 1 hour in a final volume of 100 µl of 3% MPBS. The blocked phage are added to the blocked GPCR wells and incubated for 1 hour. Wells are washed 5 times with PBST (PBS containing 0.1% v/v Tween 20) before being wash 5 times with PBS. The bound phage particles are then eluted and used to infect 10 ml exponentially growing *E. coli* TG1. The infected cells are grown in 2TY broth for 1 hour at 37° C., then spread onto 2TYAG plates and incubated overnight at 30° C. Cultures from this first round of panning selection are superinfected with helper phage and rescued to give, for example, scFv antibody-expressing phage particles for the second round of panning.

An alternative binding assay for phage display antibodies includes the use of soluble selections using biotinylated mutant GPCR protein at a final concentration typically of 100 nM. In this case, purified scFv phage (1012 tu) from a scFv phagemid library (as described above) is suspended in 1 ml 3% MPBS and blocked for 30 minutes. The biotinylated GPCR is then added and incubated at room temperature for 1 hour. The phage/antigen complexes are subsequently added to 250 µl of Dynal M280 Streptavidin magnetic beads that have been blocked for 1 hour at 37° C. in 1 ml of 3% MPBS, and incubated with the beads for a further 15 minutes at room temperature. The beads are captured using a magnetic rack and washed 4 times in 1 ml of 3% MPBS/0.1% (v/v) Tween 20 followed by 3 washes in PBS. After the last PBS wash, beads are resuspended in 100 µl PBS and used to infect 5 ml exponentially growing *E. coli*. Again, cultures from this first round of soluble selection would be superinfected with helper phage and rescued to give scFv antibody-expressing phage particles for a second round of soluble selection.

It is appreciated that screening assays which are capable of high throughput operation are particularly preferred to determine binding to a mutant GPCR, for example chip-based assays. Stabilised mutant GPCRs are particularly suited to such assays unlike their parent GPCRs which are not stable enough when purified to be used in these formats. In particular, technology called VLSIPS™ has enabled the production of extremely small chips that contain hundreds of thousands or more of different molecular probes, i.e. the test compounds. These biological chips have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

A test compound to a mutant GPCR on a chip surface may be detected by scanning the chip surface for radioactivity or fluorescence. The address of the interacting pair on the chip reveals the identity of the test compound or where there is an array of mutant GPCRs on the chip, the identity of the receptor (see, for example, Kuimelis et al., Addressable Protein Arrays, U.S. Ser. No. 60/080,686, Apr. 3, 1998, now abandoned, and U.S. Ser. No. 09/282,734, Mar. 31, 1999). In the latter case the array of mutant GPCRs may be used as a method for obtaining selectivity data on compounds either for various conformations of the same GPCR or for various GPCRs.

Alternative methods of detecting binding of a mutant GPCR to a test compound, for example DNA, RNA, proteins and phospholipids, small molecules and natural products include surface plasmon resonance assays (SPA), for example as described in Plant et al (2005) *Analyt Biochem* 226(2), 342-348. The mutant GPCR, immobilised on a SPA bead, may be incubated with a single ligand which is labelled for example with a fluorescent group or the ligand may be a radioligand. The ability of a test compound to bind to the mutant GPCR may then be determined via its ability to displace the fluorescent ligand or the radioligand. In another example, the mutant GPCR is immobilised on a chip surface and binding of test compounds is detected by surface plasmon resonance and related techniques employing evanescent waves. Changes in refractive index can be used to determine the amount of bound compound, the affinity of interaction and the association and dissociation kinetics. An example of this approach has been described for rhodopsin which was immobilised on carboxylated dextran surfaces modified with long alkyl groups. Following amine coupling of the detergent-solubilised receptor, lipid/detergent-mixed micelles were adhered over the immobilized surface. The detergent was eluted in the subsequent buffer flow and the remaining lipid formed a bilayer on the chip surface. (Karlsson O P, Lofas S. Anal Biochem. 2002 Jan. 15; 300(2):132-8.

Where the test compound is a peptide or protein, for example, a ligand for an orphan receptor or an interacting protein, the bound ligand may be eluted and then identified by mass spectrometry such as matrix assisted laser desorption/ionization time of flight mass spectrometry (MALDI-TOF) or electrospray ionization mass spectrometry (ESI-MS) (Williams C. Addona T A. Trends Biotechnol. 2000 February; 18(2):45, Williams C Curr Opin Biotechnol. 2000 February; 11(1):42-6). The mutant GPCR may be immobilised on a column or bead, or expressed in tagged form in a cell and co-purified with the ligand from such complex mixtures using reagents directed to the tag or directly to the GPCR (Rigaut G, Shevchenko A, Rutz B, Wilm M, Mann M, Séraphin B. Nat. Biotechnol. 1999 October; 17(10):1030-2).

The ability to generate high affinity conformation specific binding partners to GPCRs will facilitate the production of therapeutic GPCR binding partners. Thus, it will be appreciated that in addition to establishing binding to a GPCR, it will also be desirable to determine the functional effect of a binding partner on the GPCR.

Accordingly, in an embodiment of the invention, the method further comprises determining if the binding partner affects the function of the GPCR to which it binds and isolating a test compound that affects the function of the GPCR.

For example, in one embodiment, it is determined whether the binding partner alters the binding of the GPCR to its ligand. By ligand, we include any molecule which binds to the GPCR and which causes the GPCR to reside in a particular conformation as described above. Preferably, the ligand is the natural ligand of that GPCR or an analogue thereof. Binding of a GPCR to its ligand can be assayed using standard ligand binding methods known in the art and, for example, as described above. For example, the ligand may be radiolabelled or fluorescently labelled. The binding assay can be performed using the stabilised mutant GPCR or the parent GPCR. Typically, the stabilised GPCR is purified or expressed in a cell such a mammalian, bacterial or insect cell. Typically, the parent receptor is expressed in a cell such as a mammalian, bacterial or insect cell. The assay may be carried out on whole cells or on membranes obtained from the cells. The binding partner will be characterised by its ability to alter the binding of the labelled ligand.

In one embodiment, the binding partner decreases binding between the GPCR and its ligand. For example, the binding partner may decrease binding by a factor of at least 2 fold, 3 fold, 4 fold, 5 fold, 10 fold, 15 fold, 20, fold, 50 fold, 100 fold, 250 fold, 500 fold or 1000 fold. Preferably, the binding partner decreases binding by a factor of between 100-1000 fold, such as between 10-100 fold.

In one embodiment, the binding partner increases binding between the GPCR and its ligand. For example, the binding partner may increase binding by a factor of at least 2 fold, 3 fold, 4 fold, 5 fold, 10 fold, 15 fold, 20, fold, 50 fold, 100 fold, 250 fold, 500 fold or 1000 fold. Preferably, the binding partner increases binding by a factor of between 100-1000 fold, such as between 10-100 fold.

In a further embodiment, it is determined whether the binding partner modulates activation of a GPCR. For example, if a mutant GPCR stabilised in an agonist conformation was provided in step (a) of the method of the invention, the binding partner selected may be an agonist binding partner and thus increase activation of the GPCR. If a mutant GPCR stabilised in an antagonist conformation was provided in step (a) of the method of the invention, the binding partner selected may be an antagonist binding partner and thus decrease activation of the GPCR.

In this assay the parent GPCR or stabilised mutant GPCR is expressed in vivo, for example, in mammalian or insect cells where the GPCR is allowed to couple to well know GPCR signal transduction pathways (Eglen R. M. Functional G protein-coupled receptor assays for primary and secondary screening. Comb Chem High Throughput Screen. 2005 June; 8(4):311-8). Such assays include: calcium mobilisation (Gonzalez J E, Maher M P. Cellular fluorescent indicators and voltage/ion probe reader (VIPR) tools for ion channel and receptor drug discovery. Receptors Channels. 2002; 8(5-6): 283-95, Dupriez V J, Maes K, Le Poul E, Burgeon E, Detheux M. Aequorin-based functional assays for G-protein-coupled receptors, ion channels, and tyrosine kinase receptors. Receptors Channels. 2002; 8(5-6):319-30), changes in cAMP levels (Weber M, Ferrer M, Zheng W, Inglese J, Strulovici B, Kunapuli P. A 1536-well cAMP assay for Gs- and Gi-coupled receptors using enzyme fragmentation complementation. Assay Drug Dev Technol. 2004 February; 2(1):39-49), activation of kinase pathways (Leroy D, Missotten M, Waltzinger C, Martin T, Scheer A. G protein-coupled receptor-mediated ERK1/2 phosphorylation: towards a generic sensor of GPCR activation. J Recept Signal Transduct Res. 2007; 27(1):83-97), regulation of gene transcription for example via the use of a reporter gene (Liu B, Wu D. Analysis of the coupling of G12/13 to G protein-coupled receptors using a luciferase reporter assay. Methods Mol. Biol. 2004; 237:145-9, Kent T C, Thompson K S, Naylor L H. Development of a generic dual-reporter gene assay for screening G-protein-coupled receptors J Biomol Screen. 2005 August; 10(5):437-46), recruitment of β-arrestin (Hudson C C, Oakley R H, Sjaastad M D, Loomis C R. High-content screening of known G protein-coupled receptors by arrestin translocation Methods Enzymol. 2006; 414:63-78), activation of G proteins such as measuring GTPase activity (Jameson E E, Roof R A, Whorton M R, Mosberg H I, Sunahara R K, Neubig R R, Kennedy R T. Real-time detection of basal and stimulated G protein GTPase activity using fluorescent GTP analogues. J Biol. Chem. 2005 Mar. 4; 280(9):7712-9) or measuring [35S]GTPgamma(γ)S binding (Rodgers G, Hubert C, McKinzie J, Suter T, Statnick M, Emmerson P, Stancato L. Development of displacement binding and GTPgammaS scintillation proximity assays for the identification of antagonists of the micro-opioid receptor. Assay Drug Dev Technol. 2003 October; 1(5):627-36).

Binding partners are typically selected which modulate the activation of the receptor.

For agonist binding partners the binding partner will typically mimic the activity of the natural ligand of the receptor and produce an increase in receptor activation, G protein activation or signal transduction. This will occur in the absence of an additional agonist. An agonist binding partner may increase receptor activation by a factor of at least 2 fold, 3 fold, 4 fold, 5 fold, 10 fold, 15 fold, 20, fold, 50 fold, 100 fold, 250 fold, 500 fold, 1000 fold, or 10000 fold.

It will be appreciated that there are two ways in which a binding partner may increase receptor activation. For example, the binding partner may act as a direct agonist, in which case receptor activation is typically increased by between 2-1000 fold. In another method, the binding partner may act to amplify the activity of an agonist. For example, the binding partner may increase the potency of the agonist, in which case receptor activation is typically increased by between 2-1000 fold, such as between 10-100 fold, or the binding partner may increase the maximal response produced by the agonist, in which case receptor activation is typically increased by between 2-10 fold. It will be appreciated that activating/amplifying the activity of receptors that are already switched on by endogenous ligand may be preferable to turning on all available receptors, since it is more physiologically specific and may mitigate issues such as desensitisation and undesirable side-effects (Christopoulos A (2002) Nat Rev Drug Discov 1:198-210).

In the case of antagonist binding partners the binding partner will typically act to block the activity of the receptor or its activation by an agonist. The antagonist binding partner may do this by blocking the binding of the agonist or by locking the receptor in an inactive form such that it is unable to couple to G proteins. An antagonist binding partner may decrease receptor activation by a factor of at least 2 fold, 3 fold, 4 fold, 5 fold, 10 fold, 15 fold, 20, fold, 50 fold, 100 fold, 250 fold, 500 fold, 1000 fold or 10000 fold. Typically, an antagonist binding partner would reduce receptor activation to a non-detectable level.

It will be appreciated that it may be desirable to produce a test compound or combination of test compounds that bind to more than one GPCR. For example, the test compound may bind to more than one GPCR of the same class of family. A list of GPCR classes and families has been produced by the International Union of Pharmacology (Foord et al (2005) *Pharmacol. Rev.* 57, 279-288) and this list is periodically updated at iuphar-db.org/GPCR/ReceptorFamiliesForward. The test compound may bind to one target GPCR and at least one further GPCR. The at least one further GPCR may be a GPCR that has been implicated in a disease pathway, or a GPCR that is involved in the same signalling pathway as the target GPCR, for example a signalling pathway that regulates or modulates a disease pathway. In addition, the at least one further GPCR may be one which enhances or suppresses the action of a test compound on the target GPCR. Such enhancement or suppression of action can be determined using methods well known in the art including binding assays and functional assays as described, for example, above.

Accordingly, in one embodiment more than one mutant GPCR is provided in step (a). For example, at least 2, 3, 4 or 5 mutant GPCRs of a different parent GPCR may be provided in step (a). Thus, in this embodiment, test compounds are selected for which bind to more than one GPCR. The compound may be a cross-reactive compound including, for example, a small molecule, affibody, antibody or diabody. It will be appreciated that such an approach may lead to improvements in a binding partner's efficacy or potency.

Thus, a test compound may be selected which binds to a first and second GPCR, where the first and second GPCRs may be any pair of GPCRs. For example, the method can be used to select for a bivalent partner that binds to GPCRs which form a heterodimer, in which case the bivalent partner could bind to both receptors at the same time. Examples of appropriate GPCR heterodimers in this context include dopamine D1 and adenosine A1, opioid receptor heterodimers, cannabinoid CB1 and orexin receptors (Marshall F H. Heterodimerization of G-protein-coupled receptors in the CNS. Curr Opin Pharmacol. 2001 February; 1(1):40-4; Kent T, McAlpine C, Sabetnia S, Presland J. G-protein-coupled receptor heterodimerization: assay technologies to clinical significance. Curr Opin Drug Discov Devel. 2007 September; 10(5):580-9). Moreover, a binding partner could be selected for which binds to and modulates the activity of two independent receptors for the purpose of enhanced therapeutic activity. For example, CCK1/opioid receptor peptides bind to both CCK1 and the opoid receptor (García-López M T, González-Muñiz R, Martín-Martínez M, Herranz R. Strategies for design of non peptide CCK1R agonist/antagonist ligands. Curr Top Med Chem. 2007; 7(12):1180-94). Other appropriate examples include a combined beta 2 agonist and muscarinic antagonist; a dopamine D2 antagonist and 5HT2 antagonist; a D2 antagonist and 5HT6 antagonist; and a M1 agonist and 5HT6 antagonist.

It will be appreciated that the more than one GPCR provided in step (a) may or may not reside in the same conformation. For example, a diabody or similar bivalent binding partner may agonise at one end of the molecule and antagonise at another end, in which case the GPCRs would not have to reside in the same conformation.

Typically, where a test compound is selected that binds to more than one GPCR, the test compound binds to each GPCR with a similar potency. Typically, the $K_d$ values for the particular binding partner binding to each of the respective GPCRs are within 5-10 fold of each other, such as within 2-3 fold.

It will be appreciated that the methods of the invention allow for combinations of test compounds that bind to one or more GPCRs to be isolated, either by repeating the method with single test compounds, providing multiple test compounds in one cycle of the method or by using a library of test compounds in the method.

In a further embodiment, it may be advantageous to select those test compounds which, while still able to bind to a first GPCR, are not able to bind, or bind less strongly than to the first GPCR, to at least one other GPCR, for example a second GPCR. It will be appreciated that the first and second GPCRs may be any pair of GPCRs. Thus, for example, the test compound may be one that is selected on the basis that it binds to a first GPCR, but the test compound so selected is further tested to determine whether it binds a second GPCR (or binds less strongly to a second GPCR than the first GPCR). Test compounds are selected which do not bind (or have reduced binding to) the second GPCR. Where the binding partner is therapeutic molecule, such an approach may help to reduce the binding partner's toxicity.

It is preferred that the test compound binds the further (second) GPCR with an affinity which is less than 50% of the affinity the compound has for first GPCR, more preferably less than 10% and still more preferably less than 1% or 0.1% or 0.01% of the affinity the compound has for the first GPCR. Thus, the $K_d$ for the interaction of the test compound with the first GPCR is higher than for the second GPCR.

A second aspect of the invention provides a method for producing a binding partner of a GPCR, the method comprising synthesising a binding partner identifiable by carrying out the method according to the first aspect of the invention.

The binding partners can be synthesised by any suitable method known in the art including the techniques of organic chemistry, molecular biology or biochemistry. For example, if the binding partner is a polypeptide, the binding partner may be made by expressing the nucleic acid molecule encoding the binding partner in a suitable host cell as is known in the art. Antibodies may be synthesised using any of the methods described above including, for example, recombinant DNA technology.

A third aspect of the invention provides a binding partner obtained by any of the methods of the first aspect of the invention.

In an embodiment, the binding partner is a conformation-specific binding partner, as described above.

A fourth aspect of the invention provides a binding partner, for example a conformation-specific binding partner, obtainable by any of the methods of the first aspect of the invention.

The binding partner may be any of a polypeptide; an anticalin; a peptide; an antibody; a chimeric antibody; a single chain antibody; an aptamer; a darpin; a Fab, F(ab')$_2$, Fv, ScFv or dAb antibody fragment; a small molecule; a natural product; an affibody; a peptidomimetic; a nucleic acid; a peptide nucleic acid molecule; a lipid; a carbohydrate; a protein based on a modular framework including ankyrin repeat proteins, armadillo repeat proteins, leucine rich proteins, tetrariopeptide repeat proteins or Designed Ankyrin Repeat Proteins (DARPins); or proteins based on lipocalin or fibronectin domains or Affilin scaffolds based on either human gamma crystalline or human ubiquitin.

In a preferred embodiment, the binding partner is an antibody. For example, the antibody may be specific to a non-contiguous epitope in the GPCR or may be specific to a contiguous epitope in the GPCR. Preferably, the relevant epitopes in the parent and mutant GPCR recognised by the antibody are similar, whether they be contiguous or non-contiguous. Specifically, extracellular epitopes such as C- or N-termini or polypeptide loops of the parent and mutant GPCR are preferably similar.

Typically the binding partner to the mutant GPCR with a similar potency to its binding to the parent GPCR. Typically, the $K_d$ values for the particular binding partner binding the mutant GPCR and the parent GPCR are within 5-10 fold of each other, such as within 2-3 fold. Typically, the binding of the binding partner to the mutant GPCR compared to the parent GPCR would be not more than 5 times weaker and not more than 10 times stronger.

Typically, mutant receptors which have been stabilised in the selected conformation should bind the binding partner with approximately equal affinity (that is to say typically within 2-3 fold) or greater affinity than does the parent receptor. For agonist-conformation binding partners, the mutants typically bind the agonists with the same or higher affinity than the parent GPCR and typically bind antagonists with the same or lower affinity than the parent GPCR. Similarly for antagonist-conformation binding partners, the mutants typically bind the antagonists with the same or higher affinity than the parent GPCR and typically bind agonists with the same or lower affinity than the parent GPCR.

It is appreciated that the methods of the invention may be used as a biosensor to detect target substances such as molecules, especially biomolecules. For example, the biosensor may be used to detect biomarkers of disease or drug treatment which may be used as a diagnostic or prognostic. The mutant GPCR may be immobilised on a sensor surface and binding of compounds detected, for example, by surface plasmon resonance as described above. In a further example of a biosensor, compound binding to the receptor can be detected by changes in intrinsic tryptophan fluorescence or using fluorescence resonance energy transfer between an intrinsic tryptophan resident donor and a fluorescent acceptor (Lakowicz J R 1999. Principles of fluorescence spectroscopy, Plenum New York, Martin D D, Budamagunta M S, Ryan R O, Voss J C, Oda M N. J Biol Chem. 2006 Jul. 21; 281(29):20418-26). Alternatively, mutant GPCRs may be used in acoustic biosensors, wherein the mutant GPCRs are immobilised on quartz crystal resonator sensors (QCRS) and the acoustic sensor response used to detect compound—mutant GPCR binding interactions (Cooper M A, Drug Discov Today. 2006 December; 11(23-24):1068-74. Epub 2006 Oct. 20).

Accordingly, a fifth aspect of the invention provides a biosensor comprising a mutant GPCR of a parent GPCR wherein the mutant GPCR has increased stability in a particular conformation relative to the parent GPCR, and wherein when a target substance binds to said mutant GPCR, a detectable signal is produced.

Preferences for the mutant GPCRs and their methods of production are as defined above with respect to the first aspect of the invention.

Preferably, the biosensor is in a chip form or a bead supported form, where the mutant GPCRs are immobilised on a chip or bead and used to detect target substances. However, it will be appreciated that the mutant GPCRs may be provided in soluble form, in which case the biosensor would comprise a solution.

Immobilisation of mutant GPCRs onto a solid support for incorporation into a biosensor can be performed using methods well known in the art and as described above with respect to the first aspect of the invention. Typically, mutant GPCRs are reconstituted onto chip surfaces suitable for direct biosensor analysis via flow-mediated surface reconstitution (Karlsson et al., Analytical Biochemistry 300, 132-138 (2002)). For example, rapid immobilization and reconstitution of GPCRs on carboxylated dextran surfaces modified with long alkyl groups can be achieved following amine coupling of a detergent-solubilized receptor; lipid/detergent-mixed micelles are adhered as they are injected over the immobilized surface, taking advantage of integrated flow cells present in many biosensor systems. The detergent can then be eluted in the subsequent buffer flow leaving functional, intact mutant GPCRs for subsequent screening and analysis. Such mutant GPCR preparations containing detergent are ideally suited for use in a flow-based biosensor, such as quartz crystal microbalance biosensor, an evanescent wave biosensor, a planar wave guide biosensor, a surface Raman sensor, or a surface plasmon resonance biosensor. In the latter case, solubilized receptors can be captured on a GE Healthcare (Biacore) CM4 or CM5 dextran sensor chip. The dextran matrix of the sensor chip is activated by 35 uL of 50 mM N-hydroxysuccinimide and 200 mM N-ethyl-N-[(dimethylamino)propyl] carbodiimide at a flow rate of 5 uL/min, followed by a 7-min injection of 0.1 mg/mL detergent-solubilised GPCR receptor (for example with 25 mM CHAPS in 10 mM MOPS, pH 7.5). Any remaining reactive carboxy groups are deactivated using a 7-min pulse of 1 M ethanolamine hydrochloride, pH 8.5. After the injection, the biosensor chip is washed at high flow rate with the surface plasmon resonance running solution until a stable baseline is restored (ca. 30 min). This washing step works like a flow dialysis procedure and ensures the removal of the detergent from the sensor chip surface; however, it will be appreciated that hydrophobic parts of the GPCR may still be attached to some lipid or detergent molecules in order to maintain functional integrity.

The target substance may be any of a molecule, a biomolecule, a peptide, a protein, a carbohydrate, a lipid, a GPCR ligand, a synthetic molecule, a drug, a drug metabolite or a disease biomarker.

In an embodiment, the detectable signal is any of a change in colour; fluorescence; evanescence; surface plasmon resonance; electrical conductance or charge separation; ultraviolet, visible or infrared absorption; luminescence; chemiluminescence; electrochemiluminescence; fluorescence anisotropy; fluorescence intensity; fluorescence lifetime; fluorescence polarisation; fluorescence energy transfer; molecular mass; electron spin resonance; nuclear magnetic resonance; hydrodynamic volume or radius; specific gravity; scintillation; field effect resistance; electrical impedance; acoustic impedance; quantum evanescence; resonant scattering; fluorescent quenching; fluorescence correlation spectroscopy; acoustic load; acoustic shear wave velocity; binding force; or interfacial stress.

Example 1

Conformational Stabilisation of the β-Adrenergic Receptor in Detergent-Resistant Form Summary There are over 500 non-odorant G protein-coupled receptors (GPCRs) encoded by the human genome, many of which are predicted to be potential therapeutic targets, but there is only one structure available, that of bovine rhodopsin, to represent the whole of the family. There are many reasons for the lack of progress in GPCR structure determination, but we hypothesise that improving the detergent-stability of these receptors and simultaneously locking them into one preferred conformation will greatly improve the chances of crystallisation. A generic strategy for the isolation of detergent-solubilised thermostable mutants of a GPCR, the β-adrenergic receptor, was developed based upon alanine scanning mutagenesis followed by an assay for receptor stability. Out of 318 mutants tested, 15 showed a measurable increase in stability. After optimisation of the amino acid residue at the site of each initial mutation, an optimally stable receptor was constructed by combining specific mutations. The most stable mutant receptor, βAR-m23, contained 6 point mutations that led to a Tm 21° C. higher than the native protein and, in the presence of bound antagonist, βARm23 was as stable as bovine rhodopsin. In addition, βAR-m23 was significantly more stable in a wide range of detergents ideal for crystallisation and was preferentially in an antagonist conformation in the absence of ligand.

Results

Selection of Single Mutations that Increase the Thermostability of the β1 Adrenergic Receptor βAR from turkey erythrocytes is an ideal target for structural studies because it is well characterised and is expressed at high-levels in insect cells using the baculovirus expression system[10,11]. The best overexpression of βAR is obtained using a truncated version of the receptor containing residues 34-424 (βAR$_{34-424}$) [9] and this was used as the starting point for this work. Alanine scanning mutagenesis was used to define amino residues in βAR$_{34-424}$ that, when mutated, altered the thermostability of the receptor; if an alanine was present in the sequence it was mutated to a leucine residue. A total of 318 mutations were made to amino acid residues 37-369, a region that encompasses all seven transmembrane domains and 23 amino acid residues at the C terminus; mutations at 15 amino residues were not obtained due to strong secondary structure in the DNA template. After sequencing each mutant to ensure the presence of only the desired mutation, the receptors were functionally expressed in E. coli and assayed for stability.

Figure 7:
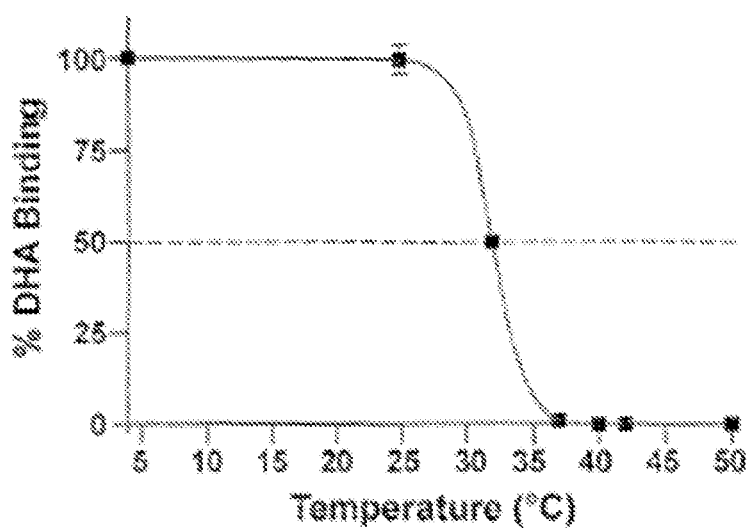
FIG. 7 Curve of thermostability of βAR$_{34-424}$ (Tm). Binding assays were performed using [$^3$H]-dihydroalprenolol (DHA) as radioligand as described under "Methods". Samples were heated for 30 minutes at different temperatures before the assay. Tm represents the temperature at which the binding decreased to the 50%, value showed as a discontinuous line. Data points are from duplicates of one single experiment. This experiment has been repeated several times with similar results.

The assay for thermostability was performed on unpurified detergent-solubilised receptors by heating the receptors at 32° C. for 30 minutes, quenching the reaction on ice and then performing a radioligand binding assay, using the antagonist [$^3$H]-dihydroalprenolol, to determine the number of remaining functional βAR$_{34-424}$ molecules compared to the unheated control. Heating the unmutated βAR$_{34-424}$ at 32° C. for 30 min before the assay reduced binding to approximately of 50% unheated control (FIG. 7); all the data for the mutants were normalised by including the unmutated βAR$_{34-424}$ as a control in every assay performed. In the first round of screening, eighteen mutants showed an apparent increase in stability, maintaining more than 75% of antagonist binding after heating and being expressed in E. coli to at least 50% of the native βAR$_{34-424}$ levels. In view of the possibility of increasing further the stability of these mutants, each of the 18 residues was mutated to 2-5 alternative amino acid residues of varying size or charge (FIG. 1). Out of these 18 mutants, 12 were not improved by further changes, 5 had better thermostability if another amino acid was present and one mutation from the first screen turned out to be a false positive. In addition, three residues that were not stabilised upon mutation to alanine (V89, S151, L221) were mutated to a range of other amino acid residues; the two positions that when mutated to alanine did not affect thermostability, were also unaffected by other changes. In contrast, V89 showed less thermostability when mutated to alanine, but thermostability increased when it was mutated to Leu. Thus the initial alanine scanning successfully gave two-thirds of the best amino acid residues of those tested for any given position.

Figure 2:
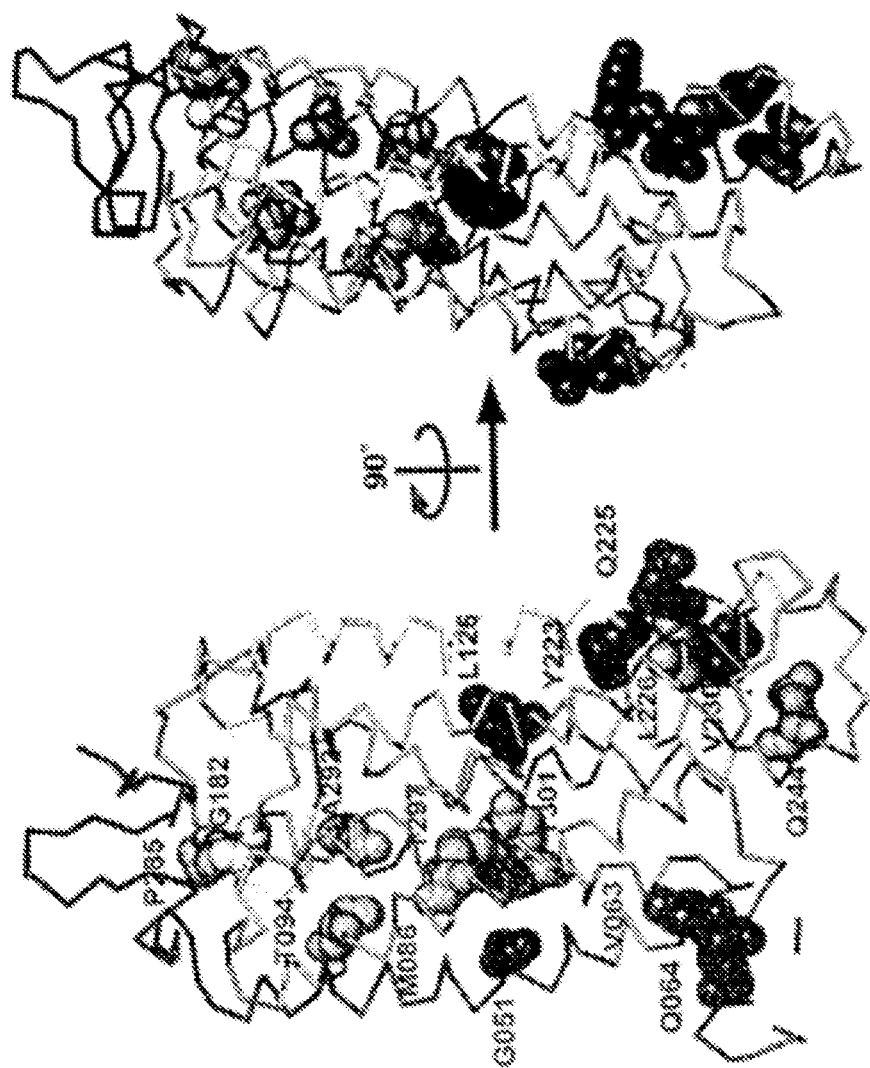
FIG. 2 Side chains in rhodopsin that are at equivalent positions to the thermostable mutations in βAR$_{34-424}$. The equivalent amino acid residues in rhodopsin to the amino acid residues mutated in βAR$_{34-424}$ were located in the rhodopsin structure, based upon an alignment among rhodopsin, β1 adrenergic receptor, neurotensin receptor, and adenosine A$_{2a}$ receptor (data not shown). Side chains in the same transmembrane helix are shown as space filling models in the same colour. The name and position of the amino acid residues are those in rhodopsin.

The position and environment predicted for each of the 16 amino residues that gave the best increases in thermostability when mutated were determined by aligning the βAR sequence with that of rhodopsin whose structure is known (FIG. 2). Fourteen of these residues were predicted to be present in transmembrane α-helices, with five of the residues predicted to be lipid-facing, 4 being deeply buried and the remainder were predicted to be at the interfaces between the helices. Some of these residues would be expected to interact with each other in the βAR structure, such as the consecutive amino acids G67 and R68 (V63 and Q64 in rhodopsin), or the amino acids within the cluster Y227, R229, V230 and A234 in helix 5 (Y223, Q225, L226 and V230 in rhodopsin). Other amino acid residues that could interact in βAR were Q194A in external loop 2 and D322A in external loop 3 (G182 and P285 in rhodopsin, respectively).

The increase in stability that each individual mutation gave to βAR$_{34-424}$ was determined by measuring the Tm for each mutant (results not shown); Tm in this context is the temperature that gave a 50% decrease in functional binding after heating the receptor for 30 minutes. Each mutation increased the Tm of βAR$_{34-424}$ by 1-3° C., with the exception of M90A and Y227A that increased the Tm by 8° C.

Combining Mutations to Make an Optimally Stable Receptor

Initially, mutations that improved thermostability that were adjacent to one another in the primary amino sequence of βAR were combined. Constructions containing the mutations G67A and R68S, or different combinations of the mutations at the end of helix 5 (Y227A, R229Q, V230A and A234L) were expressed and assayed; the Tm values (results not shown) were only 1-3° C. higher than the Tm for βAR$_{34-424}$ and one mutant was actually slightly less stable, suggesting that combining mutations that are adjacent to one another in the primary amino acid sequence does not greatly improve thermostability. Subsequently, mutations predicted to be distant from one another in the structure were combined. PCR reactions were performed using various mixes of primers to combine up to 5 different mutations in a random manner and then tested for thermostability (Table 1). The best of these combinations increased the Tm more than 10° C. compared to the Tm of βAR$_{34-424}$. In some cases, there was a clear additive effect upon the Tm with the sequential incorporation of individual mutations. This is seen in a series of 3 mutants, m4-1, m4-7 and m4-2, with the addition of V230A to m4-1 increasing the Tm by 2° C. and the additional mutation D332A in m4-7 increasing the Tm a further 3° C. Mutants that contained Y227A and M90A all showed an increase in Tm of 10° C. or more. Just these two mutations together increased the Tm of βAR$_{34-424}$ by 13° C. (m7-5), however, the total antagonist binding was less than 50% of βAR$_{34-424}$ suggesting impaired expression of this mutant. The addition of F338M to m7-5 did not increase the thermostability, but it increased levels of functional expression in E. coli.

TABLE 1

Combinations of mutations by PCR. 10 PCR reactions were performed combining different pairs of primers that contained the selected mutations. Successful PCR reactions are shown in the table. The stability of these new mutants was assayed as described in FIG. 7 and the Tm calculated. The results are shown as the mean ± S.E. from duplicates.

| PCR | Receptor | Mutations | $T_m$ (° C.) |
|---|---|---|---|
|  | βAR$_{34-424}$ |  | 31.7 ± 0.1 |
| 4 | m4-1 | G67A, G98A | 35.5 ± 0.9 |
|  | m4-2 | G67A, G98A, V230A, D322A | 40.9 ± 0.9 |
|  | m4-6 | G98A, D322A | 35.0 ± 0.2 |
|  | m4-7 | G67A, G98A, V230A | 38.0 ± 1.2 |
| 6 | m6-1 | Y227A, A234L, A282L, A334L | 41.6 ± 0.9 |
|  | m6-4 | R68S, Y227A, A234L, A282L | 41.6 ± 0.1 |
|  | m6-5 | R68S, A234L, A282L, A334L | 41.9 ± 0.5 |
|  | m6-9 | R68S, Y227A, A234L, A282L, A334L | 43.7 ± 0.4 |
|  | m6-10 | R68S, Y227A, A282L, A334L | 47.4 ± 1.1 |
|  | m6-11 | R68S, A282L, A334L | 39.1 ± 0.5 |
| 7 | m7-1 | M90V, A282L, F338M | 43.0 ± 0.8 |
|  | m7-2 | M90V, A282L | 38.9 ± 0.6 |
|  | m7-5 | M90V, Y227A | 45.2 ± 1.0 |
|  | m7-6 | M90V, I129V | 40.0 ± 0.6 |
|  | m7-7 | M90V, Y227A, F338M | 45.2 ± 2.0 |
| 10 | m10-4 | R68S, M90V, V230A, A334L | 46.9 ± 1.0 |
|  | m10-8 | R68S, M90V, V230A, F327A, A334L | 47.3 ± 1.4 |

Figure 3:
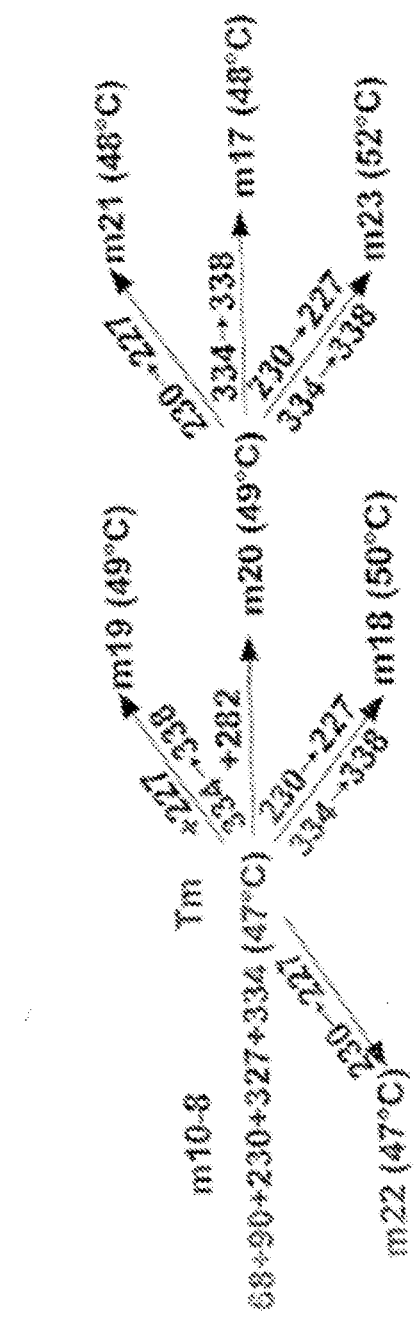
FIG. 3 Evolution of thermostability in βAR. Starting from βAR-m10-8, combinations of mutations were rearranged systematically to find the optimum combination of mutations (see also Table 2).

The most thermostable mutants obtained, which were still expressed at high levels in E. coli, were m6-10, m7-7 and m10-8. These mutants contained collectively a total of 10 different mutations, with 8 mutations occurring in at least two of the mutants. A second round of mutagenesis was performed using m10-8 as the template and adding or replacing mutations present in m6-10 and m7-7 (FIG. 3); some of these mutations were very close in the primary amino acid sequence of βAR and therefore were not additive as noted above, but many mutations improved the Tm further (Table 2). For example, exchanging two mutations in m10-8, to create m18, raised the Tm to 49.6° C. and adding A282L to make m23 increased the Tm a further 3° C. to 52.8° C. This produced the most thermostable $\beta AR_{34\text{-}424}$ mutant so far and will be referred to as $\beta AR$-m23.

TABLE 2

Improvement of best combination of mutations. These new mutants were obtained mixing the changes present in mutants m6-10, m7-7 and m10-8 by PCR. The stability of these new mutants was assayed as described in FIG. 7 and the Tm calculated. The results are shown as the mean ± S.E. from duplicates.

| | | | Mutations | | | | | | $T_m$ (° C.) |
|---|---|---|---|---|---|---|---|---|---|
| m17 | R68S | M90V | Y227A | V230A | — | F327A | A334L | — | 48.2 ± 1.4 |
| m18 | R68S | M90V | Y227A | V230A | A282L | F327A | — | F338M | 49.6 ± 0/9 |
| m19 | R68S | M90V | Y227A | — | A282L | F327A | — | F338M | 49.0 ± 0.8 |
| m20 | R68S | M90V | — | — | — | F327A | A334L | — | 48.4 ± 0.7 |
| m21 | R68S | M90V | Y227A | — | — | F327A | A334L | — | 47.0 ± 1.3 |
| m22 | R68S | M90V | Y227A | — | — | F327A | A334L | — | 47.4 ± 0.5 |
| m23 | R68S | M90V | Y227A | — | A282L | F327A | — | F338M | 52.8 ± 1.4 |

Figure 4:
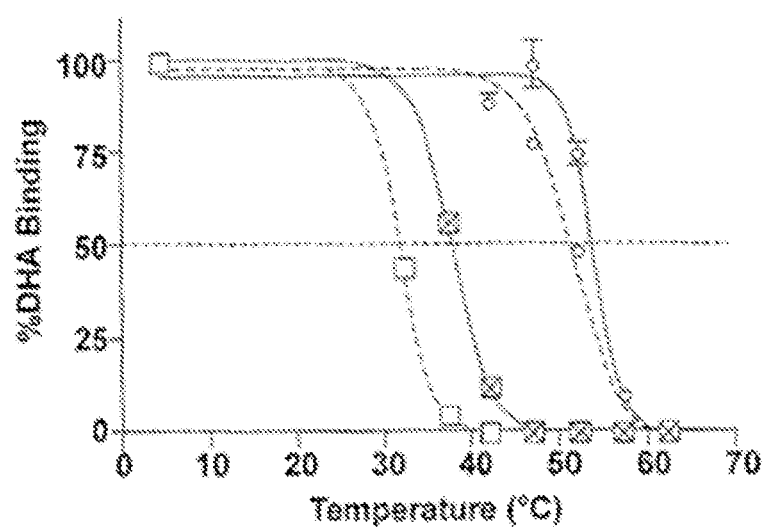
FIG. 4 Stability of βAR-m23 and βAR$_{34-424}$ in the apo-state or containing the bound antagonist [$^3$H]-DHA. To determine Tm in the absence of ligand (apo-state, discontinuous lines), detergent-solubilised receptors were incubated for 30 minutes at the temperatures indicated before carrying out the binding assay. For the Tm determination of the antagonist-bound form (continuous lines), detergent-solubilised receptors were pre-incubated with [$^3$H]-DHA, followed by incubation at the temperatures indicated. βAR-m23 (circles), and βAR$_{34-424}$ (squares). Data points are from duplicates measurements in a representative experiment.

The thermostability assays used to develop $\beta AR_{34\text{-}424}$ mutants were performed by heating the receptor in the absence of the antagonist, but it is well known that bound ligand stabilises receptors. Therefore, stability assays for $\beta AR_{34\text{-}424}$ and $\beta AR$-m23 were repeated with antagonist bound to the receptors during the heating step (FIG. 4). As expected, the Tm of the receptor that contained bound antagonist during the incubation was higher than that for the receptor without antagonist. For $\beta AR_{34\text{-}424}$ the Tm was 6° C. higher with bound antagonist and for $\beta AR$-m23 the Tm increased 2° C. to 55° C.; the smaller increase in thermostability observed for $\beta AR$-m23 when antagonist binds suggests that the receptor is already in a more stable conformation similar to the antagonist bound state than $\beta AR_{34\text{-}424}$ (see also below). The Tm of $\beta AR$-m23 with antagonist bound is very similar to the Tm of dark-state rhodopsin in dodecylmaltoside (DDM)[12], whose structure has been solved by two independent laboratories[13,14]. This suggested that $\beta AR$-m23 is sufficiently stable for crystallisation.

Characterization of $\beta AR$-m23

Figure 5A:
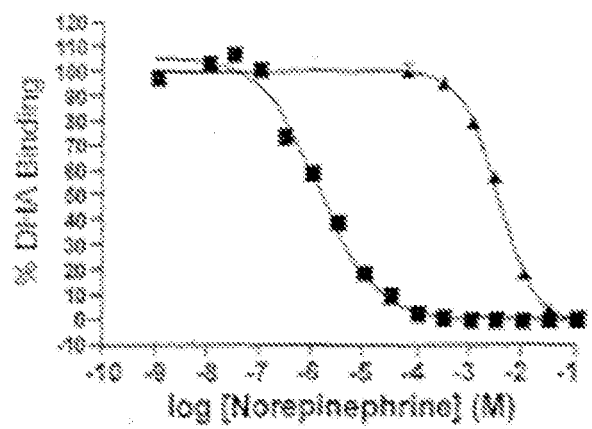
FIGS. 5A-C Competition binding of agonists to βAR-m23 and βAR$_{34-424}$. Binding assays were performed on receptors partially purified in DDM; βAR-m23 (triangles) and βAR$_{34-424}$ (squares). [$^3$H]-DHA was used at a concentration three times greater than the K$_D$ of partially purified receptor (see Methods). [$^3$H]-DHA binding was competed with increasing concentrations of the agonists, norepinephrine (a) and isoprenaline (b), or with an antagonist, alprenolol (c). LogEC$_{50}$ and corresponding EC$_{50}$ values for the different ligands were calculated by nonlinear regression using GraphPad Prism software and the error for logEC$_{50}$s were lower than 10%. The EC$_{50}$s for ligand binding to βAR$_{34-424}$ and βAR-m23 are: norepinephrine, βAR$_{34-424}$ 1.5 μM, βAR-m23 3.7 mM; isoprenaline, βAR$_{34-424}$ 330 nM, βAR-m23 20 μM; alprenolol, βAR 78 nM, βAR-m23 112 nM.
Figure 5B:
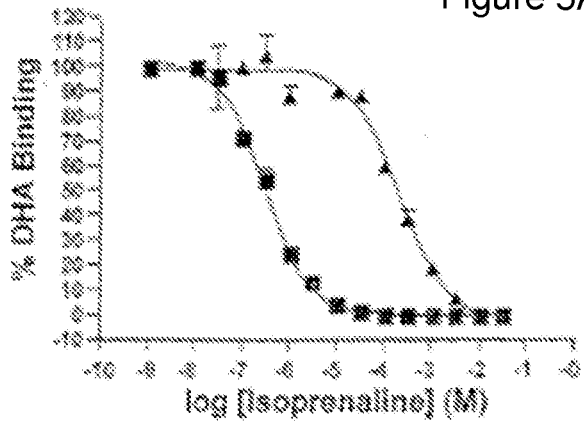
Figure 5C:
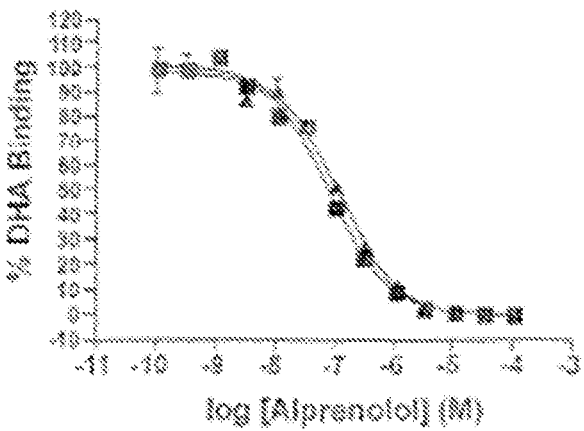
Figure 8A:
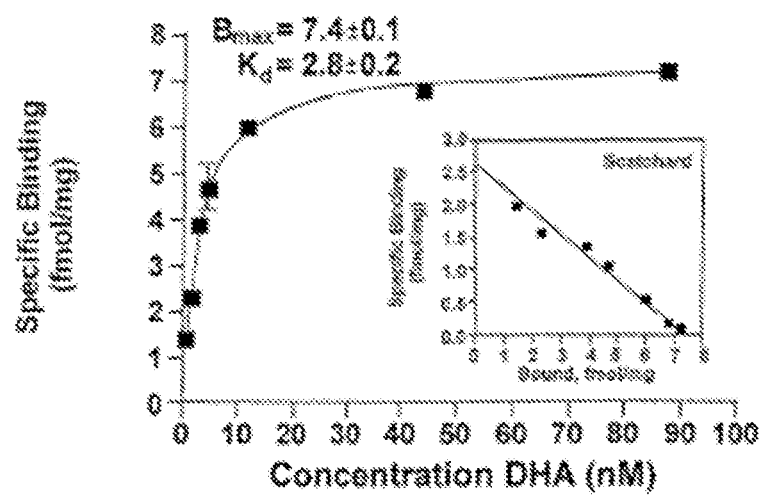
FIGS. 8A and 8B Saturation binding assays of membranes of βAR$_{34-424}$ and βAR-m23. Binding assays were performed as described in "Methods" using [$^3$H]-dihydroalprenolol (DHA) as radioligand; βAR$_{34-424}$ (a) and βAR-m23 (b). Scatchard plots are shown as insets along with the corresponding values for B$_{max}$ and K$_D$. Data points are from duplicates of two independent experiments for each protein. Data were analyzed by nonlinear regression using Prism software (Graph Pad).
Figure 8B:
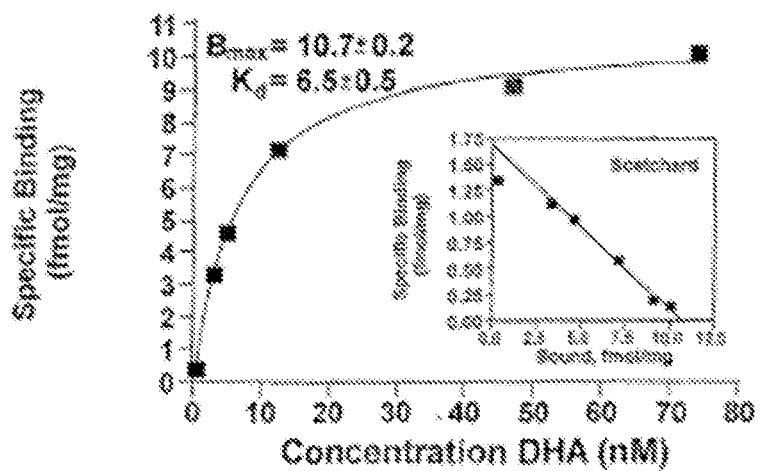

The three characteristic activities measured for $\beta AR$-m23 and $\beta AR_{34\text{-}424}$ to identify the effect of the six mutations were the affinity of antagonist binding, the relative efficacies of agonist binding and the ability of $\beta AR$-m23 to couple to G proteins. Saturation binding experiments to membranes using the antagonist [$^3$H]-dihydroalprenolol (FIGS. 8A and 8B) showed that the affinity of binding to $\beta AR$-m23 ($K_D$ 6.5±0.2 nM, n=2) was slightly lower than for $\beta AR_{34\text{-}424}$ ($K_D$ 2.8±0.1 nM, n=2), suggesting that there are no large perturbations in the structure of $\beta AR$m23 in the antagonist-bound conformation. This is consistent with the observation that none of the mutations in $\beta AR$-m23 correspond with amino acids believed to be implicated in ligand binding. In contrast to antagonist binding, the efficacy of agonist binding by $\beta AR$-m23 is 3 orders of magnitude weaker than for $\beta AR_{34\text{-}424}$ (FIG. 5). The potency of the agonist isoprenaline is consistently lower in $\beta AR$-m23 and $\beta AR_{34\text{-}424}$ than for the native agonist norepinephrine, indicating that the agonist-bound conformation for the two receptors is likely to be similar. However, the large decrease in agonist efficacy in $\beta AR$-m23 compared to $\beta AR_{34\text{-}424}$ indicates that the 6 mutations in $\beta AR$-m23 have locked the receptor preferentially in an antagonist-bound conformation. From a crystallisation perspective, this is an added bonus to thermostabilisation, because it is essential to have a conformationally homogeneous protein population for the production of diffraction-quality crystals.

Figure 6A:
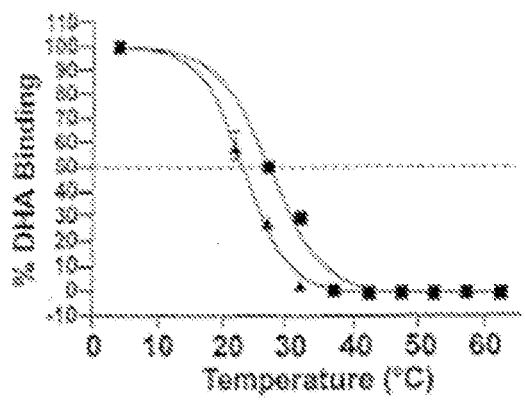
FIGS. 6A-C Stability of βAR-m23 and βAR$_{34-424}$ in five different detergents. Samples of βAR$_{34-424}$ (a), and βAR-m23 (b) solubilized in DDM were partially purified on Ni-NTA agarose columns allowing the exchange into various different detergents: DDM (squares), DM (triangles), OG (inverted triangles), LDAO (diamonds) and NG (circles). βAR is so unstable in OG, NG and LDAO that it was not possible to measure any activity after purification at 6° C. Assays were carried out as described in the Methods and the Tm is shown at the intersection between the curves and the discontinuous line. Results are from duplicate measurements in a representative experiment performed in parallel. (c) Photomicrograph of a crystal of βAR-m23 mutant, which showed good order by X-ray diffraction.
Figure 6B:
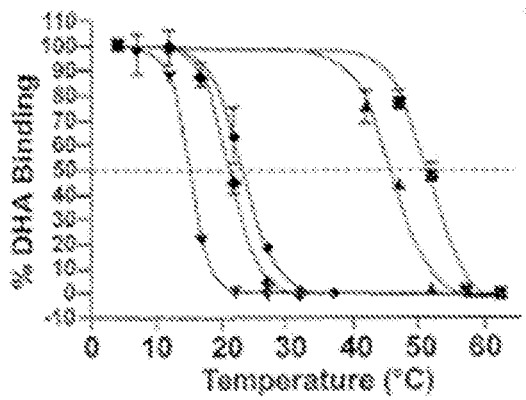
Figure 6C:
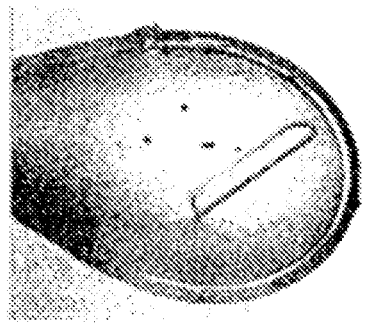

All of the thermostability assays used to derive $\beta AR$-m23 were performed on receptors solubilised in DDM. The aim of the thermostabilisation process was to produce a receptor that is ideal for crystallography, which means being stable in a variety of different detergents and not just DDM. We therefore tested the stability of $\beta AR$-m23 and $\beta AR$ in a variety of different detergents, concentrating on small detergents that are preferentially used in crystallising integral membrane proteins. Membranes prepared from $E.\ coli$ expressing $\beta AR$-m23 or $\beta AR_{34\text{-}424}$ were solubilised in DDM, bound to Ni-NTA agarose then washed with either DDM, decylmaltoside (DM), octylglucoside (OG), lauryldimethylamine oxide (LDAO) or nonylglucoside (NG). Stability assays were performed on the receptors in each of the different detergents (FIG. 6). $\beta AR_{34\text{-}424}$ was only stable in DDM and DM, with no active receptors eluting from the resin washed with OG, NG or LDAO. In contrast, functional $\beta AR$-m23 was still present in all detergents and the Tm could be determined. As expected, the smaller detergents were considerably more denaturing than either DDM (Tm 52° C.) or DM (Tm 48° C.), with $T_m$s of 25° C. (NG), 23° C. (LDAO) and 17° C. (OG). The difference in Tm between $\beta AR$-m23 and $\beta AR_{34\text{-}424}$ is about 20° C., irrespective of whether the receptors were solubilised in either DDM or DM; it is therefore not surprising that no active $\beta AR_{34\text{-}424}$ could be found in even NG, because the predicted Tm would be about 5° C., thus resulting in rapid inactivation of the receptor under the conditions used for purification. The selection strategy used for the generation of $\beta AR$-m23 was chosen deliberately to be based upon thermostability, because it is far simpler to apply than selecting for stability in detergents of increasing harshness. However, it is clear that increasing the thermostability of $\beta AR_{34\text{-}424}$ also resulted in increasing tolerance to small detergents ideal for crystallising integral membrane proteins.

Crystallisation of Mutant GPCR

Earlier attempts to crystallise several different constructs of turkey beta-adrenegic receptor failed. Despite experimenting with a variety of conditions, using both the native sequence and several truncated and loop-deleted constructs, over many years, no crystals were obtained.

However, once the stabilising mutations from $\beta AR$-m23 were transferred into the constructs, several different crystals were obtained in different detergents and different conditions.

The crystals that have been most studied so far were obtained using the purified beta-36 construct (amino acid residues 34-367 of the turkey beta receptor containing the following changes: point mutations C116L and C358A; the 6 thermostabilising point mutations in m23; replacement of amino acid residues 244-278 with the sequence ASKRK; a C terminal His6 tag) expressed in insect cells using the baculovirus expression system, after transferring the receptor into the detergent octyl-thioglucoside. The precipitant used was PEG600 or PEG1000 and the crystals obtained are elongated plates.

Experiments have also been carried out to see whether, once the crystallisation conditions had been defined using the stabilised receptor, it was possible to get crystals using the original non-stabilised construct. It was possible that similar or perhaps very small crystals could have been obtained, but, in fact, the "wild type" (i.e. the starting structure from which the mutagenesis began) never gave any crystals.

The crystals are plate-shaped with space group C2 and diffract well, though the cell dimensions do vary depending on the freezing conditions used.

In general, once a GPCR has been stabilised it may be subjected to a variety of well-known techniques for structure determination. The most common technique for crystallising membrane proteins is by vapour diffusion (20, 21), usually using initially a few thousand crystallisation conditions set up using commercial robotic devices (22). However, sometimes the crystals formed by vapour diffusion are small and disordered, so additional techniques may then be employed. One technique involves the co-crystallisation (by vapour diffusion) of the membrane protein with antibodies that bind specifically to conformational epitopes on the proteins' surface (23, 24); this increases the hydrophilic surface of the protein and can form strong crystal contacts. A second alternative is to use a different crystallisation matrix that is commonly called either lipidic cubic phase or lipidic mesophase (25, 26), which has also been developed into a robotic platform (27). This has proven very successful for producing high quality crystals of proteins with only small hydrophilic surfaces e.g. bacteriorhodopsin (28). Membrane protein structures can also be determined to high-resolution by electron crystallography (29).

The evolution of βAR-m23 from $βAR_{34-424}$ by a combination of alanine scanning mutagenesis and the selection of thermostable mutants has resulted in a GPCR that is ideal for crystallography. The Tm for βAR-m23 is 21° C. higher than for $βAR_{34-424}$ and, in the presence of antagonist, βAR-m23 has a similar stability to rhodopsin. The increased Tm of βAR-m23 has resulted in an increased stability in a variety of small detergents that inactivate $βAR_{34-424}$. In addition, the selection strategy employed resulted in a receptor that is preferentially in the antagonist-bound conformation, which will also improve the chances of obtaining crystals, because the population of receptor conformations will be more homogeneous than for wild type $βAR_{34-424}$. Thus we have achieved a process of conformational stabilisation in a single selection procedure.

It is not at all clear why the particular mutations we have introduced lead to the thermostabilisation of the receptor. Equivalent positions in rhodopsin suggest that the amino acid residues mutated could be pointing into the lipid bilayer, into the centre of the receptor or at the interfaces between these two environments. Given the difficulties in trying to understand the complexities of the thermostabilisation of soluble proteins[15], it seems unlikely that membrane proteins will be any easier to comprehend; we found that there was no particular pattern in the amino acid residues in βAR that, when mutated, led to thermostability. However, since nearly 5% of the mutants produced were more stable than the native receptor, alanine scanning mutagenesis represents an efficient strategy to rapidly identify thermostable mutants.

The procedure we have used to generate βAR-m23 is equally applicable to any membrane protein that has a convenient assay for detecting activity in the detergent solubilized form. While we have selected for stability as a function of temperature as the most convenient primary parameter, the procedure can easily be extended to test primarily for stability, for example, in a harsh detergent, an extreme of pH or in the presence of chaotropic salts. Conformational stabilisation of a variety of human receptors, channels and transporters will make them far more amenable to crystallography and will also allow the improvement in resolution of membrane proteins that have already been crystallised. It is to be hoped that conformational stabilisation will allow membrane protein crystallisation to become a far more tractable problem with a greater probability of rapid success than is currently the case. This should allow routine crystallisation of human membrane proteins in the pharmaceutical industry, resulting in valuable structural insights into drug development.

Methods

Materials.

The truncated β1 adrenergic receptor from turkey ($βAR_{34-424}$)[9] was kindly provided by Dr Tony Warne (MRC Laboratory of Molecular Biology, Cambridge, UK). This βAR construct encoding residues 34-424 contains the mutation C116L to improve expression[11], and a C-terminal tag of 10 histidines for purification. 1-[4,6-propyl-$^3$H]-dihydroalprenolol ([$^3$H]-DHA) was supplied by Amersham Bioscience, (+) L-norepinephrine bitartrate salt, (−) isoprenaline hydrochloride, (−) alprenolol tartrate salt and s-propranolol hydrochloride were from Sigma.

Mutagenesis of βAR.

The βAR cDNA was ligated into pRGIII to allow the functional expression of βAR in *E. coli* as a MalE fusion protein[16]. Mutants were generated by PCR using the expression plasmid as template using the QuikChange II methodology (Stratagene). PCR reactions were transformed into XL10-Gold ultracompetent cells (Stratagene) and individual clones were fully sequenced to check that only the desired mutation was present. Different mutations were combined randomly by PCR by including all the pairs of primers that introduced the following mutations: Mut4, G67A, G068A, V230A, D322A and F327A; Mut6, R068S, Y227A, A234L, A282L and A334L; Mut7, M90V, I129V, Y227A, A282L and F338M; Mut10, R68S, M90V, V230A, F327A and A334L. The PCR mixes were transformed and the clones sequenced to determine exactly which mutations were introduced.

Protein Expression and Membrane Preparations.

Expression of βAR and the mutants was performed in XL10 cells (Stratagene). Cultures of 50 ml of 2×TY medium containing ampicillin (100 μg/ml) were grown at 37° C. with shaking until $OD_{600}$=3 and then induced with 0.4 mM IPTG. Induced cultures were incubated at 25° C. for 4 h and then cells were harvested by centrifugation at 13,000×g for 1 min (aliquots of 2 ml) and stored at −20° C. For the assays, cells were broken by freeze-thaw (five cycles), resuspended in 500 μl of buffer [20 mM Tris pH 8, 0.4 M NaCl, 1 mM EDTA and protease inhibitors (Complete™, Roche)]. After an incubation for 1 h at 4° C. with 100 μg/ml lysozyme and DNase I (Sigma), samples were solubilized with 2% DDM on ice for 30 minutes. Insoluble material was removed by centrifugation (15,000×g, 2 min, 4° C.) and the supernatant was used directly in radioligand binding assays.

For large-scale membrane preparations, 2L and 6L of *E. coli* culture of βAR and Mut23, respectively, were grown as described above. Cells were harvested by centrifugation at 5,000×g for 20 min, frozen in liquid nitrogen and stored at −80° C. Pellets were resuspended in 10 ml of 20 mM Tris pH 7.5 containing 1× protease inhibitor cocktail (Complete™ EDTA-free, Roche); 1 mg DNase I (Sigma) was added and the final volume was made to 100 ml. Cells were broken by a French press (2 passages, 20,000 psi), and centrifuged at 12,000×g for 45 min at 4° C. to remove cell debris. The supernatant (membranes) was centrifuged at 200,000×g for 30 min at 4° C.; the membrane pellet was resuspended in 15 ml of 20 mM Tris pH 7.5 and stored in 1 ml aliquots at −80° C. after flash-freezing in liquid nitrogen. The protein concentration was determined by the amido black method[17]. These samples were used in radioligand binding assays after thawing and being solubilized in 2% DDM as above.

For competition assays, as well as testing different detergents, DDM-solubilized βAR was partially purified with Ni-NTA agarose (Qiagen). 200 µl of Ni-NTA agarose was added to 2 ml of solubilized samples (10 mg/ml of membrane protein) in 20 mM Tris pH 8, 0.4 M NaCl, 20 mM imidazole pH 8 and incubated for 1 h at 4° C. After incubation, samples were centrifuged at 13,000×g for 30 sec and washed twice with 250 µl of buffer (20 mM Tris pH 8, 0.4 M NaCl, 20 mM imidazole) containing detergent (either 0.1% DDM, 0.1% DM, 0.1% LDAO, 0.3% NG or 0.7% OG).

Receptors were eluted in 2×100 µl of buffer (0.4 M NaCl, 1 mM EDTA, 250 mM imidazole pH 8, plus the relevant detergent). The $K_D$ for [$^3$H]-DHA binding to semipurified $βAR_{34-424}$ and βAR-m23 was, respectively 3.7 nM and 12.5 nM and the final concentration of [$^3$H]-DHA used in the competition assays was 3 times the $K_D$ ie 12 nM for $βAR_{34-424}$ and 40 nM for βAR-m23.

Radioligand Binding and Thermostability Assays.

Single point binding assays contained 20 mM Tris pH 8, 0.4 M NaCl, 1 mM EDTA, 0.1% DDM (or corresponding detergent) with 50 nM [$^3$H]-DHA and 20-100 µg membrane protein in a final volume of 120 µl; equilibration was for 1 h at 4° C. Thermostability was assessed by incubating the binding assay mix, with or without [$^3$H]-DHA at the specified temperature for 30 minutes; reactions were placed on ice and [$^3$H]-DHA added as necessary and equilibrated for a further hour. Receptor-bound and free radioligand were separated by gel filtration as described previously[18]. Non-specific binding was determined in the presence of 1 µM of s-propranolol. Saturation curves were obtained using a range of [$^3$H]-DHA concentration from 0.4 nM to 100 nM. Competition assays were performed using a concentration of [$^3$H]-DHA of 12 nM for $βAR_{34-424}$ and 40 nM for βAR-m23 (ie three times the $K_D$) and various concentrations of unlabeled ligands (0-100 mM). Radioactivity was counted on a Beckman LS6000 liquid scintillation counter and data were analyzed by nonlinear regression using Prism software (Graph Pad).

Location of RAR-m23 Thermostable Mutations in Rhodopsin Structure.

The pdb file for the rhodopsin structure, accession code 1GZM[14], was downloaded from the Protein Data Bank website (pdb.org) and displayed in the program PyMOLX11Hybrid (DeLano Scientific). The equivalent amino acid residues in rhodopsin for the thermostable mutations in βAR were located in the rhodopsin structure based upon an alignment among the four GPCRs with which we are most familiar, namely rhodopsin, β1 adrenergic receptor, neurotensin receptor and adenosine $A_{2a}$ receptor[19].

Example 2

Mutants of the Adenosine $A_{2a}$ Receptor ($A_{2a}$R) with Increased Thermostability 1. 315 site-directed mutants made between residues 2-316 of $A_{2a}$R.
2. All of these mutants have been assayed for thermostability using an assay measuring agonist and antagonist binding after the heating step (Ligand(−) format as described in FIG. 12).
   a. 26 mutants showed improved thermostability when measured with $^3$H-NECA (agonist): G114 A, G118A, L167A, A184L, R199A, A203L, L208A, Q210A, S213A, E219A, R220A, S223A, T224A, Q226A, K227A, H230A, L241A, P260A, S263A, L267A, L272A, T279A, N284A, Q311A, P313A, K315A.
   b. 18 mutants showed improved thermostability when assayed with $^3$H-ZM241385 (antagonist): A54L, V57A, H75A, T88A, G114A, G118A, T119A, K122A, G123A, P149A, E151A, G152A, A203L, A204L, A231L, L235A, V239A.
3. Mutations have been combined to generate mutants in a putative antagonist conformation. Wildtype $A_{2a}$R has a Tm of 31° C. with ZM241385 bound.

| | | |
|---|---|---|
| a. Rant17 A54L + K122A + L235A | | Tm 48° C. (ZM241385 bound) |
| b. Rant19 A54L, T88A, V239A + A204L | | Tm 47° C. (ZM241385 bound) |
| c. Rant21 A54L, T88A, V239A + K122A | | Tm 49° C. (ZM241385 bound) |

4. Mutations from the agonist screen have been combined, but have led to only a very low level of improvement in Tm of +2° C.

TABLE (i)

List of A2aR stabilising mutations.

| Mutation | Expression (%) | Stability (%) |
|---|---|---|
| Agonist | | |
| wt | 100 | 100 |
| S090A | 151 | 151 |
| G114A | 62 | 143 |
| G118A | 71 | 151 |
| L167A | 41 | 174 |
| A184L | 140 | 150 |
| R199A | 73 | 202 |
| A203L | 42 | 172 |
| L208A | 276 | 215 |
| Q210A | 46 | 155 |
| S213A | 40 | 140 |
| E219A | 96 | 221 |
| R220A | 84 | 250 |
| S223A | 57 | 146 |
| T224A | 142 | 276 |
| Q226A | 119 | 217 |
| K227A | 87 | 222 |
| H230A | 57 | 154 |
| L241A | 139 | 156 |
| P260A | 70 | 169 |
| S263A | 60 | 158 |
| L267A | 40 | 187 |
| L272A | 34 | 157 |
| T279A | 125 | 158 |
| N284A | 64 | 151 |
| Q311A | 49 | 164 |
| P313A | 44 | 148 |
| K315A | 64 | 186 |
| Antagonist | | |
| wt | 100 | 100 |
| A054L | 90 | 140 |
| V057A | 44 | 144 |
| H075A | 82 | 152 |

TABLE (i)-continued

List of A2aR stabilising mutations.

| | | |
|---|---|---|
| T088A | 67 | 230 |
| G114A | 73 | 153 |
| G118A | 84 | 148 |
| T119A | 90 | 148 |
| K122A | 52 | 153 |
| G123A | 90 | 158 |
| P149A | 54 | 215 |
| E151A | 63 | 173 |
| G152A | 70 | 156 |
| A203L | 111 | 132 |
| A204L | 40 | 181 |
| A231L | 90 | 148 |
| L235A | 85 | 140 |
| V239A | 91 | 134 |

Mutants were expressed in *E. coli*, solubilised in 2% DDM + 10% glycerol and tested for ligand-binding, using the agonist [$^3$H]-NECA (on the right) and the antagonist [$^3$H]-ZM241385 (left). Concentrations of radioligands were 6-10-fold above their $K_D$ measured for the wild-type receptor. Expression of active receptor was evaluated by ligand binding at 4° C. Stability was assayed by heating the solubilised receptor in its apo-state at 30° C. for 30 minutes and then measuring residual binding activity. Under these conditions, wild-type activity decays to 50% (S.D. = 15%). Data obtained for expression and stability were normalised to wild-type values. Mutations included in subsequent rounds of mutagenesis were those whose expression was ≥30-40% and stability ≥130-140% compared to the wild-type. Bold lines indicate cluster of mutations.

TABLE ii

Stability of best combinations.

| | Tm (° C.) | | | Tm (° C.) | |
|---|---|---|---|---|---|
| | − agonist | + agonist | | − antagonist | + antagonist |
| Wt | 21 | 29 | wt | 31 | 32 |
| Rag 1 (A184L/R199A/L272A) | 26 | 34 | Rant 5 (A54L/T88A/V239A) | 42 | 46 |
| Rag 23 (Rag 1 + F79A/L208A) | 22 | 38 | Rant 21 (Rant 5 + K122A) | 41 | 49 |

Receptors were solubilised in 1% DDM (no glycerol). A melting profile was obtained by heating the solubilised receptor at different temperatures in absence (apo-state) or presence of ligand (ligand-occupied state). Data shown are representative of at least three independent experiments. S.D. is <1° C.

TABLE (iii)

Summary of results for competition assays of detergent-solubilised wild-type A2aR and thermo-stable mutant Rant 21.

| | $K_i$ (M) | |
|---|---|---|
| Competitor | wt | Rant 21 |
| XAC | $2.3 \times 10^{-6}$ | $2.3 \times 10^{-6}$ |
| Theophylline | $1.5 \times 10^{-3}$ | $0.9 \times 10^{-3}$ |
| NECA | $7.0 \times 10^{-6}$ | $>1 \times 10^{-1}$ |
| R-PIA | $1.6 \times 10^{-5}$ | $3.6 \times 10^{-3}$ |

Values are representative of two independent experiments. Each data point was assayed in triplicate and plotted as mean ± SD. Each solubilised receptor was incubated with ligands for one hour on ice in binding buffer (50 mM Tris pH 7.5 and 0.025% DDM) containing 400 mM NaCl. Binding of [3H]ZM241385 (10 nM) in the absence of unlabeled ligand was set to 100%. Data shown are from two independent experiments with each data point measured in triplicate. Incubation of samples with ligands was for 1 hour on ice with [$^3$H]ZM241385 at a concentration of 10 nM. $K_i$ values were calculated according to the Cheng and Prusoff equation using the non-linear regression equation of the software Prism, applying a $K_D$ for [$^3$H]ZM241385 of 12 nM for the wild-type and 15 nM for Rant 21. Rant 21 did not bind NECA sufficiently for an accurate $K_i$ determination (hence indicated as $>1 \times 10^{-1}$). The affinity of Rant21 for agonist binding is weakened 232 fold for R-PIA and at least by 1900 fold for NECA.

TABLE (iv)

Summary of results for saturation assays of detergent-solubilised wild-type A2aR and thermo-stable mutants.

| | $K_D$ (nM) | |
|---|---|---|
| Receptor | [$^3$H]NECA (agonist) | [$^3$H]ZM241385 (antagonist) |
| wt | 32 ± 1 | 12 ± 3 |
| Rag 1 | 26 ± 0.4 | 26 ± 0.5 |
| Rag 23 | 21 ± 1 | 62 ± 1 |
| Rant 21 | >450 | 15 ± 3 |

Values are representative of three independent experiments. Each data point was assayed in triplicate and plotted as mean ± SD. Data were fitted to the Michaelis-Menten equation using the non-linear regression equation of the software Prism.

TABLE (v)

Summary of stability of wild-type and mutant receptors in different detergents.

| | Tm (° C.) | | | |
|---|---|---|---|---|
| | Agonist-binding | | Antagonist-binding | |
| | wt | Rag 23 | wt | Rant 21 |
| 0.01% DDM | 27 | 34 | 25 | 39 |
| 0.1% DM | 23 | 29 | 10 | 28 |
| 0.3% NM | 22 | 28 | <4 | 25 |
| 0.3% NG | † | † | † | 22 |
| 0.6% OG | <9 | 16 | † | 23 |
| 0.003% LDAO | 28 | 38 | 32 | 42 |
| 0.006% FC12 | 37 | 39 | 43 | 49 |

Solubilisation of receptors and detergent exchange was performed during the IMAC step. S.D. is <1° C. It was not possible to determine the Tm for some receptor-detergent combinations, because the receptor was too unstable (†).

Example 3

Mutants of the Neurotensin Receptor (NTR) with Increased Thermostability 1. 340 site-directed mutants have been made between residues 61-400 of NTR.
2. Initially, all of these mutants were assayed for thermostability using an assay measuring $^3$H-neurotensin (agonist) binding after the heating step. 24 mutations led to a small but significant increase in thermostability: A356L, H103A, D345A, A86L, A385L, Y349A, C386A, K397A, H393A, I116A, F358A, S108A, M181A, R392A, D113A, G209A, L205A, L72A, A120L, P399A, Y351A, V268A, T207A, A155L, S362A, F189A, N262A, L109A, W391A, T179A, S182A, M293A, L256A, F147A, D139A, S100A, K176A, L111A, A90L, N270A.
3. Mutants tested for thermostability by heating in the absence of the agonist were re-tested using a slightly different assay where the mutants were heated in the presence of $^3$H-neurotensin (Ligand(+) format in FIG. 12). Mutants with improved thermostability are: A69L, A73L, A86L, A90L, H103A, V165A, E166A, G215A, V229A, M250A, I253A, A177L, R183A, I260A, T279A, T294A, G306A, L308A, V309A, L310A, V313A, F342A, F358A, V360A, S362A, N370A, S373A, F380A, A385L, P389A, G390A, R395A.
4. There are also mutants that have a significantly enhanced expression level compared to the wildtype receptor and could be used to boost preceptor production levels for crystallisation: A86L, H103A, F358A, S362A, N370A, A385L, G390A. All of these also have increased thermostability.
5. Preferred combinations are

| | | |
|---|---|---|
| a. Nag7m | F358A + A86L + I260A + F342A | Tm 51° C. (neurotensin bound) |
| b. Nag7n | F358A + H103A + I260A + F342A | Tm 51° C. (neurotensin bound) |

Wildtype NTR has a Tm of 35° C. with neurotensin bound.

Example 4

Identification of Structural Motifs in which Stabilising GPCR Mutations Reside The structure of the β2 adrenergic receptor has been determined (20, 21), which is 59% identical to the turkey β receptor, but with a distinctly different pharmacological profile (22, 23). In order to determine the structural motifs in which the stabilising mutations of the turkey β receptor reside, we mapped the mutations onto the human β2 structure (21).

The beta adrenergic receptors were first aligned using ClustalW in the MacVector package; thermostabilising mutations in turkey β1 were highlighted along with the corresponding residue in the human β2 sequence. The human β2 model (pdb accession code 2RH1) was visualised in Pymol and the desired amino acids were shown as space filling models by standard procedures known in the art. The structural motifs in which the stabilising mutations were located, were determined by visual inspection.

Table (vi) lists the equivalent positions in the β2 receptor corresponding to the thermostabilising mutations in βAR-m23 and the structural motifs in which they reside.

As seen from Table (vi), the mutations are positioned in a number of distinct localities. Three mutations are in loop regions that are predicted to be accessible to aqueous solvent (loop). Eight mutations are in the transmembrane α-helices and point into the lipid bilayer (lipid); three of these mutations are near the end of the helices and may be considered to be at the hydrophilic boundary layer (lipid boundary). Eight mutations are found at the interfaces between transmembrane α-helices (helix-helix interface), three of which are either within a kinked or distorted region of the helix (kink) and another two mutations occur in one helix but are adjacent to one or more other helices which contain a kink adjacent in space to the mutated residue (opposite kink). These latter mutations could affect the packing of the amino acids within the kinked region, which could result in thermostabilisation. Another mutation is in a substrate binding pocket (pocket).

TABLE (vi)

Position in the human β2 structure of the amino acid residues equivalent to the thermostabilising mutations found in the turkey β1 receptor and the structural motifs in which they reside.

Figure 18:
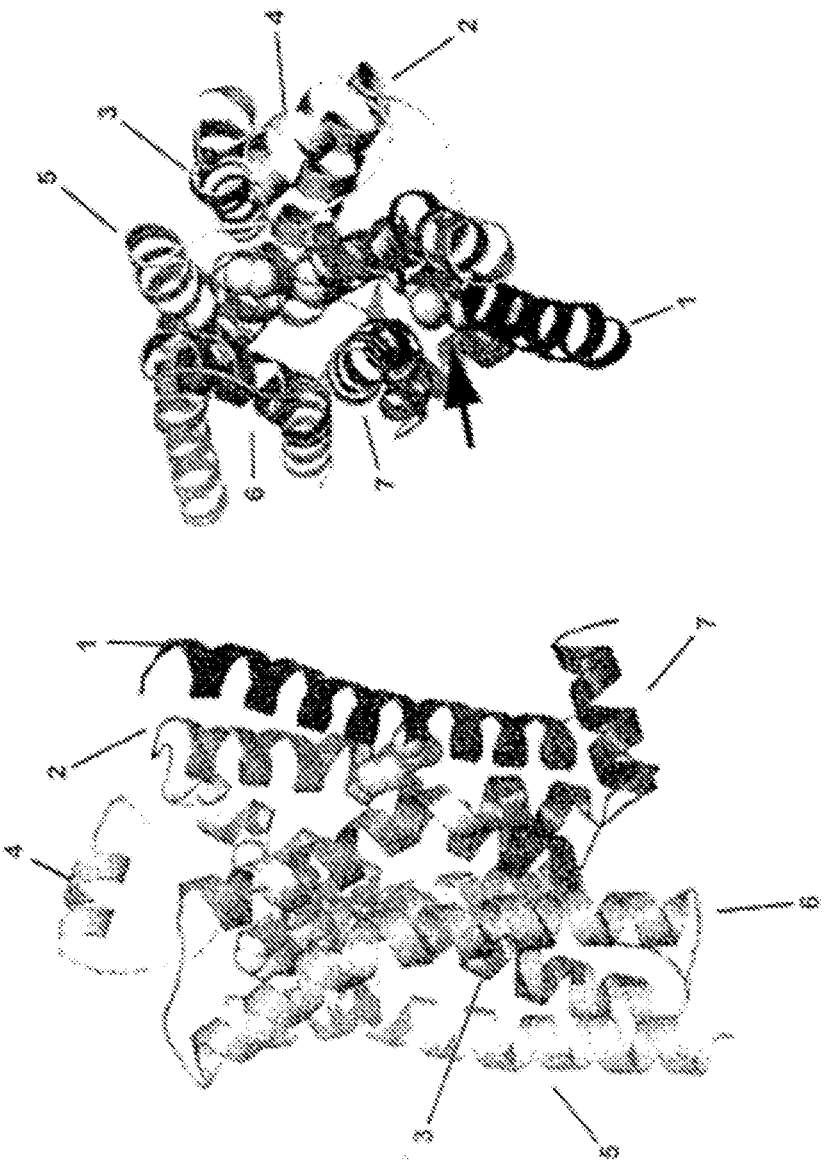
FIG. 18 Mapping of turkey beta1AR mutation I55A (human beta2AR 147) onto human beta2AR structure (pdb accession code 2RH1). Mutation is at the interface between 3 helices (H1, H2 kink, H7 kink). Left: side view; right: top view.
Figure 19:
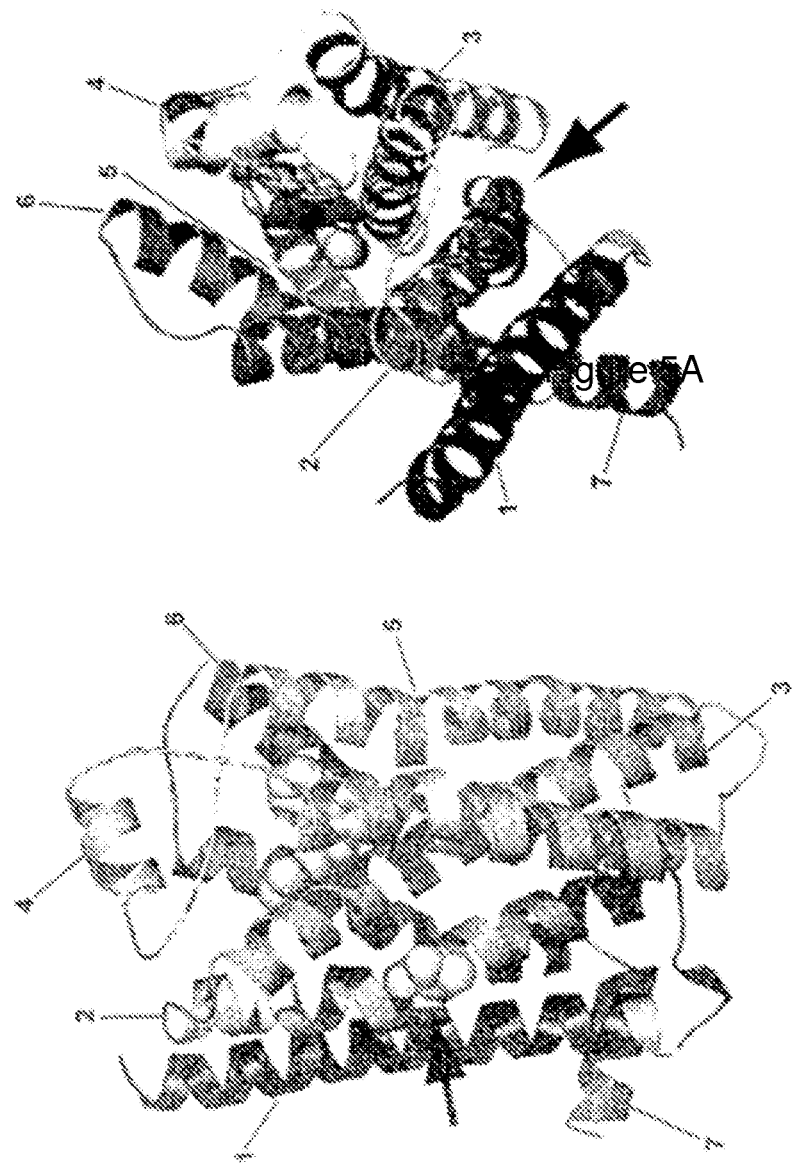
FIG. 19 Mapping of turkey beta1AR V89L mutation (human beta2AR V81) onto human beta2AR structure (pdb accession code 2RH1). Mutation is in the kink in helix 2. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.
Figure 20:
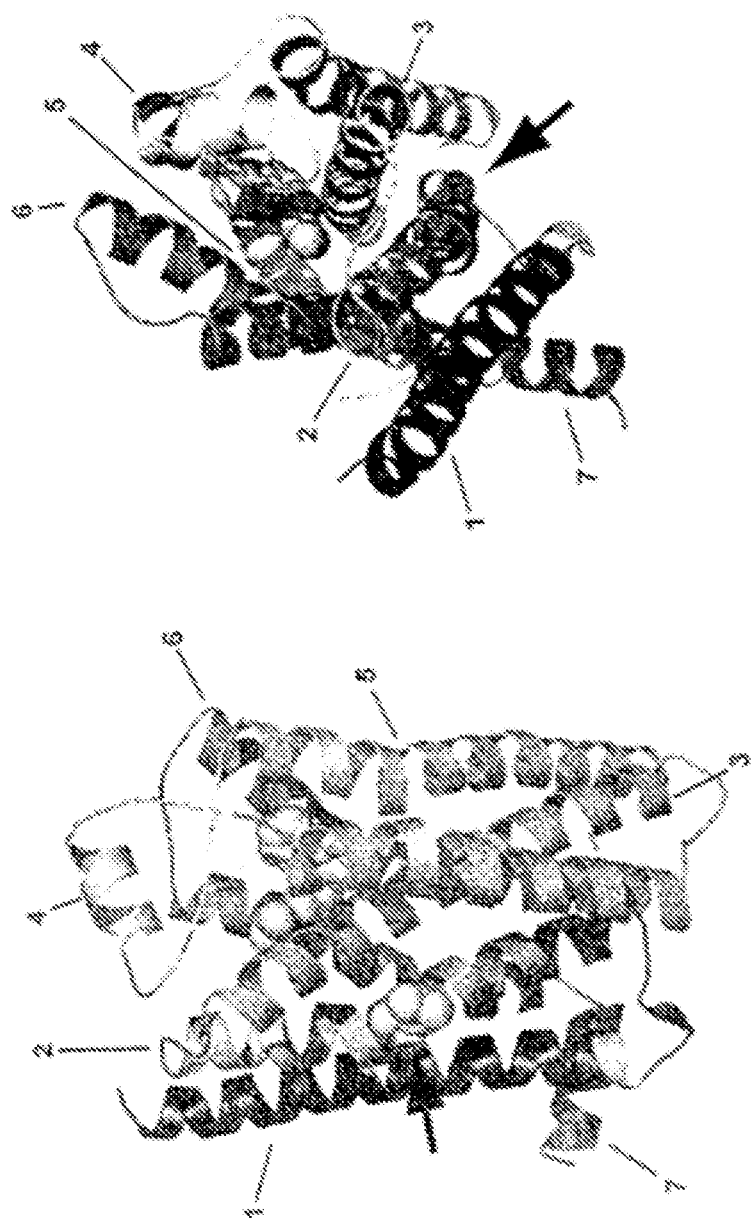
FIG. 20 Mapping of turkey beta1AR M90V mutation (human beta2AR M82) onto human beta2AR structure (pdb accession code 2RH1). Mutation is in kink in helix 2 oriented towards the binding pocket. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.
Figure 21:
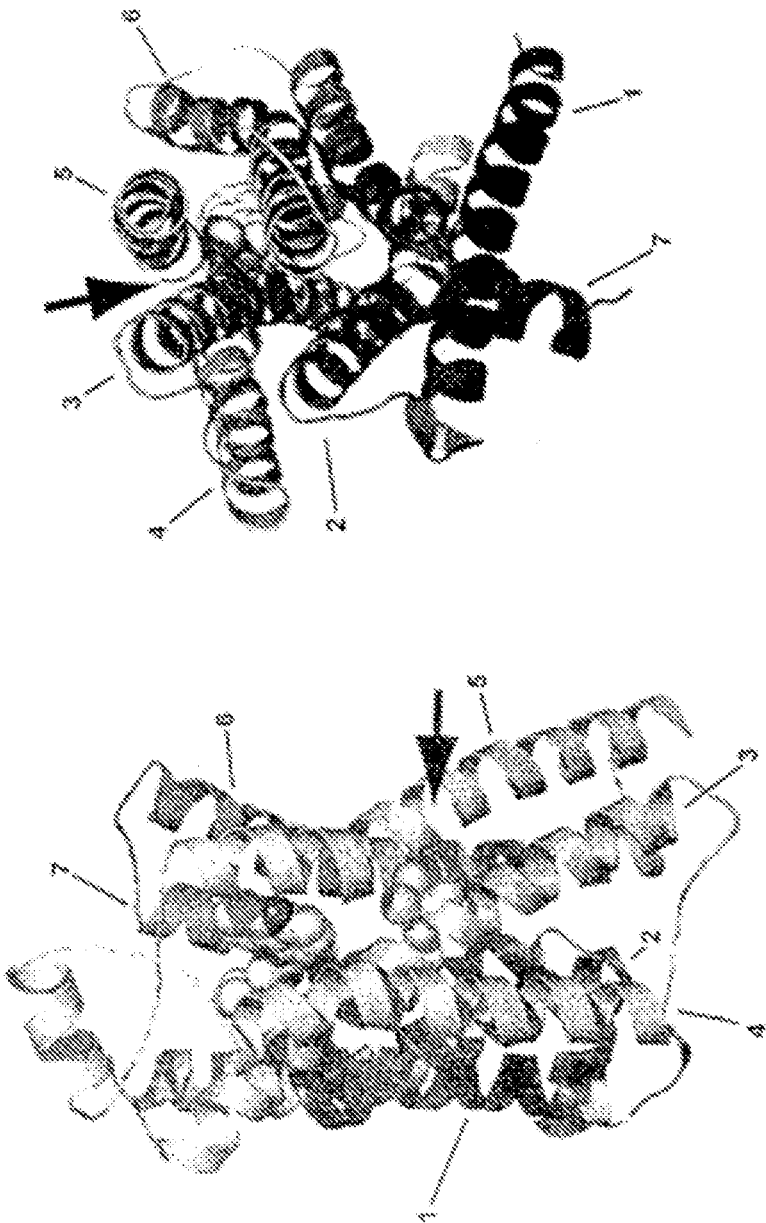
FIG. 21 Mapping of turkey beta1AR I129V mutation (human beta2AR I121) onto human beta2AR structure (pdb accession code 2RH1). Mutation is opposite a kink in helix 5. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: bottom view.
Figure 22:
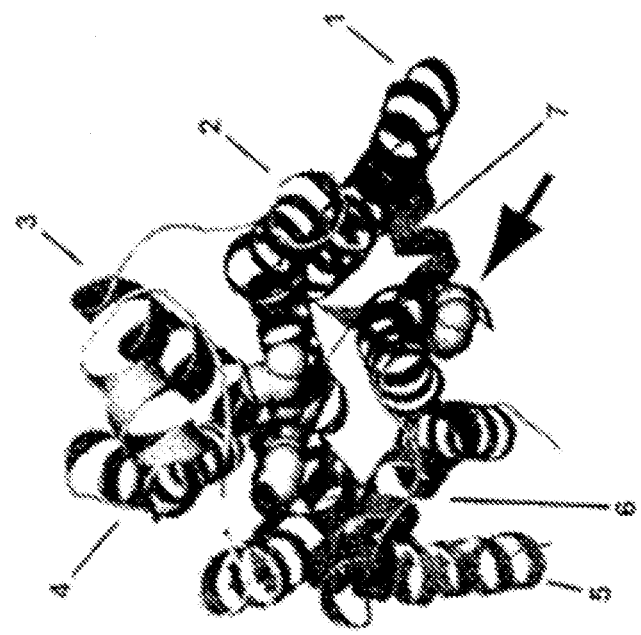
FIG. 22 Mapping of turkey beta1AR F338M mutation (human beta2AR F321) onto human beta2AR structure (pdb accession code 2RH1). Mutation is in kink in helix 7. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.
Figure 22:
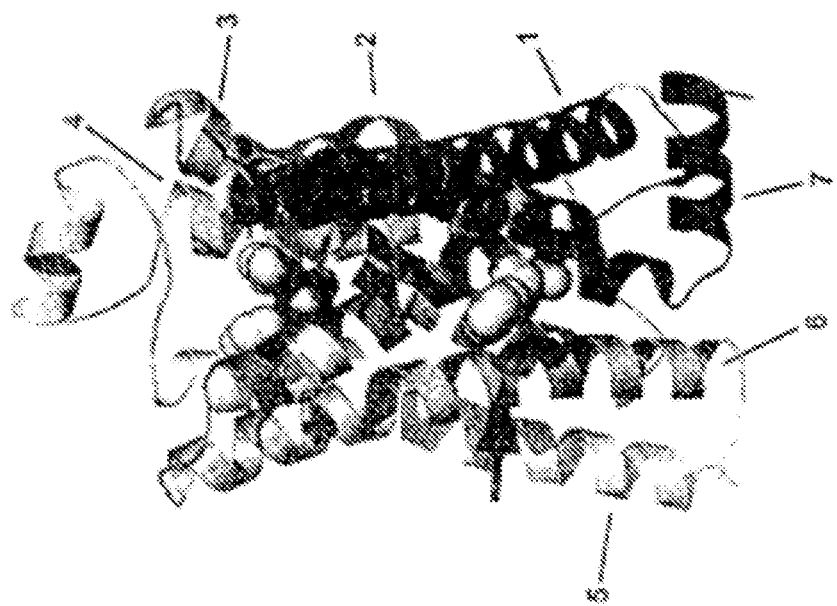
Figure 23:
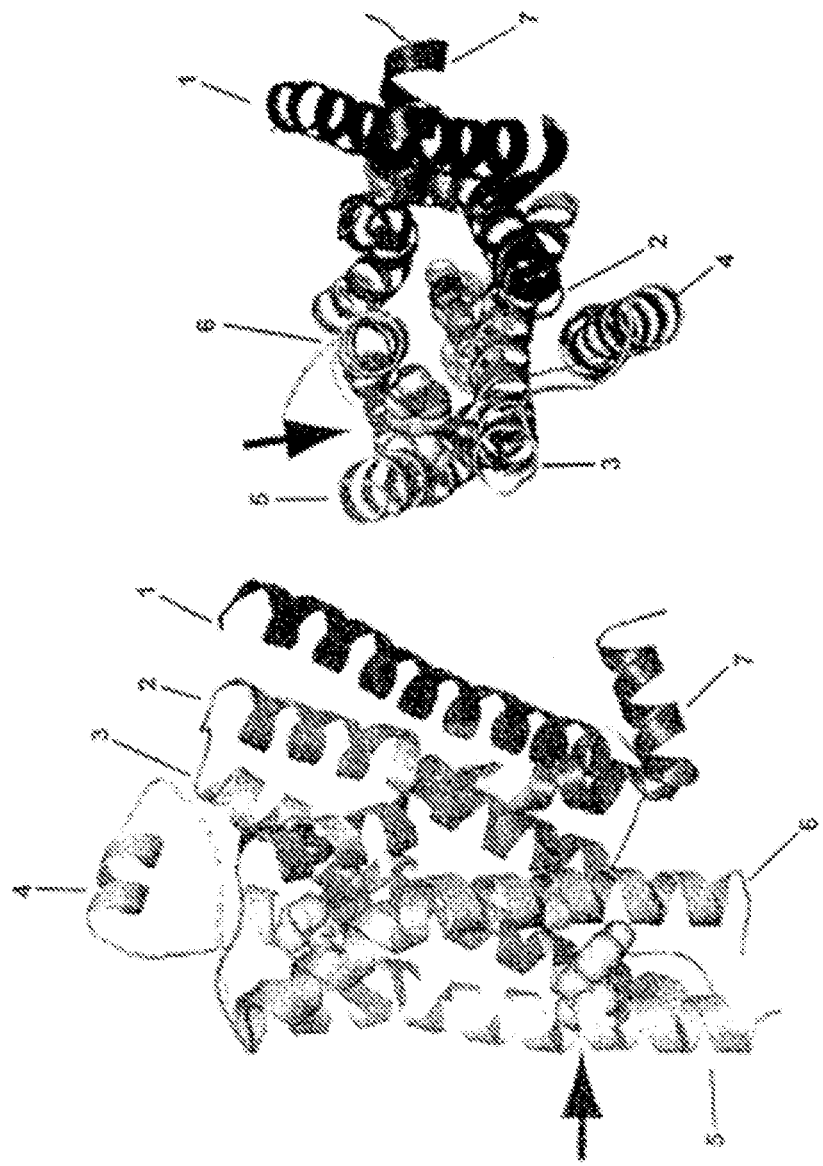
FIG. 23 Mapping of turkey beta1AR Y227A mutation (human beta2AR Y219) onto human beta2AR structure (pdb accession code 2RH1). Mutation is at helix-helix interface. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: bottom view.
Figure 24:
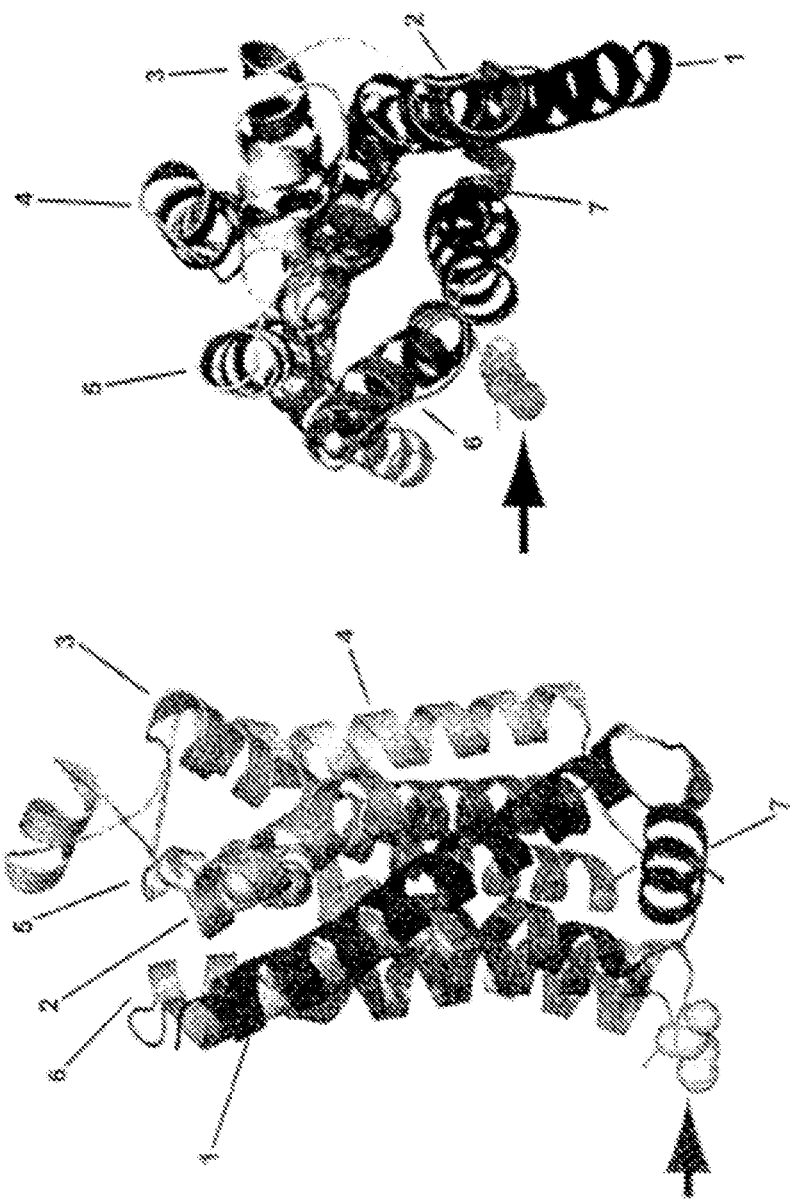
FIG. 24 Mapping of turkey beta1AR A282L mutation (human beta2AR C265) onto human beta2AR structure (pdb accession code 2RH1). Mutation is in loop region. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: top view.
Figure 25:
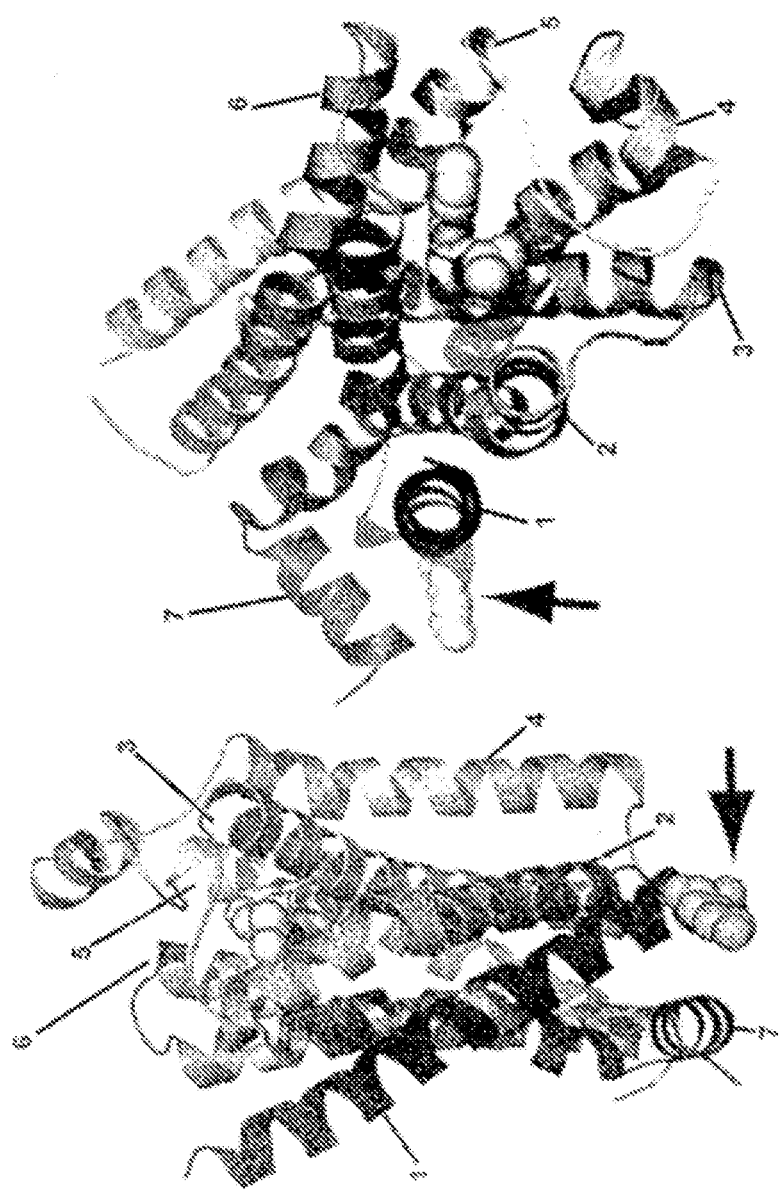
FIG. 25 Mapping of turkey beta1AR R68S mutation (human beta2AR K60) onto human beta2AR structure (pdb accession code 2RH1). Mutation is at the lipid-water boundary, pointing into the solvent. The helices are numbered and the bound antagonist is shown as a space filling model. Amino acid residues in equivalent positions to the thermostabilising mutations in the turkey β1 adrenergic receptor are shown as space filling models and are arrowed for clarity. Left: side view; right: angled top view.

| | Turkey β1 | Human β2 | Description | |
|---|---|---|---|---|
| Helix 1 | I55A | I47 | 3-helix kink interface | FIG. 18 |
| Helix 1 | G67A | A59 | lipid boundary | |
| Helix 1 | R68S | K60 | lipid boundary | FIG. 25 |
| Helix 2 | V89L | V81 | kink | FIG. 19 |
| Helix 2 | M90V | M82 | kink | FIG. 20 |
| Helix 2 | G98A | G90 | pocket | |
| Helix 3 | I129V | I121 | opposite kink | FIG. 21 |
| | S151E | S143 | loop | |
| Helix 4 | V160A | V152 | lipid | |
| | Q194A | A186 | loop | |
| Helix 5 | L221V | V213 | lipid | |
| Helix 5 | Y227A | Y219 | helix-helix interface | FIG. 23 |
| Helix 5 | R229Q | R221 | lipid | |
| Helix 5 | V230A | V222 | helix-helix interface | |
| Helix 5 | A234L | A226 | helix-helix interface | |
| Helix 6 | A282L | C265 | loop | FIG. 24 |
| | D322A | K305 | lipid boundary | |
| Helix 7 | F327A | L310 | lipid | |
| Helix 7 | A334L | V317 | lipid | |
| Helix 7 | F338M | F321 | kink | FIG. 22 |

Such structural motifs, by virtue of them containing stabilising mutations, are important in determining protein stability. Therefore, targeting mutations to these motifs will facilitate the generation of stabilised mutant GPCRs. Indeed, there were several instances where more than one mutation mapped to the same structural motif. For example, the Y227A, V230A and A234L mutations in the turkey β1 adrenergic receptor all mapped to the same helical interface, the V89L and M90V mutations mapped to the same helical kink and the F327A and A334L mutations mapped to the same helical surface pointing towards the lipid bilayer (Table (vi)). Thus, when one stabilising mutation has been identified, the determination of the structural motif in which that mutation is located will enable the identification of further stabilising mutations.

Example 5

Generation of Conformation Specific Binding Partners of GPCRs

The generation of mutant GPCRs having increased stability in a particular conformation relative to a parent GPCR provides a number of advantages for screening of binding partners. For example, the present methods reduce the amount of material required for a screen. In standard screens, GPCRs are present in whole cells or in membranes from whole cells which are usually screened by incubation with individual compounds in isolated chambers rather than libraries of compounds. Therefore the present invention provides advantages in terms of time required to carry out a compound screen. The ability to lock a GPCR in a particular conformation provides advantages in that it increases the likelihood of identifying a ligand with the required pharmacological properties. In standard binding screens GPCRs are able to assume a number of different conformations and binding compounds will be identified across different pharmacological types. Reagent costs can be reduced due to the ability to miniaturize the assay formats and this is facilitated by the present method.

Methods

Compound Screening

A mutant GPCR having increased stability in a particular conformation is immobilised on a solid surface and incubated with buffer containing an encoded library of compounds. After a suitable period of time, to allow binding between the mutant GPCR and compounds from the library which selectively bind to the mutant GPCR, the buffer is removed. Next there follows a number of wash steps to remove compounds which have not bound specifically to the mutant GPCR. The reading code, tag or address (such as DNA or RNA) is then used to identify the small molecule bound either whilst still bound to the mutant GPCR or following elution from the GPCR. The conformation specific binding partner is subsequently isolated.

Selection of Antibodies Using Immobilised GPCRS

Immobilised stabilised GPCRs can be used to select antibodies to the receptor from mixtures of antibodies such as would be present in plasma from an animal immunised with the stabilised GPCR, the native receptor or a peptide from the receptor. Antibodies could be identified from supernatants obtained from B-cells taken from immunised animals or from hybridomas obtained following immortalization of B-cells from the immunised animal or from recombinant antibody libraries which may be expressed on phage particles or through an in vitro expression system such as ribosome display. The method has the advantage of selecting antibodies to particular conformations of a receptor. A stabilised GPCR locked in the antagonist or ground state of the receptor would increase the probability of selecting an antagonistic antibody whereas a stabilised GPCR locked in the activated or R* state would increase the probability of selecting an activating antibody. In standard screens antibodies are often selected to GPCRs that bind to peptide epitopes of the receptor but do not have antagonist or agonist properties and therefore are not useful as therapeutic agents.

Example 6

Antibody Phage Selection on β-Adrenergic Receptor

Summary

We have used stabilised β-adrenergic receptor (β-AR) to generate antibodies using phage display. Positive phage clones showed specificity for β-AR and sub-cloning of selected antibody genes led to successful production of anti-β-AR specific scFv antibodies.

Introduction

The therapeutic application of antibodies in the area of receptor-ligand systems has great potential. However, the primary issue in generating antibodies (either by in vitro or in vivo methods) to G protein coupled receptors (GPCRs) concerns the immunogenic recognition of a specific conformation in a homogeneous antigen preparation, i.e. either an agonistic conformation or antagonistic conformation, rather than creating a pool of antibody binders that recognises purified antigen in multiple conformations in a heterogeneous preparation. In addition, recombinant receptor antigen is usually available only in the extracellular domain form, which precludes any tertiary structure involving other parts of the receptor. The proposed solution to this issue is the application of stabilized GPCRs as the target antigen.

We have demonstrated the utility of stabilised GPCRs (StaRs™) in the generation of recombinant antibodies by the in vitro method of phage display such that antibodies which bind the β adrenergic receptor stabilised in the antagonist conformation may be isolated. Such antibodies can then be subject to functional assays e.g. in ligand binding assays.

Overview of Process

Figure 29:
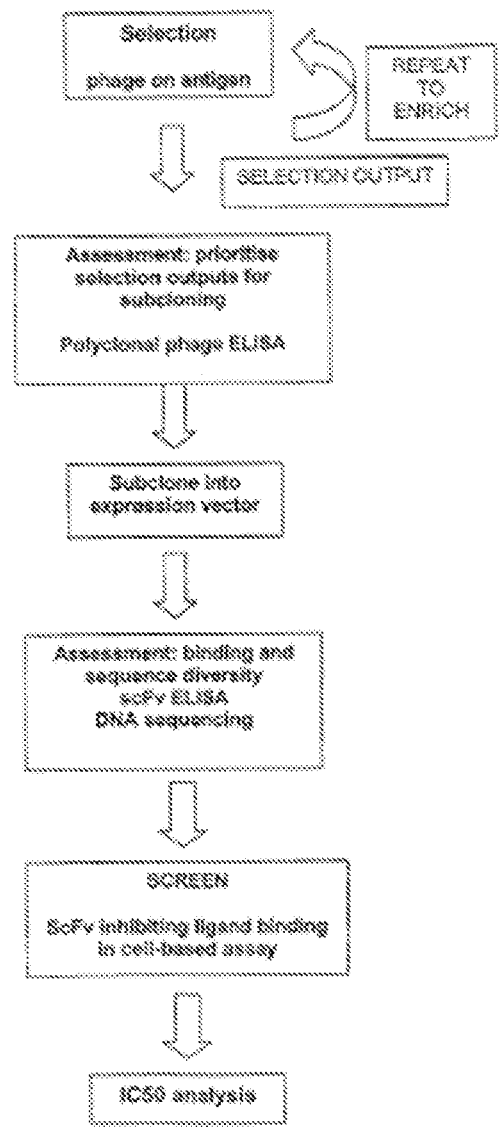
FIG. 29 Schematic representation of typical lead isolation process for the identification of inhibitory scFv binders.

A typical phage display strategy comprises several stages in the process to identify inhibitory scFv clones (FIG. 29). The first part is the selection of phage libraries on antigen to isolate a population of phage antibody binders using various methodologies (for example, panning selection, soluble selection, etc.). This resulting population of phage antibody binders is referred to as a selection output. This process is repeated 2-4 times to enrich for specific antigen binders.

A pool of clones representing a selection output (polyclonal phage ELISA) is assessed for recognition of antigen by phage ELISA. Individual clones can also be assessed by monoclonal phage ELISA and for diversity by sequence analysis, however the preferred method is to subclone the selected population into a recombinant antibody expression vector (pSANG 10-3F) and then perform the assessment by monoclonal scFv ELISA and DNA sequencing. This circumvents the problem of identifying phage antibody binders that subsequently exhibit poor expression as scFv fragments. Selection outputs yielding diverse ELISA positives can then be prioritised for functional screening of larger panels of phage antibodies.

Selection outputs are subjected to a screening campaign, employing a functional high-throughput assay, of periplasmic extracts in order to identify a population of scFv inhibitors. Lastly, the hits from the screening campaign are profiled as scFv by further functional assays, as well as IC50 analysis which assess the efficiency of their inhibitory action.

Methods and Results 2-3 rounds of antibody selections were carried out using stabilised β-AR as antigen and using the "McCafferty" antibody phage display library described in Schofield et al, 2007 (24). Selections were carried out in PBS in the presence (A) or absence (B) of 20 nM ligand (-)-alprenolol during binding and washing steps. Further, for β-AR protein handling, all coating, washing and blocking buffers were supplemented with 0.1% detergent decylmaltoside (Anatrace, Anagrade). The relative success of the selectives was determined using polyclonal phage ELISA and monoclonal phage ELISA.

Optimisation to Immobilise Antigen

Immobilisation strategies were based on taking advantage of the His tagged antigen. In the first instance, immobilisation was done using control proteins rather than βAR-m23. A variety of surfaces, including Ni-NTA plates, were employed in the initial assessment. All were compared against standard passive absorption onto Nunc plates. In all cases, the outcome was evaluated using polyclonal phage ELISA after 2 rounds of selection.

Antibody Selection

Selection, elution and rescue of the library was as described in Schofield et al (2007). 150 μl of β-AR at concentration of 20 μg/ml was coated over night at +4° C. in two (24) wells of a Nickel chelate-plate (Nunc). The receptor was diluted in coating buffer which is 20 mM Tris pH8, 100 mM NaCl, 0.1% decylmaltoside (dec-M) and also 20 nM ligand for selection A. Next day, the wells were rinsed with PBS and blocked for 1 h at room temperature with 3% Marvel milk protein in PBS supplemented with 0.1% dec-M (PBS-M). After coating, the well was rinsed in PBS and 100 μl of phage library pre-blocked in 2% Marvel/PBS was added and incubated for 1 h at room temperature. Following binding, samples were washed 6 times in PBS/0.1% Tween supplemented with 0.1% dec-M and six times in PBS supplemented with 0.1% dec-M. Bound phage was then eluted with Trypsin (24). Eluted phage were added to exponentially growing TG1 cells (at $OD_{600}$=0.5) and grown at 37° C. for 1 h. Infected cells were plated onto TY plates supplemented with 100 μg/ml ampicillin, 2% glucose and grown overnight at 30° C. Next day, plates were scraped in TY medium supplemented with 100 μg/ml ampicillin, 15% glycerol for storage. The population from this first round of selection was rescued with helper phage and PEG precipitated and 100 μl of these were used in a second round of selections using the same conditions and procedures as described for round 1.

Polyclonal Phage ELISA

Figure 30A:
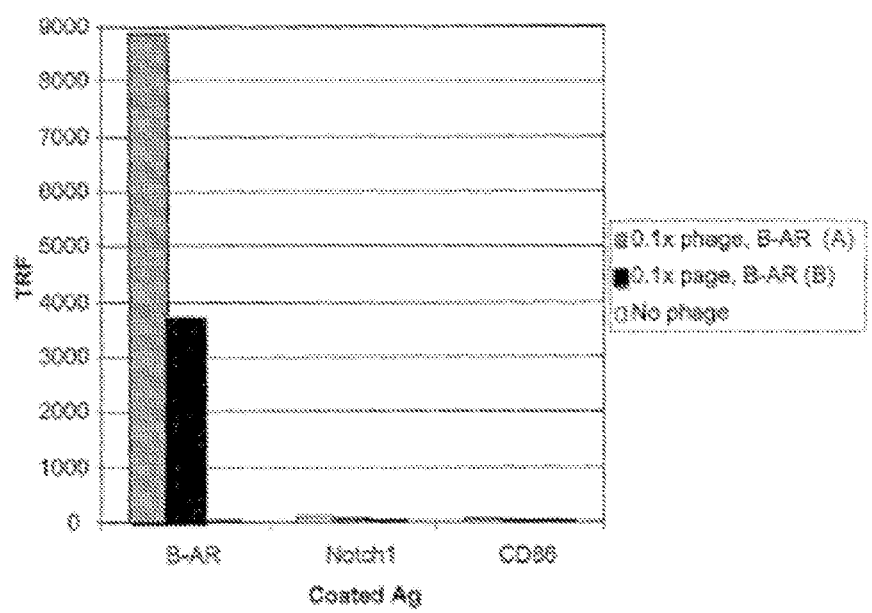
FIGS. 30A and 30B Results of (A) polyclonal and (B) monoclonal phage ELISAs. (B) Columns 1-9 rows A-H of a 96 well ELISA plate were used to screen 69 anti β-AR phage clones FIGS. 31A and 31B Specificity phage ELISA using β-andregenic receptor and 3 unrelated control proteins (CD86-CD4, Notch1-Fc and the NRR region of Notch1). Proteins coated on two ELISA plates, amino-plate (A) and His-plate (B) are shown. Beta-AR phage clones (hashed bars) from left to right (C1, E2, A3, G3, C4, D4, F4, H4, D5, F5, G5, C6, D6, C7, F7, B8 and C8) names originates from the screen shown in FIGS. 30A and 30B. In the graph, sticky anti β-AR clones are indicated by their clone names over the corresponding bar. Also shown are binding of control phage populations specific to the control proteins, anti-CD86 (grey bars), anti-N1 EGF (white bars) and anti-N1 NRR (dotted bars).

For ELISA, βAR was covalently immobilised on Amino plates (Nunc Catalog No: 436008). Coating and washing buffers were supplemented with 20 nM ligand and 0.1% dec-M. The ELISA plate was coated overnight with β-AR at 24 μg/ml and 2 control proteins (CD86 and Notch1) at 5 μg/ml. Next day the wells were washed and blocked with PBS-M. 50 μl/well of polyclonal phage from 2 rounds of selection were added (in PBS-M, at a concentration of 0.1× relative to the initial culture volume) and incubated for 1 hour at room temperature. Wells were washed and incubated with an α-M13 antibody (GE healthcare product No: 27-9421-01), for 1 hour at room temperature. Plates were washed and incubated with Europium labelled anti-mouse antibody (Perkin Elmer, product No: AD 0207), for 1 hour at room temperature. Wells were washed and 50 μl/well of enhancement solution (Perkin Elmer, product No: 4001-0010) added and incubated for 10 min. The results are shown in FIG. 30A, which suggests specific enrichment of β-AR binding phage in experiments A and B following 2 rounds of selection. Signals were higher from phage selection A (with ligand present in buffers).

Monoclonal Phage ELISA

Figure 30B:
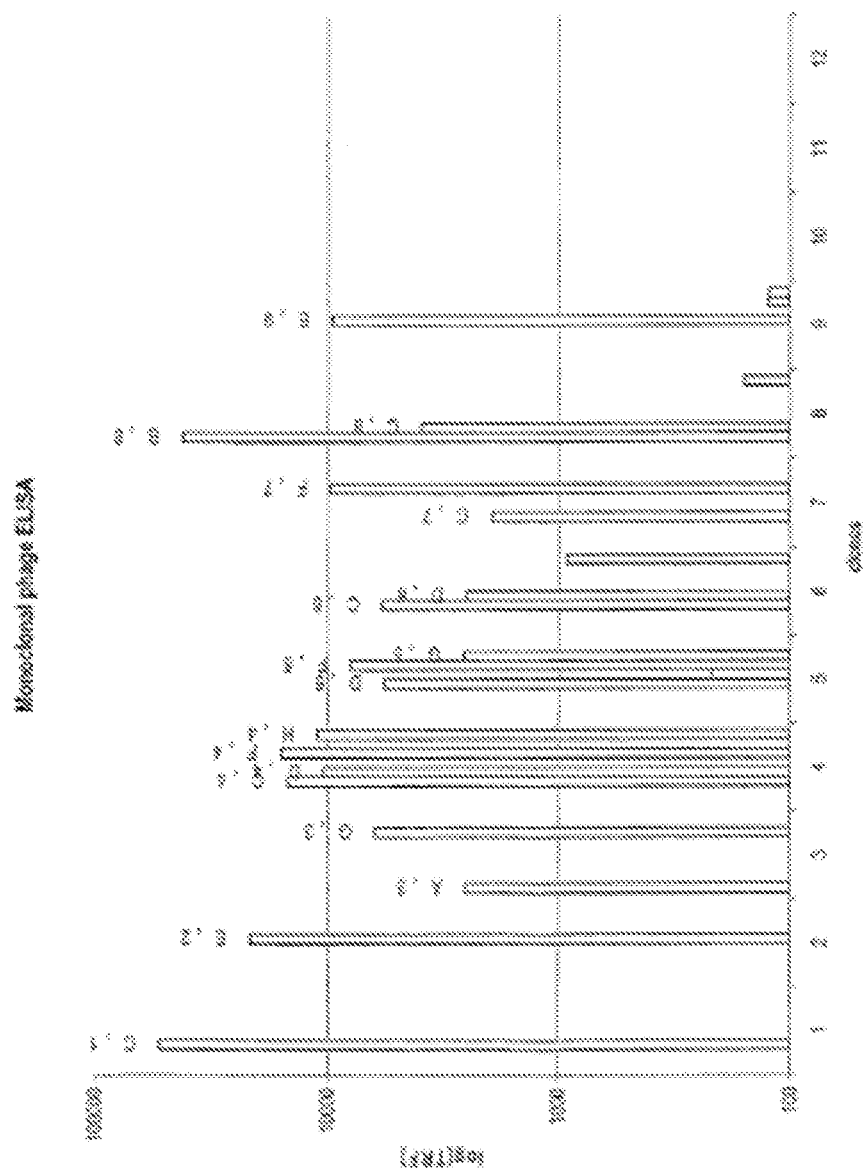

For this assay, individual clones of round 2 phage from selection A were picked, rescued and PEG precipitated. Again, coating, washing, blocking and antibody detection buffers were supplemented with 20 nM ligand and 0.1% detergent. Wells of a Nunc Amino plate were coated with β-AR for 1 h 30 minutes at room temperature. Coated wells were washed 3 times with PBST and 3 times with PBS and blocked with PBS-M and 50 ul/well of 0.1× phage was added and incubated for 1 h at room temperature. Wells were washed 6 times with PBS and incubated with α-M13 antibody for 1 h at room temperature. After washing 6 times with PBS the wells were incubated with anti-mouse-Eu antibody, 1 h at room temperature. Next, wells were washed and incubated with enhancement solution for 10 min. Out of 69 screened clones, 20 clones were detected as positive (FIG. 30B).

Figure 31A:
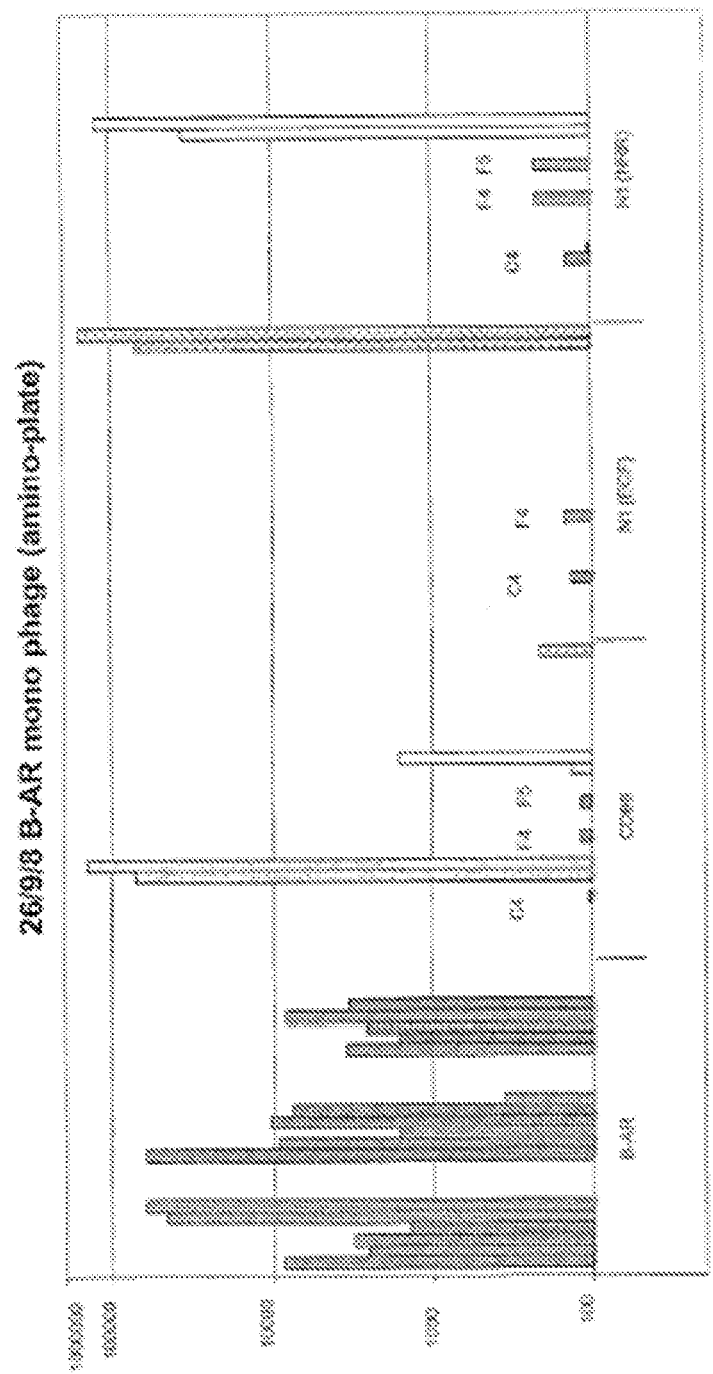
Figure 31B:
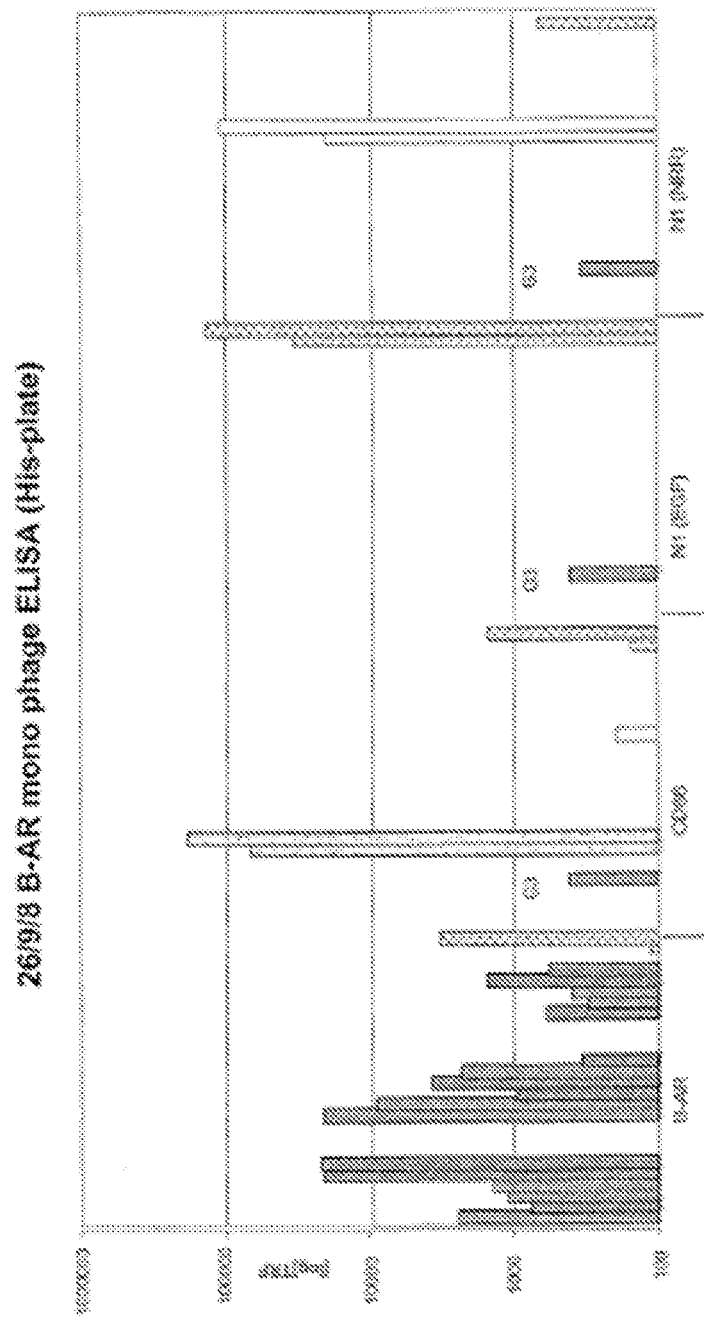

Specificity Phage ELISA 17 of the positive phage clones from the monoclonal ELISA were tested for binding specificity to β-AR and 3 unrelated proteins. This includes N1-EGF, (EGF domains 1-12 of murine Notch1 fused to a human Fc domain from R&D Systems, catalogue number 1057-TK). The other control proteins include the extracellular domain of murine CD86 and the negative regulatory region of murine Notch1 expressed as a CD4 fusion (CD86 and N1(NRR) respectively) in a transient expression system as described in Chapple et al 2006 (25). In this ELISA both nickel chelate and amino-plate were used for comparison. Again, for wells containing β-AR protein, coating, washing, blocking and antibody binding buffers were supplemented with 20 nM ligand and 0.1% detergent. Wells were washed and incubated with antibodies as described for the monoclonal ELISA in previous section. The assay showed that both His and Amino-plates can be used and that the majority of the anti-β-AR clones do not cross react with the unrelated proteins (FIGS. 31A and 31B).

Expression and Screening of Monoclonal scFv

Figure 32:
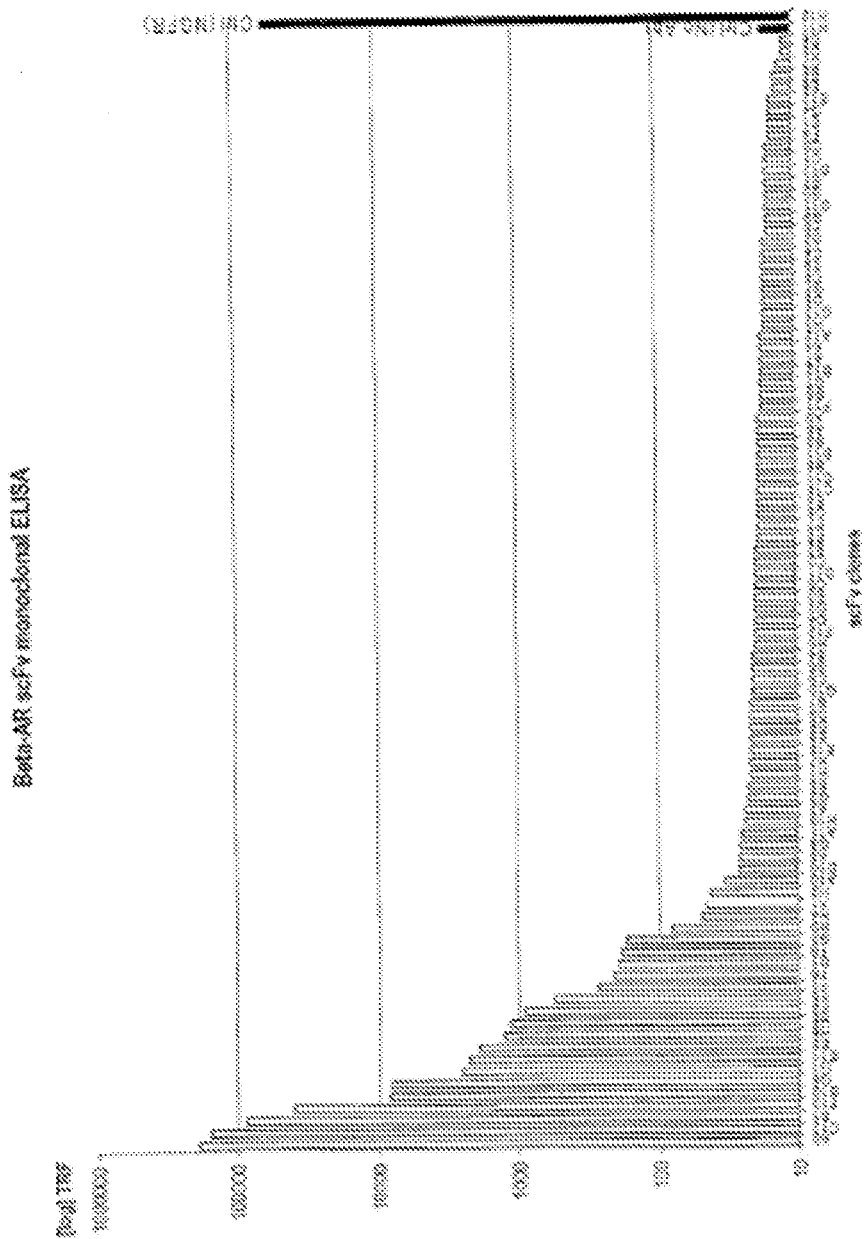
FIG. 32 Anti-β-AR antibody clones (white bars) and positive control antibody (black bar) and a no antibody negative control (black bar) are shown.

Sub-cloning, antibody single chain Fv (scFv) expression and purification were as described in Schofield et al (2007). Selected antibody genes within the round 2 phage population (selection A) were sub-cloned into the pSANG10-3F vector (26) and transformed into BL21(DE3) cells. 96 colonies were picked and periplasmic expression of the scFv antibody was induced in a 96 well format using standard methods in the art. scFv were recovered from the periplasm and used for ELISA on an Amino plate (Nunc). Washed and blocked wells were incubated for 1 h with 50 μl/well of scFv. Plates were washed and incubated with Europium labelled anti-FLAG antibody for 1 h at room temperature. 12 clones gave a signal above 1000 units with background levels of less than 50 for negative clones (FIG. 32).

Positive clones are selected with binding and specifically confirmed in a secondary ELISA, and clones of interest sequenced. Antibody sequences are analysed to identify the number of unique binding clones that have been isolated.

To test for blocking of ligand binding by isolated antibodies, unique positive antibody clones are selected for larger scale preparation (50-500 ml) using periplasmic extraction and immobilised metal affinity chromatography. This material is assessed for the ability to interfere in ligand binding to receptor using robust reporter assays (e.g. inhibition of cAMP generation or inhibition of ligand binding to transfected cells).

Example 7

Assessment of Compound Interaction with β1-AR

Methods and Results:

Binding studies were performed at 10° C. using a Biacore S51 optical biosensor equipped with a streptavidin-coated CM5 chip and equilibrated with running buffer (20 mM trisHCl, 150 mM NaCl, 1 mM EDTA, 1% DMSO, 0.1% decyl maltoside, pH 7.8).

β1AR Immobilization.

β1AR36-M23 was minimally biotinylated using EZ-link sulfo-NHS-LC-LC biotin (Pierce #21338): The biotin was added to the receptor preparation, (spiked with 100 uM alprenolol) and allowed to react for three hours at 4° C., after which free biotin was removed via column chromatography.

Figure 33A:
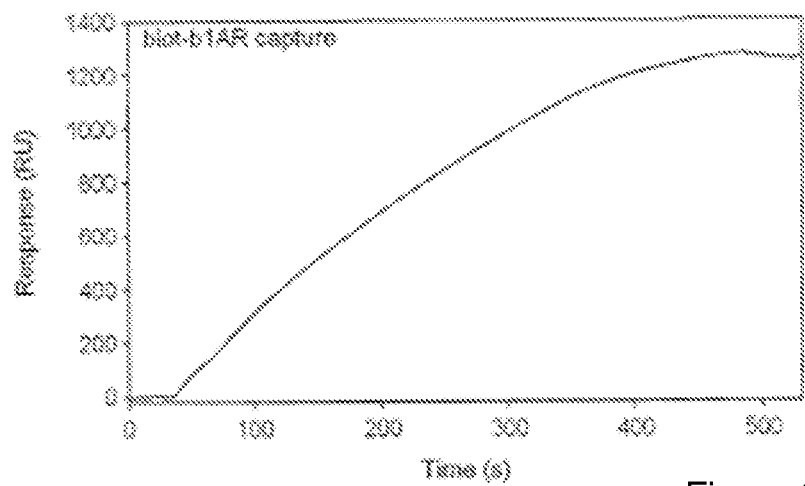
FIGS. 33A and 33B Two capture stages of the biotinylated β1 AR onto a streptavidin-coated flow cell. A ~1200 RU captured; B ~4000 RU captured.
Figure 33B:
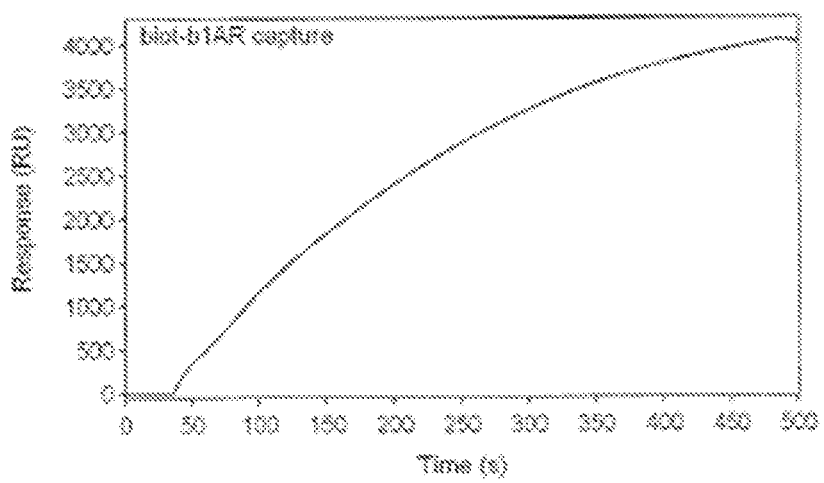

FIGS. 33A and 33B show the two capture stages of the biotinylated b1AR onto a streptavidin-coated flow cell. In the first stage, we captured ~1200 RU; in the second, ~4000 RU.

The biacore sensor chips coated in the stabilised beta receptor could be used to characterise the binding of drugs with activity at the beta receptor. Flow through of the compound allowed the on rate to be determined. Subsequent washing enabled determination of the off rate. These parameters could then be used to determine a kinetic affinity measurement (Kd).

Figure 34:
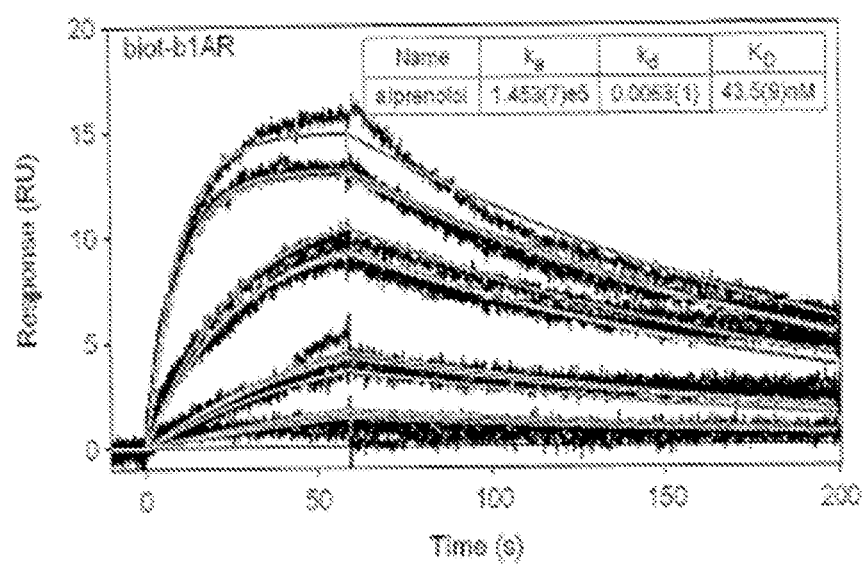
FIG. 34 Biacore responses for alprenolol. The highest concentration is 666 nM and each concentration was tested three times in a three-fold dilution series. The responses are concentration dependent and fairly reproducible. The lines depict the fit of a simple 1:1 interaction model and the parameters determined from this fit are listed in the inset (the number in parentheses is the error in the last digit).

FIG. 34 shows the responses for alprenolol which was tested in replicate in a three-fold dilution series for binding to the receptor surface The highest concentration is 666 nM and each concentration was tested three times. The responses are concentration dependent and are reproducible. The grey lines depict the fit of a simple 1:1 interaction model and the parameters determined from this fit are listed in the inset (the number in parentheses is the error in the last digit).

Figure 35:
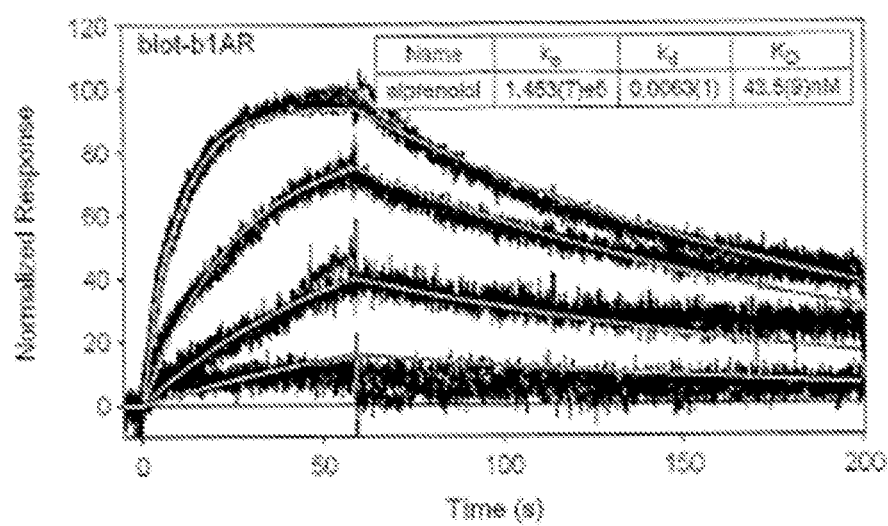
FIG. 35 Normalised responses to alprenolol. The responses are normalized with respect to the Rmax determined (from the fitting) for each curve.

FIG. 35 is an alternative depiction of the data set in FIG. 34. The responses are normalized with respect to the Rmax determined (from the fitting) for each curve.

The alprenolol data demonstrates that the biotinylated b1AR is active and this biosensor approach can be used to characterize the compound/receptor interactions.

Figure 36:
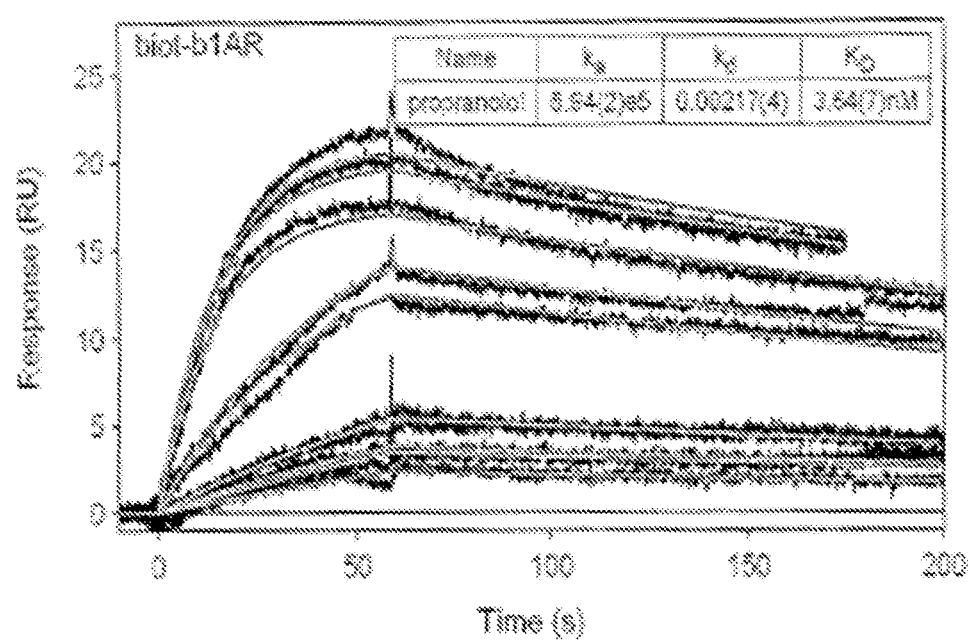
FIG. 36 Biacore responses for propranolol. The highest concentration is 111 nM and each concentration was tested two or three times in a three-fold dilution series.
Figure 37:
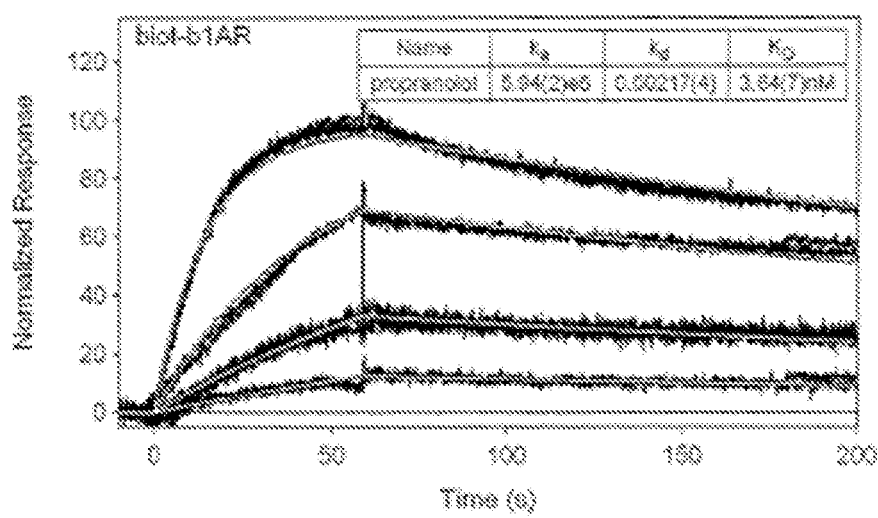
FIG. 37 Normalised responses to propranol. The responses are normalized with respect to the Rmax determined (from the fitting) for each curve.

FIG. 36 shows the responses for propranolol binding to β1AR. 111 nM is the highest concentration and each concentration was tested two or three times. The propranolol data are plotted as normalized responses in FIG. 37.

Figure 38:
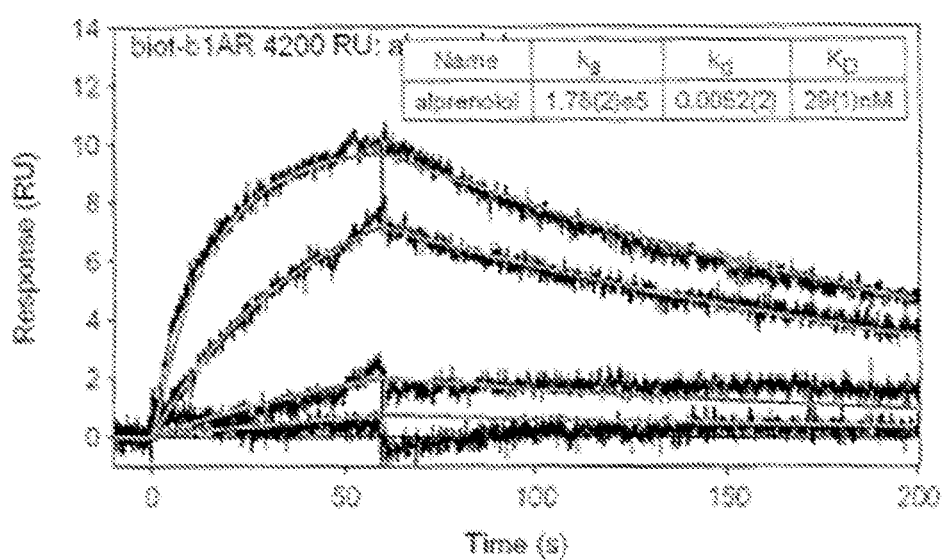
FIG. 38 Biacore responses to alprenolol on β1AR surface that was almost three days old.

When the β1AR surface was almost three days old, we retested alprenolol binding to determine how much activity the receptor had lost over time. FIG. 38 shows the alprenolol binding responses with 333 nM as the highest concentration. The receptor appeared to be nearly as active as when it was first captured.

β1AR Capture on Another Spot.

Figure 39:
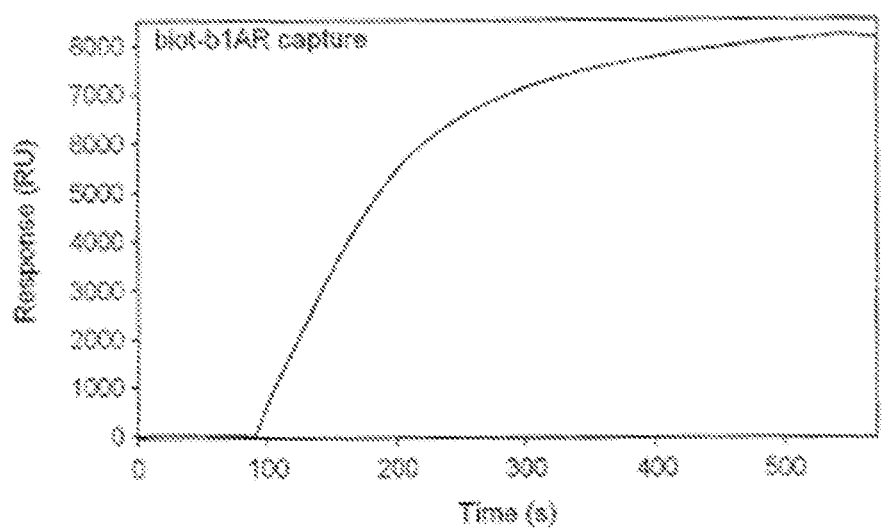
FIG. 39 Capture of β1AR to a density of 8000 RU.

The S51 biosensor has the ability to monitor two reaction spots at one time so we captured the receptor to a density of 8000 RU on another streptavidin-coated spot (FIG. 39).

Figure 40:
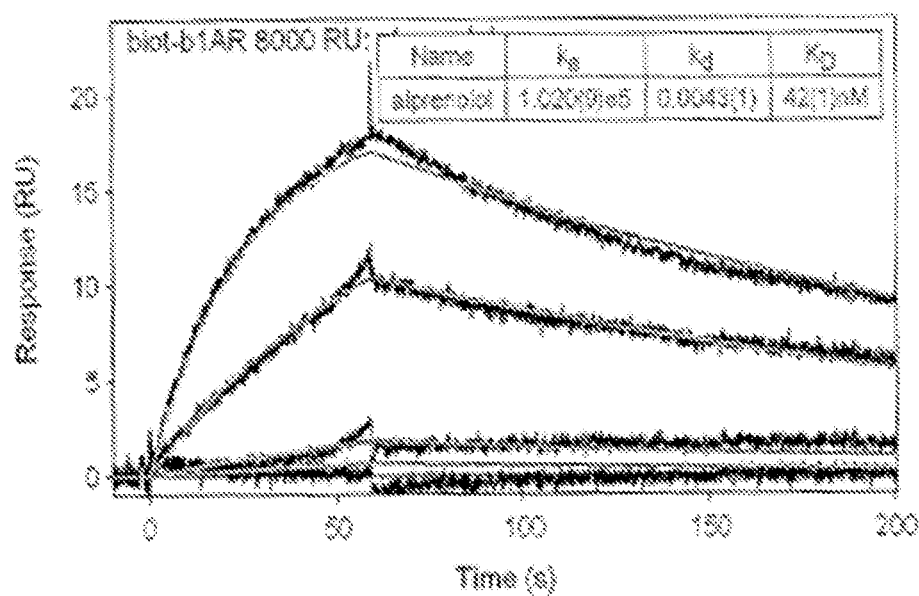
FIG. 40 Biacore response to alprenolol binding to 8000 RU β1AR surface.

The data from a test run of alprenolol binding to the 8000-RU b1AR spot are provided in FIG. 40.

Figure 41A:
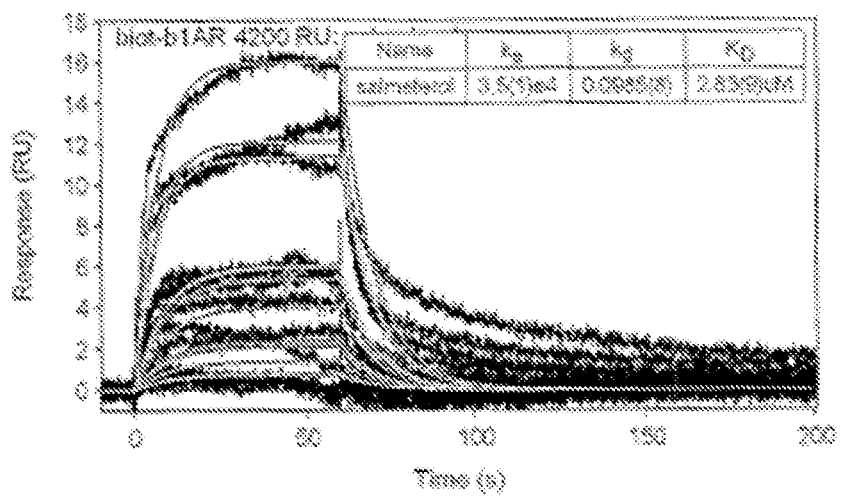
FIGS. 41A and 41B Biacore responses to salmeterol using 2 different surfaces. Salmeterol was tested using a highest concentration of 1.67 uM, with each concentration tested two or three times. A. 4200 RU surface; B. 8000 RU surface. Larger responses are observed with the 8000 RU surface.
Figure 41B:
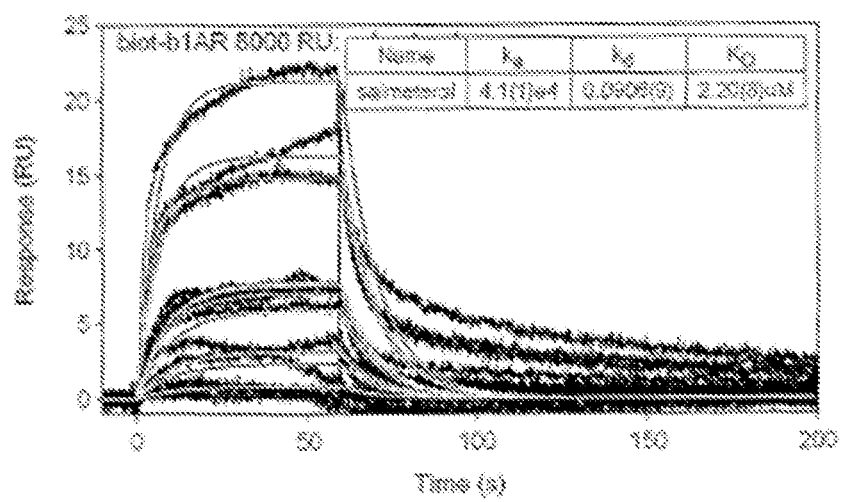

The beta receptor agonist salmeterol was tested using a highest concentration of 1.67 μM, with each concentration tested two or three times (FIGS. 41A and 41B). The responses are concentration dependent and mostly reproducible.

Also, the responses from the 8000 RU surface (FIG. 41B) were larger than from the 4200 RU surface (FIG. 41A), as expected.

Figure 42A:
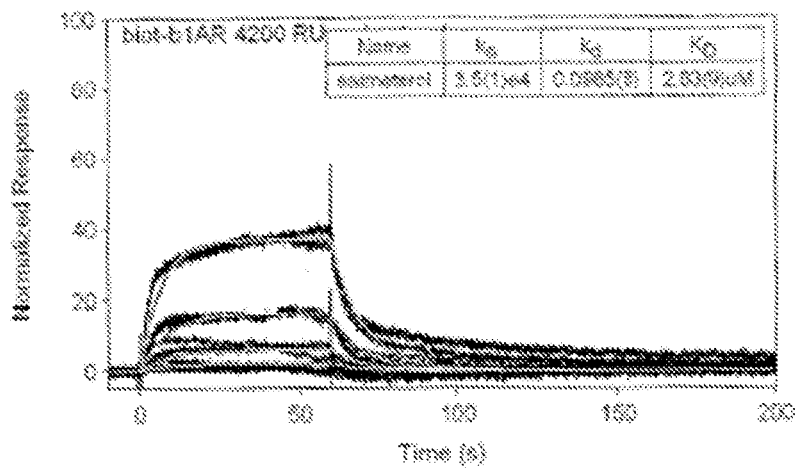
FIGS. 42A and 42B Biacore responses for salmeterol, shown as normalised responses. A. 4200 RU surface; B. 8000 RU surface.
Figure 42B:
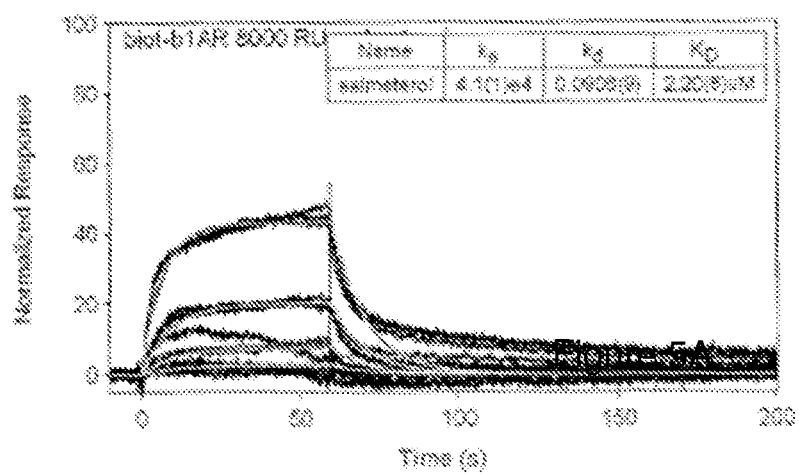

Salmeterol dissociated much faster and bound the receptor much more weakly than alprenolol or propranolol did. This is to be expected since salmeterol has a low affinity for the β1-AR and in particular has a low affinity for the antagonist stabilised form of the receptor which is used here. In addition, we detected some complexity in the interaction, as indicated by the poor fit of the model to the responses during the dissociation phase (t>60 sec). FIGS. 42A and 42B show the data plotted as normalized responses.

Figure 43A:
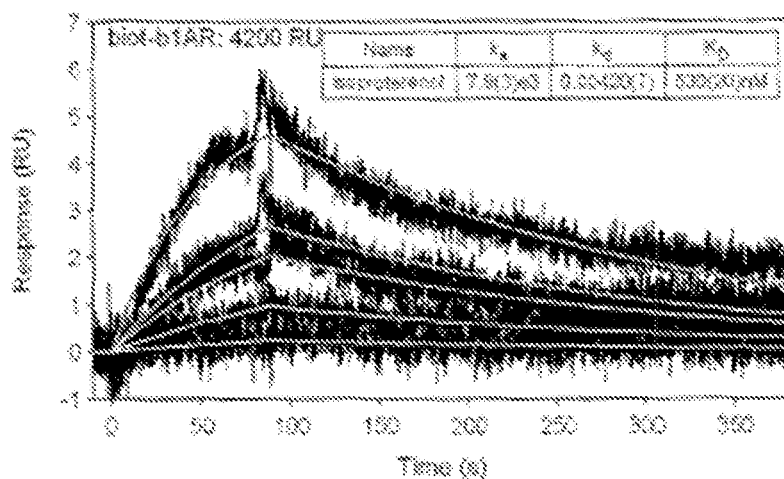
FIGS. 43A and 43B Biacore responses to isoproterenol. Isoproterenol was tested using a highest concentration of 2 μM. A. 4200 RU surface. B. 8000 RU surface.
Figure 43B:
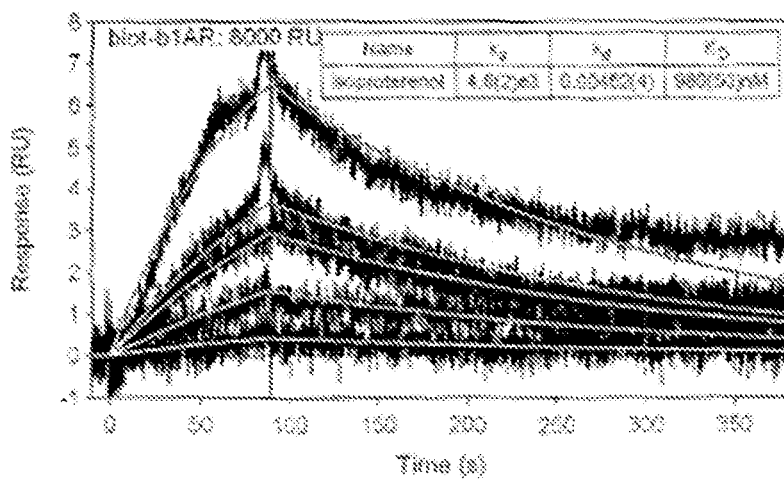

Isoproterenol, a non-selective β-adrenergic agonist, was tested using a highest concentration of 2 μM (FIGS. 43A and 43B). In this analysis, isoproterenol displayed a much slower association rate than the other compounds. The compound was injected for 90 sec.

Figure 44A:
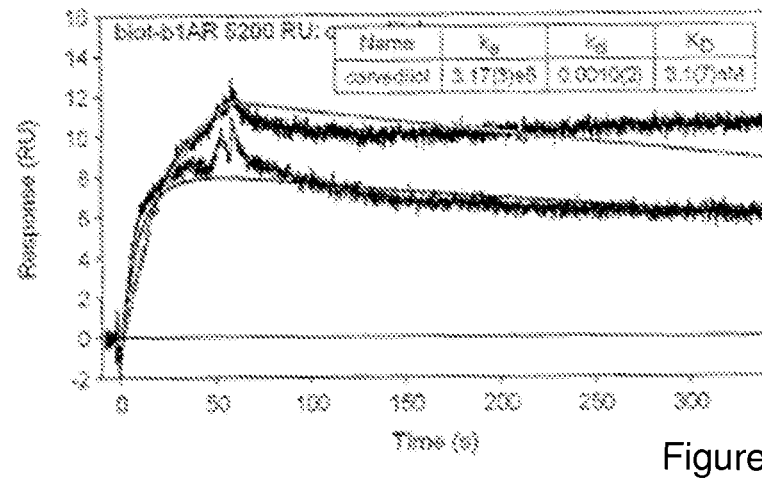
FIGS. 44A and 44B Biacore responses for carvedilol. A. 5200 RU surface; B. 8000 RU surface.
Figure 44B:
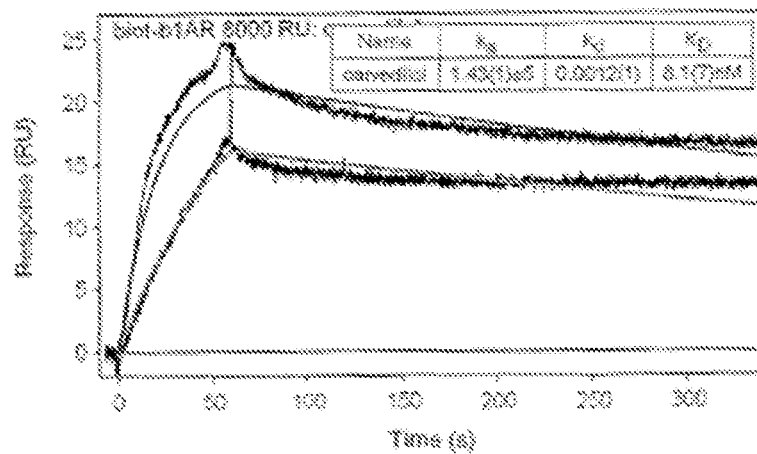

FIGS. 44A and B show responses for 111 uM and 333 nM carvedilol binding to the two b1AR surfaces. Carvedilol displays a much slower dissociation rate than the other compounds examined so far.

Conclusion

1. Minimal biotinylation and capture by streptavidin produced active b1AR surfaces that can be used to measure compound binding.
2. At 10° C., the b1AR surfaces remained active over several days.
3. For the compounds tested including agonists and antagonists, we observed differences in both the association and dissociation rates, as well as the affinities. This demonstrates the biosensor assay is a viable approach to characterising panels of compounds binding to this b1AR preparation.
4. Binding parameters were determined for several compounds as shown in Table A below, all of which were measured at 10° C.

TABLE A

|  | $k_a$ (M$^{-1}$s$^{-1}$) | $k_d$ (s$^{-1}$) | $K_D$ (nM) |
| --- | --- | --- | --- |
| Alprenolol | $(1.453 \pm 0.007) \times 10^5$ | $(6.3 \pm 0.1) \times 10^{-3}$ | $44 \pm 1$ |
| Propranolol | $(5.94 \pm 0.02) \times 10^5$ | $(2.17 \pm 0.04) \times 10^{-3}$ | $3.64 \pm 0.07$ |
| Salmeterol[1] | $(3.8 \pm 0.3) \times 10^4$ | $(9.5 \pm 0.4) \times 10^{-2}$ | $2500 \pm 300$ |
| Isoproterenol[1,2] | $(6 \pm 2) \times 10^3$ | $(4.4 \pm 0.2) \times 10^{-3}$ | $800 \pm 300$ |
| Carvedilol[1,2] | $(2.3 \pm 0.9) \times 10^5$ | $(1.1 \pm 0.1) \times 10^{-3}$ | $5 \pm 3$ |

[1]averaged from two b1AR surfaces
[2]preliminary results

Example 8

Use of the Adenosine A2a StaR for Compound Screening in Drug Discovery

Methods

A thermostabilised adenosine A2a receptor (A2a StaR) conformationally selected in the antagonist form (referred to as Rant22) was used to screen compounds from a library in order to identify compounds with activity at the A2a receptor. The StaR was generated as previously described (Magnani et al, Co-evolving stability and conformational homogeneity of the human adenosine A2a receptor. Proc Natl Acad Sci USA. 2008 Aug. 5; 105 (31):10744-9). HEK293T cells transfected with Rant22 A$_2$a receptors were grown in a monolayer in T-175 flasks at 37° C. and 5% CO$_2$ in Dulbeccos Modified Eagle Medium supplemented with 10% fetal bovine serum. Cells were harvested by scraping the cells from the T-175 surface and collected by centrifugation.

Membrane Preparation.

Cell pellets were resuspended in 10 ml 20 mM HEPES, pH 7.4 plus protease inhibitor cocktail tablets (Roche) and were homogenised for 30s at 20,500 rpm using a tissuemizer. Homogenates were centrifuged at 200×g for 15 min at 4° C. The supernatant was removed and reserved on ice. This procedure was repeated a further two times and the pooled supernatants were then centrifuged at 40,000×g for 45 min at 4° C. Membranes were resuspended in 1 ml aliquots of 20 mM HEPES, pH 7.4 plus protease inhibitor tablets. Protein concentration was determined by a BCA protein assay (Pierce).

Screening Assay.

10 μg aliquots of prepared membrane were incubated with [$^3$H]ZM241385 3.7 nM and an appropriate amount of unlabelled ligand for 60 min at room temperature. A serial dilution ranging from 10 mM-1 μM was screened in a 96 well format. The filter GFC plates were pre soaked in 0.1% PEI for 60 min. Radioactivity was determined by liquid scintillation counting using a Microbeta counter at 3 min/well.

Results

Figure 45:
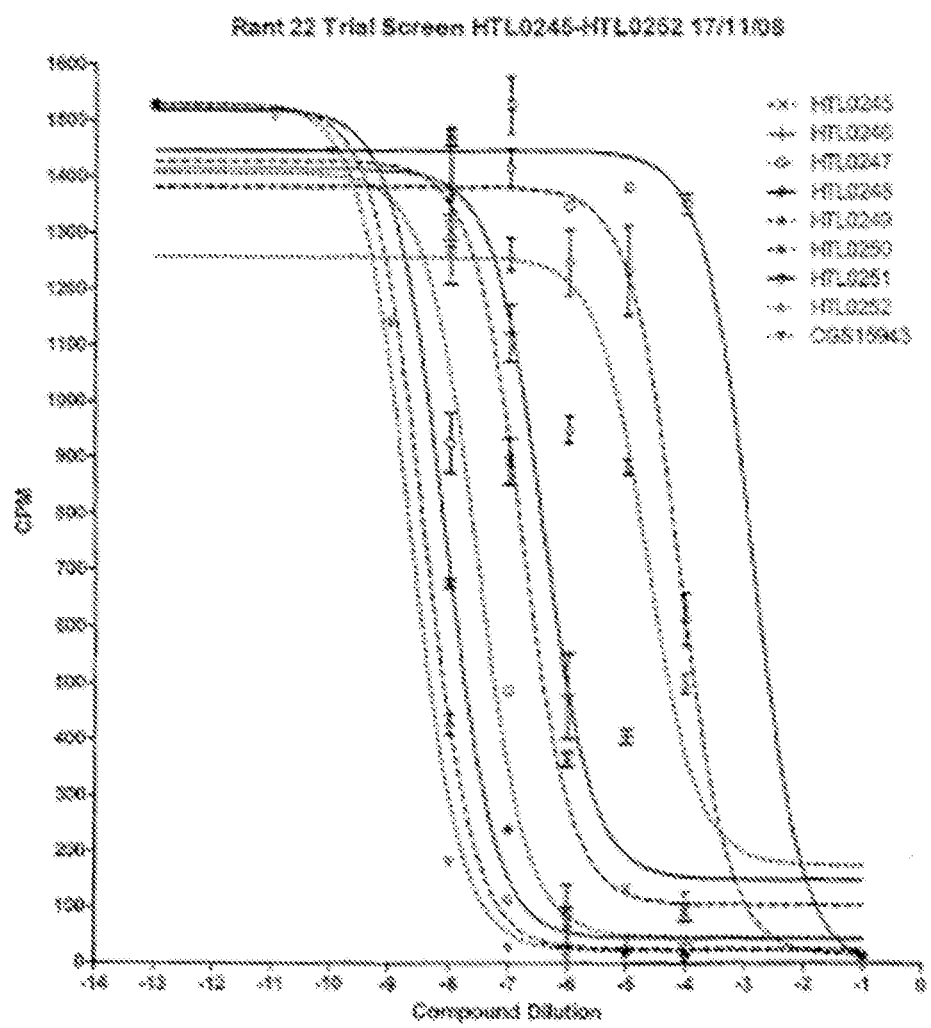
FIG. 45 Competition binding curves to a range of compounds tested for activity at the stabilised adenosine A2a receptor (Rant22) using [$^3$H]ZM241385.

Data was analysed using GraphPad prism to fit concentration response curves. The $IC_{50}$ of compounds was calculated as the concentration resulting in 50% inhibition of the specific binding of [$^3$H]ZM241385. The data presented in FIG. 45 and in Table B below demonstrates that the compounds tested were able to inhibit binding to the A2a receptor StaR and had a range of activities in this assay. This data demonstrates the utility of StaRs for compound screening.

TABLE B

|  | HTL0245 | HTL0246 | HTL0247 | HTL0248 | HTL0249 |
|---|---|---|---|---|---|
| Best-fit values | | | | | |
| Bottom | 105.2 | 151.2 | 47.23 | 44.21 | 25.74 |
| Top | 1428 | 1414 | 1406 | 1519 | 1527 |
| LogIC50 | −6.795 | −6.442 | −7.552 | −8.098 | −8.431 |
| IC50 | 1.605e−007 | 3.614e−007 | 2.804e−008 | 7.985e−009 | 3.709e−009 |
| Std. Error | | | | | |
| Bottom | 29.07 | 70.00 | 40.67 | 18.05 | 7.115 |
| Top | 44.68 | 83.73 | 96.91 | 50.84 | 20.46 |
| LogIC50 | 0.07888 | 0.1886 | 0.1338 | 0.05205 | 0.02427 |

|  | HTL0250 | HTL0251 | HTL0252 | CGS15943 |
|---|---|---|---|---|
| Best-fit values | | | | |
| Bottom | 13.98 | −5.831 | 176.4 | 22.40 |
| Top | 1382 | 1446 | 1257 | 1530 |
| LogIC50 | −4.112 | −2.874 | −4.658 | −8.661 |
| IC50 | 7.735e−005 | 0.001337 | 2.199e−005 | 2.183e−009 |
| Std. Error | | | | |
| Bottom | 104.4 | 79.15 | 154.9 | 29.97 |
| Top | 38.13 | 26.10 | 74.89 | 40.93 |
| LogIC50 | 0.1202 | 0.2821 | 0.2878 | 0.08677 |

REFERENCES

1. S. H. White (2004) *Protein Sci* 13, 1948-1949.
2. C. G. Tate (2001) *FEBS Lett* 504, 94-98.
3. R. Grisshammer, C. G. Tate (1995) *Q Rev Biophys* 28, 315-422.
4. J. U. Bowie (2001) *Curr Opin Struct Biol* 11, 397-402.
5. F. W. Lau, S. Nauli, Y. Zhou, J. U. Bowie (1999) *J Mol Biol* 290, 559-564.
6. Y. Zhou, J. U. Bowie (2000) *J Biol Chem* 275, 6975-6979.
7. S. Faham, D. Yang, E. Bare, S. Yohannan, J. P. Whitelegge, J. U. Bowie (2004) *J Mol Biol* 335, 297-305.
8. Y. Yarden, H. Rodriguez, S. K. Wong, D. R. Brandt, D. C. May, J. Burnier, R. N. Harkins, E. Y. Chen, J. Ramachandran, A. Ullrich, et al (1986) *Proc. Natl. Acad. Sci. USA* 83, 6795-6799.
9. T. Warne, J. Chirnside, G. F. Schertler (2003) *Biochim Biophys Acta* 1610, 133-140.
10. E. M. Parker, E. M. Ross (1991) *J Biol Chem* 266, 9987-9996.
11. E. M. Parker, K. Kameyama, T. Higashijima, E. M. Ross (1991) *J Biol Chem* 266, 519-527.
12. W. J. Degrip (1982) *Methods in Enzymology* 81, 256-265.
13. K. Palczewski, T. Kumasaka, T. Hori, C. A. Behnke, H. Motoshima, B. A. Fox, I. Le Trong, D. C. Teller, T. Okada, R. E. Stenkamp, et al (2000) *Science* 289, 739-745.
14. J. Li, P. C. Edwards, M. Burghammer, C. Villa, G. F. Schertler (2004) *J Mol Biol* 343, 1409-1438.
15. R. Jaenicke, G. Bohm (1998) *Current Opinion in Structural Biology* 8, 738-748.
16. J. Tucker, R. Grisshammer (1996) *Biochem J* 317 (Pt 3), 891-899.
17. W. Schaffner, C. Weissmann (1973) *Anal. Biochem.* 56, 502-514.
18. C. G. Tate (1998) *Methods Enzymol* 296, 443-455.
19. H. M. Weiss, R. Grisshammer (2002) *Eur J Biochem* 269, 82-92.
20. Rasmussen, S. G., Choi, H. J., Rosenbaum, D. M., Kobilka, T. S., Thian, F. S., Edwards, P. C., Burghammer, M., Ratnala, V. R., Sanishvili, R., Fischetti, R. F., Schertler, G. F., Weis, W. I. and Kobilka, B. K. (2007) *Nature* 15, 383-387.
21. Cherezov, V., Rosenbaum, D. M., Hanson, M. A., Rasmussen, S. G., Thian, F. S., Kobilka, T. S., Choi, H. J., Kuhn, P., Weis, W. I., Kobilka, B. K. and Stevens, R. C. (2007) *Science* 318:1258-1265.
22. Minneman, K. P., Weiland, G. A. and Molinoff, P. B. (1980) *Mol Pharmacol* 17:1-7.
23. Parker, E. M., Swigart, P., Nunnally, M. H., Perkins, J. P. and Ross, E. M. (1995) *J Biol Chem* 270:6482-6487.
24. Schofield D J, Pope A, Clementel V, Buckell J, Chapple S D J, Clarke K F, Conquer J S, Crofts A M, Crowther S R E, Dyson M R, Flack G, Griffin G J, Hooks Y, Howat W J, Kolb-Kokocinski A, Kunze S, Martin C D, Maslen G L, Mitchell J M, O'Sullivan M, Perera R L, Roake W, Shadbolt S P, Vincent K J, Warford A, Wilson W E, Xie J, Young J L, McCafferty J (2007) Application of phage display to high throughput antibody generation and characterisation. Genome Biology. 8 (11) R254
25. Chapple S D, Crofts A M, Shadbolt S P, McCafferty J, Dyson M R. (2006) Multiplexed expression and screening for recombinant protein production in mammalian cells. BMC Biotechnol. 2006 Dec. 22; 6:49. biomedcentral.com/1472-6750/6/49
26. Martin C, Rojas G, Mitchell J N, Vincent K J, Wu J, McCafferty J, Schofield D J (2006) A simple vector system to improve performance and utilisation of recombinant antibodies. BMC Biotechnology 6:46 doi:10.1186/1472-6750-6-46 biomedcentral.com/1472-6750/6/46/abstract
27. Warne et al (2008) Structure of a β adrenergic G protein coupled receptor *Nature* 454: 486-491

The invention claimed is:

1. A method of selecting a binding partner of a GPCR, the method comprising:
   a) providing a mutant GPCR of a parent GPCR, wherein the mutant GPCR has increased stability in a particular conformation under denaturing conditions relative to the parent GPCR in the same particular conformation under denaturing conditions;
   b) providing one or more test compounds;
   c) determining whether the or each test compound binds to the mutant GPCR when residing in a particular conformation; and
   d) isolating one or more test compounds that bind to the mutant GPCR when residing in the particular conformation.

2. A method according to claim 1, the method further comprising:
   e) determining whether the or each test compound binds to the parent GPCR when residing in the particular conformation and
   f) isolating the or each test compound that also binds the parent GPCR when residing in the particular conformation.

3. A method according to claim 1, wherein the mutant GPCR is immobilised onto a solid support.

4. A method according to claim 1, wherein more than one mutant GPCR is provided in step (a), it is determined whether the test compound binds to each mutant GPCR when residing in a particular conformation; and the test compound which binds to each mutant GPCR when residing in the particular conformation is isolated.

5. A method according to claim 1, wherein more than one mutant GPCR is provided in step (a) and a test compound is selected that binds to a first mutant GPCR but which does not bind, or binds less strongly than to the first mutant GPCR, to at least one other mutant GPCR.

6. A method according to claim 1, further comprising determining if the isolated test compound affects the function of the GPCR to which it binds.

7. A method according to claim 6, wherein it is determined if the isolated test compound affects the binding of the GPCR to its natural ligand or analog thereof.

8. A method according to claim 7, wherein the isolated test compound increases or decreases binding between the GPCR and its natural ligand or analog thereof.

9. A method according to claim 6, wherein it is determined if the isolated test compound modulates activation of the GPCR to which it binds.

10. A method according to claim 9, wherein the isolated test compound modulates any of calcium mobilisation, cAMP levels, kinase pathway activity, gene transcription from a reporter gene under control of the GPCR to which the test compound binds, β-arrestin recruitment, activation of G proteins, GTPase activity or [35S]GTPγS binding.

11. A method according to claim 9, wherein the isolated test compound is an agonist test compound that increases activation of the GPCR to which it binds.

12. A method according to claim 9, wherein the isolated test compound is an antagonist test compound that decreases activation of the GPCR to which it binds.

13. A method according to claim 1, wherein the mutant GPCR is provided by:
   (a) providing one or more mutants of a parent GPCR,
   (b) selecting a ligand, the ligand being one which binds to the parent GPCR when the GPCR is residing in a particular conformation,
   (c) determining whether the or each mutant GPCR has increased stability with respect to binding the selected ligand under denaturing conditions compared to the stability of the parent GPCR with respect to binding that ligand under denaturing conditions, and
   (d) selecting those mutants that have an increased stability compared to the parent GPCR with respect to binding the selected ligand under denaturing conditions.

14. A method according to claim 1, wherein the mutant GPCR is provided by:
   (a) providing one or more mutants of a parent GPCR,
   (b) selecting a ligand, the ligand being one which binds to the parent GPCR when the GPCR is residing in a particular conformation,
   (c) determining whether the or each mutant GPCR has increased stability with respect to binding the selected ligand under denaturing conditions compared to the stability of the parent GPCR with respect to binding that ligand under denaturing conditions,
   (d) selecting those mutants that have an increased stability compared to the parent GPCR with respect to binding the selected ligand,
   (e) identifying the position or positions of the mutated amino acid residue or residues in the mutant GPCR or GPCRs which has been selected for increased stability, and
   (f) synthesising a mutant GPCR which contains a replacement amino acid at one or more of the positions identified.

15. A method according to claim 1, wherein the mutant GPCR is provided by:
   (i) identifying in the amino acid sequence of one or more mutants of a first parent GPCR with increased stability in a particular conformation under denaturing conditions relative to the first parent GPCR in the same particular conformation under denaturing conditions, the position or positions at which the one or more mutants have at least one different amino acid residue compared to the first parent GPCR, and
   (ii) making one or more mutations in the amino acid sequence that defines a second GPCR at the corresponding position or positions, to provide one or more mutants of a second parent GPCR with increased stability in a particular conformation under denaturing conditions relative to the second parent GPCR in the same particular conformation under denaturing conditions.

16. A method according to claim 1, wherein the mutant GPCR is provided by:
   (i) providing one or more mutants of a first parent GPCR with increased stability in a particular conformation under denaturing conditions relative to the first parent GPCR in the same particular conformation under denaturing conditions
   (ii) identifying in a structural membrane protein model the structural motif or motifs in which the one or more mutants have at least one different amino acid residue compared to the first parent GPCR, and
   (iii) making one or more mutations in the amino acid sequence that defines a corresponding structural motif or motifs in a second parent GPCR, to provide one or more mutants of a second parent GPCR with increased stability in a particular conformation under denaturing conditions relative to the second parent GPCR in the same particular conformation under denaturing conditions.

17. A method according to claim 15, further comprising:
(I) selecting a ligand, the ligand being one which binds to the second parent GPCR when the GPCR is residing in a particular conformation
(II) determining whether the or each mutant of the second parent GPCR when residing in a particular conformation has increased stability with respect to binding the selected ligand compared to the stability of the second parent GPCR when residing in the same particular conformation with respect to binding that ligand, and
(III) selecting those mutants that have an increased stability compared to the second parent GPCR with respect to binding the selected ligand.

* * * * *

UNITED STATES PATENT AND TRADEMARK OFFICE
CERTIFICATE OF CORRECTION

PATENT NO. : 8,790,933 B2
APPLICATION NO. : 12/809181
DATED : July 29, 2014
INVENTOR(S) : Malcolm Peter Weir et al.

It is certified that error appears in the above-identified patent and that said Letters Patent is hereby corrected as shown below:

On the Title page:

Title: "SCREENING" should be replaced to read --METHODS FOR SCREENING FOR BINDING PARTNERS OF G-PROTEIN COUPLED RECEPTORS--

Inventors: For both inventor addresses, "Welwyn Garden" should be replaced to read --Welwyn Garden City--

In the Specification:

Column 3, Line 2, "Titremax" should be replaced to read --Titermax--

Column 49, Line 57, "Titremax" should be replaced to read --Titermax--

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

Page 1 of 1

PATENT NO. : 8,790,933 B2
APPLICATION NO. : 12/809181
DATED : July 29, 2014
INVENTOR(S) : Malcolm Peter Weir et al.

It is certified that error appears in the above-identified patent and that said Letters Patent is hereby corrected as shown below:

Title page, item (54) and in the Specification, Column 1, line 1, Title: "SCREENING" should be replaced to read --METHODS FOR SCREENING FOR BINDING PARTNERS OF G-PROTEIN COUPLED RECEPTORS--

Inventors: For both inventor addresses, "Welwyn Garden" should be replaced to read --Welwyn Garden City--

In the Specification:

Column 3, Line 2, "Titremax" should be replaced to read --Titermax--

Column 49, Line 57, "Titremax" should be replaced to read --Titermax--

This certificate supersedes the Certificate of Correction issued April 21, 2015.

Signed and Sealed this
Seventh Day of July, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 483
<212> TYPE: PRT
<213> ORGANISM: Meleagris gallopavo

<400> SEQUENCE: 1

```
Met Gly Asp Gly Trp Leu Pro Pro Asp Cys Gly Pro His Asn Arg Ser
1               5                   10                  15

Gly Gly Gly Ala Thr Ala Ala Pro Thr Gly Ser Arg Gln Val Ser
            20                  25                  30

Ala Glu Leu Leu Ser Gln Gln Trp Glu Ala Gly Met Ser Leu Leu Met
            35                  40                  45

Ala Leu Val Val Leu Leu Ile Val Ala Gly Asn Val Leu Val Ile Ala
        50                  55                  60

Ala Ile Gly Arg Thr Gln Arg Leu Gln Thr Leu Thr Asn Leu Phe Ile
65                  70                  75                  80

Thr Ser Leu Ala Cys Ala Asp Leu Val Met Gly Leu Leu Val Val Pro
                85                  90                  95

Phe Gly Ala Thr Leu Val Val Arg Gly Thr Trp Leu Trp Gly Ser Phe
            100                 105                 110

Leu Cys Glu Cys Trp Thr Ser Leu Asp Val Leu Cys Val Thr Ala Ser
            115                 120                 125

Ile Glu Thr Leu Cys Val Ile Ala Ile Asp Arg Tyr Leu Ala Ile Thr
        130                 135                 140

Ser Pro Phe Arg Tyr Gln Ser Leu Met Thr Arg Ala Arg Ala Lys Val
145                 150                 155                 160

Ile Ile Cys Thr Val Trp Ala Ile Ser Ala Leu Val Ser Phe Leu Pro
                165                 170                 175

Ile Met Met His Trp Trp Arg Asp Glu Asp Pro Gln Ala Leu Lys Cys
            180                 185                 190

Tyr Gln Asp Pro Gly Cys Cys Asp Phe Val Thr Asn Arg Ala Tyr Ala
            195                 200                 205

Ile Ala Ser Ser Ile Ile Ser Phe Tyr Ile Pro Leu Leu Ile Met Ile
        210                 215                 220

Phe Val Tyr Leu Arg Val Tyr Arg Glu Ala Lys Glu Gln Ile Arg Lys
225                 230                 235                 240

Ile Asp Arg Cys Glu Gly Arg Phe Tyr Gly Ser Gln Glu Gln Pro Gln
                245                 250                 255

Pro Pro Pro Leu Pro Gln His Gln Pro Ile Leu Gly Asn Gly Arg Ala
            260                 265                 270

Ser Lys Arg Lys Thr Ser Arg Val Met Ala Met Arg Glu His Lys Ala
        275                 280                 285

Leu Lys Thr Leu Gly Ile Ile Met Gly Val Phe Thr Leu Cys Trp Leu
        290                 295                 300

Pro Phe Phe Leu Val Asn Ile Val Asn Val Phe Asn Arg Asp Leu Val
305                 310                 315                 320

Pro Asp Trp Leu Phe Val Phe Asn Trp Leu Gly Tyr Ala Asn Ser
                325                 330                 335

Ala Phe Asn Pro Ile Ile Tyr Cys Arg Ser Pro Asp Phe Arg Lys Ala
            340                 345                 350

Phe Lys Arg Leu Leu Cys Phe Pro Arg Lys Ala Asp Arg Arg Leu His
        355                 360                 365
```

```
Ala Gly Gly Gln Pro Ala Pro Leu Pro Gly Gly Phe Ile Ser Thr Leu
    370             375             380

Gly Ser Pro Glu His Ser Pro Gly Gly Thr Trp Ser Asp Cys Asn Gly
385             390             395             400

Gly Thr Arg Gly Gly Ser Glu Ser Ser Leu Glu Glu Arg His Ser Lys
            405             410             415

Thr Ser Arg Ser Glu Ser Lys Met Glu Arg Glu Lys Asn Ile Leu Ala
            420             425             430

Thr Thr Arg Phe Tyr Cys Thr Phe Leu Gly Asn Gly Asp Lys Ala Val
            435             440             445

Phe Cys Thr Val Leu Arg Ile Val Lys Leu Phe Glu Asp Ala Thr Cys
    450             455             460

Thr Cys Pro His Thr His Lys Leu Lys Met Lys Trp Arg Phe Lys Gln
465             470             475             480

His Gln Ala

<210> SEQ ID NO 2
<211> LENGTH: 477
<212> TYPE: PRT
<213> ORGANISM: Homo sapiens

<400> SEQUENCE: 2

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255
```

```
Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475

<210> SEQ ID NO 3
<211> LENGTH: 413
<212> TYPE: PRT
<213> ORGANISM: Homo sapiens

<400> SEQUENCE: 3

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160
```

-continued

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 4
<211> LENGTH: 408
<212> TYPE: PRT
<213> ORGANISM: Homo sapiens

<400> SEQUENCE: 4

Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
            20                  25                  30

Val Pro Trp Glu Ala Ala Leu Ala Gly Ala Leu Leu Ala Leu Ala Val
        35                  40                  45

Leu Ala Thr Val Gly Gly Asn Leu Leu Val Ile Val Ala Ile Ala Trp
    50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
            100                 105                 110

Trp Thr Ser Val Asp Val Leu Cys Val Thr Ala Ser Ile Glu Thr Leu

```
            115                 120                 125
Cys Ala Leu Ala Val Asp Arg Tyr Leu Ala Val Thr Asn Pro Leu Arg
130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
        195                 200                 205

Ser Ser Val Ser Phe Tyr Leu Pro Leu Leu Val Met Leu Phe Val Tyr
    210                 215                 220

Ala Arg Val Phe Val Val Ala Thr Arg Gln Leu Arg Leu Leu Arg Gly
225                 230                 235                 240

Glu Leu Gly Arg Phe Pro Pro Glu Gly Ser Pro Ala Pro Ser Arg
                245                 250                 255

Ser Leu Ala Pro Ala Pro Val Gly Thr Cys Ala Pro Pro Glu Gly Val
                260                 265                 270

Pro Ala Cys Gly Arg Arg Pro Ala Arg Leu Leu Pro Leu Arg Glu His
            275                 280                 285

Arg Ala Leu Cys Thr Leu Gly Leu Ile Met Gly Thr Phe Thr Leu Cys
        290                 295                 300

Trp Leu Pro Phe Phe Leu Ala Asn Val Leu Arg Ala Leu Gly Gly Pro
305                 310                 315                 320

Ser Leu Val Pro Gly Pro Ala Phe Leu Ala Leu Asn Trp Leu Gly Tyr
                325                 330                 335

Ala Asn Ser Ala Phe Asn Pro Leu Ile Tyr Cys Arg Ser Pro Asp Phe
            340                 345                 350

Arg Ser Ala Phe Arg Arg Leu Leu Cys Arg Cys Gly Arg Arg Leu Pro
        355                 360                 365

Pro Glu Pro Cys Ala Ala Ala Arg Pro Ala Leu Phe Pro Ser Gly Val
    370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
                405

<210> SEQ ID NO 5
<211> LENGTH: 412
<212> TYPE: PRT
<213> ORGANISM: Homo sapiens

<400> SEQUENCE: 5

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80
```

```
Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
            115                 120                 125

Trp Val Leu Ser Phe Ala Ile Gly Leu Thr Pro Met Leu Gly Trp Asn
130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
                180                 185                 190

Met Leu Gly Val Tyr Leu Arg Ile Phe Leu Ala Ala Arg Arg Gln Leu
            195                 200                 205

Lys Gln Met Glu Ser Gln Pro Leu Pro Gly Glu Arg Ala Arg Ser Thr
            210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
                260                 265                 270

Ala Ile Val Leu Ser His Thr Asn Ser Val Val Asn Pro Phe Ile Tyr
            275                 280                 285

Ala Tyr Arg Ile Arg Glu Phe Arg Gln Thr Phe Arg Lys Ile Ile Arg
            290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
                340                 345                 350

His Pro Glu Arg Arg Pro Asn Gly Tyr Ala Leu Gly Leu Val Ser Gly
            355                 360                 365

Gly Ser Ala Gln Glu Ser Gln Gly Asn Thr Gly Leu Pro Asp Val Glu
370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410

<210> SEQ ID NO 6
<211> LENGTH: 332
<212> TYPE: PRT
<213> ORGANISM: Homo sapiens

<400> SEQUENCE: 6

Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
            20                  25                  30

Gly Thr Ala Asn Thr Leu Gln Thr Pro Thr Asn Tyr Phe Leu Val Ser
            35                  40                  45
```

```
Leu Ala Ala Ala Asp Val Ala Val Gly Leu Phe Ala Ile Pro Phe Ala
 50                  55                  60

Ile Thr Ile Ser Leu Gly Phe Cys Thr Asp Phe Tyr Gly Cys Leu Phe
 65                  70                  75                  80

Leu Ala Cys Phe Val Leu Val Leu Thr Gln Ser Ser Ile Phe Ser Leu
                 85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
        115                 120                 125

Leu Trp Val Leu Ala Phe Gly Ile Gly Leu Thr Pro Phe Leu Gly Trp
130                 135                 140

Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                165                 170                 175

Val Pro Met Ser Tyr Met Val Tyr Phe Asn Phe Phe Gly Cys Val Leu
            180                 185                 190

Pro Pro Leu Leu Ile Met Leu Val Ile Tyr Ile Lys Ile Phe Leu Val
        195                 200                 205

Ala Cys Arg Gln Leu Gln Arg Thr Glu Leu Met Asp His Ser Arg Thr
210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
            260                 265                 270

Asn Met Ala Ile Leu Leu Ser His Ala Asn Ser Val Val Asn Pro Ile
        275                 280                 285

Val Tyr Ala Tyr Arg Asn Arg Asp Phe Arg Tyr Thr Phe His Lys Ile
290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330

<210> SEQ ID NO 7
<211> LENGTH: 318
<212> TYPE: PRT
<213> ORGANISM: Homo sapiens

<400> SEQUENCE: 7

Met Pro Asn Asn Ser Thr Ala Leu Ser Leu Ala Asn Val Thr Tyr Ile
 1               5                  10                  15

Thr Met Glu Ile Phe Ile Gly Leu Cys Ala Ile Val Gly Asn Val Leu
                20                  25                  30

Val Ile Cys Val Val Lys Leu Asn Pro Ser Leu Gln Thr Thr Thr Phe
            35                  40                  45

Tyr Phe Ile Val Ser Leu Ala Leu Ala Asp Ile Ala Val Gly Val Leu
        50                  55                  60

Val Met Pro Leu Ala Ile Val Val Ser Leu Gly Ile Thr Ile His Phe
 65                  70                  75                  80

Tyr Ser Cys Leu Phe Met Thr Cys Leu Leu Leu Ile Phe Thr His Ala
```

```
                    85                  90                  95
Ser Ile Met Ser Leu Leu Ala Ile Ala Val Asp Arg Tyr Leu Arg Val
                100                 105                 110

Lys Leu Thr Val Arg Tyr Lys Val Thr Thr His Arg Arg Ile Trp
            115                 120                 125

Leu Ala Leu Gly Leu Cys Trp Leu Val Ser Phe Leu Val Gly Leu Thr
130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
                165                 170                 175

Met Val Tyr Phe Ser Phe Leu Thr Trp Ile Phe Ile Pro Leu Val Val
                180                 185                 190

Met Cys Ala Ile Tyr Leu Asp Ile Phe Tyr Ile Ile Arg Asn Lys Leu
                195                 200                 205

Ser Leu Asn Leu Ser Asn Ser Lys Glu Thr Gly Ala Phe Tyr Gly Arg
            210                 215                 220

Glu Phe Lys Thr Ala Lys Ser Leu Phe Leu Val Leu Phe Leu Phe Ala
225                 230                 235                 240

Leu Ser Trp Leu Pro Leu Ser Ile Ile Asn Cys Ile Ile Tyr Phe Asn
                245                 250                 255

Gly Glu Val Pro Gln Leu Val Leu Tyr Met Gly Ile Leu Leu Ser His
                260                 265                 270

Ala Asn Ser Met Met Asn Pro Ile Val Tyr Ala Tyr Lys Ile Lys Lys
            275                 280                 285

Phe Lys Glu Thr Tyr Leu Leu Ile Leu Lys Ala Cys Val Val Cys His
290                 295                 300

Pro Ser Asp Ser Leu Asp Thr Ser Ile Glu Lys Asn Ser Glu
305                 310                 315

<210> SEQ ID NO 8
<211> LENGTH: 326
<212> TYPE: PRT
<213> ORGANISM: Homo sapiens

<400> SEQUENCE: 8

Met Pro Pro Ser Ile Ser Ala Phe Gln Ala Ala Tyr Ile Gly Ile Glu
1               5                   10                  15

Val Leu Ile Ala Leu Val Ser Val Pro Gly Asn Val Leu Val Ile Trp
                20                  25                  30

Ala Val Lys Val Asn Gln Ala Leu Arg Asp Ala Thr Phe Cys Phe Ile
            35                  40                  45

Val Ser Leu Ala Val Ala Asp Val Ala Val Gly Ala Leu Val Ile Pro
50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
                85                  90                  95

Ala Leu Leu Ala Ile Ala Val Asp Arg Tyr Leu Arg Val Lys Ile Pro
            100                 105                 110

Leu Arg Tyr Lys Met Val Val Thr Pro Arg Arg Ala Val Ala Ile
            115                 120                 125

Ala Gly Cys Trp Ile Leu Ser Phe Val Val Gly Leu Thr Pro Met Phe
130                 135                 140
```

```
Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175

Met Glu Tyr Met Val Tyr Phe Asn Phe Phe Val Trp Val Leu Pro Pro
            180                 185                 190

Leu Leu Leu Met Val Leu Ile Tyr Leu Glu Val Phe Tyr Leu Ile Arg
            195                 200                 205

Lys Gln Leu Asn Lys Lys Val Ser Ala Ser Ser Gly Asp Pro Gln Lys
        210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
                245                 250                 255

Thr Leu Phe Cys Pro Ser Cys His Lys Pro Ser Ile Leu Thr Tyr Ile
            260                 265                 270

Ala Ile Phe Leu Thr His Gly Asn Ser Ala Met Asn Pro Ile Val Tyr
        275                 280                 285

Ala Phe Arg Ile Gln Lys Phe Arg Val Thr Phe Leu Lys Ile Trp Asn
290                 295                 300

Asp His Phe Arg Cys Gln Pro Ala Pro Pro Ile Asp Glu Asp Leu Pro
305                 310                 315                 320

Glu Glu Arg Pro Asp Asp
                325

<210> SEQ ID NO 9
<211> LENGTH: 424
<212> TYPE: PRT
<213> ORGANISM: Rattus norvegicus

<400> SEQUENCE: 9

Met His Leu Asn Ser Ser Val Pro Gln Gly Thr Pro Gly Glu Pro Asp
1               5                   10                  15

Ala Gln Pro Phe Ser Gly Pro Gln Ser Glu Met Glu Ala Thr Phe Leu
                20                  25                  30

Ala Leu Ser Leu Ser Asn Gly Ser Gly Asn Thr Ser Glu Ser Asp Thr
            35                  40                  45

Ala Gly Pro Asn Ser Asp Leu Asp Val Asn Thr Asp Ile Tyr Ser Lys
        50                  55                  60

Val Leu Val Thr Ala Ile Tyr Leu Ala Leu Phe Val Val Gly Thr Val
65                  70                  75                  80

Gly Asn Ser Val Thr Ala Phe Thr Leu Ala Arg Lys Lys Ser Leu Gln
                85                  90                  95

Ser Leu Gln Ser Thr Val His Tyr His Leu Gly Ser Leu Ala Leu Ser
                100                 105                 110

Asp Leu Leu Ile Leu Leu Leu Ala Met Pro Val Glu Leu Tyr Asn Phe
            115                 120                 125

Ile Trp Val His His Pro Trp Ala Phe Gly Asp Ala Gly Cys Arg Gly
        130                 135                 140

Tyr Tyr Phe Leu Arg Asp Ala Cys Thr Tyr Ala Thr Ala Leu Asn Val
145                 150                 155                 160

Ala Ser Leu Ser Val Glu Arg Tyr Leu Ala Ile Cys His Pro Phe Lys
                165                 170                 175

Ala Lys Thr Leu Met Ser Arg Ser Arg Thr Lys Lys Phe Ile Ser Ala
            180                 185                 190
```

```
Ile Trp Leu Ala Ser Ala Leu Leu Ala Ile Pro Met Leu Phe Thr Met
        195                 200                 205

Gly Leu Gln Asn Arg Ser Gly Asp Gly Thr His Pro Gly Gly Leu Val
210                 215                 220

Cys Thr Pro Ile Val Asp Thr Ala Thr Val Lys Val Val Ile Gln Val
225                 230                 235                 240

Asn Thr Phe Met Ser Phe Leu Phe Pro Met Leu Val Ile Ser Ile Leu
                245                 250                 255

Asn Thr Val Ile Ala Asn Lys Leu Thr Val Met Val His Gln Ala Ala
                260                 265                 270

Glu Gln Gly Arg Val Cys Thr Val Gly Thr His Asn Gly Leu Glu His
            275                 280                 285

Ser Thr Phe Asn Met Thr Ile Glu Pro Gly Arg Val Gln Ala Leu Arg
        290                 295                 300

His Gly Val Leu Val Leu Arg Ala Val Val Ile Ala Phe Val Val Cys
305                 310                 315                 320

Trp Leu Pro Tyr His Val Arg Arg Leu Met Phe Cys Tyr Ile Ser Asp
                325                 330                 335

Glu Gln Trp Thr Thr Phe Leu Phe Asp Phe Tyr His Tyr Phe Tyr Met
                340                 345                 350

Leu Thr Asn Ala Leu Phe Tyr Val Ser Ser Ala Ile Asn Pro Ile Leu
            355                 360                 365

Tyr Asn Leu Val Ser Ala Asn Phe Arg Gln Val Phe Leu Ser Thr Leu
        370                 375                 380

Ala Cys Leu Cys Pro Gly Trp Arg His Arg Arg Lys Lys Arg Pro Thr
385                 390                 395                 400

Phe Ser Arg Lys Pro Asn Ser Met Ser Ser Asn His Ala Phe Ser Thr
                405                 410                 415

Ser Ala Thr Arg Glu Thr Leu Tyr
            420

<210> SEQ ID NO 10
<211> LENGTH: 418
<212> TYPE: PRT
<213> ORGANISM: Homo sapiens

<400> SEQUENCE: 10

Met Arg Leu Asn Ser Ser Ala Pro Gly Thr Pro Gly Thr Pro Ala Ala
1               5                   10                  15

Asp Pro Phe Gln Arg Ala Gln Ala Gly Leu Glu Glu Ala Leu Leu Ala
                20                  25                  30

Pro Gly Phe Gly Asn Ala Ser Gly Asn Ala Ser Glu Arg Val Leu Ala
            35                  40                  45

Ala Pro Ser Ser Glu Leu Asp Val Asn Thr Asp Ile Tyr Ser Lys Val
50                  55                  60

Leu Val Thr Ala Val Tyr Leu Ala Leu Phe Val Val Gly Thr Val Gly
65                  70                  75                  80

Asn Thr Val Thr Ala Phe Thr Leu Ala Arg Lys Lys Ser Leu Gln Ser
                85                  90                  95

Leu Gln Ser Thr Val His Tyr His Leu Gly Ser Leu Ala Leu Ser Asp
                100                 105                 110

Leu Leu Thr Leu Leu Leu Ala Met Pro Val Glu Leu Tyr Asn Phe Ile
            115                 120                 125

Trp Val His His Pro Trp Ala Phe Gly Asp Ala Gly Cys Arg Gly Tyr
```

```
                130                 135                 140
Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
                180                 185                 190

Trp Leu Ala Ser Ala Leu Leu Ala Val Pro Met Leu Phe Thr Met Gly
            195                 200                 205

Glu Gln Asn Arg Ser Ala Asp Gly Gln His Ala Gly Gly Leu Val Cys
        210                 215                 220

Thr Pro Thr Ile His Thr Ala Thr Val Lys Val Ile Gln Val Asn
225                 230                 235                 240

Thr Phe Met Ser Phe Ile Phe Pro Met Val Val Ile Ser Val Leu Asn
                245                 250                 255

Thr Ile Ile Ala Asn Lys Leu Thr Val Met Val Arg Gln Ala Ala Glu
                260                 265                 270

Gln Gly Gln Val Cys Thr Val Gly Gly Glu His Ser Thr Phe Ser Met
            275                 280                 285

Ala Ile Glu Pro Gly Arg Val Gln Ala Leu Arg His Gly Val Arg Val
        290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
                325                 330                 335

Phe Leu Tyr Asp Phe Tyr His Tyr Phe Tyr Met Val Thr Asn Ala Leu
                340                 345                 350

Phe Tyr Val Ser Ser Thr Ile Asn Pro Ile Leu Tyr Asn Leu Val Ser
            355                 360                 365

Ala Asn Phe Arg His Ile Phe Leu Ala Thr Leu Ala Cys Leu Cys Pro
        370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
                405                 410                 415

Leu Tyr

<210> SEQ ID NO 11
<211> LENGTH: 409
<212> TYPE: PRT
<213> ORGANISM: Homo sapiens

<400> SEQUENCE: 11

Met Glu Thr Ser Ser Pro Arg Pro Pro Arg Pro Ser Ser Asn Pro Gly
1               5                   10                  15

Leu Ser Leu Asp Ala Arg Leu Gly Val Asp Thr Arg Leu Trp Ala Lys
            20                  25                  30

Val Leu Phe Thr Ala Leu Tyr Ala Leu Ile Trp Ala Leu Gly Ala Ala
        35                  40                  45

Gly Asn Ala Leu Ser Val His Val Val Leu Lys Ala Arg Ala Gly Arg
    50                  55                  60

Ala Gly Arg Leu Arg His His Val Leu Ser Leu Ala Leu Ala Gly Leu
65                  70                  75                  80

Leu Leu Leu Leu Val Gly Val Pro Val Glu Leu Tyr Ser Phe Val Trp
```

85                  90                  95
Phe His Tyr Pro Trp Val Phe Gly Asp Leu Gly Cys Arg Gly Tyr Tyr
                100                 105                 110

Phe Val His Glu Leu Cys Ala Tyr Ala Thr Val Leu Ser Val Ala Gly
            115                 120                 125

Leu Ser Ala Glu Arg Cys Leu Ala Val Cys Gln Pro Leu Arg Ala Arg
        130                 135                 140

Ser Leu Leu Thr Pro Arg Arg Thr Arg Trp Leu Val Ala Leu Ser Trp
145                 150                 155                 160

Ala Ala Ser Leu Gly Leu Ala Leu Pro Met Ala Val Ile Met Gly Gln
                165                 170                 175

Lys His Glu Leu Glu Thr Ala Asp Gly Glu Pro Glu Pro Ala Ser Arg
            180                 185                 190

Val Cys Thr Val Leu Val Ser Arg Thr Ala Leu Gln Val Phe Ile Gln
        195                 200                 205

Val Asn Val Leu Val Ser Phe Val Leu Pro Leu Ala Leu Thr Ala Phe
210                 215                 220

Leu Asn Gly Val Thr Val Ser His Leu Leu Ala Leu Cys Ser Gln Val
225                 230                 235                 240

Pro Ser Thr Ser Thr Pro Gly Ser Ser Thr Pro Ser Arg Leu Glu Leu
                245                 250                 255

Leu Ser Glu Gly Leu Leu Ser Phe Ile Val Trp Lys Lys Thr Phe
            260                 265                 270

Ile Gln Gly Gly Gln Val Ser Leu Val Arg His Lys Asp Val Arg Arg
        275                 280                 285

Ile Arg Ser Leu Gln Arg Ser Val Gln Val Leu Arg Ala Ile Val Val
290                 295                 300

Met Tyr Val Ile Cys Trp Leu Pro Tyr His Ala Arg Arg Leu Met Tyr
305                 310                 315                 320

Cys Tyr Val Pro Asp Asp Ala Trp Thr Asp Pro Leu Tyr Asn Phe Tyr
                325                 330                 335

His Tyr Phe Tyr Met Val Thr Asn Thr Leu Phe Tyr Val Ser Ser Ala
            340                 345                 350

Val Thr Pro Leu Leu Tyr Asn Ala Val Ser Ser Ser Phe Arg Lys Leu
        355                 360                 365

Phe Leu Glu Ala Val Ser Ser Leu Cys Gly Glu His His Pro Met Lys
370                 375                 380

Arg Leu Pro Pro Lys Pro Gln Ser Pro Thr Leu Met Asp Thr Ala Ser
385                 390                 395                 400

Gly Phe Gly Asp Pro Pro Glu Thr Arg
                405

<210> SEQ ID NO 12
<211> LENGTH: 460
<212> TYPE: PRT
<213> ORGANISM: Homo sapiens

<400> SEQUENCE: 12

Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Leu Ile
        35                  40                  45

-continued

```
Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
        115                 120                 125

Arg Pro Leu Ser Tyr Arg Ala Lys Arg Thr Pro Arg Arg Ala Ala Leu
    130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
            180                 185                 190

Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
    210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
            260                 265                 270

Ser Trp Lys Glu Glu Glu Glu Asp Glu Gly Ser Met Glu Ser Leu
        275                 280                 285

Thr Ser Ser Glu Gly Glu Glu Pro Gly Ser Glu Val Val Ile Lys Met
    290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
            340                 345                 350

Lys Thr Phe Ser Leu Val Lys Glu Lys Lys Ala Ala Arg Thr Leu Ser
        355                 360                 365

Ala Ile Leu Leu Ala Phe Ile Leu Thr Trp Thr Pro Tyr Asn Ile Met
    370                 375                 380

Val Leu Val Ser Thr Phe Cys Lys Asp Cys Val Pro Glu Thr Leu Trp
385                 390                 395                 400

Glu Leu Gly Tyr Trp Leu Cys Tyr Val Asn Ser Thr Ile Asn Pro Met
                405                 410                 415

Cys Tyr Ala Leu Cys Asn Lys Ala Phe Arg Asp Thr Phe Arg Leu Leu
            420                 425                 430

Leu Leu Cys Arg Trp Asp Lys Arg Arg Trp Arg Lys Ile Pro Lys Arg
        435                 440                 445

Pro Gly Ser Val His Arg Thr Pro Ser Arg Gln Cys
    450                 455                 460
```